(12) United States Patent
Ding et al.

(10) Patent No.: US 9,909,104 B2
(45) Date of Patent: Mar. 6, 2018

(54) GENERATING DEFINITIVE ENDODERM AND PANCREATIC PROGENITOR CELLS

(71) Applicant: The J. David Gladstone Institutes, a testamentary trust established under the Will of J. David Gladstone, San Francisco, CA (US)

(72) Inventors: Sheng Ding, Orinda, CA (US); Ke Li, San Francisco, CA (US); Saiyong Zhu, San Francisco, CA (US)

(73) Assignee: The J. David Gladstone Institutes, a testamentary trust established under the Will of J. David Gladstone, San Francisco, CA (US)

( * ) Notice: Subject to any disclaimer, the term of this patent is extended or adjusted under 35 U.S.C. 154(b) by 0 days.

(21) Appl. No.: 14/907,056

(22) PCT Filed: Jul. 25, 2014

(86) PCT No.: PCT/US2014/048258
§ 371 (c)(1),
(2) Date: Jan. 22, 2016

(87) PCT Pub. No.: WO2015/013653
PCT Pub. Date: Jan. 29, 2015

(65) Prior Publication Data
US 2016/0272944 A1    Sep. 22, 2016

Related U.S. Application Data

(60) Provisional application No. 61/859,025, filed on Jul. 26, 2013.

(51) Int. Cl.
*A61K 35/39* (2015.01)
*C12N 5/071* (2010.01)
*C12N 5/074* (2010.01)

(52) U.S. Cl.
CPC ............ *C12N 5/0678* (2013.01); *A61K 35/39* (2013.01); *C12N 5/0676* (2013.01); *C12N 5/0696* (2013.01); *C12N 2500/38* (2013.01); *C12N 2501/11* (2013.01); *C12N 2501/115* (2013.01); *C12N 2501/117* (2013.01); *C12N 2501/119* (2013.01); *C12N 2501/15* (2013.01); *C12N 2501/16* (2013.01); *C12N 2501/385* (2013.01); *C12N 2501/40* (2013.01); *C12N 2501/41* (2013.01); *C12N 2501/415* (2013.01); *C12N 2501/999* (2013.01); *C12N 2506/02* (2013.01); *C12N 2506/1307* (2013.01)

(58) Field of Classification Search
None
See application file for complete search history.

(56) References Cited

FOREIGN PATENT DOCUMENTS

| EP | 2288692 A1 | 3/2011 |
|---|---|---|
| WO | WO-2009157593 A1 | 12/2009 |
| WO | WO-201159726 A2 | 12/2011 |
| WO | WO-2015013653 A1 | 1/2015 |

OTHER PUBLICATIONS

"International Application Serial No. PCT/US2014/048258, International Search Report dated Oct. 28, 2014", 5 pgs.
"International Application Serial No. PCT/US2014/048258, Written Opinion dated Oct. 28, 2014", 9 pgs.
Ji, Shuyi, et al., "Cell fate conversion: Direct induction of hepatocyte-like cells from fibroblasts", Journal of Cellular Biochemistry, vol. 114, (Feb. 2013), 256-265.
Li, Ke, et al., "Small Molecules Facilitate the Reprogramming of Mouse Fibroblasts into Pancreatic Lineages", Cell Stem Cell14, (Feb. 16, 2014), 228-236.
Masaki, Hosoya, "Preparation of pancreatic β-cells from human iPS cells with small molecules", ISLETS, vol. 4, No. 3, (May 1, 2012), 249-252.
Thatava, T, et al., "Indolactarn V/GLP-1-mediated differentiation of human iPS cells into glucose-responsive insulin-secreting progeny", Gene Therapy, Nature Publishing Group, GB vol. 18, No. 3, (Mar. 1, 2011), 283-293.
"European Application Serial No. 14752486.2, Communication Pursuant to Article 94(3) EPC dated Nov. 24, 2016", 6 pgs.
"European Application Serial No. 14752486.2, Response filed Mar. 14, 2017 to Communication Pursuant to Article 94(3) EPC dated Nov. 24, 2016", 9 pgs.
"International Application Serial No. PCT/US2014/048258, International Preliminary Report on Patentability dated Feb. 4, 2016", 11 pgs.
"European Application Serial No. 14752486.2, Communication Pursuant to Article 94(3) EPC dated Oct. 17, 2017", 9 pgs.

*Primary Examiner* — David W Berke-Schlessel
(74) *Attorney, Agent, or Firm* — Schwegman Lundberg & Woessner, P.A.

(57) ABSTRACT

Compositions and methods of producing mammalian cell populations that include a high proportion of definitive endoderm cells, posterior foregut-like progenitor cells, pancreatic progenitor cells and/or pancreatic beta cells are described herein. Such cell populations are useful for treatment of diabetes.

21 Claims, 45 Drawing Sheets

Sox17/Foxa2    Cer/Foxa2    CXCR4/Foxa2

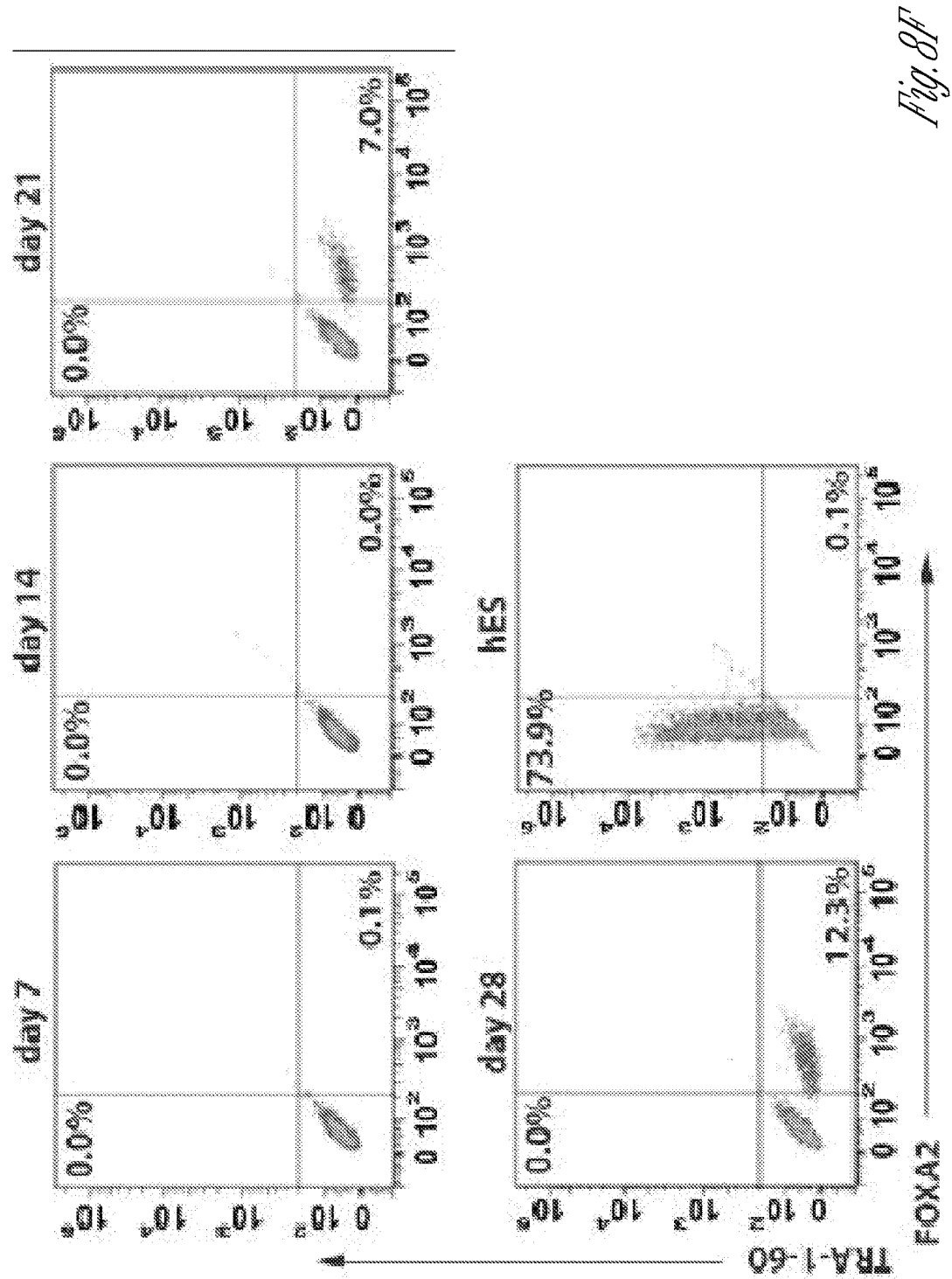

DAPI SOX17 FOXA2    DAPI HNFA FOXA2    DAPI HNF6 FOXA2

DAPI SOX17 FOXA2        DAPI HNFA FOXA2

DAPI HNF6 FOXA2         DAPI SOX9 FOXA2

DAPI PDX1 FOXA2 panKeratin HuNu

HNF4A b-catenin

SOX9 e-cadherin

PDX1 HuNu

DAPI FOXA2 PDX1    DAPI SOX9 PDX1    DAPI HNF6 PDX1

DAPI PDX1 NKX6.1

DAPI PDX1 NKX6.1

INS GCG PDX1

INS GCG NKX6.1

C-PEPTIDE PDX1

GENERATING DEFINITIVE ENDODERM AND PANCREATIC PROGENITOR CELLS

RELATED APPLICATIONS

This application is a U.S. National Stage Application under 35 U.S.C. 371 from International Application No. PCT/US2014/048258, filed. Jul. 25, 2014 and published as WO 2015/013653 A1 on Jan. 29, 2015, which application claims the benefit of priority to U.S. Provisional Patent Application Ser. No. 61/859,025 entitled "Generating Definitive Endoderm and Pancreatic Progenitor Cells," filed Jul. 26, 2013, the disclosure of which applications are incorporated by reference herein in their entireties.

BACKGROUND

Type-1 diabetes results from autoimmune destruction of the insulin-secreting beta cells within pancreatic islets. Typically it affects children and young adults. Proper management of type 1 diabetes requires frequent glucose monitoring and life-long insulin administration. In conjunction with new strategies to induce immune tolerance, the transplantation of healthy islet and beta cells to replace the lost cells may be a cure for the disease. However, a primary challenge remains—the scarcity of functional, glucose-responsive beta cells.

Researchers have been hopeful that stem cells could provide an unlimited source of functional beta cells. Stepwise differentiation conditions have been proposed that recapitulate developmental signaling and that purportedly differentiate pluripotent stem cells through a definitive endoderm stage all the way into functional pancreatic beta cells (D'Amour, Agulnick et al. 2005; Yasunaga, Tada et al. 2005; Gouon-Evans, Boussemart et al. 2006; Jiang, Shi et al. 2007; Kroon, Martinson et al. 2008; Green, Chen et al. 2011). However, use of stem cells as the starting material for generating pancreatic cells has problems, including lack of availability, potential immunological rejection, and social concerns.

Direct beta-cell reprogramming methods could be faster and more efficient than preparing induced pluripotent stem cells (iPSCs). However, a general approach to converting non-endoderm cells, such as fibroblast cells, across the germ-layer boundary towards an endoderm-beta cell lineage has not yet been developed. Cell types derived from the endoderm lineage, such as acinar cells or hepatocytes, might be easier to reprogram into a beta cell lineage owing to their similarity to beta cells. However, these methods have not been successfully applied to cell-based therapy or in vivo therapy because of the practicality of obtaining useful starting cells. In addition, beta-like cells generated by conventional direct reprogramming are post-mitotic and have very limited regenerative ability. Pancreatic progenitor cells would be a better cell source for transplantation because of their potential for sustained proliferation and proper differentiation. However, successful methods for reliably obtaining clinically useful numbers of pancreatic progenitor cells are not available.

SUMMARY

The problem of how to obtain or generate significant numbers of these pancreatic progenitor cells has been solved by use of the compositions and methods described herein. Compositions and methods are described herein for producing mammalian cell populations that include a high proportion of definitive endoderm cells, pancreatic progenitor cells and/or pancreatic cells. The pancreatic progenitor cells and/or pancreatic beta cells so produced are particularly useful for treatment of diabetes.

One aspect of the invention is a method that involves: (a) contacting starting mammalian cells with a first composition comprising an effective amount of a TGFβ family member and a WNT activator, while the mammalian cells express pluripotency factors comprising OCT4, SOX2, and KLF4, wherein the effective amount is sufficient to generate a first cell population comprising definitive endoderm cells and wherein at least about 5% of the cells in the first population express Sox17 and/or Foxa2, but where the first cell population does not express detectable NANOG; and (b) contacting cells from the first cell population with a second composition comprising an effective amount of a TGFβ receptor inhibitor, a hedgehog pathway inhibitor, and a retinoic acid receptor agonist to generate a second cell population comprising pancreatic progenitor cells, wherein at least about 10% of the cells in the second population express Pdx1, Nkx6.1, Hnf6, or a combination thereof.

Another aspect of the invention is a method that involves contacting an endodermal cell population with an expansion composition that includes growth factors, a WNT activator, and a TGFβ receptor inhibitor for a time sufficient to expand cell numbers by at least ten-fold and thereby generate an expanded population of posterior foregut-like progenitor cells.

The methods can further include administering the second cell population, posterior foregut-like progenitor cells, pancreatic progenitor cells obtained from the second cell population, functional pancreatic beta-like cells obtained therefrom, or a combination thereof, to a mammal in need thereof. For example, such a mammal can have type I diabetes, type II diabetes, or type 1.5 diabetes.

DESCRIPTION OF THE FIGURES

FIG. 1A schematically illustrates two approaches for reprogramming fibroblasts. Approach-1 (App1) involved transient iPSC-factor expression (induced by doxycycline (Dox) addition to the culture medium) in fibroblasts followed by adding definitive endoderm induction factors Activin A (AA) and lithium chloride (LiCl); Approach-2 (App2) involved addition of definitive endoderm induction factors AA and LiCl during the transient doxycycline-induced iPSC-factor expression. FIG. 1B graphically illustrates expression of Sox17 and Foxa2 on Day 12 (day 12) after treating fibroblasts by either Approach 1 or Approach 2, where expression levels were assessed by quantitative PCR. The results are the average of 3 independent experiments. *P<0.05. FIG. 1C graphically illustrates the total number of all the colonies (cross-hatched bar) as well as Sox17$^+$/Foxa2$^+$ double positive colonies (open bar), where the colonies were generated by using Approach 1 or Approach 2. The results are the average of three independent experiments. FIG. 1D graphically illustrates the percentage of Sox17$^+$/Foxa2$^+$ double positive colonies generated by Approach 1 or Approach 2. The results are the average of three independent experiments.

FIG. 2A is a schematic diagram of the approach to generating pancreatic-like cells from fibroblasts by Approach 2. Med-IV contains laminin, nicotinamide, and B27 etc., based on a previous report (Schroeder et al., 2006). FIG. 2B shows images of cells immunostained to identify expression of definitive endoderm markers Sox17, CXCR4, Foxa2 and Cerberus1 in cells on day 12 (D12) of the process outlined in FIG. 2A. FIG. 2C graphically illustrates expression of Sox17, Foxa2, Cerberus1, and CXCR4 (left to right panels) in cells treated for twelve days (D0 to D12) by the method shown in FIG. 2A. NGFP1 induced pluripotent stem cell-derived definitive endoderm like cells (DE) were used as a positive control. FIG. 2D shows images of cells immunostained on D18 for pancreatic progenitor markers Pdx1, Hnf6, Pax6, and Nkx6.1 (left to right panels). FIG. 2E graphically illustrates expression of Pdx1, Nkx6.1, Hnf6, and Pax6 in cells treated from days D12 to D18 with the method shown in FIG. 2A. FIG. 2F shows images of cells immunostained for pancreatic β cell markers insulin (Ins) and C-peptide (C-PEP) on D27. FIG. 2G graphically illustrates expression of Ins1 and Ins2 in cells treated from D18 to D27 with the method shown in FIG. 2A. The results in FIGS. 2C, 2E, and 2G are the average of at least three independent experiments. *P<0.05, **P<0.01.

FIG. 3A graphically illustrates expression of Pdx1 and Nkx6.1 on day 16 (D16) when the indicated factors of the protocol outlined in FIG. 4A are employed. Cells were treated with indicated small molecules from day 12 to day 16 (D12 to D16). The results shown are the average of 3 independent experiments. *P<0.05. FIG. 3B shows images of cells immunostained on day 16 (D16) for Pdx1 and Nkx6.1 after treatment with the indicated conditions.

FIG. 4A is a schematic diagram of the advanced approach where additional small molecules (Bix (Bix-01294), and pVc (2-Phospho-L-ascorbic acid trisodium salt), A83, and/or SB (SB203580)) are employed that significantly improve induction of the pancreatic progenitor-like phenotype. As illustrated, mouse embryonic fibroblasts (MEFs) are redirected to form Intermediate Cells (IMCs) by exposure to doxycycline (which induces pluripotency factor expression), Activin A, LiCl, Bix (Bix-01294), and pVc (2-Phospho-L-ascorbic acid trisodium salt) between days 0-6. Further exposure of the IMCs to Activin A, LiCl, and pVc directs the cells to differentiate into definitive endoderm-like cells (DELCs) by day 12. When the DELCs are exposed to retinoic acid (RA), A83-01, LDE225 and pVc, they differentiate into pancreatic progenitor-like cells (PPLCs) by day 16, which can be further differentiated into insulin-producing pancreatic-like cells (PLCs) by day 25. FIG. 4B shows images of cells immunostained on Day 16 for pancreatic progenitor markers, Nkx6.1, Pdx1, Sox9, Pax6, and Hnf6. Cells were treated with the combination of four small molecules (RA, A83-01, LDE225 and pVc) from D12 to D16 to generate the cells shown in FIG. 4B. FIG. 4C graphically illustrates expression of the indicated markers at days 12, 14 and 16 during the pancreatic progenitor induction process as detected by quantitative PCR. The results are the average of 3 independent experiments. *P<0.05, **P<0.01. FIG. 4D shows images of cells immunostained on D16 for Pdx1 and Nkx6.1. FIG. 4E graphically illustrates Pdx1$^+$/Nkx6.1$^+$ colony numbers on D16 after treatment of cells with the indicated conditions. 4000 cells were seeded into each well of a 24-well plate on D0. The results are the average of 3 independent experiments. *P<0.05. FIG. 4F shows images of cells immunostained on day 12 (D12) for expression of Sox17, Foxa2, Cerberus1 and CXCR4. Bix (Bix-01294) at 1 µM was added from D0 to D6 and pVc (2-Phospho-L-ascorbic acid trisodium salt) at 280 µM was added to the cells from D0 to D12 before the images shown in FIGS. 4B, 4D, and 4F were taken.

FIG. 5A shows images of cells immunostained on day 25 (D25) to show which cells express Pdx1 and insulin, after SB (SB203580) at 5 µM was added from D16 to D25, and pVc (2-Phospho-L-ascorbic acid trisodium salt) at 28004 was added from D16 to D25. FIG. 5B graphically illustrates expression of Ins1, Ins2, Pdx1 and Nkx6.1 during the process as assessed by quantitative PCR. The results are the average of 3 independent experiments. *P<0.05, **P<0.01. FIG. 5C shows images of cells immunostained on day 25 (D25) to show which cells express the pancreatic cell markers insulin, Glucagon, Somatostatin, Amylase and Nkx6.1. FIG. 5D graphically illustrates insulin release on day 25 by cells treated as described herein. The results are the average of 4 independent experiments. *P<0.05. As indicated, the pancreatic cells produced by the methods described herein express insulin in a glucose dose-responsive manner.

FIG. 6A graphically illustrates gene expression of the indicated markers as a function of time during the reprogramming process, as assessed by quantitative PCR. The expression levels of pluripotency genes, Nanog and Rex1; of definitive endoderm marker genes, Sox17 and Foxa2; of pancreatic progenitor markers Pdx1 and Nkx6.1; and of pancreatic beta cell markers Ins1 and Ins2 are shown. NGFP1 iPS cells (iPS) are used as positive control for Nanog and Rex1 expression. Definitive endoderm like cells (DE) derived from NGFP1 iPS cells were used as a positive control for Sox17 and Foxa2 expression. The results are the average of four independent experiments. *P<0.05, **P<0.01. FIG. 6B shows images of cells tracing the direct reprogramming process over time from mouse embryonic fibroblasts (MEF; at day 0) to definitive endodermal like cells (DELCs) at day 12. Bright-field and fluorescence images were taken at the indicated times. Representative immunostaining of Sox17 and Foxa2 on Day 12 is also shown (last panel, D12). Secondary MEF cells that were cultured in Med-I with Dox and LIF for 17 days are shown as a positive control (first panel, Ctrl). FIG. 6C shows images of cells tracing the induction/differentiation process of DELC to PPLC. The last image shows representative immunostaining of cells to identify Pdx1 and Nkx6.1 expression on Day 16. FIG. 6D shows images of cells tracing the induction/differentiation process of PPLC to pancreatic like cells. The right-most image shows representative immunostaining of cells exhibiting Ins and Glu expression on Day 25.

FIG. 7A graphically illustrates blood glucose levels of normal mice and STZ-induced type I diabetic mice transplanted with MEF or PPLC cells (or controls not transplanted with cells) during the eight weeks (0 W, 1 W, etc.) following transplantation. Under anesthesia, diabetic mice received a renal subcapsular transplant of about $3\times10^6$ pancreatic progenitor like cells (n=14; filled diamond symbols) or $3 \times 10^6$ secondary MEF cells (n=10; filled square symbols). Untreated normal mice (n=4, lower line with X symbols) and mice treated with STZ only (n=4; filled triangle symbols) were used as controls. *P<0.05, P<0.01. FIGS. 7B and 7C show images of kidney sections from mice engrafted with PPLCs, where the immunofluorescence identifies sites of gene expression. The C regions show images of regions containing transplanted cells, while the K regions identify kidney tissues. FIG. 7D graphically illustrates serum insulin levels in the serum of animals from each experimental or control group. The group of mice transplanted with MEF cells was set as control. P<0.01.

FIGS. 8A-8G illustrate direct conversion of human fibroblasts into definitive endodermal progenitor cells. FIG. 8A is a schematic diagram of the procedure used to convert human fibroblasts into definitive endodermal progenitor cells (cDE cells) by combining non-integrating episomal reprogramming plasmids with specific initiation and conversion conditions. FIG. 8B shows bright-field images of control fibroblasts and a definitive endodermal progenitor cell (cDE) colony at day 21. Scale bar, 20 µm. FIG. 8C illustrates immunofluorescence staining of representative definitive endodermal progenitor cell (cDE) colonies at day 21 for the endodermal progenitor markers SOX17 and FOXA2. Scale bar, 20 µm. FIG. 8D graphically illustrates the colony number of number of FOXA2 positive colonies scored at day 28 after treatment of cells with various small molecule factors. Small molecules sodium butyrate (NaB), Parnate (Par), RG108 (RG), CHIR99021 (CHIR), and 5'-N-ethylcarboxamidoadenosine (NECA) added to the basal condition to further enhance endodermal reprogramming efficiency. Data represent the number of FOXA2 positive colonies scored at day 28 (Mean values±standard error (s.e.m.) of three experiments). FIG. 8E graphically illustrates expression levels (relative quantity, RQ, values) of endodermal genes SOX17 and FOXA2, and endogenous pluripotent genes OCT4 (endoOCT4) and NANOG (endoNANOG) during the conversion process. Human ESCs (hES) served as a control. Mean values±s.e.m. of expression for the indicated gene were normalized to Glyceraldehyde 3-phosphate dehydrogenase (GAPDH) expression for day 28 (d28) definitive endodermal progenitor cell cultures and hESCs, respectively (n=3 experiments). FIG. 8F graphically illustrates the percentage of cells expressing human pluripotent surface marker TRA-1-60 and endodermal marker FOXA2 during the conversion process as assessed by fluorescence-activated cell sorting. Human ESCs (hES) served as control for comparison. FIG. 8G shows images of definitive endodermal progenitor cell colonies at day 28, illustrating expression of early endodermal progenitor markers SOX17 and FOXA2 (upper panels, lighter areas), but not of the primitive gut tube marker HNF4A, posterior foregut marker HNF6, and pluripotency marker NANOG (middle panels) where only DAPI staining of nuclei is visible. Note that hESC served as positive control for NANOG staining (right panel in the middle row). Control fibroblasts (lower panels) do not express any marker analyzed. Scale bar, 20 µm.

FIG. 9A is a schematic representation of culture conditions for the amplification of definitive endodermal progenitor cells (cDE cells) that resulted in further specification into expandable posterior foregut-like progenitor cells (cPF cells). FIG. 9B illustrates that improved culture conditions allow amplification of cDE/cPF cell colonies. Mean values±s.e.m. represent three experiments. FIG. 9C shows images of colonies after 4 passages in improved expansion media indicating that the cells exhibit specification towards cPF cells as detected by immunofluorescence analysis. Scale bar, 20 µm. FIG. 9D is a schematic diagram of the process for cPF expansion. FIG. 9E graphically illustrates growth curves of cPF cells. Note that the cPF cell number increases at least a trillion fold. FIG. 9F graphically illustrates the effects of four media supplements, EGF, bFGF, A83-01, and CHIR99021 upon cell growth. As shown, the combination ("ALL") of these factors improves cPF cell growth and self-renewal. FIG. 9G shows a bright field image of established cPF cells illustrating epithelial colony morphology. Scale bar, 20 µm. FIG. 9H illustrates expression of SOX17, FOXA2, HNF4A, HNF6, SOX9, and PDX1 in cPF cells at passage 15 as detected by immunofluorescence staining Scale bar, 20 µm. FIG. 9I graphically illustrates enrichment of transcripts for SOX17, FOXA2, HNF1A, HNF1B, HNF4A, HNF6, SOX9, and PDX1 transcripts, but not SOX1, BRY, OCT4 and NANOG in p15 cPF cells as detected by qPCR analysis. Mean values±s.e.m. were normalized to GAPDH relative to control fibroblasts. (n=3 experiments). FIG. 9J graphically illustrates qPCR analysis for the presence of episomal reprogramming vectors in established cPF cells (cPF p17) compared to fibroblasts 4 days after electroporation with episomal plasmids, serving as positive control (pos. CTR). Note that episomal vectors were undetectable by this method in cPF cells. Mean values±s.e.m. are shown (n=3 experiments). FIG. 9K shows images of kidney tissues after transplantation of hESC-derived definitive endodermal cells and cPF cells under the kidney capsule of immune deficient mice. None of the cPF cell grafts result in tumor formation, even after prolonged periods of up to 12 weeks in vivo (n=10 mice), while hESC-derived endodermal cell grafts (n=4 mice) resulted in tumorigenic structures with big cysts and increased graft size already after 7 weeks in vivo. FIG. 9L shows images of cPF cell grafts exhibiting epithelial structures that express E-cadherin, HNF4a, PDX1, SOX9, and pan-cytokeratin as detected by immunofluorescence analysis. Human nuclear antigen (HuNu) identifies the human cell origin. Scale bar, 20 µm.

FIG. 10A is a schematic diagram of a process for the differentiation of cPF cells into pancreatic endodermal progenitor cells (cPE cells). FIG. 10B and FIG. 10C illustrate expression (lighter areas) of pancreatic endodermal markers FOXA2, SOX9, HNF6, PDX1 and NKX6.1 in p1 cPE cells as detected by immunofluorescence staining. Scale bar, 20 µm. FIG. 10D graphically illustrates the percentage of cells that express PDX1 and NKX6.1 in p1 cPE cells compared to control (Isotype CTR) as detected by flow cytometry. FIG. 10E is a schematic diagram illustrating procedures for the expansion of cPE cells. FIG. 10F graphically illustrates growth of cPE cells over time. Note that cPE cell number increases at least two hundred million fold. FIG. 10G illustrates expression of pancreatic endodermal markers PDX1 and NKX6.1 in p12 cPE cells as detected by immunofluorescence staining Scale bar, 20 µm. FIG. 10H graphically illustrates the percentage of p12 cPE cells that express PDX1 and NKX6.1 as detected by flow cytometry. FIG. 10I graphically illustrates enrichment of NKX2.2, NKX6.1, PDX1, FOXA2, HNF4A, HNF6, HLXB9, PTF1A, and NGN3 transcripts, while SOX17 expression is down regulated, in cPE cells relative to cPF cells. Gene expression was detected by qPCR analysis. Mean expression values±s.e.m. of the indicated genes were normalized to GAPDH and (n=3 experiments). FIG. 10J graphically illustrates that detectable levels of human c-peptide (as detected by ELISA analysis) are present in the serum of 67% of mice bearing cPE cell grafts for 15 weeks and within 1 hour after glucose challenge. Moreover, human C-peptide levels as well as the percentage of mice exhibiting detectable levels of human C-peptide increase over time. Numbers on top of each bar indicate human C-peptide positive mice out of total mice assayed. FIG. 10K graphically illustrates human C-peptide levels before and after glucose challenge of mice bearing cPE cell grafts for 23-24 weeks as detected by ELISA analysis. As shown, the mice exhibit a functional response to glucose administration. The line at about 15 pM human C-peptide identifies the lower detection limit of the ELISA assay. The p-value was calculated using a two tailed students t-test. FIG. 10L illustrates co-expression of insulin (INS) and the beta cell transcription factors PDX1 and NKX6.1 but not of the hormone Glucagon (GCG) as detected by immunofluorescence analysis of 15-week-old cPE cell graft sections. Scale bar, 20 μm.

FIG. 11A is a schematic diagram of the strategy employed to mature pancreatic endodermal progenitor cells (cPE cells) into pancreatic beta-like cells (cPB cells) in vitro. FIG. 11B illustrates expression of PDX1 and C-peptide in beta-like cells generated with basal pancreatic differentiation conditions in vitro as detected by immunofluorescence staining. Scale bar, 20 μm. Basal pancreatic differentiation media contains A83-01 (A83), Nicotinamide (NIC), Forskolin (FSK), Dexamethasone (DEX) and Exendin-4 (Ex-4). FIG. 11C graphically illustrates the effects of several small molecules, Compound E (C-E), Vitamin C (Vc), and BayK-8644 (BayK) on the percentage of C-peptide positive cells. Note that combined treatment of all molecules results in an additive effect, further increasing the percentage of C-peptide positive cells. (n=3 experiments) FIG. 11D illustrates expression of several genes in converted pancreatic beta-like cells (cPB cells) as detected by immunofluorescence analysis. The cPB cells were generated with the improved pancreatic maturation conditions. Many of the insulin (INS) positive cells co-express key beta cell transcription factors including, PDX1, NKX6.1, NKX2.2, and NeuroD, but only rarely co-express endocrine progenitor marker NGN3 and the endocrine hormones, Glucagon (GCG) and Somatostatin (SST). Scale bar, 20 μm. FIG. 11E graphically illustrates human C-peptide levels (a marker for insulin release) during in vitro glucose stimulation of insulin secretion (GSIS) assays (n=7 cell cultures of 4 experiments). As shown, the cPB cells release insulin in response to physiological levels of glucose. Depolarization by higher KCl concentration further increased insulin secretion. Insulin release was measured by human specific C-peptide ELISA assay. The line at about 10-15 pM human C-peptide identifies the lower detection limit of the ELISA assay. The p-value was calculated using a two tailed students t-test. FIG. 11F illustrates the percentage of cPB cells converted from fibroblasts that express endodermal and pluripotency markers (PDX1, NKX6.1, NKX2.2) in as detected by flow cytometry of fluorophores A-488 and A-647. The first panel shows fluorescence by the secondary antibody only. FIG. 11G illustrates expression of several genes in cPB cells. Many of the insulin (INS) positive cells co-express key beta cell transcription factors PDX1, NKX6.1, NKX2.2, and NeuroD, but only rarely co-express endocrine progenitor marker NGN3. Scale bar, 20 μm. FIG. 11H shows high magnification micrographs of cPB cells. As shown, insulin (INS) and C-peptide staining is co-localized, excluding insulin uptake from the media as an explanation for C-peptide staining Scale bar, 20 μm.

DETAILED DESCRIPTION

The methods and compositions described herein provide populations of definitive endoderm cells, pancreatic progenitor cells and pancreatic beta cells. Such cells are useful for treatment of diabetes.

The definitive endoderm cells generated as described herein express Sox17, Foxa2, Cerberus1, CXCR4, or a combination thereof. Definitive endoderm cells can be prepared from stem cells or by re-directing differentiated cells from an established lineage to the endoderm lineage. Compositions and procedures for such preparation of definitive endoderm cells are described herein. For example, embryonic fibroblasts can be redirected into the endoderm lineage to form definitive endoderm cells by inducing expression of pluripotency factors at the same time as the embryonic fibroblasts are mixed with a first composition containing a TGFβ family member such as Activin A and a WNT activator such as CHIR99021 and/or lithium chloride. The yield of definitive endoderm cells can be increased by including growth factors (e.g., epidermal growth factor (EGF), basic fibroblast growth factor (bFGF), or a combination thereof), phospho-L-ascorbic acid, a histone deacetylase inhibitor (e.g., Na butyrate), a histone demethylase inhibitor (e.g., parnate), a DNA methyltransferase inhibitor (e.g., RG108), an adenosine agonist (e.g., 5'-N-ethylcarboxamido-adenosine (NECA)), and/or a G9a histone methyltransferase inhibitor in the first composition (e.g., in the culture medium).

Pancreatic progenitor cells can be obtained from definitive endoderm cells by contacting or mixing the definitive endoderm cells with a second composition. For example, pancreatic progenitor cells can be obtained from definitive endoderm cells by contacting or mixing the definitive endoderm cells with a second composition that includes a TGFβ receptor inhibitor, a hedgehog pathway inhibitor, a retinoic acid receptor agonist, or a combination thereof. The yield of pancreatic progenitor cells can be increased by including a WNT activator, 2-phospho-L-ascorbic acid, a Notch signaling inhibitor, a BMP4 signaling inhibitor, growth factors (e.g., epidermal growth factor (EGF), basic fibroblast growth factor (bFGF), fibroblast growth factor 7 (FGF7), fibroblast growth factor 10 (FGF10), or a combination thereof).

Figure 4A:
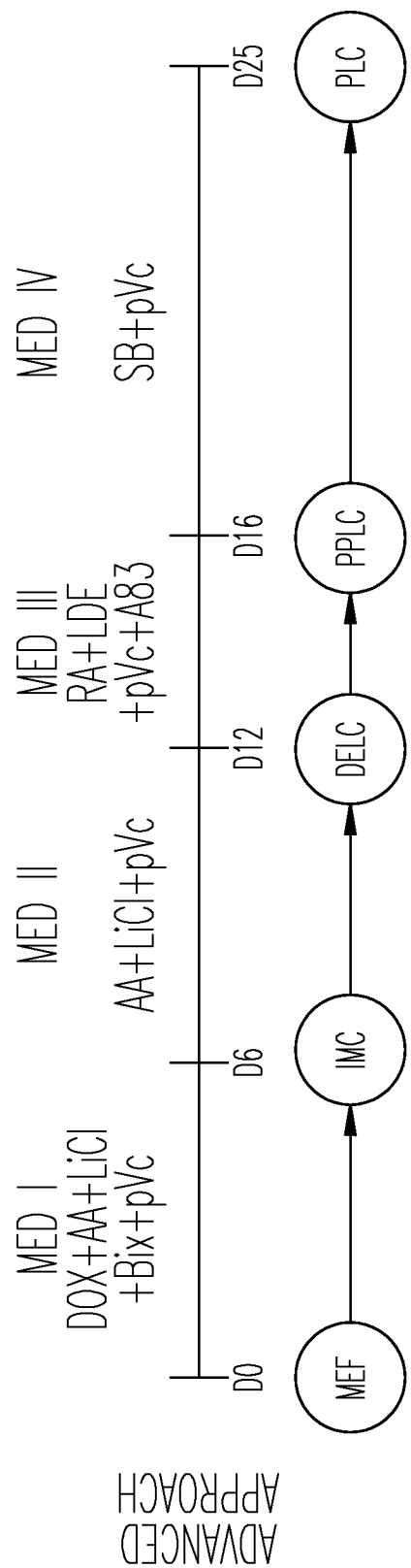
FIGS. 4A-4F illustrates identification of novel small molecule conditions that enhanced generation of pancreatic progenitor-like cells that are readily converted in the pancreatic beta cells.

An example of a process for obtaining definitive endoderm cells and pancreatic precursor cells is outlined in FIG. 4A and in Table 1, shown below.

TABLE 1

| Stage* | Stages I & II<br>Days 0-12<br>Definitive Endodermal<br>Cells that<br>Express Sox17 &<br>Foxa2 (Cer & Cxcr4) | Stage III<br>Days 12-16<br>Pancreatic<br>Progenitor<br>Cells that<br>Express Pdx1<br>& Nkx6.1<br>(Hnf6 & Pax6) | Stage IV<br>Days 16-25<br>Functional<br>Pancreatic<br>Beta-Like<br>Cells that<br>Express<br>glucagon &<br>insulin |
|---|---|---|---|
| Factor | Approach 1 Approach 2 | | Add laminin, nicotinamide, B27, etc. (per Schroeder 2006) |

TABLE 1-continued

| Stage* | Stages I & II Days 0-12 Definitive Endodermal Cells that Express Sox17 & Foxa2 (Cer & Cxcr4) | Stage III Days 12-16 Pancreatic Progenitor Cells that Express Pdx1 & Nkx6.1 (Hnf6 & Pax6) | Stage IV Days 16-25 Functional Pancreatic Beta-Like Cells that Express glucagon & insulin |
|---|---|---|---|
| TGFβ family member | 6 days pluripotency factors, then 6 days of Activin A | 6 days Activin A + pluripotency factors, then 6 days of Activin A | |
| WNT activator | 6 days pluripotency factors, then 6 days of LiCl | With pluripotency factors 6 days, then 6 days of LiCl | |
| RAR Agonist | | Add retinoic acid at day 12 for 1 day or when Sox17 & Foxa2 expressed | |
| TGFβ receptor Inhibitor | | Add A83-01 at day 12 for 1 day, or when Sox17 & Foxa2 expressed; then add A83-01 for 3 more days | |
| Vitamin C | | Add Phospho-L-ascorbic acid | Add pVc at day 12 for 1 day, or when Sox17 & | Add pVc when cells express Pdx1 & |
| Hedgehog Inhibitor | trisodium salt (pVc) day 0-12 | Foxa2 expressed; then add pVc for 3 more days Add LDE225 at day 12 for 1 day, or when Sox17 & Foxa2 expressed; then add LDE225 for 3 more days | Nkx6.1 |
| G9a histone methyl-transferase Inhibitor | | Add Bix-01294 day 0-6 | |
| p38 mitogen-activated protein (MAP) kinase inhibitor | | | Add SB203580 when cells express Pdx1 & Nkx6.1 |

* Stage I is induction of pluripotency, which can include contacting cells with Activin A and LiCl; but if the cells are already pluripotent (or of an appropriate stem cell type) then stage I may not be needed. See FIG. 1A.

In another example, a related procedure for obtaining definitive endoderm cells and pancreatic precursor cells is outlined in Table 2, shown below.

TABLE 2

| | Generating Definitive Endodermal Progenitor Cells from fibroblasts | | Generating Pancreatic Progenitor Cells Stage | Generating Functional Beta-Like Cells |
|---|---|---|---|---|
| Factor | Initiation Days 0-7 | Endo-dermal Conversion Days 7-28 (cDE) Induces expression of SOX17, FOXA2 | Posterior foregut-like progenitor cells (cPF) Induces expression of SOX17, FOXA2, HNF4α, HNF6, SOX9, and/or PDX1 | Endodermal progenitor cells (cPE) Induces expression of FOXA2, HNF6, SOX9, PDX1 & NKX6.1. | Functional Beta-Like Cells (cPB) Induces expression of INSULIN, PDX1, NKX6.1, NEUROD1, and NKX2.2 |
| Pluripotency factor expression | 7 days recovery after inducing pluri-potency factor expression | | | | |
| Growth Factors | | EGF & bFGF | | EGF & bFGF | FGF7 & FGF10 (2 days) |

TABLE 2-continued

| | Generating Definitive Endodermal Progenitor Cells from fibroblasts | | Generating Pancreatic Progenitor Cells Stage | | Generating Functional Beta-Like Cells |
|---|---|---|---|---|---|
| Factor | Initiation Days 0-7 | Endodermal Conversion Days 7-28 (cDE) Induces expression of SOX17, FOXA2 | Posterior foregut-like progenitor cells (cPF) Induces expression of SOX17, FOXA2, HNF4α, HNF6, SOX9, and/or PDX1 | Endodermal progenitor cells (cPE) Induces expression of FOXA2, HNF6, SOX9, PDX1 & NKX6.1. | Functional Beta-Like Cells (cPB) Induces expression of INSULIN, PDX1, NKX6.1, NEUROD1, and NKX2.2 |
| TGFβ family member (e.g., Activin A) | | Activin A (100 ng/ml) | | | |
| WNT activator (e.g., LiCl, CHIR-99021) | CHIR99021 | CHIR99021 | CHIR99021 | | |
| RAR Agonist | | | | Retinoic Acid (2 days) | |
| TGFβ receptor Inhibitor | | | A83-01 | A83-01 (2 days) | A83-01 (3 days) |
| Vitamin C | | | | | Vitamin C |
| Hedgehog Inhibitor | | | | GDC-0449 | |
| Histone deacetylase inhibitor | | Na butyrate | Na butyrate | | |
| Histone demethylase inhibitor | | Parnate | Parnate | | |
| DNA methyl-transferase inhibitor | | RG108 | RG108 | | |
| Adenosine agonist | | 5'-N-ethylcarbox-amido-adenosine (NECA) | 5'-N-ethylcarbox-amido-adenosine (NECA) | | |
| Notch Inhibitor | | | | Compound E (2 days) | Compound E (3 days) |
| BMP4 signaling inhibitor | | | | LDN-193189 (2 days) | |
| Agonist of Glucagon-like Peptide-1 | | | | | Extendin-4 (3 days) |
| polyADP-ribose synthetase inhibitor | | | | | Nicotinamide (3 days) |
| Adenylyl cyclase activator | | | | | Forskolin |
| Gluco-corticoid receptor agonist | | | | | Dexamethasone |
| $Ca^{2+}$ channel agonist | | | | | BayK-8644 |

The exact type of factors employed and the incubation times can be varied over what is exemplified in Tables 1 and 2, as is described in more detail below.

Definitive Endoderm Induction

Definitive endoderm cells can be identified by their expression of Sox17, Foxa2, Cerberus1, CXCR4, or a combination thereof.

Starting Cells

Definitive endoderm cells can be obtained in several ways. The extent of differentiation of the initial cell type selected can impact what initial steps are chosen to make definitive endoderm cells. For example, if pluripotent stem cells are used as the starting cells, induction of pluripotency factors is not needed. However, if differentiated cells are employed as the starting cells, then introduction and/or induction of pluripotency factor expression facilitates conversion of the cells into definitive endoderm cells. There is no need to induce full pluripotency in the starting cells. Instead, the starting cells can be converted directly to definitive endodermal cells.

A variety of cell types can therefore be used to generate definitive endodermal cells. For example, definitive endodermal cells can be generated from induced pluripotent stem cells (iPSCs), from embryonic stem cells, from multipotent stem cells, and by manipulation of other cell types. In some instances, definitive endodermal cells can be generated by re-directing cells from one lineage to another. For example, the endodermal cells can be obtained from starting cells of epidermal lineage, hematopoietic lineage, endothelial lineage, muscle cell lineage, epithelial cell lineage, and/or neural cell lineage. Examples of starting cells that can be converted into endodermal cells include fibroblasts, epidermal cells, lymphocytes, hepatocytes, myoblasts, neurons, osteoblasts, osteoclasts, T-cells, and combinations thereof. As illustrated by experiments described herein, embryonic fibroblasts can be redirected to an endodermal lineage by the methods disclosed herein.

Starting cells for generation of definitive endoderm cells can include a selected cell population that contains nonpluripotent cells that are induced to transiently express one or more pluripotency factors such as SSEA1, SSEA-3, SSEA-4, TRA-1-60, TRA-1-81, TRA-2-49/6E, ALP, Sox2, E-cadherin, UTF-1, Oct4, Klf4, Sox2, c-Myc, a short hairpin RNA (shRNA) against p53, or a combination thereof. The selected population can include pluripotent stem cells, induced pluripotent stem cells (iPSCs), embryonic stem cells, multipotent stem cells, and combinations thereof. The selected cell population can be re-directed from one lineage to the endodermal lineage. For example, partially and/or fully differentiated cells of the epithelial cell lineage, hematopoietic lineage, endothelial cell lineage, muscle cell lineage, neural cell lineage, and combinations thereof can be re-directed to the endodermal lineage and to become pancreatic progenitor cells.

The initial starting population of cells can be a nonpluripotent cell population, for example, a cell population that does not express detectable levels of endogenous NANOG, but that is induced to transiently express pluripotency factors while being directed to the endodermal lineage.

Expression of endogenous or recombinantly introduced pluripotency factors can also be induced to facilitate redirection of a selected cell population to the endodermal lineage. For example, pluripotent expression vectors can be transfected into a selected cell population, and expression of the pluripotency factors encoded by those expression vectors can be induced. The pluripotent expression vectors can be integrated into the genomes of the cells, or the pluripotent expression vectors can be maintained episomally for the time needed to redirect the cells to the endodermal lineage. Episomal introduction and expression of pluripotency factors is desirable because the mammalian cell genome is not altered by insertion of the episomal vectors and because the episomal vectors are lost over time. Hence, use of episomal expression vectors allows expression of pluripotency factors for the short time that is needed to convert nonpluripotent mammalian cells to definitive endodermal progenitor cells, while avoiding possible chromosomal mutation and expression of pluripotency factors during later stages of differentiation into pancreatic progenitor cells and pancreatic beta cells.

Episomal plasmid vectors encoding p53 suppression factors and other pluripotency factors can be introduced into mammalian cells as described for example, in Yu et al., *Human induced pluripotent stem cells free of vector and transgene sequences*, Science 324(5928): 797-801 (2009); United States Patent Application 20120076762, and Okita et al., *A more efficient method to generate integration-free human iPS cells*, NATURE METHODS 8: 409-412 (2011), the contents of which are specifically incorporated herein by reference in their entireties.

For example, the pluripotency factors can be encoded within and expressed from an episomal vector that has EBNA-1 (Epstein-Barr nuclear antigen-1) and oriP, or Large T and SV40ori sequences so that the vectors can be episomally present and replicated without incorporation into a chromosome.

Cells from various lineages can be induced to a stem cell-like phenotype by procedures described by United States Patent Application Nos. 20130059385, 20120190059, 20110110899, 20100267141, 20100233804 and WO/2011/123572, the contents of which are specifically incorporated herein by reference in their entireties.

The pluripotency factors can be introduced into mammalian cells in the form of DNA, protein or mature mRNA by a technique such as lipofection, binding with a cell membrane-permeable peptide, liposomal transfer/fusion, or microinjection. When in the form of DNA, a vector such as a virus, a plasmid, or an artificial chromosome can be employed. Examples of viral vectors include retrovirus vectors, lentivirus vectors (e.g., according to Takahashi, K. and Yamanaka, S., *Cell*, 126: 663-676 (2006); Takahashi, K. et al., *Cell*, 131: 861-872 (2007); Yu, J. et al., *Science*, 318: 1917-1920 (2007)), adenovirus vectors (e.g., Okita K, et al., *Science* 322: 949 (2008)), adeno-associated virus vectors, and Sendai virus vectors (*Proc Jpn Acad Ser B Phys Biol Sci.* 85: 348-62, 2009), the contents of each of which references are incorporated herein by reference in their entireties. Also, examples of artificial chromosome vectors that can be used include human artificial chromosome (HAC), yeast artificial chromosome (YAC), and bacterial artificial chromosome (BAC and PAC) vectors. As a plasmid, a plasmid for mammalian cells can be used (e.g., Okita K, et al., *Science* 322: 949 (2008)). A vector can contain regulatory sequences such as a promoter, an enhancer, a ribosome binding sequence, a terminator, and a polyadenylation site, so that a pluripotency factor can be expressed. A vector may further contain, if desired, a selection marker sequence such as a drug resistant gene (e.g., a neomycin resistant gene, an ampicillin resistant gene, and a puromycin resistant gene), a thymidine kinase gene, and a diphtheria toxin gene, a reporter gene sequence such as a green fluorescent protein (GFP), β glucuronidase (GUS), FLAG, or combinations thereof. Also, the above vector may have LoxP sequences located before and after the segment encoding the pluripotency factor to permit cleavage at the ends of the pluripotency factor segment (before and after) or at both ends of the segment encoding a promoter and the pluripotency factor after introduction into the mammalian cells.

The nucleic acid segment encoding a pluripotency factor can be operably linked to a promoter. The promoter is typically selected from promoters which are functional in mammalian cells, although prokaryotic promoters and promoters functional in other eukaryotic cells may be used. The promoter can be derived from promoter sequences of viral or eukaryotic genes. For example, it may be a promoter derived from the genome of a cell in which expression is to occur. However, a heterologous promoter is often desirable. Examples of eukaryotic promoters that can be employed include those promoters that function in a ubiquitous manner (such as promoters of a-actin, b-actin, tubulin) or, alternatively, a tissue-specific manner (such as promoters of the genes for pyruvate kinase). Tissue-specific promoters can be specific for lymphocytes, dendritic cells, skin, brain cells and epithelial cells. Examples of promoters include CD2, CD11c, keratin 14, Wnt-1 and Rhodopsin promoters. An epithelial cell promoter such as SPC can be used. Viral promoters may also be used, for example the Moloney murine leukemia virus long terminal repeat (MMLV LTR) promoter, the rous sarcoma virus (RSV) LTR promoter or the human cytomegalovirus (CMV) IE promoter. The promoters employed for expression of pluripotency factors can be inducible promoters that respond to specific stimuli. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, steroid, or a physiological stress imposed directly by, for example heat, or indirectly through the action of a pathogen or disease agent such as a virus. It may be advantageous for the promoters to be inducible so that the levels of expression of the heterologous gene can be regulated during the lifetime of the cell. In addition, any of these promoters may be modified by the addition of further regulatory sequences, for example enhancer sequences. Chimeric promoters may also be used comprising sequence elements from two or more different promoters described above.

There is no need to induce pluripotency to the extent that pluripotency markers such as Nanog and Rex1 are expressed. Instead, cells are exposed to or induced to express pluripotency factors to redirect the cells from their current differentiation lineage and toward the endodermal differentiation lineage.

The selected cell population is treated with Activin A and lithium chloride to generate definitive endoderm cells. Addition of phospho-L-ascorbic acid and/or a G9a histone methyl-transferase inhibitor can increase the yield of definitive endoderm cells from the selected cell population. Such treatment is for a time and at a concentration of Activin A, lithium chloride, phospho-L-ascorbic acid and/or a G9a histone methyl-transferase inhibitor that is sufficient to induce differentiation or re-direction of the selected cell population to the endoderm lineage. Further details on treatment of a selected cell population to generate definitive endoderm cells are provided below.

Growth Factors

The composition used to convert starting cells to definitive endoderm cells can contain growth factors such as epidermal growth factor, basic fibroblast growth factor, fibroblast growth factor (e.g., FGF7 and/or FGF10), and combinations thereof. Such growth factors can also improve conversion of definitive endoderm cells to pancreatic progenitor cells.

Epidermal growth factor can stimulate cell growth, cell proliferation, and cellular differentiation. Human epidermal growth factor is a small protein (approximately 6045 daltons) with about 53 amino acids and three intramolecular disulfide bonds. Epidermal growth factor is available commercially, for example, from MP Biomedicals (see, e.g., mpbio.com), PeproTech (see, e.g., peprotech.com), and Cell Signaling Technology (see, e.g., cellsignal.com).

The fibroblast growth factor (FGF) family is comprised of at least nine polypeptides that show a variety of biological activities toward cells of mesenchymal, neuronal and epithelial origin. All FGFs have two conserved cysteine residues and share 30-50% sequence identity at the amino acid level.

Basic fibroblast growth factor can help maintain cells in an undifferentiated state. Basic fibroblast growth factor is commercially available, for example, from BD Biosciences (see, e.g., bdbiosciences.com), and EMD Millipore (see, e.g., Millipore.com).

Fibroblast growth factor 7 (FGF-7) is also called keratinocyte growth factor (KGF) and is encoded by the FGF7 gene. KGF/FGF-7 was originally isolated from the conditioned medium of a human embryonic lung fibroblast cell line as a mitogen that is specific for epithelial cells. The transcript for KGF/FGF-7 can be detected in stromal but not epithelial cells from various epithelial tissues. It has been proposed that KGF is a mesenchymal cell-derived paracrine growth factor that specifically stimulates epithelial cell growth. The KGF cDNA encodes a 194 amino acid precursor protein from which the N-terminal 31 amino acid residues are cleaved to generate the mature KGF. Human KGF exhibits species cross-reactivity and is active on mouse, monkey, and porcine cells. A high affinity receptor for KGF has been cloned and shown to be an alternatively spliced isoform of FGF R2/bek. Whereas FGF R2 binds FGF acidic and FGF basic but not KGF with high affinity, the alternately spliced KGF/FGF-7 R can bind KGF and FGF acidic with high affinity. FGF7 is commercially available from R&D Systems (see website at www.rndsystems.com/Products/251-KG).

Fibroblast growth factor 10 (FGF10) is a protein that in humans is encoded by the FGF10 gene. The human FGF10 cDNA encodes a 208 amino acid residue protein with a hydrophobic amino-terminal signal peptide. Based on its in vitro biological activities and in vivo expression pattern, FGF10 has been proposed to play unique roles in the brain, in lung development, wound healing and limb bud formation. FGF10 is commercially available from R&D Systems (see website at rndsystems.com/product_results.aspx?m=1448 or rndsystems.com/Products/345-FG).

As illustrated herein epidermal growth factor, basic fibroblast growth factor, fibroblast growth factor 7, fibroblast growth factor 10, and combinations thereof can facilitate reprogramming of differentiated cells to the endodermal lineage. Experiments described herein show that addition of such growth factors to a selected population of cells during or after expression of pluripotency factors can increase the proportion and yield of cells that express endodermal markers. In particular, addition of such growth factors to starting cells induces those cells to express markers indicative of a endoderm phenotype such as Sox17, Foxa2, Cerberus 1 (Cer), C-X-C chemokine receptor type 4 (Cxcr4), or a combination thereof.

Similarly, epidermal growth factor, basic fibroblast growth factor, fibroblast growth factor 7, fibroblast growth factor 10, and combinations thereof can facilitate reprogramming of definitive endodermal cells to pancreatic progenitor cells. Experiments described herein show that addition of such growth factors to a definitive endodermal cells can increase the proportion and yield of cells that express pancreatic progenitor cell markers. In particular, addition of such growth factors to definitive endodermal cells induces those cells to express markers indicative of the pancreatic progenitor phenotype such as Pdx1, Nkx6.1, Pax6, Hnf6, or a combination thereof.

In some cases, a combination of two growth factors is employed in the first or second composition, such as epidermal growth factor and basic fibroblast growth factor (or alternatively, for example, FGF7 and FGF10). In other cases, a combination of three growth factors, or a combination of four growth factors is employed.

For example, treatment of a selected population of cells with epidermal growth factor, basic fibroblast growth factor, fibroblast growth factor 7, fibroblast growth factor 10, or combinations thereof can convert or induce at least about 0.5%, or at least about 1%, or at least about 2%, or at least about 3%, or at least about 4%, or at least about 5%, or at least about 6%, or at least about 7%, or at least about 8% of cells in the selected mammalian cell population to express Sox17, Foxa2, Cerberus 1 (Cer), C-X-C chemokine receptor type 4 (Cxcr4), or a combination thereof. Similarly, treatment of a definitive endodermal population of cells with epidermal growth factor, basic fibroblast growth factor, fibroblast growth factor 7, fibroblast growth factor 10, or combinations thereof can convert or induce at least about 0.5%, or at least about 1%, or at least about 2%, or at least about 3%, or at least about 4%, or at least about 5%, or at least about 6%, or at least about 7%, or at least about 8% of cells in the selected mammalian cell population to express Pdx1, Nkx6.1, Pax6, Hnf6, or a combination thereof.

For example, concentrations of such growth factors that are at least about 1 ng/ml, or at least about 2 ng/ml, or at least about 3 ng/ml, or at least about 5 ng/ml in a first composition are useful for converting starting cells to definitive endodermal cells. Similarly, concentrations of such growth factors of at least about 1 ng/ml, or at least about 2 ng/ml, or at least about 3 ng/ml, or at least about 5 ng/ml, or about 10 ng/ml in a second composition are useful for converting definitive endodermal cells to pancreatic progenitor cells.

To increase the proportion of cells that express markers indicative of an endoderm phenotype or pancreatic progenitor phenotype, a selected population of cells is contacted or mixed with one or more growth factors for a time and at a concentration sufficient to differentiate or re-direct the cells to an endoderm lineage.

The time of contacting or mixing one or more growth factors with a starting population of cells to generate definitive endodermal cells can vary, for example, from about 2 days to about 20 days, or from 3 days to about 15 days, or from 4 days to about 10 days, or from 5 days to about 9 days, or from 6 days to about 8 days, or about 7 days.

The time of contacting or mixing one or more growth factors with a definitive endodermal population of cells to generate pancreatic progenitor cells can vary, for example, from about 3 days to about 130 days, or from 5 days to about 120 days, or from 7 days to about 110 days, or from 10 days to about 100 days, or from 20 days to about 95 days, or about 30 days to about 95 days.

The growth factor(s) can be added to a selected cell population during induced pluripotency and while directing the cells into the endoderm lineage.

The growth factors can be employed in the compositions and methods described herein in a variety of amounts and/or concentrations. For example, the growth factor(s) can be employed at a concentration of about 0.01 ng/ml to about 1 mg/ml, or about 0.1 ng/ml to about 300 ng/ml in a solution, or about 0.5 ng/ml to about 100 ng/ml in a solution, or about 1 ng/ml to about 50 ng/ml, or about 5 ng/ml to about 20 ng/ml in a solution, or about 10 ng/ml in a solution. In a dry formulation, the epidermal growth factor and basic fibroblast growth factor can be present in amounts of about 0.01 mg to about 1000 mg, or about 0.1 mg to about 100 mg, or about 1 mg to about 10 mg.

TGFβ Family Members

Transforming growth factor beta (TGF-β) is a protein that is involved in the control of proliferation, cellular differentiation, and other functions in most cells. It is a cytokine that has a role in immunity, cancer, bronchial asthma, heart disease, diabetes, Hereditary hemorrhagic telangiectasia, Marfan syndrome, Vascular Ehlers-Danlos syndrome, Loeys-Dietz syndrome, Parkinson's disease and AIDS. Proteins of the TGF-beta family are active as homodimers or heterodimers, with the two chains being linked by a single disulfide bond. Examples of TGF-β family members include the Activin/Inhibin subfamily, the decapentaplegic-Vg-related (DVR) related subfamily (that includes bone morphogenetic proteins and the growth differentiation factors), and the TGF-β subfamily.

Activin A is a member of the TGFβ family first identified in late 1980s as an inducer of follicle-stimulating hormone. Activin A is highly conserved in evolution and throughout the animal kingdom. It regulates a variety of biologic processes including cell proliferation, hematopoiesis, wound healing, and fibrosis. Activin A signals through the activin type I (Alk2, 4, or 7) and type II (ActRII or ActRIIB) receptors and shares with TGFβ the activation of the Smad cascade. See, Phillips et al., *Cytokine Growth Factor Rev.* 20(2): 153-64 (2009); Werner, *Cytokine Growth Factor Rev.* 17(3): 157-71 (2006).

As shown herein, addition of Activin A to a selected population of cells during expression of pluripotency factors increases the proportion and yield of definitive endodermal like cells generated. In particular, addition of Activin A to cells that express SSEA1, SSEA-3, SSEA-4, TRA-1-60, TRA-1-81, TRA-2-49/6E, ALP, Sox2, E-cadherin, UTF-1, Oct4, or a combination thereof, increases the proportion of cells that express markers indicative of a definitive endoderm phenotype such as Sox17, Foxa2, Cerberus 1 (Cer), C-X-C chemokine receptor type 4 (Cxcr4), or a combination thereof. For example, after treatment of a selected population of cells with Activin A, at least about 5%, or at least about 10%, or at least about 15%, or at least about 20%, or at least about 22%, or at least about 23%, or at least about 24%, or at least about 25% of cells in the selected mammalian cell population express Sox17, Foxa2, Cerberus 1 (Cer), C-X-C chemokine receptor type 4 (Cxcr4), or a combination thereof.

To increase the proportion of cells that express markers indicative of a definitive endoderm phenotype, a selected population of cells is contacted or mixed with Activin A for a time and at a concentration sufficient to differentiate or re-direct the cells to an endodermal lineage.

The time of contacting or mixing Activin A with the selected population of cells can vary, for example, from about 1 days to about 20 days, or from 2 days to about 18 days, or from 3 days to about 16 days, or from 4 days to about 15 days, or from 5 days to about 14 days, or from about 6 days to about 12 days.

Activin A can be added to a selected cell population during induced pluripotency and while directing the cells into the definitive endoderm lineage.

Activin A can be used at a variety of concentrations, for example, at about 5 ng/ml to about 200 ng/ml, or from about 10 ng/ml to about 175 ng/ml, or from about 15 ng/ml to about 150 ng/ml, or from about 20 ng/ml to about 150 ng/ml, or from about 25 ng/ml to about 125 ng/ml, or from about 30 ng/ml to about 100 ng/ml, or from about 35 ng/ml to about 80 ng/ml, or from about 40 ng/ml to about 60 ng/ml, or about 50 ng/ml.

Activin A is available commercially from various suppliers, for example, from Invitrogen, PeproTech, StemRD, R&D Systems, and other vendors.

Nucleic acid and protein sequences for Activin A are available, for example, in the sequence database maintained by the National Center for Biotechnology Information (see website at www.ncbi.nlm.nih.gov/). One example of a human Activin A amino acid sequence is available as accession number EAW94141.1 (GI:119614547) and provided below as SEQ ID NO:1.

```
  1   MPLLWLRGFL LASCWIIVRS SPTPGSEGHS AAPDCPSCAL
 41   AALPKDVPNS QPEMVEAVKK HILNMLHLKK RPDVTQPVPK
 61   AALLNAIRKL HVGKVGENGY VEIEDDIGRR AEMNELMEQT
121   SEIITFAESG TARKTLHFEI SKEGSDLSVV ERAEVWLFLK
161   VPKANRTRTK VTIRLFQQQK HPQGSLDTGE EAEEVGLKGE
201   RSELLLSEKV VDARKSTWHV FPVSSSIQRL LDQGKSSLDV
241   RIACEQCQES GASLVLLGKK KKKEEEGEGK KKGGGEGGAG
281   ADEEKEQSHR PFLMLQARQS EDHPHRRRRR GLECDGKVNI
321   CCKKQFFVSF KDIGWNDWII APSGYHANYC EGECPSHIAG
361   TSGSSLSFHS TVINHYRMRG HSPFANLKSC CVPTKLRPMS
401   MLYYDDGQNI IKKDIQNMIV EECGCS
```

WNT Activators

The WNT signaling pathway includes a series of events that occur when a WNT protein binds to a cell-surface receptor of a Frizzled receptor family member. Such events result in the activation of Dishevelled family proteins which inhibit a complex of proteins that includes axin, GSK-3, and the protein APC to degrade intracellular beta-catenin. The resulting enriched nuclear beta-catenin enhances transcription by TCF/LEF family transcription factors. A WNT activator can therefore include an agent that activates TCF/LEF-mediated transcription in a cell. WNT activators can be selected from true WNT agonists that bind and activate a Frizzled receptor family member including any and all of the WNT family proteins, an inhibitor of intracellular beta-catenin degradation, activators of TCF/LEF, and inhibitors of GSK-3.

As illustrated herein WNT activators are useful for converting starting cells to definitive endodermal cells and for converting definitive endodermal cells to pancreatic progenitor cells.

Examples of WNT activators that can be employed include one or more of the following compounds:

CHIR99021 (6-(2-(4-(2,4-dichlorophenyl)-5-(4-methyl-1H-imidazol-2-yl)pyrimidin-2-ylamino)ethylamino) nicotinonitrile);

1-azakenpaullone (9-Bromo-7,12-dihydro-pyrido[3',2':2,3]azepino[4,5-b]indol-6(5H)-one), BIO ((2'Z,3'E)-6-Bromoindirubin-3'-oxime);

AR-A014418 (N-(4-Methoxybenzyl)-N'-(5-nitro-1,3-thiazol-2-yl)urea);

Indirubin-3'-monoxime;

5-Iodo-indirubin-3'-monoxime;

kenpaullone (9-Bromo-7,12-dihydroindolo-[3,2-d][1]benzazepin-6(5H)-one);

SB-415286 (3-[(3-Chloro-4-hydroxyphenyl)amino]-4-(2-nitrophenyl)-1H-pyrrole-2,5-dione);

SB-216763 (3-(2,4-Dichlorophenyl)-4-(1-methyl-1H-indol-3-yl)-1H-pyrrole-2,5-dione);

Maybridge SEW00923SC (2-anilino-5-phenyl-1,3,4-oxadiazole);

(Z)-5-(2,3-Memylenedioxyphenyl)imidazolidine-2,4-dione,

TWS119 (3-(6-(3-aminophenyl)-7H-pyrrolo[2,3-d]pyrimidin-4-yloxy)phenol);

CHIR98014 (N2-(2-(4-(2,4-dichlorophenyl)-5-(1H-imidazol-1-yl)pyrimidin-2-ylamino)ethyl)-5-nitropyridine-2,6-diamine);

SB415286 (3-(3-chloro-4-hydroxyphenylamino)-4-(2-nitrophenyl)-1H-pyrrole-2,5-dione);

Tideglusib (also known as NP031112, or NP-12; 1,2,4-Thiadiazolidine-3,5-dione, 2-(1-naphthalenyl)-4-(phenylmethyl));

LY2090314 (1H-Pyrrole-2,5-dione, 3-imidazo[1,2-a]pyridin-3-yl-4-[1,2,3,4-tetrahydro-2-(1-piperidinylcarbonyl)pyrrolo[3,2,1-jk][1,4]benzodiazepin-7-yl]);

lithium salt (e.g., LiCl); or any combination thereof.

WNT activators can also include small-interfering RNAs (siRNA, Cell Signaling) that act as GSK-inhibitors, lithium (Sigma), kenpaullone (Biomol International, Leost, Metal (2000) *Eur J Biochem* 267, 5983-5994), 6-Bromoindirubin-30-acetoxime (Meyer, Let al (2003) *Chem Biol* 10, 1255-1266), SB 216763 and SB 415286 (Sigma-Aldrich), and FRAT-family members and FRAT-derived peptides that prevent interaction of GSK-3 with axin. An overview is provided by Meijer et al, (2004) *Trends in Pharmacological Sciences* 25, 471-480, which is hereby incorporated by reference in its entirety. WNT activators (GSK3 inhibitors) that can be used in the compositions and methods described herein can also include those disclosed in US 20120329152 by Pera et al., which is specifically incorporated herein in its entirety.

The WNT activators can, for example, be CHIR99021, SB216763, TWS119, CHIR98014, Tideglusib, SB415286, LY2090314, or any combination thereof. In some embodiments, the WNT activators can be CHIR99021, whose structure is shown below.

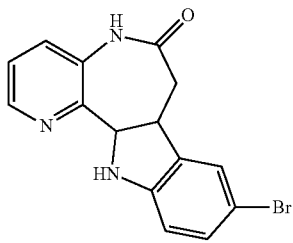 [SMILES: O=C1CC2c3cc(Br)ccc3NC2c2ncccc2N1]

The WNT activators can also be in the form of a salt or hydrate of any of the foregoing compounds.

To increase the proportion of cells that express markers indicative of an endodermal or pancreatic progenitor phenotype, a selected population of cells is contacted or mixed with one or more WNT activators for a time and at a concentration sufficient to differentiate or re-direct the cells to an endodermal and/or pancreatic progenitor lineage.

The time of contacting or mixing WNT activator(s) with a starting population of cells (to generate definitive endodermal cells) can vary, for example, from about 2 days to about 50 days, or from 3 days to about 40 days, or from 4 days to about 35 days, or from 5 days to about 33 days, or from 6 days to about 30 days, or about 14 to 28 days. The time of contacting or mixing WNT activator(s) with a population of definitive endodermal cells (to generate pancreatic progenitor cells) can vary, for example, from about 3 days to about 130 days, or from 5 days to about 120 days, or from 7 days to about 110 days, or from 10 days to about 100 days, or from 20 days to about 95 days, or about 30 days to about 95 days.

WNT activators can be added to a selected starting cell population during induced pluripotency and while directing the cells into the endoderm lineage. WNT activators can also be added to a definitive endodermal cell population to be converted to pancreatic progenitor cells.

The WNT activators can be employed in the compositions and methods described herein in a variety of amounts and/or concentrations. For example, the WNT activators can be employed at a concentration of about 0.01 micromolar to about 1 millimolar in a solution, or about 0.1 micromolar to about 100 micromolar in a solution, or about 0.5 micromolar to about 10 micromolar in a solution, or about 1 micromolar to about 5 micromolar in a solution. In a dry formulation, the WNT activators can be present in amounts of about 0.01 mg to about 1000 mg, or about 1 mg to about 100 mg, or about 1 mg to about 10 mg can be present in amounts of about 0.01 mg to about 1000 mg, or about 0.1 mg to about 100 mg, or about 1 mg to about 10 mg.

Methods and assays for determining a level of WNT activation or GSK-3 inhibition are available to a skilled person and include, for example, the methods and assays described in Liao et al., *Endocrinology*, 145(6): 2941-2949 (2004); and in U.S. Pat. No. 8,323,919, both of which are specifically incorporated by reference herein in their entireties.

Lithium

Lithium is an activator of WNT. The lithium can be in the form of a salt, where the anion includes, but is not limited to, chloride, bromide, carbonate, citrate, sulfate, or other biologically compatible monovalent anion (see, for example, US 2004/0028656 and WO 2008/055224).

As shown herein, addition of lithium salts to a selected population of cells during expression of pluripotency factors increases the proportion and yield of definitive endodermal like cells generated. In particular, addition of lithium salts to cells that express SSEA1, SSEA-3, SSEA-4, TRA-1-60, TRA-1-81, TRA-2-49/6E, ALP, Sox2, E-cadherin, UTF-1, Oct4, or a combination thereof, increases the proportion of cells that express markers indicative of a definitive endoderm phenotype such as Sox17, Foxa2, Cerberus 1 (Cer), C-X-C chemokine receptor type 4 (Cxcr4), or a combination thereof. For example, after treatment of a selected population of cells with lithium salts at least about 10%, or at least about 15%, or at least about 20%, or at least about 22%, or at least about 23%, or at least about 24%, or at least about 25% of cells in the selected mammalian cell population express Sox17, Foxa2, Cerberus 1 (Cer), C-X-C chemokine receptor type 4 (Cxcr4), or a combination thereof.

To increase the proportion of cells that express markers indicative of a definitive endoderm phenotype, a selected population of cells is contacted or mixed with lithium salts for a time and at a concentration sufficient to differentiate or re-direct the cells to an endoderm lineage.

The time of contacting or mixing lithium salts with the selected population of cells can vary, for example, from about 1 days to about 20 days, or from 2 days to about 18 days, or from 3 days to about 16 days, or from 4 days to about 15 days, or from 5 days to about 14 days, or from about 6 days to about 12 days.

Lithium salts can be added to a selected cell population during induced pluripotency and while directing the cells into the definitive endoderm lineage. Lithium salts can be employed at a variety of concentrations, for example, at about 0.01 mM to about 10 mM, or from about 0.05 mM to about 9 mM, or from about 0.1 mM to about 8 mM, or from about 0.2 mM to about 7 mM, or from about 0.3 mM to about 6 mM, or from about 0.4 mM to about 5 mM, or from about 0.5 mM to about 3 mM, or about 1 mM.

Vitamin C (Ascorbic Acid and/or Phospho-L-Ascorbic Acid)

As shown herein, addition of vitamin C or phospho-L-ascorbic acid to a selected population of cells during expression of pluripotency factors increases the proportion and yield of definitive endodermal like cells generated. In particular, addition of phospho-L-ascorbic acid to cells that express SSEA1, SSEA-3, SSEA-4, TRA-1-60, TRA-1-81, TRA-2-49/6E, ALP, Sox2, E-cadherin, UTF-1, Oct4, or a combination thereof, increases the proportion of cells that express markers indicative of a definitive endoderm phenotype such as Sox17, Foxa2, Cerberus 1 (Cer), C-X-C chemokine receptor type 4 (Cxcr4), or a combination thereof. For example, after treatment of a selected population of cells with vitamin C or phospho-L-ascorbic acid at least about 10%, or at least about 15%, or at least about 20%, or at least about 22%, or at least about 23%, or at least about 24%, or at least about 25% of cells in the selected mammalian cell population express Sox17, Foxa2, Cerberus 1 (Cer), C-X-C chemokine receptor type 4 (Cxcr4), or a combination thereof.

Also as shown herein, addition of 2-phospho-L-ascorbic to definitive endoderm cells increases the proportion and yield of Pdx1$^+$ and/or Nkx6.1$^+$ pancreatic progenitor cells. For example, more than about 5%, or more than about 10%, or more than about 15%, or more than about 20%, or about 25% of the cells were Pdx1 positive and/or Nkx6.1 positive. The 2-phospho-L-ascorbic acid can therefore be added to cells that already express Sox17, Foxa2, Cerberus 1 (Cer), C-X-C chemokine receptor type 4 (Cxcr4), or a combination thereof.

In addition, the presence of vitamin C or phospho-L-ascorbic acid in cell culture media can improve conversion of pancreatic progenitor cells to pancreatic beta cells.

To increase the proportion of cells that express markers indicative of a definitive endoderm phenotype, a pancreatic progenitor phenotype, or a pancreatic beta cell phenotypes a selected starting population of cells is contacted or mixed with vitamin C or phospho-L-ascorbic acid for a time and at a concentration sufficient to differentiate or convert the cells to the desired phenotype.

The time of contacting or mixing vitamin C or phospho-L-ascorbic acid with the selected population of cells can vary, for example, from about 1 days to about 50 days, or from 2 days to about 45 days, or from 3 days to about 40 days, or from 4 days to about 35 days, or from 5 days to about 33 days, or from about 6 days to about 30 days, or for about 20-25 days.

Phospho-L-ascorbic acid or vitamin C can be added to a starting cell population during induced pluripotency and while directing the cells into the definitive endoderm lineage.

Phospho-L-ascorbic acid or vitamin C can be employed at a variety of concentrations, for example, at about 1 µM to about 1000 µM, or from about 10 µM to about 700 µM, or from about 20 µM to about 500 µM, or from about 30 µM to about 400 µM, or from about 40 µM to about 350 µM, or from about 45 µM to about 300 µM, or from about 50 µM to about 310 µM, or about 280 µM.

To increase the proportion of cells that express markers indicative of a pancreatic progenitor cell phenotype, a selected population of definitive endoderm cells is contacted or mixed with 2-phospho-L-ascorbic acid or vitamin C for a time and at a concentration sufficient to differentiate at least some of the cells into pancreatic progenitor cells.

The time of contacting or mixing phospho-L-ascorbic acid or vitamin C with the definitive endoderm cells or pancreatic progenitor cells can vary, for example, from about 1 days to about 50 days, or from 2 days to about 45 days, or from 3 days to about 40 days, or from 4 days to about 35 days, or from 5 days to about 33 days, or from about 6 days to about 30 days, or for about 20-25 days.

Phospho-L-ascorbic acid and/or vitamin C can be added to definitive endoderm cells while directing those cells to differentiate into pancreatic progenitor cells. Phospho-L-ascorbic acid or vitamin C can be employed at a variety of concentrations, for example, at about 1 µM to about 1000 µM, or from about 20 µM to about 700 µM, or from about 50 µM to about 500 µM, or from about 100 µM to about 400 µM, or from about 150 µM to about 350 µM, or from about 200 µM to about 325 µM, or from about 250 µM to about 310 µM, or about 280 µM.

Phospho-L-ascorbic acid and/or vitamin C can be added to pancreatic progenitor cells while directing those cells to differentiate into pancreatic beta cells. Phospho-L-ascorbic acid or vitamin C can be employed at a variety of concentrations, for example, at about 1 µM to about 100 µM, or from about 10 µM to about 80 µM, or from about 25 µM to about 75 µM, or from about 30 µM to about 70 µM, or from about 35 µM to about 65 µM, or from about 40 µM to about 60 µM, or from about 45 µM to about 55 µM, or about 50 µM.

G9a Histone Methyl-Transferase Inhibitor

The G9a histone methyltransferase enzymatically methylates histone lysines. The G9a histone methyltransferase is also named euchromatin histone methyltransferase 2 (EHMT2). Histone lysine methylation has important roles in the organization of chromatin domains and the regulation of gene expression.

As shown herein, addition of inhibitors of G9a histone methyltransferase to a selected population of cells during expression of pluripotency factors increases the proportion and yield of definitive endodermal like cells generated. In particular, addition of such inhibitors to cells that express SSEA1, SSEA-3, SSEA-4, TRA-1-60, TRA-1-81, TRA-2-49/6E, ALP, Sox2, E-cadherin, UTF-1, Oct4, or a combination thereof increases the proportion of cells that express markers indicative of a definitive endoderm phenotype such as Sox17, Foxa2, Cerberus 1 (Cer), C-X-C chemokine receptor type 4 (Cxcr4), or a combination thereof. For example, after treatment of a selected population of cells with inhibitors of G9a histone methyltransferase at least about 10%, or at least about 15%, or at least about 20%, or at least about 22%, or at least about 23%, or at least about 24%, or at least about 25% of cells in the selected mammalian cell population express Sox17, Foxa2, Cerberus 1 (Cer), C-X-C chemokine receptor type 4 (Cxcr4), or a combination thereof.

To increase the proportion of cells that express markers indicative of a definitive endoderm phenotype, a selected population of cells is contacted or mixed with an inhibitor of G9a histone methyltransferase for a time and at a concentration sufficient to differentiate or redirect the cells to an endoderm lineage.

The time of contacting or mixing a G9a histone methyltransferase inhibitor with the selected population of cells can vary, for example, from about 1 days to about 15 days, or from 1 days to about 14 days, or from 2 days to about 13 days, or from 3 days to about 10 days, or from 3 days to about 9 days, or from about 4 days to about 8 days, or from about 5 days to about 7 days.

The G9a histone methyltransferase inhibitors can be added during induction of pluripotency, for example, for 2 days, or for 3 days, or for 4 days, or for 5 days, or for about 6 days while the cells are exposed to, or are induced to express, pluripotency factors.

G9a histone methyltransferase inhibitors can be used at a variety of concentrations, for example, at about 0.01 µM to about 10 µM, or from about 0.05 µM to about 9 µM, or from about 0.1 µM to about 8 µM, or from about 0.2 µM to about 7 µM, or from about 0.3 µM to about 6 µM, or from about 0.4 µM to about 5 µM, or from about 0.5 µM to about 3 µM, or about 1 µM.

A variety of G9a histone methyl-transferase inhibitors can be employed. For example, the G9a histone methyl-transferase inhibitor can be Bix-01294, chaetocin, 3-deazaneplanocin hydrochloride, UNC 0224, UNC 0638, UNC 0646, and combinations thereof. G9a histone methyl-transferase inhibitors can be obtained commercially, for example, from Tocris Bioscience (see website at tocris.com/pharmacologicalBrowser.php?ItemId=236264&Type=Inhibitors#.UdYcHeDD85s). Another type of G9a histone methyl-transferase inhibitor is BRD4770 (Yuan et al., *ACS Chem. Biol.* 7(7): 1152-1157 (2012)(incorporated herein by reference in its entirety).

Histone Deacetylase (HDAC) Inhibitors

Histone deacetylases (HDAC) are a class of enzymes that remove acetyl groups from an ε-N-acetyl lysine amino acid on a histone. Exemplary HDACs include those Class I HDAC: HDAC1, HDAC2, HDAC3, HDAC8; and Class II HDACs: HDAC4, HDAC5, HDAC6, HDAC7A, HDAC9, HDAC10. Type I mammalian HDACs include: HDAC1, HDAC2, HDAC3, HDAC8, and HDAC11. Type II mammalian HDACs include: HDAC4, HDAC5, HDAC6, HDAC7, HDAC9, and HDAC1.

As illustrated herein use of one or more histone deacetylase inhibitors can facilitate conversion of starting cells into the endodermal lineage. The histone deacetylase inhibitors can inhibit one or more of these histone deacetylases. In some instances the histone deacetylase inhibitors are inhibitors of HDAC1.

Inhibitors of HDACs (HDAC inhibitors) can include, for example, butyrate, small molecular weight carboxylates (e.g., less than about 250 amu), hydroxamic acids, benzamides, epoxyketones, cyclic peptides, and hybrid molecules. (See, for example, Drummond et al., *Annu Rev Pharmacol Toxicol* 45: 495-528 (2005), (including specific examples therein) which is hereby incorporated by reference in its entirety). Non-limiting examples of negative regulators of type I/II HDACs include:

Sodium butyrate, phenyl butyrate, or butyrate;

Suberoylanilide Hydroxamic Acid (SAHA; also called Vorinostat and MK0683), which inhibits the activities of HDAC1 and HDAC3, for example, with IC50 values of about 10 nM and 20 nM, respectively;

BML-210 (N1-(2-aminophenyl)-N8-phenyl-octanediamide, available from Sigma-Aldrich); in HeLa extracts, the IC50 of BML-210 for inhibition of HDAC activity can, for example, be about 80 µM;

Depudecin (e.g., (−)-Depudecin; 4,5:8,9-Dianhydro-1,2,6,7,11-pentadeoxy-D-threo-D-ido-undeca-1,6-dienitol), which can, for example, have an IC50 for HDAC1 of about 4.7 µM;

HC Toxin ((6R,9S,14aR)-3,6R-dimethyl-9S-(7-((S)-oxiran-2-yl)-7-oxoheptyl)decahydropyrrolo[1,2-a][1,4,7,10]tetraazacyclododecine-1,4,7,10-tetranone, available from Cayman Chemical); HC Toxin is a cell-permeable, reversible inhibitor of histone deacetylases (HDACs) (e.g., $IC_{50}$=30 nM);

Scriptaid (N-Hydroxy-1,3-dioxo-1H-benz[de]isoquinoline-2(3H)-hexananmide);

Phenylbutyrate (e.g., sodium phenylbutyrate), Sodium Butyrate, pivaloyloxymethyl butyrate (Pivanex, AN-9);

Valproic Acid ((VPA) and other short chain fatty acids), Suramin (e.g., Suramin Sodium);

Trichostatin A (TSA; (R,2E,4E)-6-(4-(dimethylamino) benzoyl)-N-hydroxy-4-methylhepta-2,4-dienamide), for example, with an IC50 of about 1.8 nM;

APHA Compound 8 (3-(1-Methyl-4-phenylacetyl-1H-2-pyrrolyl)-N-hydroxy-2-propenamide), which is HDAC class I-selective;

Apicidin (Cyclo[(2S)-2-Amino-8-oxodecanoyl-1-methoxy-L-tryptophyl-L-isoleucyl-(2R)-2-piperidinecarbonyl]), which is a potent histone deacetylase with, for example, an IC50=0.7 nM;

Trapoxin B (3,6-dibenzyl-9-[6-(oxiran-2-yl)-6-oxohexyl]-1,4,7,10-tetrazabicyclo[10.3.0]pentadecane-2,5,8,11-tetrone), an HDAC1 inhibitor with, for example, an IC50 of about 0.1 nM;

Chlamydocin ((3R)-3-benzyl-6,6-dimethyl-9-[6-[(2R)-oxiran-2-yl]-6-oxohexyl]-1,4,7,10-tetrazabicyclo [10.3.0]pentadecane-2,5,8,11-tetrone), with, for example, an IC50 of about 0.15 nM;

Depsipeptide (also known as romidepsin, FR901228 or FK228; (1 S,4S,7Z,10S,16E,21R)-7-ethylidene-4,21-di (propan-2-yl)-2-oxa-12,13-dithia-5,8,20,23-tetrazabicyclo[8.7.6]tricos-16-ene-3,6,9,19,22-pentone);

CI-994 (also known as acetyldinaline or Tacedinaline; 4-acetamido-N-(2-aminophenyl)benzamide), with, for example, a Ki of 0.05 for HDAC1;

MS-27-275 (also known as MS275 or entinostat; pyridin-3-ylmethyl-N-[[4-[(2-aminophenyl)carbamoyl]phenyl] methyl]carbamate), with, for example, an IC50 of about 0.1-1 µM;

MGCD0103 (also known as Mocetinostat, N-(2-aminophenyl)-4-[[(4-pyridin-3-ylpyrimidin-2-yl)amino] methyl]benzamide), with, for example, an 1050 of about 0.1 µM;

NVP-LAQ-824 (also known as Dacinostat or LAQ824, (E)-N-hydroxy-3-[4-[[2-hydroxyethyl-[2-(1H-indol-3-yl)ethyl]amino]methyl]phenyl]prop-2-enamide), with, for example, an IC50 for HDAC1 of about 0.003-0.008 µM;

CBHA (also known as m-carboxycinnaminic acid bishydroxamic acid; N-hydroxy-3-[(E)-3-(hydroxyamino)-3-oxoprop-1-enyl]benzamide);

JNJ16241199 (also known as R306465; N-hydroxy-2-(4-(naphthalen-2-ylsulfonyl)piperazin-1-yl)pyrimidine-5-carboxamide), a potent inhibitor of HDAC1 with, for example, IC50 values of about 30 to 300 nM;

Tubacin (also known as 537049-40-4, AC1O7Y2P, CHEMBL356769, CTK8E6516, DIOX-H_003551, Y6280; N-[4-[(2R,4R,6S)-4-[(4,5-diphenyl-1,3-oxazol-2-yl)sulfanylmethyl]-6-[4-(hydroxymethyl)phenyl]-1,3-dioxan-2-yl]phenyl]-N'-hydroxyoctanediamide), with, for example, a Ki for HDAC1 of about 0.028 µM;

A-161906 (7-[4-(4-cyanophenyl)phenoxy]-heptanohydroxamic acid);

Proxamide (see WO2007031853A2);

Oxamflatin ((E)-5-[3-(benzenesulfonamido)phenyl]-N-hydroxypent-2-en-4-ynamide);

3C1-UCHA (6-(3-chlorophenylureido)caproic hydroxamic acid);

AOE (2-amino-8-oxo-9,10-epoxydecanoic acid);

CHAP31 ((2S)—N'-hydroxy-N-[(2R)-3-(4-methoxyphenyl)-1-[[(2S,3R)-3-methyl-1-oxopentan-2-yl]amino]-1-oxopropan-2-yl]-2-(pyrrolidine-2-carbonylamino) octanediamide); or any combination thereof.

See WO2007031853A2, which is incorporated by reference herein in its entirety, for structures of many of these HDAC inhibitors.

Other inhibitors include, for example, dominant negative forms of the HDACs (e.g., catalytically inactive forms), siRNA inhibitors of the HDACs, and antibodies that specifically bind to the HDACs. Inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

In some embodiments the HDAC inhibitor(s) can include sodium butyrate.

The time of contacting or mixing HDAC inhibitor(s) with the selected population of cells can vary, for example, from about 2 days to about 50 days, or from 3 days to about 40 days, or from 4 days to about 35 days, or from 5 days to about 33 days, or from 6 days to about 30 days, or about 21-28 days.

The HDAC inhibitor(s) can be added to a selected cell population during induced pluripotency and while directing the cells into the endoderm lineage.

The HDAC inhibitor can be employed in the compositions and methods described herein in a variety of amounts and/or concentrations. For example, the HDAC inhibitor can be employed at a concentration of about 1 micromolar to about 20 millimolar, or about 10 micromolar to about 15 millimolar, or about 25 micromolar to about 5 millimolar, or about 40 micromolar to about 1 millimolar, or about 60 micromolar to about 0.5 millimolar, or about 0.1 millimolar in a solution. In a dry formulation, the HDAC inhibitor can be present in amounts of about 0.01 mg to about 100 mg, or about 0.05 mg to about 50 mg, or about 0.1 mg to about 25 mg, or about 1 mg to about 8 mg. For example, entinostat (MS275) has been administered during clinical trials at dosages of about 4-5 mg/m$^2$ (Pili et al., *Br J Cancer* 106(1): 77-84 (2012)), where mg/m$^2$ is mg per body surface area of patient. The adult average body surface is about 2.2 m$^2$ and formulae are available converting height and weight into body surface area.

Histone Demethylase Inhibitors

Histone demethylases remove methyl groups from histone. The lysine-specific demethylase 1 (LSD1, also called KDM1, AOF2, or BHC110) is a histone demethylase that suppresses gene expression by converting di-methylated lysines on histone H3 to monomethylated and unmethylated lysines. Histone methylation can influence epigenetic patterns of gene expression due to association with active promoters. As illustrated herein use of one or more inhibitors of histone demethylase enzymes can facilitate conversion of differentiated cells into the endodermal lineage.

Exemplary inhibitors of histone demethylase include, but are not limited to, parnate (also called tranylcypromine sulfate) or an equivalent salt of parnate, and phenelzine (Nardil, 2-phenylethylhydrazine). See, also, Huang et al., *Proc Natl Acad Sci USA*. 104(19): 8023-8028 (2007); Bi, X. et al., *Bioorg. Med. Chem. Lett.* 16:3229-3232 (2006); International Patent Application Nos. WO2007/021839 and WO2008/127734. MAO inhibitors can also serve as epigenetic modulators.

In some embodiments, the histone demethylase inhibitor is parnate

The time of contacting or mixing histone demethylase inhibitor(s) with the selected population of cells can vary, for example, from about 2 days to about 50 days, or from 3 days to about 40 days, or from 4 days to about 35 days, or from 5 days to about 33 days, or from 6 days to about 30 days, or about 21-28 days.

The histone demethylase inhibitor(s) can be added to a selected cell population during induced pluripotency and while directing the cells into the endoderm lineage.

The histone demethylase inhibitor can be employed in the compositions and methods described herein in a variety of amounts and/or concentrations. For example, the histone demethylase inhibitor can be employed at a concentration of about 0.01 micromolar to about 20 micromolar, or about 0.05 micromolar to about 10 micromolar, or about 0.1 micromolar to about 5 micromolar, or about 0.5 micromolar to about 3 micromolar, or about 1 micromolar to about 3 micromolar, or about 1 micromolar in a solution. In a dry formulation, the lysine-specific demethylase 1 inhibitor can be present in amounts of about 0.01 mg to about 100 mg, or about 0.05 mg to about 50 mg, or about 0.1 mg to about 25 mg, or about 1 mg to about 8 mg.

DNA Methyltransferase (DNMT) Inhibitors

DNA methyltransferases are enzymes that transfer methyl groups to DNA Inhibitors of DNA methyltransferases can reactivate the expression of genes that have been repressed by DNA methylation. As illustrated herein, DNA methyltransferase inhibitors can improve the conversion of starting cells to definitive endodermal cells.

Exemplary DNA methyltransferase (DNMT) inhibitors can include antibodies that bind to DNA methyltransferases, dominant negative variants of DNA methyltransferases, and siRNA and antisense nucleic acids that suppress expression of DNMT. DNA methyltransferase inhibitors include, but are not limited to, RG108 (available, e.g., from Sigma-Aldrich), 5-aza-C(5-azacitidine or azacitidine) (see, e.g., Schermelleh, et al., *Nature Methods* 2:751-6 (2005)), 5-aza-2'-deoxycytidine (5-aza-CdR) (see, e.g., Zhu, *Clinical Medicinal Chemistry* 3(3):187-199 (2003)), decitabine (see, e.g., Gore, *Nature Clinical Practice Oncology* 2:S30-S35 (2005)), doxorubicin (see, e.g., Levenson, *Molecular Pharmacology* 71:635-637 (2007)), EGCG ((−)-epigallocatechin-3-gallate) (see, e.g., Fang, et al., *Cancer Research* 63:7563-7570 (2003)), RG108 (see, e.g., Carninci, et al., WO2008/126932, incorporated herein by reference) and zebularine (see, Carninci, supra).

In some embodiments, the DNA methyltransferase inhibitor is RG108, which has the following structure.

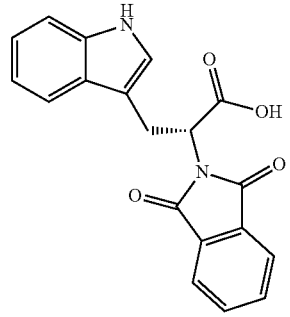 [SMILES: O=C(O)[C@@H](Cc1c[nH]c2ccccc12)N1C(=O)c2ccccc2C1=O]

The time of contacting or mixing DNA methyltransferase inhibitor(s) with the selected population of cells can vary, for example, from about 2 days to about 50 days, or from 3 days to about 40 days, or from 4 days to about 35 days, or from 5 days to about 33 days, or from 6 days to about 30 days, or about 7-28 days.

The DNA methyltransferase inhibitor(s) can be added to a selected starting cell population during induced pluripotency and while directing the cells into the endoderm lineage. The DNA methyltransferase inhibitor can be employed in the compositions and methods described herein in a variety of amounts and/or concentrations. For example, the DNA methyltransferase inhibitor can be employed at a concentration of about 0.01 micromolar to about 20 micromolar, or about 0.03 micromolar to about 10 micromolar, or about 0.05 micromolar to about 5 micromolar, or about 0.1 micromolar to about 2 micromolar, or about 0.2 micromolar to about 1 micromolar, or about 0.5 micromolar in a solution. In a dry formulation, the DNA methyltransferase inhibitor can be present in amounts of about 0.01 mg to about 100 mg, or about 0.05 mg to about 50 mg, or about 0.1 mg to about 25 mg, or about 1 mg to about 8 mg.

Adenosine Receptor Agonists

Adenosine receptor agonists bind to and/or activate adenosine receptors. Adenosine receptor agonists can activate any, two or more, or all of the adenosine receptor subtypes, including $A_1$, $A_{2a}$, $A_{2b}$, and $A_3$ adenosine receptors. Various adenosine receptor subtypes and agonists are described in the scientific literature, including, e.g., Muller C E, "Medicinal chemistry of adenosine A3 receptor ligands," *Curr Top Med Chem*. 3(4):445-62, 2003; Cristalli G et al., "Medicinal chemistry of adenosine A2A receptor agonists," *Curr Top Med Chem*. 3(4):387-401, 2003; Gao Z G, et al., "Partial agonists for A(3) adenosine receptors," *Curr Top Med Chem*. 4(8):855-62, 2004; Zablocki J A et al., "Partial A(1) adenosine receptor agonists from a molecular perspective and their potential use as chronic ventricular rate control agents during atrial fibrillation (AF)," *Curr Top Med Chem*. 4(8):839-54, 2004; Dalpiaz A et al., "Adenosine A(1) receptor: analysis of the potential therapeutic effects obtained by its activation in the central nervous system," *Curr Med Chem*. 9(21):1923-37, 2002 November; Cristalli G et al., "Medicinal chemistry of adenosine A2A receptor agonists," *Curr Top Med Chem*. 3(4):387-401, 2003; Gao Z G et al., "Allosteric modulation of the adenosine family of receptors," *Mini Rev Med Chem*. 5(6):545-53, 2005 June; Headrick J P et al., "A3 adenosine receptor-mediated protection of the ischemic heart," *Vascul Pharmacol.* 42(5-6): 271-9, 2005 April-May, Epub 2005 Apr. 19; Hutchinson S A et al., "A(1) adenosine receptor agonists: medicinal chemistry and therapeutic potential," *Curr Pharm Des.* 10(17): 2021-39, 2004; Cerqueira M D, "The future of pharmacologic stress: selective A2A adenosine receptor agonists," *Am J Cardiol.* 94(2A):33D-40D, 2004 Jul. 22, discussion 40D-42D; Lukashev D et al., "Targeting hypoxia—A(2A) adenosine receptor-mediated mechanisms of tissue protection," *Drug Discov Today.* 9(9):403-9, 2004 May 1; Yan L et al., "Adenosine receptor agonists: from basic medicinal chemistry to clinical development, "*Expert Opin Emerg Drugs.* 8(2):537-76, 2003 November; Sullivan G W, "Adenosine A2A receptor agonists as anti-inflammatory agents," *Curr Opin Investig Drugs.* 4(11):1313-9, 2003 November; Jacobson K A et al., "Adenosine receptors as therapeutic targets, *Nat Rev Drug Discov.* 5(3):247-64, 2006 March; Gross, G. J. and Auchampach, J. A. "Reperfusion injury: Does it exist?" *J. Mol. Cell. Cardiol.* (2006), 42: 12; Baraldi, P. G. et al., "Ligands for A2B adenosine receptor subtype" *Curr. Med. Chem.* (2006) 13:3467; Yuzlenko, O.; Kiec-Kononowicz, K. "Potent adenosine A1 and A2A receptors antagonists: Recent developments." *Curr. Med. Chem.* (2006), 13:3609, Cronstein, B. N. Adenosine receptors and wound healing, revised," *The Scientific World Journal* (2006) 6:984; Akkari, R. et al., "Recent progress in the development of Adenosine receptor ligands anti-inflammatory drugs," *Curr. Top. Med. Chem.* (2006) 6:1375; Vallon, V. et al., "Adenosine and kidney function," *Physiol. Rev.* (2006) 86:901; Bours, M. J. L., et al., "Adenosine 5'-triphosphate and adenosine as endogenous signaling molecules in immunity and inflammation," *Pharmacol. Ther.* (2006) 112: 358, the contents of which are specifically incorporated herein by reference in their entireties.

A variety of adenosine receptor agonists can be used in the methods and compositions described herein. For example, as illustrated herein 5'-N-ethylcarbox-amido-adenosine (NECA) can improve the conversion of starting cells to definitive endodermal cells. The structure of NECA is shown below.

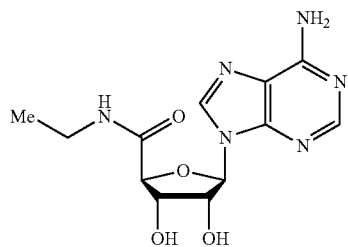

Other adenosine receptor agonists that can be employed include the following.

The 8-butylamino-adenosine compound is a partial agonist for the adenosine $A_1$ receptor. Prototypical $A_2$ agonists include 2-[p-(2-carboxyethyl)phenethyl-amino]-5'-N-ethyl-carboxamidoadenosine (CGS-2 1680) and HENECA. Another example of a NECA-modified adenosine analog is 4-(3-[6-amino-9-(5-ethylcarbamoyl-3,4-dihydroxy-tetra-hydro-furan-2-yl]-9H-purin-2-yl]-prop-2-ynyl)-cyclohexanecarboxylic acid methyl ester) from Adenosine Therapeutics. Agonists selective for the $A_1$ adenosine receptor subtype include, but are not limited to, $N^6$-cyclopentyladenosine (CPA), 2-chloro-$N^6$-cyclopentyl-adenosine (CCPA), (2S)—N6-[2-endo-Norbornyl]adenosine ((S)-ENBA), N-(2-aminoethyl)-2-[4-[[2-[4-[[9-[(2R,3R,4S,5R)-3,4-dihydroxy-5-(hydroxymethyl)oxolan-2-yl]purin-6-yl]amino]phenyl]acetyl]amino]phenyl]acetamide hydrate (ADAC), AMP579, NNC-21-0136, GR79236, CVT-510 (Tecadenoson), SDZ WAG 994, and Selodenoson.

Agonists selective for the $A_{2A}$ adenosine receptor subtype include, but are not limited to, NECA, CGS21680, DPMA, Binodenoson, ATL-146e, and CV-3146. Agonists selective for the $A_{2B}$ adenosine receptor subtype include, but are not limited to, LUF5835.

Agonists selective for the $A_3$ adenosine receptor subtype include, but are not limited to, IB-MECA, Cl-IB-MECA, 11568, CP-608039, MRS3558, and MRS1898. In various embodiments, the agonist is AmP579, a mixed adenosine agonist with both $A_1$ and $A_2$ effects (Rhone-Poulenc Rorer, Collegeville, Pa.). The analog may also be DPMA, a selective adenosine $A_2$ receptor agonist, CPA, a selective adenosine $A_1$ receptor agonist, Benzyl-NECA, a selective $A_3$ receptor agonist, 2-chloroadenosine, a non-selective $A_2/A_1$ agonist, or NECA, a non-selective $A_2/A_1$ agonist.

The time of contacting or mixing adenosine receptor agonists with the selected population of cells can vary, for example, from about 2 days to about 50 days, or from 3 days to about 40 days, or from 4 days to about 35 days, or from 5 days to about 33 days, or from 6 days to about 30 days, or from about 7 to about 28 days, or from about 14 to about 21 days.

The adenosine receptor agonists can be added to a selected starting cell population during induced pluripotency and while directing the cells into the endoderm lineage. The adenosine receptor agonists can be employed in the compositions and methods described herein in a variety of amounts and/or concentrations. For example, the adenosine receptor agonists can be employed at a concentration of about 0.01 micromolar to about 20 micromolar, or about 0.03 micromolar to about 10 micromolar, or about 0.05 micromolar to about 5 micromolar, or about 0.1 micromolar to about 2 micromolar, or about 0.2 micromolar to about 1 micromolar, or about 0.5 micromolar in a solution. In a dry formulation, the adenosine receptor agonists can be present in amounts of about 0.01 mg to about 100 mg, or about 0.05 mg to about 50 mg, or about 0.1 mg to about 25 mg, or about 1 mg to about 8 mg.

Expansion of Endodermal Cells

Endodermal cells can be expanded by culturing the cells in a medium containing an activator of WNT signaling and an inhibitor of TGFβ signaling. The WNT activator and the TGFβ signaling inhibitor can be any of those listed above. One example of a useful WNT activator for expansion is CHIR99021. An example of a TGFβ signaling inhibitor useful for cellular expansion is A83-01. Addition of two growth factors (e.g., EGF and bFGF) can improve the expansion and serial passage of the definitive endodermal cells. The cells proliferate rapidly with an average doubling time of 2 days. After 15 passages an increase in cell number was obtained of at least a trillion-fold.

The expanded cells maintained their epithelial colony morphology and had a posterior foregut-like phenotype as determined by immunofluorescence staining for SOX17, FOXA2, HNF4a, HNF6, and SOX9. Following gastrulation, definitive endoderm migrates to form the primitive gut, which initially consists of a single flattened sheet of cells surrounded by mesoderm. Simultaneously, as migration is occurring, the primitive gut is becoming regionalized along the dorsal-ventral and anterior-posterior axes into foregut, midgut, and hindgut domains. The foregut region gives rise to many of the major organ systems such as the liver, thyroid, lungs, the upper airways, the biliary system, stomach, and pancreas. Hence, a posterior foregut-like phenotype is indicative of cells that can give rise to pancreatic progenitor cells.

When the methods and compositions described herein are employed, high levels of expression of multiple posterior foregut progenitor gene transcripts are detected in expanded posterior foregut-like cells, including SOX17, FOXA2, HNF1A, HNF1B, HNF4A, HNF6, SOX9 and PDX1, as compared to parental fibroblasts. In contrast, ectodermal marker gene SOX1, mesodermal marker gene BRACHYURY, and pluripotency marker genes OCT4 and NANOG were not induced. Notably, the episomal vectors were undetectable by qPCR assays in established posterior foregut-like cells (abbreviated as cPF cells).

Transplantation of expanded cPF cells under the kidney capsule of immune deficient mice did not result in any tumor formation even after prolonged periods of up to 12 weeks in vivo. Analysis of the cPF grafts demonstrated epithelial structures expressing different endoderm-specific markers, including E-cadherin, HNF4α, PDX1, SOX9, and pan-cytokeratin. Thus, the cPF cells can be greatly expanded in culture while maintaining their posterior foregut endodermal phenotype.

The cPF cells can be differentiated into more committed pancreatic endodermal progenitor cells using the methods described below.

For example, the cPF cells can first be cultured in the presence of growth factors, an inhibitor of TGFβ, an inhibitor of Notch signaling, a retinoic acid receptor agonist, a hedgehog antagonist, an inhibitor of BMP4 signaling, and combinations thereof for several days. The cPF cells can be cultured in the presence of these agents for about 1 to 10 days, or about 2 to 5 days, or about 2 to 4 days. The growth factors employed can be FGF7 and FGF10. The inhibitor of TGFβ can be A83-01. The inhibitor of Notch signaling can be Compound-E. The hedgehog antagonist can be GDC-0449, and the inhibitor of BMP4 signaling can be LDN-193189.

In a second step, the differentiating cells can be cultured for several more days, for example, in the presence of different growth factors (e.g., EGF), an agonist of glucagon-like peptide-1 (e.g., Extendin-4), an inhibitor of TGFβ (e.g., A83-01), an inhibitor of BMP4 signaling (e.g., LDN-193189), an activator of protein kinase C (e.g., phorbol 12,13-dibutyrate), an inhibitor of Notch signaling (e.g., Compound-E), an inhibitor of polyADP-ribose synthetase (e.g. nicotinamide), and combinations thereof. For example, the differentiating cells can be cultured in the presence of these agents for about 1 to 10 days, or about 2 to 5 days, or about 2 to 4 days.

The resulting pancreatic progenitor cells express FOXA2, HNF6, SOX9, and PDX1, NKX6.1, or combinations thereof.

Further details on generating pancreatic progenitor cells are described below.

Pancreatic Progenitor Cells

Pancreatic progenitor cells can be identified by their expression of Pdx1, Nkx6.1, Pax6, Hnf6, FoxA2, Sox9, or a combination thereof. Pancreatic progenitor cells can be obtained from the definitive endoderm cells and/or posterior foregut-like cells generated as described herein. The conversion to pancreatic progenitor cells can involve contacting or mixing the cells with a second composition. For example, pancreatic progenitor cells can be obtained from definitive endoderm cells by contacting or mixing the definitive endoderm cells with a second composition that includes a TGFβ receptor inhibitor, a hedgehog pathway inhibitor, a retinoic acid receptor agonist, or a combination thereof. The yield of pancreatic progenitor cells can be increased by including a WNT activator, 2-phospho-L-ascorbic acid, a Notch signaling inhibitor, a BMP4 signaling inhibitor, an activator of protein kinase C, growth factors (e.g., epidermal growth factor (EGF), basic fibroblast growth factor (bFGF), fibroblast growth factor 7 (FGF7), fibroblast growth factor 10 (FGF10), or a combination thereof).

Starting Cells for Generating Pancreatic Progenitor Cells

Pancreatic progenitor cells can be obtained from definitive endoderm cells, for example, cells that express Sox17, Foxa2, Cerberus 1 (Cer), C-X-C chemokine receptor type 4 (Cxcr4), or a combination thereof. Pancreatic progenitor cells can also be obtained from posterior foregut-like cells, which express Sox17, Foxa2, Hnf4a, Sox9, or a combination thereof.

The starting cells are treated with a TGFβ receptor inhibitor, a hedgehog pathway inhibitor, a retinoic acid receptor agonist, 2-phospho-L-ascorbic acid, an inhibitor of Notch signaling, an inhibitor of BMP4 signaling, one or more growth factors, or a combination thereof, to generate pancreatic progenitor cells. Additional factors that can improve conversion to pancreatic progenitor cells include an agonist of glucagon-like peptide-1, an inhibitor of BMP4 signaling, an activator of protein kinase C, an inhibitor of polyADP-ribose synthetase, and combinations thereof. Several of these factors and details for use of these factors are described above in the section describing conversion of starting cells to definitive endodermal cells. Other factors and more details for converting definitive endoderm cells to pancreatic progenitor cells are described below.

Retinoic Acid Receptor Agonists

As shown herein, addition of retinoic acid receptor agonists (without addition of any growth factors) to definitive endoderm cells increases the proportion and yield of Pdx1$^+$ and/or Nkx6.1$^+$ pancreatic progenitor cells. For example, more than about 5%, or more than about 10%, or more than about 15%, or more than about 20%, or about 25% of the cells were Pdx1 positive and/or Nkx6.1 positive.

The retinoic acid receptor agonists can be added to cells that express Sox17, Foxa2, Cerberus 1 (Cer), C-X-C chemokine receptor type 4 (Cxcr4), or a combination thereof.

To increase the proportion of cells that express markers indicative of a pancreatic progenitor cell phenotype, a selected population of cells (e.g., definitive endoderm cells) is contacted or mixed with a retinoic acid receptor agonist for a time and at a concentration sufficient to differentiate at least some of the cells into pancreatic progenitor cells.

The time of contacting or mixing a retinoic acid receptor agonist with the selected population of cells can vary, for example, from about 0.5 days to about 12 days, or from 1 days to about 10 days, or from 1.5 days to about 8 days, or from 2 days to about 7 days, or from 2.5 days to about 6 days, or from about 3 days to about 5 days, or about 4 days.

Retinoic acid receptor agonists can be used at a variety of concentrations, for example, at about 0.01 μM to about 10 μM, or from about 0.05 μM to about 9 μM, or from about 0.1 μM to about 8 μM, or from about 0.3 μM to about 7 μM, or from about 0.5 μM to about 6 μM, or from about 0.75 μM to about 5 μM, or from about 1 μM to about 3 μM, or about 2 μM.

A variety of retinoic acid receptor agonists can be employed. Examples of retinoic acid receptor agonists include, for example, retinoic acid. The retinoic acid receptor agonists can be a naturally-occurring retinoid, or chemically synthesized retinoid, a retinoic acid receptor agonist compound free of retinoid skeleton, or a naturally-occurring substance having a retinoic acid receptor agonist activity. Examples of the natural retinoid having a RAR agonist activity include retinoic acid (stereoisomers of all-trans retinoic acid (all-trans RA) and 9-cis-retinoic acid (9-cis RA) are known). A chemically synthesized retinoid is known in this field (see, e.g., U.S. Pat. Nos. 5,234,926, and 4,326,055). Examples of the retinoic acid receptor agonist compound free of retinoid skeleton include Am80, AM580, TTNPB and AC55649. Examples of a naturally-occurring substance having a retinoic acid receptor agonist activity includes honokiol and magnolol (Annual Report of Research Institute for Biological Function 9:55-61, 2009). The RAR agonist to be used in this step is preferably retinoic acid, AM580 (4-[[5,6,7,8-tetrahydro-5,5,8,8-tetramethyl-2-naphthalenyl]carboxamide]benzoic acid), TTNPB (4-[[E]-2-[5,6,7,8-tetrahydro-5,5,8,8-tetramethyl-2-naphthalenyl]-1-propenyl]benzoic acid), AC55649 (4'-octyl-[1,1'-biphenyl]-4-carboxylic acid), more preferably retinoic acid. While the concentration of an RAR agonist in the medium is appropriately determined according to the kind of the RAR agonist to be used, the concentration of retinoic acid when used as a RAR agonist is generally 0.1-100 μM, preferably 0.5-10 μM. The concentration of TTNPB when used as an RAR agonist is generally 0.02-20 μM, preferably 0.05-10 μM. The concentration of AM580 when used as an RAR agonist is generally 0.02-20 μM, preferably 0.05-10 μM. The concentration of AC55649 when used as an RAR agonist is generally 0.02-20 μM, preferably 0.1-10 μM.

TGFβ Receptor Inhibitors

TGFβ receptor is a serine/threonine kinase receptor. The transforming growth factor beta (TGFβ) signaling pathway is involved in many cellular processes in both the adult organism and in the developing embryo including cell growth, cell differentiation, apoptosis, cellular homeostasis and other cellular functions. In spite of the wide range of cellular processes that the TGFβ signaling pathway regulates, the process is relatively simple. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression. The TGFβ receptor inhibitor also includes TGFβ receptor antagonists.

As shown herein, addition of inhibitors of TGFβ receptors (without addition of any growth factors) to definitive endoderm cells increases the proportion and yield of Pdx1$^+$ and/or Nkx6.1$^+$ pancreatic progenitor cells. For example, more than about 5%, or more than about 10%, or more than about 15%, or more than about 20%, or about 25% of the cells were Pdx1 positive and/or Nkx6.1 positive.

Also as shown herein, addition of inhibitors of TGFβ receptors (without addition of any growth factors) to pancreatic progenitor cells can improve the conversion of such cells to pancreatic beta cells. For example, more than about 0.1%, or more than about 0.2%, or more than about 0.5%, or more than about 1%, or about 2% of the cells, or more than about 5%, or more than about 7% of cells treated with such inhibitors of TGFβ receptors were positive for C-peptide and/or insulin production.

The TGFβ receptor inhibitors can be added to cells that express Sox17, Foxa2, Cerberus 1 (Cer), C-X-C chemokine receptor type 4 (Cxcr4), or a combination thereof. The TGFβ receptor inhibitors can be added to cells that express Pdx1 and/or Nkx6.1.

To increase the proportion of cells that express markers indicative of a pancreatic progenitor cell phenotype or a mature pancreatic beta cell phenotype, a selected population of cells (e.g., definitive endoderm cells or pancreatic progenitor cells) is contacted or mixed with an inhibitor of TGFβ receptors for a time and at a concentration sufficient to differentiate at least some of the cells into pancreatic progenitor cells, or pancreatic beta cells, respectively.

Examples of TGF-β inhibitors include, but are not limited to:

3-(6-Methyl-2-pyridinyl)-N-phenyl-4-(4-quinolinyl)-1H-pyrazole-1-carbothioamide (also known as A83-01, and available from Tocris Bioscience), which is a TGFβ kinase/Activin receptor like kinase (ALK5) inhibitor that blocks the phosphorylation of Smad2 and inhibits TGFβ-induced epithelial-to-mesenchymal transition;

SB431542 (also known as 4-[4-(1,3-benzodioxol-5-yl)-5-(2-pyridinyl)-1H-imidazol-2-yl]benzamide; available from Tocris Bioscience), which is a potent and selective inhibitor of the transforming growth factor-β (TGF-β) type I receptor Activin receptor-like kinase ALK5 ($IC_{50}$=94 nM), and its relatives ALK4 and ALK7;

4-[4-(1,3-benzodioxol-5-yl)-5-(2-pyridinyl)-1H-imidazol-2-yl]benzamide (also known as SB 431542 and available from Tocris Bioscience; a potent and selective inhibitor of TGF-β type I receptor Activin receptor-like kinase ALK5 (e.g., with $IC_{50}$=94 nM), and its relatives ALK4 and ALK7);

3-(6-Methyl-2-pyridinyl)-N-phenyl-4-(4-quinolinyl)-1H-pyrazole-1-carbothioamide (also known as A83-01 from Tocris Bioscience; a selective inhibitor of TGF-β type I receptor ALK5 kinase, type I Activin/nodal receptor ALK4 and type I nodal receptor ALK7 (IC50 values can, e.g., be 12, 45 and 7.5 nM respectively);

2-(3-(6-Methylpyridine-2-yl)-IH-pyrazol-4-yl)-1,5-naphthyridine (also known as SJN 2511 from Tocris Bioscience; selective inhibitor of the TGF-β type I receptor ALK5 (IC50 values can, e.g., be 0.004 and 0.023 μM for ALK5 autophosphorylation and ALK5 binding, respectively);

4-[4-(2,3-Dihydro-1,4-benzodioxin-6-yl)-5-(2-pyridinyl)-IH-imidazol-2-yl]benzamide (also known as D 4476 from Tocris Bioscience; a selective inhibitor of casein kinase 1 (CK1) and TGF-β type-1 receptor (ALK5) that displays greater than 20-fold selectivity over SAPK2/p38);

4-[3-(2-Pyridinyl)-1H-pyrazol-4-yl]-quinoline (also known as LY 364947 from Tocris Bioscience; a selective inhibitor of TGF-β type-I receptor (TGF-β R1, TGFR-I, TβR-1, ALK-5) (IC50 values can, e.g., be 59, 400 and 1400 nM for TGR-β RI, TGF-β RII and MLK-7K respectively);

2-(4-(benzo[d][1,3]dioxol-5-yl)-2-tert-butyl-1H-imidazol-5-yl)-6-methylpyridine (also known as SB505124, and available from Selleckchem.com; a selective inhibitor of ALK4 and ALK5 (e.g., with IC50 of 129 nM and 47 nM, respectively);

6-[2-(1,1-Dimethylethyl)-5-(6-methyl-2-pyridinyl)-1H-imidazol-4-yl]quinoxaline (also known as SB 525334 from Sigma-Aldrich; a selective inhibitor of transforming growth factor-β receptor I (ALK5, TGF-βRI), with IC50=14.3 nM, for example);

2-(5-Chloro-2-fluorophenyl)-4-[(4-pyridyl)amino]pteridine (also known as SD 208 from Tocris Bioscience; a potent, orally active ATP-competitive transforming growth factor-(3 receptor 1 (TGF-βRI) inhibitor, e.g., with IC50=49 nanomolar);

4-(6-(4-(piperazin-1-yl)phenyl)pyrazolo[1,5-a]pyrimidin-3-yl)quinoline (also known as LDN-193189 from Miltenyi Biotec); and any combination thereof.

The inhibitor that directly or indirectly negatively regulates TGF-beta signaling can, for example, be selected from the group consisting of SB431542, A83-01, SB-431542, A83-01, SJN-2511, LY-36494, SB-505124, SB-525334, and SD-208. In some embodiments, an inhibitor that directly or indirectly negatively regulates TGF-beta signaling can inhibit ALK4, ALK5 and/or ALK7. For example, the inhibitor that directly or indirectly negatively regulates TGF-beta signaling can be A83-01, with the following structure.

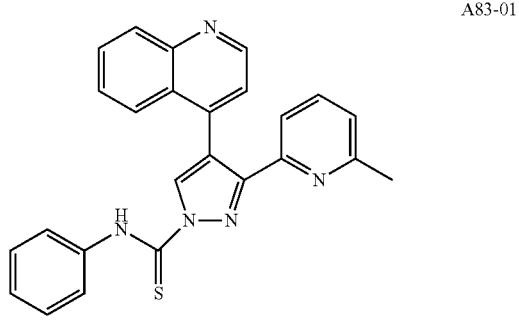 [SMILES: Cc1cccc(-c2nn(C(=S)Nc3ccccc3)cc2-c2ccnc3ccccc23)n1]

A83-01

The TGF-beta inhibitor can also be in the form of a salt or hydrate of any of the foregoing compounds.

The time of contacting or mixing a TGFβ receptor inhibitor with a population of definitive endodermal cells can vary, for example, from about 0.5 days to about 10 days, or from 1 days to about 10 days, or from 1.5 days to about 8 days, or from 2 days to about 7 days, or from 2 days to about 6 days, or from about 2 days to about 5 days, or about 2 days to 4 days.

The time of contacting or mixing a TGFβ receptor inhibitor with a population of pancreatic progenitor cells can vary, for example, from about 0.5 days to about 10 days, or from 1 days to about 8 days, or from 1.5 days to about 6 days, or from 1.5 days to about 5 days, or from 2 days to about 4 days, or about 3 days.

TGFβ receptor inhibitors can be used at a variety of concentrations, for example, at about 0.01 µM to about 10 µM, or from about 0.05 µM to about 9 µM, or from about 0.1 µM to about 8 µM, or from about 0.2 µM to about 7 µM, or from about 0.3 µM to about 6 µM, or from about 0.4 µM to about 5 µM, or from about 0.5 µM to about 3 µM, or about 1 µM.

Various methods for determining if a substance is a TGF-beta inhibitor are available. For example, a cell-based assay can be employed in which cells are stably transfected with a reporter construct comprising the human PAI-1 promoter or Smad binding sites, driving a luciferase reporter gene Inhibition of luciferase activity relative to control groups can be used as a measure of compound activity (De Gouville et al., *Br J Pharmacol*. 2005 May; 145(2): 166-177). Another example is the ALPHASCREEN® phospho-sensor assay for measurement of kinase activity (Drew A E et al., Comparison of 2 Cell-Based Phosphoprotein Assays to Support Screening and Development of an ALK Inhibitor, *J Biomol Screen* 16(2) 164-173, 2011).

Hedgehog Pathway Inhibitors

As shown herein, addition of inhibitors of the hedgehog pathway (without addition of any growth factors) to definitive endoderm cells increases the proportion and yield of Pdx1$^+$ and/or Nkx6.1$^+$ pancreatic progenitor cells. For example, more than about 5%, or more than about 10%, or more than about 15%, or more than about 20%, or about 25% of the cells were Pdx1 positive and/or Nkx6.1 positive.

The hedgehog pathway inhibitors can be added to cells that express Sox17, Foxa2, Cerberus 1 (Cer), C-X-C chemokine receptor type 4 (Cxcr4), or a combination thereof.

To increase the proportion of cells that express markers indicative of a pancreatic progenitor cell phenotype, a selected population of cells (e.g., definitive endoderm cells) is contacted or mixed with a hedgehog pathway inhibitor for a time and at a concentration sufficient to differentiate at least some of the cells into pancreatic progenitor cells.

The time of contacting or mixing a hedgehog pathway inhibitor with the selected population of cells can vary, for example, from about 0.5 days to about 12 days, or from 1 days to about 10 days, or from 1.5 days to about 8 days, or from 2 days to about 7 days, or from 2.5 days to about 6 days, or from about 3 days to about 5 days, or about 4 days.

Hedgehog pathway inhibitors can be used at a variety of concentrations, for example, at about 0.01 µM to about 10 µM, or from about 0.05 µM to about 9 µM, or from about 0.1 µM to about 8 µM, or from about 0.3 µM to about 7 µM, or from about 0.5 µM to about 6 µM, or from about 0.75 µM to about 5 µM, or from about 1 µM to about 3 µM, or about 2 µM.

A variety of hedgehog pathway inhibitors can be employed. Examples of hedgehog pathway inhibitors include, for example, LDE 225 (Novartis), cyclopamine, MK-4101 (Merck), GDC-0449 (Genentech), XL-139 (BMS-833923) (Bristol Myers Squibb), PF-04449913 (Pfizer), robotnikinin, and Cur-61414 (G-024856).

Notch Inhibitor

As shown herein, addition of inhibitors of Notch to definitive endoderm cells increases the proportion and yield of Pdx1$^+$ and/or Nkx6.1$^+$ pancreatic progenitor cells. For example, more than about 5%, or more than about 10%, or more than about 15%, or more than about 20%, or about 25% of the cells were Pdx1 positive and/or Nkx6.1 positive. In addition Notch inhibitors can also increase the proportion and yield of mature pancreatic beta cells.

The Notch inhibitor can operate in any manner that inhibits Notch function. For example, the Notch inhibitor can inhibit Notch signaling, inhibit Notch transcription, inhibit Notch translation, or competitively inhibit Notch. Examples of Notch inhibitors include gamma secretase inhibitors, Notch interfering RNA, and dominant negative Notch proteins.

Notch signaling can be modulated by altering the activity of the gamma-secretase complex. This complex cleaves the Notch receptor releasing the Notch intracellular domain (reviewed in Fortini, *Nature Reviews Molecular and Cell Biology* 3: 673-684 (2002)). Gamma-secretase inhibitors reduce the level of Notch signaling and lead to effects that resemble or are identical to the phenotypes produced by loss of function mutations in Notch genes in a variety of organisms and experimental systems (Dovey et al., *Journal of Neurochemistry* 76:173-181 (2001); Hadland et al., *Proceedings of the National Academy of Sciences USA* 98: 7487-7491 (2001); Doerfler et al., *Proceedings of the*

*National Academy of Sciences USA* 98: 9312-9317 (2001); Micchelli et al., *The FASEB Journal* 17: 79-81 (2002)).

A variety of Notch and/or gamma-secretase inhibitors can be employed, including any of the following:

Compound E (C-E) is a cell permeable, potent, selective, non-transition state and non-competitive inhibitor of γ-secretase (IC$_{50}$=0.3 nM for total β-amyloid) and Notch processing, which inhibits cell differentiation. At higher concentrations (20-4000/1), compound E only weakly affects the presenilase activity. Compound E is commercially available from a variety of sources, including Enzo Life Sciences (enzolifesciences.com/ALX-270-415/compound-e/). The structure of compound E is shown below.

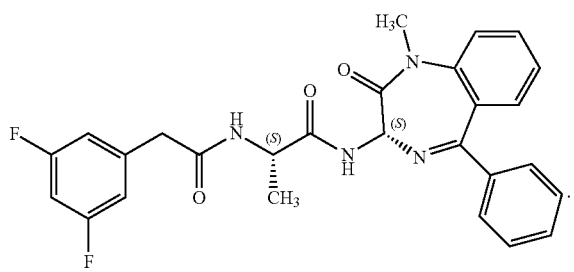

Compound E

RO4929097 is a γ secretase inhibitor (available from Selleckcehem.com) with IC50 of 4 nM, inhibiting cellular processing of Aβ40 and Notch with EC50 of 14 nM and 5 nM, respectively. RO4929097 has the following structure:

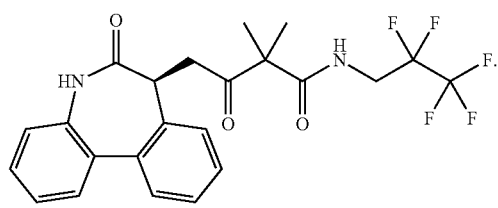

RO4929097

DAPT (GSI-IX) is a γ-secretase inhibitor (available from Sigma-Aldrich) that inhibits Aβ production. DAPT has the following structure:

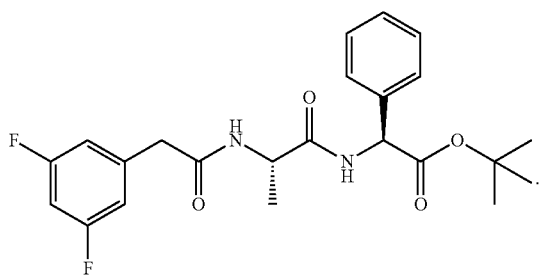

DAPT

Gamma-Secretase Inhibitor I, which has the following structure: Z-Leu-Leu-Nle-CHO (Nle=Norleucine) (available from EMD Millipore (see, emdmillipore.com/life-science-research/gamma-secretase-inhibitor).

Gamma-Secretase Inhibitor II, which is a cell-permeable, reversible and selective peptidomimetic inhibitor of γ-secretase (IC$_{50}$=13 μM for Aβ). It displays only weak inhibitory activity against calpain II (IC$_{50}$=100 μM in a purified enzyme assay). Gamma-Secretase Inhibitor II has the following structure:

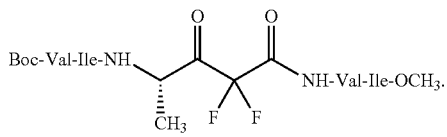

In some embodiments, the Notch inhibitor is compound E.

The Notch inhibitor can be used in various concentrations. For example, the Notch inhibitor can be employed at a concentration of about 0.001 micromolar to about 200 micromolar, or about 0.01 micromolar to about 100 micromolar, or about 0.05 micromolar to about 10 micromolar, or about 0.1 micromolar in a solution. In a dry formulation, Notch inhibitor can be present in amounts of about 0.01 mg to about 1000 mg, or about 0.1 mg to about 100 mg, or about 1 mg to about 10 mg.

Cells can be incubated in a medium containing a Notch inhibitor (e.g., compound E (C-E)), for varying amounts of time. For example, the cells can be incubated in a medium containing a Notch inhibitor until at least some of the cells express pancreatic progenitor markers such as Pdx1$^+$ and/or Nkx6.1$^+$. The incubation time can vary, for example, from about 0.5 days to about 5 days, or from about 1 day to about 4 days, or from about 1 days to about 3 days, or about 2 days.

Alternatively, when converting pancreatic progenitor cells to mature pancreatic beta cells, the cells can be incubated until markers such as insulin and/or Pdx1. The incubation time for conversion of pancreatic progenitor cells to mature pancreatic beta cells can vary, for example, from about 2 days to about 20 days, or from about 4 days to about 16 days, or from about 6 days to about 15 days, or from about 9 days to about 14 days, or about 12 days.

BMP4 Signaling Inhibitor

BMP4 is a potent growth factor that has a role in mesodermal differentiation, basic body plan formation, and determination of the proximal-distal, left-right, and dorsal-ventral axes. BMP4 elicits different biological responses depending on the concentration of the secreted form. For example, high levels of BMP4 in early embryonic development are associated with commitment to a ventral fate, while low levels are associated with a commitment to dorsal neural and muscular tissue. Secreted active BMP4 can be inhibited at the extracellular level by interacting with secreted BMP4 antagonists, such as noggin, chordin, CeM, DAN, and Gremlin.

BMP4 signaling inhibitors are available. For example, the methods and compositions described herein can include any of the BMP4 inhibitors described in U.S. Pat. No. 8,507,501, the contents of which are hereby incorporated by reference in their entirety. Another example of a BMP4 signaling inhibitor is 3-(6-amino-5-(3,4,5-trimethoxyphenyl)pyridin-3-yl)phenol (K02288), which inhibits BMP4 mediated phosphorylation of Smad1/5/8 (Sanvitale et al., A New Class of Small Molecule Inhibitor of BMP Signaling, *PLOS One* 8(4): e62721 (Apr. 30, 2013). In some embodiments, the BMP4 signaling inhibitor can be 4-(6-(4-(piperazin-1-yl)phenyl)pyrazolo[1,5-a]pyrimidin-3-yl)quinoline (LDN-193189).

The BMP4 signaling inhibitor can be used in various concentrations. For example, the BMP4 signaling inhibitor can be employed at a concentration of about 0.001 micromolar to about 200 micromolar, or about 0.01 micromolar to about 100 micromolar, or about 0.05 micromolar to about 10 micromolar, or about 0.1 micromolar in a solution. In a dry formulation, BMP4 signaling inhibitor can be present in amounts of about 0.01 mg to about 1000 mg, or about 0.1 mg to about 100 mg, or about 1 mg to about 10 mg.

Cells can be incubated in a medium containing a BMP4 signaling inhibitor (e.g., LDN-193189), for varying amounts of time. For example, the cells can be incubated in a medium containing a BMP4 signaling inhibitor until at least some of the cells express pancreatic progenitor markers such as Pdx1$^+$ and/or Nkx6.1$^+$. The incubation time can vary, for example, from about 0.5 days to about 5 days, or from about 1 day to about 4 days, or from about 1 day to about 3 days, or about 2 or 3 days.

Activators of Protein Kinase C

Protein kinase C is an enzyme that regulates the function of other proteins by phosphorylation of serine and/or threonine hydroxy groups on those proteins.

Activators of protein kinase C include phorbol 12,13-dibutyrate (PBDu), Bryostatin, FR 236924, (−)-Indolactam V, PEP 005, phorbol 12,13-dibutyrate, phorbol 12-myristate13-acetate, PKC fragment (530-558), pseudo RACK1, SC-10, SC-9, and combinations thereof. These protein kinase C activators are available from Tocris (see website at tocris.com/pharmacologicalBrowser.php?ItemId=164170&Te=Activators#.U8mK601OU5t).

The protein kinase C activator can be used in various concentrations. For example, the protein kinase C activator can be employed at a concentration of about 0.01 nanomolar to about 3 nanomolar, or about 0.05 nanomolar to about 1 nanomolar, or about 0.1 nanomolar to about 0.5 nanomolar, or about 0.2 nanomolar in a solution. In a dry formulation, protein kinase C activator can be present in amounts of about 0.01 mg to about 1000 mg, or about 0.1 mg to about 100 mg, or about 1 mg to about 10 mg.

Cells can be incubated in a medium containing a protein kinase C activator (e.g., phorbol 12,13-dibutyrate), for varying amounts of time. For example, the cells can be incubated in a medium containing a protein kinase C activator until at least some of the cells express pancreatic progenitor markers such as Pdx1$^+$ and/or Nkx6.1$^+$. The incubation time can vary, for example, from about 0.5 days to about 7 days, or from about 1 day to about 5 days, or about 2 to 4 days.

Expansion of Pancreatic Progenitor Cells

Pancreatic progenitor cells can be expanded using the same procedures as for expansion of endodermal cells. However the pancreatic progenitor cell colonies easily detached from culture plates when such procedures were employed. Removal of the WNT activator, and increased amounts of growth factors (e.g., EGF) obviated this problem and improved pancreatic progenitor cell expansion. Under these optimized culture conditions, pancreatic progenitor cells were expanded more than two hundred million fold with an approximate doubling time of 3 days for up to 14 passages. Moreover, the cells maintained their bi-potent progenitor identity as evidenced by the presence of PDX1 and NKX6.1 double-positive cells at passage 12.

Pancreatic progenitor cells are ideal for transplantation and treatment due to their potential for sustained proliferation and proper differentiation. The expansion methods and compositions described herein facilitate production of sufficient numbers of cells to be therapeutically useful.

Pancreatic Cells

Pancreatic beta cells can be identified by their expression of insulin, C-peptide, PDX1, NKX6.1, NEUROD1, NKX2.2, glucagon, or any combination thereof. The procedures and compositions described herein can convert more than about 1%, or more than about 2%, or more than about 3%, or more than about 4%, or about 5% of pancreatic progenitor cells to pancreatic beta cells as illustrated by expression of insulin, C-peptide, PDX1, NKX6.1, NEUROD1, NKX2.2, glucagon, or any combination thereof.

Pancreatic beta cells can be generated from pancreatic progenitor cells by incubation in media that includes a TGFβ receptor inhibitor (e.g. A83-01), a polyADP-ribose synthetase inhibitor (e.g. nicotinamide), an agonist of glucocorticoid receptor (e.g., dexamethasone), a Notch Signaling Inhibitor (e.g., Compound E), and combinations thereof. Conversion of pancreatic progenitor cells to pancreatic beta cells is improved by inclusion of all four of the foregoing agents in the culture medium. Conversion of pancreatic progenitor cells to pancreatic beta cells is also improved by addition of vitamin C, an activator of adenylyl cyclase (e.g. Forskolin), an agonist of Glucagon-like Peptide-1 (e.g., Exendin-4), a Ca$^{2+}$ channel agonist (e.g. BayK-8644), or any combination thereof to the culture medium.

Pancreatic beta cells can also be generated in cell culture media containing laminin, nicotinamide, and B27 etc. as previously reported (Schroeder et al., 2006). As described herein, small molecules such as 2-phospho-L-ascorbic acid and inhibitors of a p38 mitogen-activated protein (MAP) kinase strongly and synergistically increased the number of insulin$^+$/Pdx1$^+$ cells in the mixture. For example, the SB203580 inhibitor of a p38 mitogen-activated protein (MAP) kinase and/or 2-phospho-L-ascorbic acid promote pancreatic beta-cell maturation and increased the number of insulin$^+$/Pdx1$^+$ cells in the mixture.

Several of the factors employed to convert pancreatic progenitor cells to pancreatic beta cells have been described in the foregoing sections. Further information about other factors useful for converting pancreatic progenitor cells to pancreatic beta cells is described below.

PolyADP-Ribose Synthetase Inhibitors

PolyADP-ribose synthetase is also referred to as polyADP-ribose polymerase (PARD). PolyADP-ribose synthetase is an enzyme that catalyzes the poly-ADP ribosylation reaction; this enzyme has an important role in DNA repair or transcriptional regulation.

As shown herein, addition of polyADP-ribose synthetase inhibitor to pancreatic progenitor cells increases the proportion and yield of cells that express genes indicative of the pancreatic beta cell phenotype. To increase the proportion of cells that convert to pancreatic beta cells (and express markers indicative of a pancreatic beta cell phenotype), a selected population of cells (e.g., pancreatic progenitor cells) is contacted or mixed with one or more polyADP-ribose synthetase inhibitors for a time and at a concentration sufficient to differentiate at least some of the cells into pancreatic beta cells.

Examples of a polyADP-ribose synthetase inhibitor include nicotinamide, 3-aminobenzamide, 1,5-isoquinolinediol and combinations thereof.

The polyADP-ribose synthetase inhibitor can be used in various concentrations. For example, the polyADP-ribose synthetase inhibitor can be employed at a concentration of about 0.1 millimolar to about 100 millimolar, or about 1 millimolar to about 50 millimolar, or about 3 millimolar to about 30 millimolar, or about 5 micromolar to about 15 millimolar, or about 10 millimolar in a solution. In a dry formulation, polyADP-ribose synthetase inhibitor can be present in amounts of about 1 mg to about 1000 mg, or about 10 mg to about 100 mg.

Cells can be incubated in a medium containing a polyADP-ribose synthetase inhibitor (e.g., nicotinamide), for varying amounts of time. For example, the cells can be incubated in a medium containing a polyADP-ribose synthetase inhibitor until at least some of the cells express pancreatic beta cell markers such as $Pdx1^+$, insulin, C-peptide, or a combination thereof. The incubation time can vary, for example, from about 0.5 days to about 5 days, or from about 1 day to about 4 days, or from about 1 days to about 3 days, or about 2 or 3 days.

p38 Mitogen-Activated Protein (MAP) Kinase Inhibitors

Inhibitors of a p38 mitogen-activated protein (MAP) kinase can be added to $Pdx1^+/Nkx6.1^+$ pancreatic progenitor cells to generate pancreatic beta cells.

To increase the proportion of cells that convert to pancreatic beta cells (and express markers indicative of a pancreatic beta cell phenotype), a selected population of cells (e.g., pancreatic progenitor cells) is contacted or mixed with p38 mitogen-activated protein inhibitors for a time and at a concentration sufficient to differentiate at least some of the cells into pancreatic beta cells.

Examples of p38 mitogen-activated protein inhibitors that can be used in the methods and compositions described herein include, but are not limited to, p38 inhibitors SB203580 (i.e., 4-(4-fluorophenyl)-2-(4-methylsulfinylphenyl)-5-(4-pyridyl)-1H-imidazole), SB202190 (i.e., 4-(4-fluorophenyl)-2-(4-hydroxyphenyl)-5-(4-pyridyl) imidazole), SB239063 (i.e., trans-1-(-Hydroxycyclohexyl)-4-(4-fluorophenyl)-5-(2-methoxypyrimidin-4-yl)imidazole), SB220025 (5-(2-Aminopyrimidin-4-yl)-4-(4-fluorophenyl)-1-(4-piperidinyl)imidazole trihydrochloride), PD169316 (4-(4-Fluorophenyl)-2-(4-nitrophenyl)-5-(4-pyridyl)-1H-imidazole), RPR200765A ([2-[4-(4-fluorophenyl)-5-pyridin-4-yl-1H-imidazol-2-yl]-5-methyl-1,3-dioxan-5-yl]-morpholin-4-ylmethanone; methanesulfonic acid) AMG 548 (2-[[(2S)-2-amino-3-phenylpropyl]amino]-3-methyl-5-naphthalen-2-yl-6-pyridin-4-ylpyrimidin-4-one), BIRB-796 (1-[5-tert-butyl-2-(4-methylphenyl)pyrazol-3-yl]-3-[4-(2-morpholin-4-ylethoxy)naphthalen-1-yl]urea), SCIO-469 (6-Chloro-5-[[(2R,5S)-4-[(4-fluorophenyl)methyl]-2,5-dimethyl-1-piperazinyl]carbonyl]-N,N,1-trimethyl-α-oxo-1H-Indole-3-acetamide), SCIO-323 and VX-702 disclosed in Nikas et al. (*Curr Opin Drug Discov Devel.* 8, 421-430. (2005)), FR167653 disclosed in Yamamoto et al. (*Eur. J. Pharmacol* 314, 137-142 (1996)), and combinations thereof.

The time of contacting or incubating p38 mitogen-activated protein inhibitors with pancreatic progenitor cells can vary, for example, from about 1 days to about 20 days, or from 2 days to about 15 days, or from 3 days to about 13 days, or from 4 days to about 12 days, or from 5 days to about 11 days, or from about 6 days to about 11 days, or for about 9 days.

For example, inhibitors of a p38 mitogen-activated protein (MAP) kinase can be added to a selected cell population (pancreatic progenitor cells) while directing the cells to differentiate into pancreatic beta cells Inhibitors of a p38 mitogen-activated protein (MAP) kinase such as SB203580 can be employed at a variety of concentrations, for example, at about 0.1 μM to about 500 μM, or about 0.5 μM to about 400 μM, or about 1 μM to about 200 μM, or from about 2 μM to about 100 μM, or from about 2.5 μM to about 50 μM, or from about 3 μM to about 25 μM, or from about 4 μM to about 10 μM, or about 5 μM.

Agonists of Glucagon-Like Peptide-1

Glucagon-like peptide-1 agonists are a group of medications that mimic the actions of glucagon-like peptide-1 (GLP-1). GLP-1 is one of several naturally occurring incretin compounds that affect the body after they are released from the gut during digestion. Because of its name, GLP-1 might seem to act like glucagon that increases glucose production by the liver and raises glucose levels. Instead, GLP-1 lowers both glucose and glucagon levels. Despite their different actions, GLP-1 and glucagon are both derived from the same parent compound called proglucagon, hence the similarity in names.

To increase the proportion of cells that convert to pancreatic beta cells (and express markers indicative of a pancreatic beta cell phenotype), a selected population of cells (e.g., pancreatic progenitor cells) is contacted or mixed with GLP-1 agonists for a time and at a concentration sufficient to differentiate at least some of the cells into pancreatic beta cells.

Examples of GLP-1 agonists that can be used in the methods and compositions described herein include, but are not limited to, Extendin-4, exenatide (Byetta/Bydureon), liraglutide (Victoza), lixisenatide (Lyxumia), albiglutide (Eperzan), dulaglutide, and combinations thereof.

The time of contacting or incubating GLP-1 agonists with pancreatic progenitor cells can vary, for example, from about 5 days to about 40 days, or from 8 days to about 35 days, or from 10 days to about 30 days, or from 12 days to about 25 days, or for about 8 to 12 days followed by a second incubation of about 8 days to about 12 days.

For example, GLP-1 agonists can be added to a selected cell population (pancreatic progenitor cells) while directing the cells to differentiate into pancreatic beta cells. GLP-1 agonists such as Extendin-4 can be employed at a variety of concentrations, for example, at about 5 ng/ml to about 200 ng/ml, or from about 10 ng/ml to about 175 ng/ml, or from about 15 ng/ml to about 150 ng/ml, or from about 20 ng/ml to about 150 ng/ml, or from about 25 ng/ml to about 125 ng/ml, or from about 30 ng/ml to about 100 ng/ml, or from about 35 ng/ml to about 80 ng/ml, or from about 40 ng/ml to about 60 ng/ml, or about 50 ng/ml.

Adenylyl Cyclase Activators

Adenylyl cyclase is an enzyme that employs pyrophosphate to catalyze the conversion of ATP to 3',5'-cyclic ATP, which is a second messenger involved in several biological processes. Although there are six distinct classes of adenylyl cyclase enzymes, all catalyze the same reaction.

To increase the proportion of cells that convert to pancreatic beta cells (and express markers indicative of a pancreatic beta cell phenotype), a selected population of cells (e.g., pancreatic progenitor cells) is contacted or mixed with one or more adenylyl cyclase activators for a time and at a concentration sufficient to differentiate at least some of the cells into pancreatic beta cells.

Examples of adenylyl cyclase activators that can be used in the methods and compositions described herein include, but are not limited to, Forskolin, NKH 477, PACAP 1-27, PACAP 1-38, and combinations thereof. Each of these adenylyl cyclase activators is available from Tocris (see, e.g., the website at tocris.com/pharmacologicalBrowser.php?ItemId=5136&Type=Activators#.U8kzv01OU5s).

The time of contacting or incubating adenylyl cyclase activators with pancreatic progenitor cells can vary, for example, from about 5 days to about 40 days, or from 8 days to about 35 days, or from 10 days to about 30 days, or from 12 days to about 25 days, or for about 8 to 12 days followed by a second incubation of about 8 days to about 12 days.

For example, adenylyl cyclase activators can be added to a selected cell population (pancreatic progenitor cells) while directing the cells to differentiate into pancreatic beta cells. Adenylyl cyclase activators such as Forskolin can be employed at a variety of concentrations, for example, at about 0.1 µM to about 500 µM, or from about 0.5 µM to about 400 µM, or from about 1 µM to about 200 µM, or from about 2 µM to about 100 µM, or from about 2.5 µM to about 50 µM, or from about 3 µM to about 25 µM, or from about 5 µM to about 15 µM, or about 10 µM.

Glucocorticoid Receptor Agonist

Glucocorticoid receptors bind cortisol and glucocorticoids and regulate transcription of genes involved in development, metabolism, and immune responses. Glucocorticoid receptors are expressed in almost every cell in the body.

To increase the proportion of cells that convert to pancreatic beta cells (and express markers indicative of a pancreatic beta cell phenotype), a selected population of cells (e.g., pancreatic progenitor cells) is contacted or mixed with glucocorticoid receptor agonists for a time and at a concentration sufficient to differentiate at least some of the cells into pancreatic beta cells.

Examples of glucocorticoid receptor agonists that can be used in the methods and compositions described herein include, but are not limited to, dexamethasone, corticosterone, fluticasone propionate, GSK 9027, methylprednisolone, mometasone furoate, and combinations thereof.

The time of contacting or incubating glucocorticoid receptor agonists with pancreatic progenitor cells can vary, for example, from about 5 days to about 40 days, or from 8 days to about 35 days, or from 10 days to about 30 days, or from 12 days to about 25 days, or for about 8 to 12 days followed by a second incubation of about 8 days to about 12 days.

For example, glucocorticoid receptor agonists can be added to a selected cell population (pancreatic progenitor cells) while directing the cells to differentiate into pancreatic beta cells. Glucocorticoid receptor agonists such as dexamethasone can be employed at a variety of concentrations, for example, at about 0.1 µM to about 500 µM, or from about 0.5 µM to about 400 µM, or from about 1 µM to about 200 µM, or from about 2 µM to about 100 µM, or from about 2.5 µM to about 50 µM, or from about 3 µM to about 25 µM, or from about 5 µM to about 15 µM, or about 10 µM.

$Ca^{2+}$ Channel Agonists $Ca^{2+}$ channel agonists can increase calcium influx into calcium channels of excitable tissues. To increase the proportion of cells that convert to pancreatic beta cells (and express markers indicative of a pancreatic beta cell phenotype), a selected population of cells (e.g., pancreatic progenitor cells) is contacted or mixed with $Ca^{2+}$ channel agonists for a time and at a concentration sufficient to differentiate at least some of the cells into pancreatic beta cells.

Examples of $Ca^{2+}$ channel agonists that can be used in the methods and compositions described herein include, but are not limited to, BayK-8644 (3-pyridinecarboxylic acid, 1,4-dihydro-2,6-dimethyl-5-nitro-4-(2-(trifluoromethyl)phenyl), methyl ester), CGP 28392 (2-methyl-3-methoxycarbonyl-4-(2'-difluoromethoxyphenyl)-5-oxo-1,4,5,7-tetrahydrofuro (3,4-b)pyridine), calcitriol, 1-ethyl-2-benzimidazolinone, FPL 64176 (methyl 2,5-dimethyl-4-(2-(phenylmethyl)benzoyl)-1H-pyrrole-3-carboxylate), PN 202-791 (4-isopropyl-(2,1,3-benzoxadiazol-4-yl)-1,4-dihydro-2,6-dimethyl-5-nitro-3-pyridinecarboxylate), SAN 202791, and combinations thereof.

The time of contacting or incubating $Ca^{2+}$ channel agonists with pancreatic progenitor cells can vary, for example, from about 5 days to about 40 days, or from 8 days to about 35 days, or from 10 days to about 30 days, or from 12 days to about 25 days, or for about 8 to 12 days followed by a second incubation of about 8 days to about 12 days.

For example, $Ca^{2+}$ channel agonists can be added to a selected cell population (pancreatic progenitor cells) while directing the cells to differentiate into pancreatic beta cells. $Ca^{2+}$ channel agonists such as BayK-8644 can be employed at a variety of concentrations, for example, at about 0.05 µM to about 200 µM, or from about 0.1 µM to about 100 µM, or from about 0.2 µM to about 50 µM, or from about 0.3 µM to about 25 µM, or from about 0.5 µM to about 10 µM, or from about 1 µM to about 5 µM, or from about 1.5 µM to about 4 µM, or about 2 µM.

Basement Membrane Proteins

Basement membrane proteins can increase calcium influx into calcium channels of excitable tissues. To increase the proportion of cells that convert to pancreatic beta cells (and express markers indicative of a pancreatic beta cell phenotype), a selected population of cells (e.g., pancreatic progenitor cells) is contacted or mixed with one or more basement membrane proteins for a time and at a concentration sufficient to differentiate at least some of the cells into pancreatic beta cells.

Examples of basement membrane proteins that can be used in the methods and compositions described herein include, but are not limited to, laminin, collagens, fibrillins, integrins, entactins, dystroglcans, and combinations thereof.

The time of contacting or incubating one or more basement membrane proteins with pancreatic progenitor cells can vary, for example, from about 1 days to about 30 days, or from about 2 days to about 25 days, or from about 3 days to about 20 days, or from about 5 days to about 15 days, or for about 7 to 12 days.

For example, basement membrane proteins can be added to a selected cell population (pancreatic progenitor cells) while directing the cells to differentiate into pancreatic beta cells. Glucocorticoid receptor agonists such as dexamethasone can be employed at a variety of concentrations, for example, at about 0.05 µM to about 200 µM, or from about 0.1 µM to about 100 µM, or from about 0.2 µM to about 50 µM, or from about 0.3 µM to about 25 µM, or from about 0.5 µM to about 10 µM, or from about 1 µM to about 5 µM, or from about 1.5 µM to about 4 µM, or about 2 µM.

BRIEF DESCRIPTION OF EXPERIMENTAL DATA

Experimental results described herein provide the first proof-of-principle demonstration that functional definitive endoderm cells, posterior foregut-like progenitor cells, and pancreatic progenitor cells can be generated from fibroblast cells without going through a pluripotent state. Compared with other approaches for generating such cells, the compositions and methods described herein can provide sufficient numbers of functional progenitor cells for transplantation and other applications.

Because pluripotent stem cells are not generated and the overall culture time to obtain pancreatic cells is shortened, these methods are faster and potentially safer than methods that utilize iPSCs. In addition to validating and extending the lineage-specific reprogramming paradigm to generate cells of definitive endoderm and pancreatic lineages, several novel procedures illuminate to how lineage specification can be achieved, facilitated and maintained.

First, the methods and compositions include lineage specification signals (e.g., via TGFβ family members and WNT activators) at the beginning of iPSC-factor-mediated epigenetic activation to significantly improve the efficiency of direct endodermal reprogramming. Such a process may transcriptionally program downstream lineage-specification signals to specifically re-direct iPSC-factor-mediated epigenome remodeling before pluripotency is established. Thus, in addition to the benefits of improved reprogramming efficiency, providing lineage-specification signals early also ensures that pluripotent cells are not generated.

Prolonging the first step to 7 or 8 days increases the total colony number while dramatically decreasing the percentage of Sox17 and Foxa2 double-positive colonies during expression of the pluripotency factors. The data provided herein indicate that temporary expression of reprogramming factors is sufficient and even beneficial for achieving successful conversion of cells to the endoderm lineage. Episomal expression of pluripotency factors allows such transient expression, without insertion and potential mutation of chromosomal DNA. Such transient expression of reprogramming factors may be achieved without integration of pluripotency expression cassettes into the genome of starting cells, to enhance the safety of this method (see, Kim, Kim et al. 2009; Zhou, Wu et al. 2009; Warren, Manos et al. 2010).

Secondly, the data described herein shows that while Pdx1 or Nkx6.1 single-positive cells could be readily generated from definitive endoderm cells, the cells so treated rarely co-express the other master pancreatic specification genes and consequently fail to mature into terminally differentiated, authentic pancreatic endocrine cells. To overcome this challenge, unique combinations of small molecules were identified to generate $Pdx1^+/Nkx6.1^+$ cells. For example, a combination of just four small molecules (retinoic acid, A83-01, LDE225 and pVc), in the absence of any growth factors used in other protocols (such as FGF10 and EGF), could not only effectively induce $Pdx1^+/Nkx6.1^+$ cells from definitive endoderm cells, but also increase the percentage of $Pdx1^+/Nkx6.1^+$ cells produced by about 11-fold. The definitive endodermal progenitor cells can rapidly be specified toward the posterior foregut state (cPF), illustrating efficient transdifferentiation of the fibroblasts towards the endodermal germ layer. Moreover, the posterior foregut-like progenitor cells can be greatly expanded without loss of their specific identity by culture in media that activates the WNT pathway and inhibits the TGFβ pathway while providing pro-proliferative growth factors EGF and bFGF. A somewhat unexpected finding was that not only could foregut-like progenitor cells be greatly expanded, but one could also expand pancreatic progenitor cells that were committed towards a pancreatic phenotype. The expansion of pancreatic progenitor cells by at least two hundred million fold involved the addition of a selective set of factors, including growth factors (e.g., bFGF and EGF) as well as a TGFβ receptor inhibitor (e.g., A83-1).

Thirdly, experiments described herein show that influencing the early steps of lineage induction can significantly impact later specification steps. To date, efforts to influence lineage induction to a particular stage of development or differentiation have mostly focused on the step immediately preceding the particular stage, while earlier steps were largely overlooked. For example, the search for small molecules that improve induction of $Pdx1^+$ pancreatic cells, $MHC^+$ cardiac cells, or $TH^+$ dopamine neurons had always focused on using definitive endoderm cells, cardiac precursor cells, or neural precursor cells, respectively, for screening. While this traditional approach is straightforward, the successful procedures described herein demonstrate that enhanced attention at other differentiation stages can have significant benefits. To further improve conversion to pancreatic cells, new small molecules were tested and evaluated during the first two steps of reprogramming toward definitive endoderm cells using expression of Pdx1 and Nkx6.1 as indicators of differentiation into pancreatic progenitor cells. For example, when used in early cell-induction steps two small molecules, Bix-01294 and pVc, were found to substantially increase the number or percentage of $Pdx1^+/Nkx6.1^+$ cells ultimately obtained. It should also be noted that treatment with Bix-01294 and pVc during the first two steps of reprogramming did not affect the numbers of Sox17/Foxa2 positive cells obtained at about day 12 of the process. These results demonstrate new strategies for improving the outcome of later differentiation stages in a step-wise cellular reprogramming and induction process by modifying earlier steps, an approach that until now has been largely overlooked.

Novel combinations of small molecules that promote pancreatic beta-cell maturation were also identified. For example, SB203580 and pVc strongly and synergistically increased the number of $insulin^+/Pdx1^+$ cells. Notch inhibitor Compound-E, Vitamin C, and the $Ca^{2+}$ channel agonist BayK-8644 also improved the differentiation efficiency into pancreatic beta-like cells independently as well as in combination. Not only did these screenings reveal conditions that enable the reprogramming of fibroblasts into endodermal and pancreatic progenitor cells that can mature into glucose-responsive insulin-secreting beta cells in vitro and in vivo, those newly identified small molecules for each step also provide new chemical tools for further mechanistic studies.

The potential of the pancreatic progenitor cells generated as described herein was demonstrated in vivo. The in vitro differentiated beta-like cells exhibited a mature, functional beta cell phenotype as judged by their ability to secrete insulin in response to physiological levels of glucose as well as their co-expression of critical beta cell transcription factors. Compared with cells generated by previous conditions, the pancreatic progenitor cells generated by the advanced approach described herein can much more efficiently generate all three pancreatic lineages, including functional insulin secreting beta like cells, and ameliorate hyperglycemia in vivo. These results demonstrate the therapeutic benefits of the methods and compositions described herein.

Compositions

The invention also relates to compositions useful for generating definitive endoderm cells, posterior foregut-like progenitor cells, pancreatic precursor cells, and/or mature pancreatic beta cells. The compositions can be formulated as cell culture media with one or more of the compounds and agents described herein at concentrations sufficient to generate definitive endoderm cells, posterior foregut-like progenitor cells, pancreatic precursor cells, and/or pancreatic beta cells. Alternatively, the compounds and agents described herein can be present in concentrated or dry form within the compositions, so that the composition can conveniently be added to a cell culture medium to generate a cell culture medium with an appropriate concentration of the selected compounds and/or agents for generating definitive endoderm cells, posterior foregut-like progenitor cells, pancreatic precursor cells, and/or pancreatic beta cells.

Therefore, the invention relates to a first composition containing a TGFβ family member and a WNT activator. The first composition can contain the TGFβ family member and the WNT activator in an effective amount that is sufficient to generate a first cell population comprising definitive endoderm cells. The first composition can contain other factors. For example, the first composition can contain one or more growth factors (e.g., epidermal growth factor (EGF), basic fibroblast growth factor (bFGF), or a combination thereof). The first composition can also contain a G9a histone methyltransferase inhibitor, 2-phospho-L-ascorbic acid, a histone deacetylase inhibitor, a histone demethylase inhibitor, a DNA methyltransferase inhibitor, an adenosine agonist, or a combination thereof. The first composition can include one or more of the agents or compounds listed above. Alternatively, the first compositions can contain two or more, or three or more, or four or more, or five or more, or six or more, or seven or more of these agents. In some embodiments, the first composition has less than ten of the agents listed above, or less than nine of the agents listed above.

For example, Activin A (a TGFβ family member) can be present in the compositions (useful e.g., for generating definitive endoderm cells) at a variety of concentrations, for example, at about 5 ng/ml to about 200 ng/ml, or from about 10 ng/ml to about 175 ng/ml, or from about 15 ng/ml to about 150 ng/ml, or from about 20 ng/ml to about 150 ng/ml, or from about 25 ng/ml to about 125 ng/ml, or from about 30 ng/ml to about 100 ng/ml, or from about 35 ng/ml to about 80 ng/ml, or from about 40 ng/ml to about 60 ng/ml, or about 50 ng/ml. Alternatively, the Activin A can be present in concentrated form, for example, for addition to a cell culture medium so that the cell culture medium contains Activin A at a desired concentration. For example, a concentrated composition can contain Activin A at a concentration that is about 10×, 50×, 100×, or 1000× of the concentration at which it would be employed, for example, to generate definitive endoderm cells.

Lithium chloride and/or CHIR99021 (WNT activators) can be present in the compositions (useful e.g., for generating definitive endoderm cells) at a variety of concentrations. For example, a WNT activator can be included at about 0.01 mM to about 10 mM, or from about 0.05 mM to about 9 mM, or from about 0.1 mM to about 8 mM, or from about 0.2 mM to about 7 mM, or from about 0.3 mM to about 6 mM, or from about 0.4 mM to about 5 mM, or from about 0.5 mM to about 3 mM, or about 1 mM. CHIR99021 can be present at 0.01 µM to about 10 µM, or from about 0.1 µM to about 8 µM, or from about 1 µM to about 5 µM, or from about 2 µM to about 4 µM. Alternatively, the WNT activators can be present in concentrated form, for example, for addition to a cell culture medium so that the cell culture medium contains lithium chloride at a desired concentration. For example, a concentrated composition can contain lithium chloride and/or CHIR99021 at a concentration that is about 10×, 50×, 100×, or 1000× of the concentration at which it would be employed, for example, to generate definitive endoderm cells.

Phospho-L-ascorbic acid or Vitamin C can be employed in the first composition (useful e.g., for generating definitive endoderm cells) at a variety of concentrations, for example, at about 1 µM to about 1000 µM, or from about 20 µM to about 700 µM, or from about 50 µM to about 500 µM, or from about 100 µM to about 400 µM, or from about 150 µM to about 350 µM, or from about 200 µM to about 325 µM, or from about 250 µM to about 310 µM, or about 280 µM. Alternatively, phospho-L-ascorbic acid or Vitamin C can be present in concentrated form, for example, for addition to a cell culture medium so that the cell culture medium contains phospho-L-ascorbic acid at a desired concentration. For example, a concentrated composition can contain phospho-L-ascorbic acid a concentration that is about 10×, 50×, 100×, or 1000× of the concentration at which it would be employed, for example, to generate definitive endoderm cells.

One or more G9a histone methyl-transferase inhibitors can be employed in the first composition (useful e.g., for generating definitive endoderm cells) at a variety of concentrations, for example, at about 0.01 µM to about 10 µM, or from about 0.05 µM to about 9 µM, or from about 0.1 µM to about 8 µM, or from about 0.2 µM to about 7 µM, or from about 0.3 µM to about 6 µM, or from about 0.4 µM to about 5 µM, or from about 0.5 µM to about 3 µM, or about 1 µM. Alternatively, the G9a histone methyl-transferase inhibitor can be present in concentrated form, for example, for addition to a cell culture medium so that the cell culture medium contains the G9a histone methyl-transferase inhibitor at a desired concentration. For example, a concentrated composition can contain the G9a histone methyl-transferase inhibitor at a concentration that is about 10×, 50×, 100×, or 1000× of the concentration at which it would be employed, for example, to generate definitive endoderm cells.

One or more histone deacetylase inhibitors can be employed in the first composition (useful e.g., for generating definitive endoderm cells) at a variety of concentrations, for example, at about 1 micromolar to about 20 millimolar, or about 10 micromolar to about 15 millimolar, or about 25 micromolar to about 5 millimolar, or about 40 micromolar to about 1 millimolar, or about 60 micromolar to about 0.5 millimolar, or about 0.1 millimolar in a solution. For example, a concentrated composition can contain one or more HDAC inhibitors at concentrations that are about 10×, 50×, 100×, or 1000× of the concentration at which it would be employed, for example, to generate definitive endoderm cells.

One or more histone demethylase inhibitors can be employed in the first composition (useful e.g., for generating definitive endoderm cells) at a variety of concentrations, for example, about 0.01 micromolar to about 20 micromolar, or about 0.05 micromolar to about 10 micromolar, or about 0.1 micromolar to about 5 micromolar, or about 0.5 micromolar to about 3 micromolar, or about 1 micromolar to about 3 micromolar, or about 1 micromolar in a solution. For example, a concentrated composition can contain one or more histone demethylase inhibitors at concentrations that are about 10×, 50×, 100×, or 1000× of the concentration at which it would be employed, for example, to generate definitive endoderm cells.

One or more DNA methyltransferase inhibitors can be employed in the first composition (useful e.g., for generating definitive endoderm cells) at a variety of concentrations, for example, at about 0.01 micromolar to about 20 micromolar, or about 0.03 micromolar to about 10 micromolar, or about 0.05 micromolar to about 5 micromolar, or about 0.1 micromolar to about 2 micromolar, or about 0.2 micromolar to about 1 micromolar, or about 0.5 micromolar in a solution. For example, a concentrated composition can contain one or more DNA methyltransferase inhibitors at concentrations that are about 10×, 50×, 100×, or 1000× of the concentration at which it would be employed, for example, to generate definitive endoderm cells.

One or more adenosine agonists can be employed in the first composition (useful e.g., for generating definitive endoderm cells) at a variety of concentrations, for example, at about 0.01 micromolar to about 20 micromolar, or about 0.03 micromolar to about 10 micromolar, or about 0.05 micromolar to about 5 micromolar, or about 0.1 micromolar to about 2 micromolar, or about 0.2 micromolar to about 1 micromolar, or about 0.5 micromolar in a solution. For example, a concentrated composition can contain one or more adenosine agonists at concentrations that are about 10×, 50×, 100×, or 1000× of the concentration at which it would be employed, for example, to generate definitive endoderm cells.

The invention also relates to second compositions containing one or more TGFβ receptor inhibitors, hedgehog pathway inhibitors, retinoic acid receptor agonists, or combinations thereof. The second composition can contain other factors. For example, the second composition can also contain one or more growth factors, WNT activators, vitamins (e.g., vitamin C), Notch signaling inhibitors, BMP4 signaling inhibitors, or combinations thereof. Any of such factors can be included in the second composition in amounts sufficient to generate pancreatic progenitor cells from definitive endoderm cells.

One or more TGFβ receptor inhibitors can be employed in the second composition (useful e.g., for generating pancreatic progenitor cells) at a variety of concentrations, for example, at about 0.01 µM to about 10 µM, or from about 0.05 µM to about 9 µM, or from about 0.1 µM to about 8 µM, or from about 0.2 µM to about 7 µM, or from about 0.3 µM to about 6 µM, or from about 0.4 µM to about 5 µM, or from about 0.5 µM to about 3 µM, or about 1 µM. For example, a concentrated composition can contain one or more TGFβ receptor inhibitors at concentrations that are about 10×, 50×, 100×, or 1000× of the concentration at which it would be employed, for example, to generate pancreatic progenitor cells.

One or more hedgehog pathway inhibitors can be employed in the second composition (useful e.g., for generating pancreatic progenitor cells) at a variety of concentrations, for example, at about 0.01 µM to about 10 µM, or from about 0.05 µM to about 9 µM, or from about 0.1 µM to about 8 µM, or from about 0.3 µM to about 7 µM, or from about 0.5 µM to about 6 µM, or from about 0.75 µM to about 5 µM, or from about 1 µM to about 3 µM, or about 2 µM. For example, a concentrated composition can contain one or more hedgehog pathway inhibitors at concentrations that are about 10×, 50×, 100×, or 1000× of the concentration at which it would be employed, for example, to generate pancreatic progenitor cells.

One or more retinoic acid receptor agonists can be employed in the second composition (useful e.g., for generating pancreatic progenitor cells) at a variety of concentrations, for example, at about 0.01 µM to about 10 µM, or from about 0.05 µM to about 9 µM, or from about 0.1 µM to about 8 µM, or from about 0.3 µM to about 7 µM, or from about 0.5 µM to about 6 µM, or from about 0.75 µM to about 5 µM, or from about 1 µM to about 3 µM, or about 2 µM. For example, a concentrated composition can contain one or more retinoic acid receptor agonists at concentrations that are about 10×, 50×, 100×, or 1000× of the concentration at which it would be employed, for example, to generate pancreatic progenitor cells.

One or more growth factors can be employed in the second composition (useful e.g., for generating pancreatic progenitor cells) at a variety of concentrations, for example, at least about 1 ng/ml, or at least about 2 ng/ml, or at least about 3 ng/ml, or at least about 5 ng/ml, or about 10 ng/ml. For example, a concentrated composition can contain one or more growth factors at concentrations that are about 10×, 50×, 100×, or 1000× of the concentration at which it would be employed, for example, to generate pancreatic progenitor cells.

One or more WNT activators can be employed in the second composition (useful e.g., for generating pancreatic progenitor cells) at a variety of concentrations, for example, at about 0.01 micromolar to about 1 millimolar in a solution, or about 0.1 micromolar to about 100 micromolar in a solution, or about 0.5 micromolar to about 10 micromolar in a solution, or about 1 micromolar to about 5 micromolar in a solution. For example, a concentrated composition can contain one or more WNT activators at concentrations that are about 10×, 50×, 100×, or 1000× of the concentration at which it would be employed, for example, to generate pancreatic progenitor cells.

One or more vitamins (e.g., vitamin C or phospho-L-ascorbic acid) can be employed in the second composition (useful e.g., for generating pancreatic progenitor cells) at a variety of concentrations, for example, at about 1 µM to about 1000 µM, or from about 20 µM to about 700 µM, or from about 50 µM to about 500 µM, or from about 100 µM to about 400 µM, or from about 150 µM to about 350 µM, or from about 200 µM to about 325 µM, or from about 250 µM to about 310 µM, or about 280 µM. For example, a concentrated composition can contain one or more vitamins at concentrations that are about 10×, 50×, 100×, or 1000× of the concentration at which it would be employed, for example, to generate pancreatic progenitor cells.

One or more Notch signaling inhibitors can be employed in the second composition (useful e.g., for generating pancreatic progenitor cells) at a variety of concentrations, for example, at about 0.001 micromolar to about 200 micromolar, or about 0.01 micromolar to about 100 micromolar, or about 0.05 micromolar to about 10 micromolar, or about 0.1 micromolar in a solution. For example, a concentrated composition can contain one or more Notch signaling inhibitors at concentrations that are about 10×, 50×, 100×, or 1000× of the concentration at which it would be employed, for example, to generate pancreatic progenitor cells.

One or more BMP4 signaling inhibitors can be employed in the second composition (useful e.g., for generating pancreatic progenitor cells) at a variety of concentrations, for example, at about 0.001 micromolar to about 200 micromolar, or about 0.01 micromolar to about 100 micromolar, or about 0.05 micromolar to about 10 micromolar, or about 0.1 micromolar in a solution. BMP4 signaling inhibitors at concentrations that are about 10×, 50×, 100×, or 1000× of the concentration at which it would be employed, for example, to generate pancreatic progenitor cells.

The invention also relates to third compositions containing one or more TGFβ receptor inhibitors, Notch inhibitors, polyADP ribose synthetase inhibitors, or a combination thereof useful for generating pancreatic beta cells from pancreatic progenitor cells. The third composition can contain other factors. For example, the third composition can also contain one or more glucagon-like peptide-1 agonists, vitamins, p38 mitogen-activated protein (MAP) kinase inhibitors, basement membrane proteins, adenylyl cyclase activators, glucocorticoid receptor agonists, $Ca^{2+}$ channel agonists, or combinations thereof.

One or more TGFβ receptor inhibitors can be employed in the third composition (useful e.g., for generating pancreatic beta cells) at a variety of concentrations, for example, at about 0.01 µM to about 10 µM, or from about 0.05 µM to about 9 µM, or from about 0.1 µM to about 8 µM, or from about 0.2 µM to about 5 µM, or from about 0.3 µM to about 3 µM, or from about 0.3 µM to about 2 µM, or from about 0.4 µM to about 1 µM, or about 0.5 µM. For example, a concentrated composition can contain one or more TGFβ receptor inhibitors at concentrations that are about 10×, 50×, 100×, or 1000× of the concentration at which it would be employed, for example, to generate pancreatic beta cells.

One or more Notch inhibitors can be employed in the third composition (useful e.g., for generating pancreatic beta cells) at a variety of concentrations, for example, at about 0.001 micromolar to about 200 micromolar, or about 0.01 micromolar to about 100 micromolar, or about 0.05 micromolar to about 10 micromolar, or about 0.1 micromolar in a solution. For example, a concentrated composition can contain one or more Notch inhibitors at concentrations that are about 10×, 50×, 100×, or 1000× of the concentration at which it would be employed, for example, to generate pancreatic beta cells.

One or more polyADP ribose synthetase inhibitors can be employed in the third composition (useful e.g., for generating pancreatic beta cells) at a variety of concentrations, for example, at about 0.1 millimolar to about 100 millimolar, or about 1 millimolar to about 50 millimolar, or about 3 millimolar to about 30 millimolar, or about 5 micromolar to about 15 millimolar, or about 10 millimolar in a solution. For example, a concentrated composition can contain one or more polyADP ribose synthetase inhibitors at concentrations that are about 10×, 50×, 100×, or 1000× of the concentration at which it would be employed, for example, to generate pancreatic beta cells.

One or more glucagon-like peptide-1 agonists can be employed in the third composition (useful e.g., for generating pancreatic beta cells) at a variety of concentrations, for example, at about 5 ng/ml to about 200 ng/ml, or from about 10 ng/ml to about 175 ng/ml, or from about 15 ng/ml to about 150 ng/ml, or from about 20 ng/ml to about 150 ng/ml, or from about 25 ng/ml to about 125 ng/ml, or from about 30 ng/ml to about 100 ng/ml, or from about 35 ng/ml to about 80 ng/ml, or from about 40 ng/ml to about 60 ng/ml, or about 50 ng/ml. For example, a concentrated composition can contain one or more glucagon-like peptide-1 agonists at concentrations that are about 10×, 50×, 100×, or 1000× of the concentration at which it would be employed, for example, to generate pancreatic beta cells.

One or more vitamins (e.g., vitamin C and/or phospho L-ascorbic acid) can be employed in the third composition (useful e.g., for generating pancreatic beta cells) at a variety of concentrations, for example, at about 1 µM to about 100 µM, or from about 10 µM to about 80 µM, or from about 25 µM to about 75 µM, or from about 30 µM to about 70 µM, or from about 35 µM to about 65 µM, or from about 40 µM to about 60 µM, or from about 45 µM to about 55 µM, or about 50 µM. For example, a concentrated composition can contain one or more vitamins (e.g., vitamin C and/or phospho L-ascorbic acid) at concentrations that are about 10×, 50×, 100×, or 1000× of the concentration at which it would be employed, for example, to generate pancreatic beta cells.

One or more p38 mitogen-activated protein (MAP) kinase inhibitors can be employed in the third composition (useful e.g., for generating pancreatic beta cells) at a variety of concentrations, for example, at about 0.1 µM to about 500 µM, or from about 0.5 µM to about 400 µM, or from about 1 µM to about 200 µM, or from about 2 µM to about 100 µM, or from about 2.5 µM to about 50 µM, or from about 3 µM to about 25 µM, or from about 4 µM to about 10 µM, or about 5 µM. For example, a concentrated composition can contain one or more p38 mitogen-activated protein (MAP) kinase inhibitors at concentrations that are about 10×, 50×, 100×, or 1000× of the concentration at which it would be employed, for example, to generate pancreatic beta cells.

One or more basement membrane proteins can be employed in the third composition (useful e.g., for generating pancreatic beta cells) at a variety of concentrations, for example, at about 0.05 µM to about 200 µM, or from about 0.1 µM to about 100 µM, or from about 0.2 µM to about 50 µM, or from about 0.3 µM to about 25 µM, or from about 0.5 µM to about 10 µM, or from about 1 µM to about 5 µM, or from about 1.5 µM to about 4 µM, or about 2 µM. For example, a concentrated composition can contain one or more basement membrane proteins at concentrations that are about 10×, 50×, 100×, or 1000× of the concentration at which it would be employed, for example, to generate pancreatic beta cells.

One or more adenylyl cyclase activators can be employed in the third composition (useful e.g., for generating pancreatic beta cells) at a variety of concentrations, for example, at about at about 0.1 µM to about 500 µM, or from about 0.5 µM to about 400 µM, or from about 1 µM to about 200 µM, or from about 2 µM to about 100 µM, or from about 2.5 µM to about 50 µM, or from about 3 µM to about 25 µM, or from about 5 µM to about 15 µM, or about 10 µM. For example, a concentrated composition can contain one or more adenylyl cyclase activators at concentrations that are about 10×, 50×, 100×, or 1000× of the concentration at which it would be employed, for example, to generate pancreatic beta cells.

One or more glucocorticoid receptor agonists can be employed in the third composition (useful e.g., for generating pancreatic beta cells) at a variety of concentrations, for example, at about 0.1 µM to about 500 µM, or from about 0.5 µM to about 400 µM, or from about 1 µM to about 200 µM, or from about 2 µM to about 100 µM, or from about 2.5 µM to about 50 µM, or from about 3 µM to about 25 µM, or from about 5 µM to about 15 µM, or about 10 µM. For example, a concentrated composition can contain one or more glucocorticoid receptor agonists at concentrations that are about 10×, 50×, 100×, or 1000× of the concentration at which it would be employed, for example, to generate pancreatic beta cells.

One or more $Ca^{2+}$ channel agonists can be employed in the third composition (useful e.g., for generating pancreatic beta cells) at a variety of concentrations, for example, at about 0.05 µM to about 200 µM, or from about 0.1 µM to about 100 µM, or from about 0.2 µM to about 50 µM, or from about 0.3 µM to about 25 µM, or from about 0.5 µM to about 10 µM, or from about 1 µM to about 5 µM, or from about 1.5 µM to about 4 µM, or about 2 µM. For example, a concentrated composition can contain one or more $Ca^{2+}$ channel agonists at concentrations that are about 10×, 50×, 100×, or 1000× of the concentration at which it would be employed, for example, to generate pancreatic beta cells.

The compositions can be a cell culture medium, or include components of a culture medium.

Kits

Also provided are kits for generating definitive endoderm cells and/or pancreatic precursor cells and/or pancreatic cells. The kits can contain any of the compositions described herein and instructions for using the compositions for generating definitive endoderm cells and/or pancreatic precursor cells and/or pancreatic cells. Each of the compositions can be separately packaged. Each composition can contain any of the compounds or proteins described herein at a concentration that is convenient for addition to a culture of cells. For example, compositions can be concentrated to about 10×, 50×, 100×, or 1000× of the concentration at which it would be employed to generate definitive endoderm cells and/or pancreatic precursor cells and/or posterior foregut-like progenitor cells and/or pancreatic beta cells. The instructions can provide guidance for appropriate addition (dilution) of the compositions into a cell culture, and/or guidance on other culture conditions (e.g., appropriate cell culture media, an appropriate duration of exposure to the compositions, etc.). The instructions can also provide guidance on the selection of cells for generating definitive endoderm cells and/or pancreatic precursor cells and/or posterior foregut-like progenitor cells and/or pancreatic cells. In addition, the instructions can provide information for testing and/or recognition of the generated definitive endoderm cells and/or pancreatic precursor cells and/or posterior foregut-like progenitor cells and/or pancreatic cells.

The kits can also provide components and instructions for administering definitive endoderm cells and/or pancreatic precursor cells and/or posterior foregut-like progenitor cells and/or pancreatic beta cells to mammalian subjects. The instructions can provide guidance on the numbers and the type(s) (phenotype) of cells to be administered. The instructions can also provide instructions for administration of definitive endoderm cells and/or pancreatic precursor cells and/or posterior foregut-like progenitor cells and/or pancreatic beta cells by surgical implantation or by infusion. For example, the kits can provide diluents, pharmaceutically acceptable carriers, scalpels, syringes, catheters, bandages, antiseptics, and the like to permit administration of cells.

Mixtures

The definitive endoderm cells and/or posterior foregut-like progenitor cells and/or pancreatic precursor cells and/or pancreatic cells can be present in any of the foregoing compositions. The definitive endoderm cells and/or posterior foregut-like progenitor cells and/or pancreatic precursor cells and/or pancreatic cells can also be present in a therapeutically acceptable carrier such as saline, phosphate buffered saline, or other aqueous carrier. Such a combination of the compositions described herein, or a therapeutically acceptable carrier, with definitive endoderm cells and/or posterior foregut-like progenitor cells and/or pancreatic precursor cells and/or pancreatic cells is called a mixture.

The mixtures can contain about 1 to about $10^{10}$ definitive endoderm cells and/or posterior foregut-like progenitor cells and/or pancreatic precursor cells and/or pancreatic (e.g., beta) cells.

The definitive endoderm cells and/or posterior foregut-like progenitor cells and/or pancreatic precursor cells and/or pancreatic cells generated as described herein can be isolated, separated, or purified from the composition, mixture or media in which they are generated. The definitive endoderm cells and/or posterior foregut-like progenitor cells and/or pancreatic precursor cells and/or pancreatic cells generated as described herein can be enriched or cultured to increase the proportion or numbers of desired cells in the population. Any such isolate, separation, purification, enrichment or culture is a mixture of the invention.

An isolating step can include providing the cells in the cell culture with a reagent which binds to a marker expressed in the desired cell type (e.g., definitive endoderm cells, pancreatic precursor cells and/or pancreatic cells) but which is not substantially expressed in other cells present in the cell culture. The reagent-bound cells can be separated from the non-reagent-bound cells by numerous methods. For example, an antibody against a marker that is selectively present on the desired cells can be provided to cells in a cell culture. Antibody-bound cells can then be separated from other cells in the culture by, for example, fluorescent activated cell sorting (FACS), binding the antibody to a solid support or isolating appropriately tagged antibody in a magnetic field. In some embodiments, the antibody is released from the cells after the separation process.

As an alternative means of separation, at least some of the desired cells can be separated from at least some of the other cells in the culture by specifically fluorescently labeling the desired cells in culture and then separating the labeled cells from the unlabeled cells by FACS.

An enriched cell population of definitive endoderm cells, posterior foregut-like progenitor cells, pancreatic progenitor cells, and/or pancreatic beta cells produced, for example, by an isolating step can be substantially free of cells other than definitive endoderm cells, posterior foregut-like progenitor cells, pancreatic progenitor cells, and/or pancreatic beta cells. In other embodiments, the enriched cell populations can have at least about 50% to at least about 100% definitive endoderm cells, posterior foregut-like progenitor cells, pancreatic progenitor cells, and/or pancreatic beta cells. In still other embodiments, the enriched cell populations comprise from at least about 75%, at least about 80%, at least about 85%, at least about 90%, at least about 95%, at least about 96%, at least about 97%, at least about 99%, or at least about 100% definitive endoderm cells, posterior foregut-like progenitor cells, pancreatic progenitor cells, and/or pancreatic beta cells.

In some instances, the definitive endoderm cells, posterior foregut-like progenitor cells, pancreatic progenitor cells, and/or pancreatic beta cells are expanded, for example, by culturing the cells under conditions that permit cell division. For example, some embodiments include a culturing step that comprises plating a cell population on a surface such as a culture plate. In some embodiments, the cells are plated on a surface coated with a protein, poly-amino acid or carbohydrate (e.g., collagen, fibronectin, polylysine, poly-ornithine).

In other embodiments, the culturing step comprises incubating the cell population or portion thereof in an expansion medium comprising about 2% (v/v) serum. In some embodiments, the serum concentration can range from about 0% (v/v) to about 20% (v/v). For example, in some methods described herein, the serum concentration of the medium can be about 0.05% (v/v), about 0.1% (v/v), about 0.2% (v/v), about 0.3% (v/v), about 0.4% (v/v), about 0.5% (v/v), about 0.6% (v/v), about 0.7% (v/v), about 0.8% (v/v), about 0.9% (v/v), about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v) or about 20% (v/v). In some embodiments, serum replacement is included in the medium, and no serum is employed.

Using the methods described herein, cell populations or cell cultures can be enriched in definitive endoderm, posterior foregut-like progenitor, pancreatic progenitor, and/or pancreatic beta cell content by at least about 2-fold to about 1000-fold as compared to cell populations or cell cultures produced by the methods and compositions described herein. In some embodiments, definitive endoderm, posterior foregut-like progenitor, pancreatic progenitor, and/or pancreatic beta cells can be enriched by at least about 5-fold to about 500-fold as compared to cell populations or cell cultures produced by the methods and compositions described herein. In other embodiments, definitive endoderm, posterior foregut-like progenitor, pancreatic progenitor, and/or pancreatic beta cells can be enriched from at least about 10- to about 200-fold as compared to cell populations or cell cultures produced by the methods and compositions described herein. In still other embodiments, definitive endoderm, posterior foregut-like progenitor, pancreatic progenitor, and/or pancreatic beta cells can be enriched from at least about 20- to about 100-fold as compared to cell populations or cell cultures produced by the methods and compositions described herein. In yet other embodiments, definitive endoderm, posterior foregut-like progenitor, pancreatic progenitor, and/or pancreatic beta cells can be enriched from at least about 40- to about 80-fold as compared to cell populations or cell cultures produced by the methods and compositions described herein. In certain embodiments, definitive endoderm, posterior foregut-like progenitor, pancreatic progenitor, and/or pancreatic beta cells can be enriched from at least about 2- to about 20-fold as compared to cell populations or cell cultures produced by the methods and compositions described herein.

Some embodiments described herein relate to cell cultures or cell populations comprising from at least about 5% definitive endoderm, posterior foregut-like progenitor, pancreatic progenitor, and/or pancreatic beta cells to at least about 95% definitive endoderm, pancreatic progenitor, and/or pancreatic beta cells. In some embodiments the cell cultures or cell populations comprise mammalian cells. In preferred embodiments, the cell cultures or cell populations comprise human cells. For example, certain specific embodiments relate to cell cultures comprising human cells, wherein from at least about 5% to at least about 95% of the human cells are definitive endoderm, posterior foregut-like progenitor, pancreatic progenitor, and/or pancreatic beta cells. Other embodiments relate to cell cultures comprising human cells, wherein at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the human cells are definitive endoderm, posterior foregut-like progenitor, pancreatic progenitor, and/or pancreatic beta cells. In embodiments where the cell cultures or cell populations comprise human feeder cells, the above percentages are calculated without respect to the human feeder cells in the cell cultures or cell populations.

Therapy

Also described herein is a method for treating a patient suffering from, or at risk of developing, diabetes. The diabetes can, for example, be type 1, type 2, or type 1.5 diabetes. This method involves obtaining definitive endoderm, pancreatic progenitor, and/or pancreatic beta cells as described herein, and administering or implanting the cells into a mammalian subject.

The definitive endoderm, pancreatic progenitor, and/or pancreatic beta cells can be implanted as dispersed cells or formed into clusters. Alternatively, the definitive endoderm, pancreatic progenitor, and/or pancreatic beta cells can be infused into the subject, for example, via a hepatic portal vein. Alternatively, cells may be provided in biocompatible degradable polymeric supports, porous non-degradable devices or encapsulated to protect from host immune response. Cells may be implanted into an appropriate site in a subject. The implantation sites include, for example, the liver, natural pancreas, renal subcapsular space, omentum, peritoneum, subserosal space, intestine, stomach, or a subcutaneous pocket.

The amount of cells used in implantation depends on a number of various factors including the subject's condition and response to the therapy, and can be determined by one skilled in the art. For example, the number of cells administered can range from about 1000 to about $10^{10}$.

In one aspect, this invention provides a method for treating a patient suffering from, or at risk of developing diabetes. This method involves culturing a selected cell population, differentiating or redirecting the cultured cells in vitro into a definitive endoderm lineage to generate a first cell population containing definitive endoderm cells, differentiating the first cell population into a second population containing pancreatic progenitor cells and administering the second population of cells to a subject. In some instances pancreatic progenitor cells are enriched within the second population or purified from the second population of cells to generate a third population of cells that is substantially free of non-pancreatic cells.

The cells to be administered can be incorporated into a three-dimensional support. The cells can be maintained in vitro on this support prior to implantation into the subject. Alternatively, the support containing the cells can be directly implanted in the subject without additional in vitro culturing. The support can optionally be incorporated with at least one pharmaceutical agent that facilitates the survival and function of the transplanted cells.

Support materials suitable for use include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods described herein. See, for example, the materials disclosed in U.S. Pat. No. 5,770,417, U.S. Pat. No. 6,022,743, U.S. Pat. No. 5,567,612, U.S. Pat. No. 5,759,830, U.S. Pat. No. 6,626,950, U.S. Pat. No. 6,534,084, U.S. Pat. No. 6,306,424, U.S. Pat. No. 6,365,149, U.S. Pat. No. 6,599,323, U.S. Pat. No. 6,656,488, U.S. Published Application 2004/0062753 A1, U.S. Pat. No. 4,557,264 and U.S. Pat. No. 6,333,029, each of which is specifically incorporated by reference herein in its entirety.

The mammalian subject can be a human patient, a domestic animal, or a laboratory animal.

Definitions

As used herein and in the appended claims, the singular forms "a," "an," and "the" include plural reference unless the context clearly dictates otherwise. Thus, for example, a reference to "a compound," "a cell," "a nucleic acid" or "a polypeptide" includes a plurality of such compounds, cells, nucleic acids or polypeptides (for example, a solution of cells, nucleic acids or polypeptides, a suspension of cells, or a series of compound, cell, nucleic acid or polypeptide preparations), and so forth.

The terms "diabetes" and "diabetes mellitus" are used interchangeably herein. The World Health Organization indicates that diabetes involves a fasting plasma glucose concentration of 7.0 mmol/1 (126 mg/dl) and above for Diabetes Mellitus (whole blood 6.1 mmol/1 or 110 mg/dl), or 2-hour glucose level 11.1 mmol/L or higher (200 mg/dL or higher). Other values suggestive of or indicating high risk for Diabetes Mellitus include elevated arterial pressure 140/90 mm Hg or higher; elevated plasma triglycerides (1.7 mmol/L; 150 mg/dL) and/or low HDL-cholesterol (less than 0.9 mmol/L, 35 mg/dl for men; less than 1.0 mmol/L, 39 mg/dL women); central obesity (males: waist to hip ratio higher than 0.90; females: waist to hip ratio higher than 0.85) and/or body mass index exceeding 30 kg/m2; microalbuminuria, where the urinary albumin excretion rate 20 µg/min or higher, or albumin to creatinine ratio 30 mg/g or higher). The term diabetes encompasses all forms of diabetes, including Type I, Type II and Type 1.5.

As used herein, the term "treating" and "treatment" refers to administering to a subject an effective amount of a composition so that the recipient has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. The term "treatment" includes prophylaxis. Treatment is "effective" if the progression of a disease is reduced or halted. "Treatment" can also mean prolonging survival as compared to expected survival if not receiving treatment. Those in need of treatment include those already diagnosed with a condition (e.g., diabetes), as well as those likely to develop a condition due to genetic susceptibility or other factors such as weight, diet, and health.

The term "episomal" refers to the extra-chromosomal state of an expression cassette, plasmid or vector in a cell. Episomal expression cassettes, plasmids or vectors are nucleic acid molecules that are not part of the chromosomal DNA and replicate independently thereof.

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Oct polypeptides include, Oct-1, Oct-2, Oct-3/4, Oct-6, Oct-7, Oct-8, Oct-9, and Oct-11. e.g., Oct3/4 (referred to herein as "Oct4") contains the POU domain, a 150 amino acid sequence conserved among Pit-1, Oct-1, Oct-2, and uric-86. See, Ryan, A. K. & Rosenfeld, M. G. *Genes Dev.* 11, 1207-1225 (1997). In some embodiments, variants have at least 85%, 90%, or 95% amino acid sequence identity across their whole sequence compared to a naturally occurring Oct polypeptide family member such as to those listed above or such as listed in Genbank accession number NP-002692.2 (human Oct4) or NP-038661.1 (mouse Oct4). Oct polypeptides (e.g., Oct3/4) can be from human, mouse, rat, bovine, porcine, or other animals. Generally, the same species of protein will be used with the species of cells being manipulated. The Oct polypeptide(s) can be a pluripotency factor.

A "Klf polypeptide" refers to any of the naturally-occurring members of the family of Krüppel-like factors (Klfs), zinc-finger proteins that contain amino acid sequences similar to those of the *Drosophila* embryonic pattern regulator Krüppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, Dang, D. T., Pevsner, J. & Yang, V. W. *Cell Biol.* 32, 1103-1121 (2000). Exemplary Klf family members include, Klf1, Klf2, Klf3, Klf-4, Klf5, Klf6, Klf7, Klf8, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. See, Nakagawa, et al., *Nature Biotechnology* 26:101-106 (2007). In some embodiments, variants have at least 85%, 90%, or 95% amino acid sequence identity across their whole sequence compared to a naturally occurring Klf polypeptide family member such as to those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. To the extent a Klf polypeptide is described herein, it can be replaced with an estrogen-related receptor beta (Essrb) polypeptide. Thus, it is intended that for each Klf polypeptide embodiment described herein, a corresponding embodiment using Essrb in the place of a Klf4 polypeptide is equally described. The Klf polypeptide(s) can be a pluripotency factor.

A "Myc polypeptide" refers any of the naturally-occurring members of the Myc family (see, e.g., Adhikary, S. & Eilers, M. *Nat. Rev. Mol. Cell Biol.* 6:635-645 (2005)), or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as to those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated. The Myc polypeptide(s) can be a pluripotency factor.

A "Sox polypeptide" refers to any of the naturally-occurring members of the SRY-related HMG-box (Sox) transcription factors, characterized by the presence of the high-mobility group (HMG) domain, or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, e.g., Dang, D. T., et al., *Int. J. Biochem Cell Biol.* 32:1103-1121 (2000). Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. See, Nakagawa, et al., Nature Biotechnology 26:101-106 (2007). In some embodiments, variants have at least 85%, 90%, or 95% amino acid sequence identity across their whole sequence compared to a naturally occurring Sox polypeptide family member such as to those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated. The Sox polypeptide(s) can be a pluripotency factor.

"H3K9" refers to histone H3 lysine 9. H3K9 modifications associated with gene activity include H3K9 acetylation and H3K9 modifications associated with heterochromatin, include H3K9 di-methylation or tri-methylation. See, e.g., Kubicek, et al., *Mol. Cell* 473-481 (2007).

A "p53 inhibitor" refers to a molecule that reduces p53 activity and expression. Such a p53 inhibitor can reduce the activity of a p53 protein, the translation of the p53 protein, the expression of a p53 gene, or a combination thereof. Examples of a p53 inhibitor include, but are not limited to nucleic acids, proteins, dominant negative proteins, peptides, oligosaccharides, polysaccharides, lipids, phospholipids, glycolipids, monomers, polymers, small molecules and organic compounds. The p53 inhibitor can be a polynucleotide such as a nucleic acid segment operably linked to a promoter. In some embodiments, the p53 inhibitor is a short hairpin RNA. In other embodiments, the p53 inhibitor is a small interfering RNA. The p53 inhibitor may be a protein. In some embodiments, the p53 inhibitor is a dominant negative protein. Information on such p53 inhibitors is available, for example, in U.S. Pat. No. 8,530,238 by Yamanka et al.; Yu et al., Human induced pluripotent stem cells free of vector and transgene sequences, *Science* 324 (5928): 797-801 (2009); United States Patent Application 20120076762, and Okita et al., A more efficient method to generate integration-free human iPS cells, *Nature Methods* 8: 409-412 (2011), the contents of which are specifically incorporated herein by reference in their entireties. The "p53 shRNA" can, for example, be a shRNA against p53 with the sequence described in U.S. Pat. No. 8,530,238 by Yamanka et al. or Hong et al. (Nature. 460: 1132-1135 (2009)), both of which are incorporated herein by reference in their entirety.

"NANOG" as referred to herein includes any of the naturally-occurring forms of the Nanog transcription factor, or variants thereof that maintain NANOG transcription factor activity (e.g. with at least 50%, 80%, 90% or 100% activity of the activity of natural NANOG). In some embodiments, variants have at least 90% or 95% amino acid sequence identity across their whole sequence compared to the naturally occurring NANOG polypeptide. For example, the NANOG protein can have the sequence identified by the NCBI reference gi:153945816.

The terms "transfection" or "transfected" are defined by a process of introducing nucleic acid molecules into a cell by non-viral and viral-based methods. The nucleic acid molecules may be gene sequences encoding complete proteins or functional portions thereof.

The term "pluripotent" or "pluripotency" refers to cells with the ability to give rise to progeny cells that can undergo differentiation, under the appropriate conditions, into cell types that collectively demonstrate characteristics associated with cell lineages from all of the three germinal layers (endoderm, mesoderm, and ectoderm). Pluripotent stem cells can contribute to all embryonic derived tissues of a prenatal, postnatal or adult animal. A standard art-accepted test, such as the ability to form a teratoma in 8-12 week old SCID mice, can be used to establish the pluripotency of a cell population, however identification of various pluripotent stem cell characteristics can also be used to detect pluripotent cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least some, and in some embodiments, all of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics.

As used herein, "multipotent" or "multipotent cell" refers to a cell type that can give rise to a limited number of other particular cell types.

As used herein, "non-pluripotent cells" refer to mammalian cells that are not pluripotent cells. Examples of such cells include differentiated cells as well as progenitor cells. Examples of differentiated cells include, but are not limited to, cells from a tissue selected from bone marrow, skin, skeletal muscle, fat tissue and peripheral blood. Exemplary cell types include, but are not limited to, fibroblasts, epidermal cells, lymphocytes, hepatocytes, myoblasts, neurons, osteoblasts, osteoclasts, and T-cells.

Where an individual is to be treated with definitive endoderm cells, pancreatic progenitor cells, and/or pancreatic beta cells, the individual's own non-pluripotent cells can be used to generate definitive endoderm cells, pancreatic progenitor cells, and/or pancreatic beta cells according to the methods of the invention.

Mammalian cells can be from humans or non-human mammals. Exemplary non-human mammals include, but are not limited to, mice, rats, cats, dogs, rabbits, guinea pigs, hamsters, sheep, pigs, horses, bovines, and non-human primates (e.g., chimpanzees, macaques, and apes).

"Inhibitors," "activators," and "modulators" of expression or of activity are used to refer to inhibitory, activating, or modulating molecules, respectively, identified using in vitro and in vivo assays for expression or activity of a described target protein (or encoding polynucleotide), e.g., ligands, agonists, antagonists, and their homologs and mimetics. The term "modulator" includes inhibitors and activators. Inhibitors are agents that, e g, inhibit expression or bind to, partially or totally block stimulation or protease inhibitor activity, reduce, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100% Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more higher.

The following examples are offered to illustrate, but not to limit the claimed invention.

Example 1: Materials and Methods

This Example describes some of the materials and methods employed in development of the invention.

Dox-Inducible Secondary MEF Preparation

NGFP1 Dox-inducible induced pluripotent stem (iPS) cells (Stemgent) were injected into C57BL/6 blastocysts and implanted into surrogate mice (CD1, Harlan). Chimeric embryos were isolated at E12.5-13.5. Heads, developing organs and spinal cords were carefully removed from the embryos, and MEFs were prepared and specifically selected as reported (Hanna, Markoulaki et al. 2008; Wernig, Lengner et al. 2008; Hanna, Saha et al. 2009).

Direct Reprogramming of Fibroblasts into Definitive Endoderm-Like Cells

Dox-inducible secondary mouse embryonic fibroblasts (MEFs) (cells at passage 3-4 were regularly used) were plated on Matrigel-coated culture dishes at a cell density of $1 \times 10^4$ cells/cm$^2$. Cells were cultured in MEF medium (Dulbecco's modified Eagle's medium with 10% fetal bovine serum and 2 mM Glutamax) for an additional day. The medium was then changed to Med I (Knock-out DMEM with 10% knock-out serum replacer, 5% FBS, 2 mM Glutamax, 0.1 mM non-essential amino acids (NEAA), and 0.055 mM β-mercaptoethanol) supplemented with 4 μg/ml Dox, 50 ng/ml Activin A and 1 mM LiCl for the indicated time. Thereafter, the medium was changed to Med II (75% Iscove's modified Dulbecco's medium, 25% Ham's F12 medium, supplemented with 1×N2 supplements, 0.05% bovine serum albumin, 2 mM Glutamax, and 0.45 mM monothiolglycerol (MTG)) supplemented with 50 ng/ml Activin A and 1 mM LiCl for the indicated time. All reagents were purchased from Invitrogen if not specified, and all cytokines were from R&D Systems.

Differentiation of Definitive Endoderm-Like Cells (DELCs) to Pancreatic Progenitor-Like Cells (PPLCs)

DELCs were further cultured in Med III (DMEM supplemented with 1×B27, 2 mM Glutamax), and treated with 2 μM retinoic acid (RA), 1 μM A83-01, 2 μM LDE225 and 280 μM 2-phospho-L-ascorbic acid trisodium salt (pVc) for 1 day, and then with 1 μM A83-01, 2 μM LDE225 and 280 μM pVc for another 3 days. At the end of treatment, lineage specific markers were analyzed by immunostaining and/or real-time PCR.

Immunocytochemistry

Immunocytochemistry analysis was performed as previously described (Efe et al. 2011). Primary antibodies used were Sox17 (R&D), Foxa2 (Millipore), Pdx1 (R&D), Hnf6 (Santa Cruz), Pax6 (Covance), Sox9 (Santa Cruz), Nkx6.1 (Developmental Studies Hybridoma Bank), Insulin (Dako), Glucagon (Sigma), Somatostatin (Abcam), Amylase (Abcam), and CK19 (Abcam). Nuclei were visualized by DAPI (Sigma-Aldrich) staining Images were captured using a Nikon Eclipse TE2000-U microscope.

Gene Expression Analysis by Real-Time PCR

Total RNA was extracted using the RNeasy Plus Mini Kit in combination with QIAshredder (Qiagen). First-strand reverse transcription was performed with 2 μg RNA with the iScript™ cDNA Synthesis Kit (BioRad). Expression of pluripotency and lineage-specific marker genes was analyzed by real-time PCR with iQ SYBR Green Supermix (Bio-Rad).

Transplantation Assay

Male, 8-10-week-old NOD.Cg-Prkdcscid Il2rgtm1Wjl/SzJ (NSG) mice (Jackson Laboratory, Bar Harbor, Me.) were injected intraperitoneally with 35 mg/kg Streptozocin (STZ; Sigma-Aldrich, St. Louis, Mo.) daily for 4 days. Blood glucose levels were assayed from tail-vein blood with a standard blood glucose meter (Diabetic Care Services, Eastlake, Ohio). Hyperglycemia developed 5-7 days after the STZ injection. Mice were considered to be diabetic if blood glucose measurements were >300 mg/dl for 4 consecutive days, after which they were used as transplant recipients. Under anesthesia, diabetic mice received a renal subcapsular transplant of about $3 \times 10^6$ pancreatic progenitor-like cells (n=14) or $3 \times 10^6$ secondary MEF cells (n=10). Untreated normal mice (n=4) and mice treated with STZ only (n=4) were used as controls. Non-fasting blood glucose levels were measured weekly after surgery for 8 weeks. Serum insulin was measured by ELISA (Millipore, Billerica, Mass.) at the end of 8 weeks. All animal work was approved by the institutional IACUC committee.

Immunohistochemistry

Left kidneys were removed from euthanized mice, fixed in 4% paraformaldehyde and used for paraffin section and cryosection. Kidneys were transversally sectioned and stained with primary antibodies. Then, the antigen-primary antibody immune complex was visualized with fluorescent secondary antibodies (Invitrogen). Cell nuclei were counterstained with DAPI.

Insulin Detection Assay

An insulin-release assay was performed as described (Schroeder et al. 2006). Briefly, cells were washed five times with PBS and pre-incubated in freshly prepared Krebs' Ringer bicarbonate HEPES buffer (KRBH; 118 mM NaCl, 4.7 mM KCl, 1.1 mM $KH_2PO_4$, 25 mM $NaHCO_3$, 3.4 mM $CaCl_2$, 2.5 mM $MgSO_4$, 10 mM HEPES and 2 mg/ml BSA, pH 7.4) with 2.5 mM glucose for 90 min at 37° C. KRBH buffer was then replaced with KRBH buffer containing either 27.7 or 5.5 mM glucose for another 90 min at 37° C. Supernatants were collected to determine insulin release. For serum insulin detection, 0.1 ml of tail-vein blood was collected from each mouse at the end of 8 weeks after surgery, and serum was used for insulin detection. Insulin was measured by ELISA (Millipore, Billerica, Mass.).

Statistical Analysis

Data were presented as mean±SD. Differences were analyzed by Student's t-test. P<0.05 was considered statistically significant.

Example 2: Direct Reprogramming of Fibroblasts into Definitive Endoderm-Like Cells (DELCs)

This Example describes procedures for generating definitive endoderm-like cells from mouse embryonic fibroblasts.

The doxycycline (Dox)-inducible secondary mouse embryonic fibroblast (MEF) system (Wernig, Lengner et al. 2008; Hanna, Saha et al. 2009) was employed to enable expression of the conventional four iPSC factors (the Yamanaka factors or Oct4, Sox2, Klf4, and c-Myc) with precise temporal control. MEFs were carefully prepared using standard procedures and used for reprogramming after 3-4 passages. Although endoderm cells may exist in starting MEF populations, no such contamination of these cells was observed in the cultures employed.

To extend and test the iPSC-factor-based lineage-specific reprogramming paradigm to endoderm, a two-step process was first devised to directly reprogram secondary MEF cells into definitive endoderm-like cells (DELCs). The first step (step I) involved culturing secondary MEF cells in media (Med-I) that is supplemented with 4 µg/ml Dox to initiate epigenetic activation. The second step (step II) was culturing the epigenetically activated cells in Med-II supplemented with 50 ng/ml Activin A and 1 mM LiCl (hereafter referred to as Activin/Li). Activin A plus LiCl was used as the definitive endoderm induction condition because chemical activation of the canonical WNT signaling pathway by LiCl synergized with Activin A-mediated Nodal signaling to promote induction of definitive endoderm cells from mouse ES cells (Li et al. 2011). Sox17 and Foxa2, two relatively specific markers for definitive endoderm (Tam, Kanai-Azuma et al. 2003; Qu, Pan et al. 2008), were examined by immunostaining at the end of Step II. By observing the results of different durations of Step I and Step II, it was determined that 6-days of Step I followed by 6 days of Step II was an effective condition to generate Sox17$^+$/Foxa2$^+$ cells with relatively high efficiency. Consistent with results observed by the inventors in studies on cardiac and neural inductions using this paradigm, a shortened first step induction of down to 4 days could still produce homogenous Sox17/Foxa2 double positive colonies with fewer numbers, while prolonged first step induction, such as 7 days or 8 days, dramatically decreased the percentage of Sox17/Foxa2 double positive colonies. Hereafter these Sox17/Foxa2 double-positive cells are referred to as definitive endoderm-like cells (DELCs).

In previous cardiac and neural reprogramming studies and the initial endoderm reprogramming using the iPSC-factor-based lineage-specific reprogramming paradigm, cell specification by lineage-specific signals was only induced after initial epigenetic activation with iPSC factors. Therefore, whether lineage-specific signals could overlap with epigenetic activation to enhance the efficiency of reprogramming (towards a lineage-specific fate) is unclear.

Figure 1A:
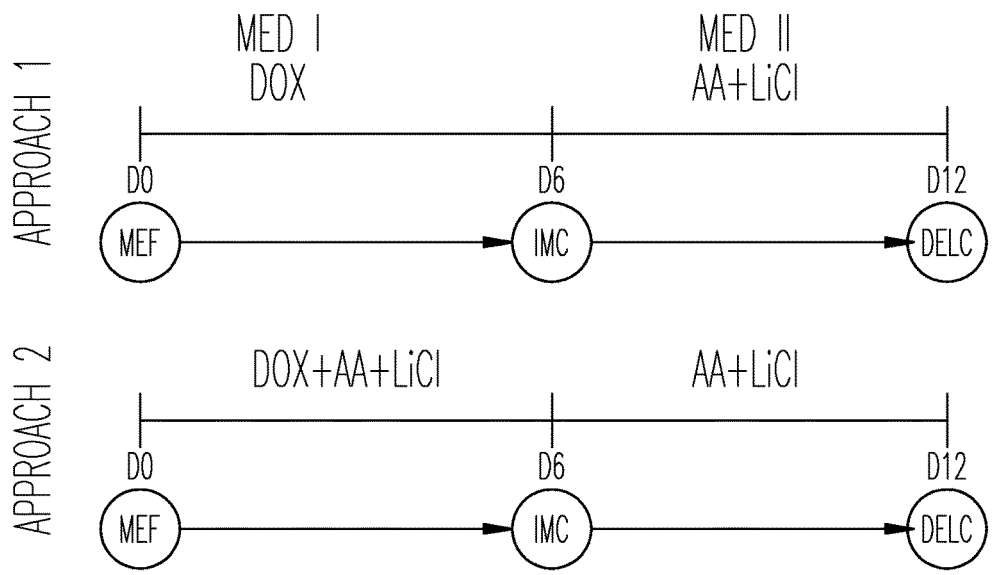
FIGS. 1A-1D illustrate reprogramming of fibroblasts to definitive endodermal like cells (DELCs) with an iPSC-factor-based lineage-specific reprogramming paradigm.
Figure 1B:
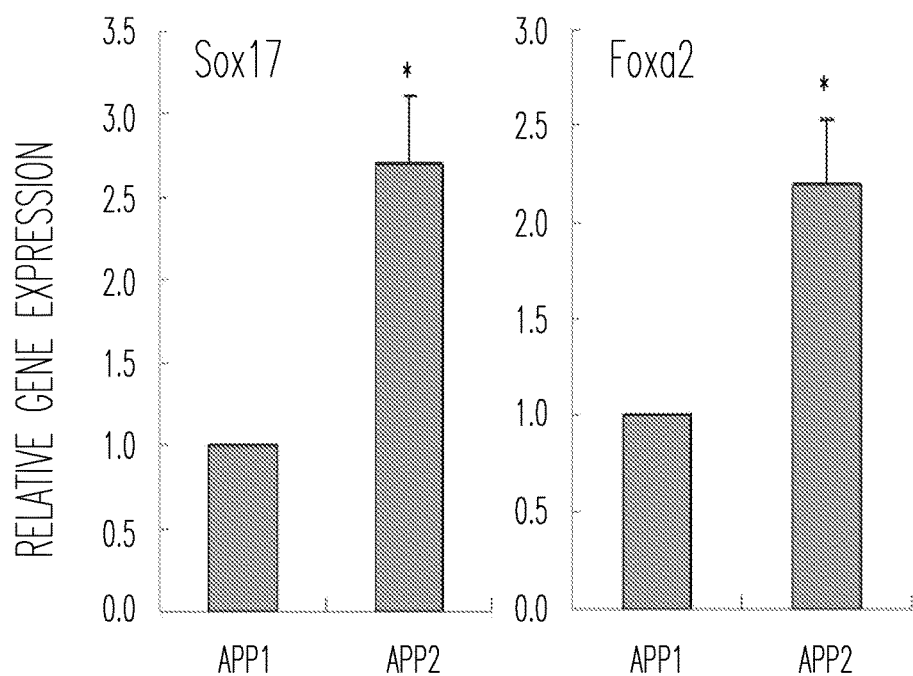
Figure 1C:
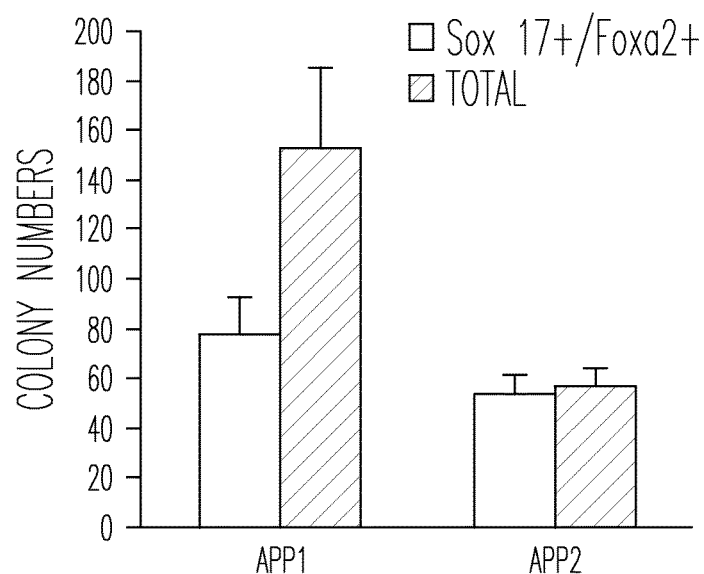
Figure 1D:
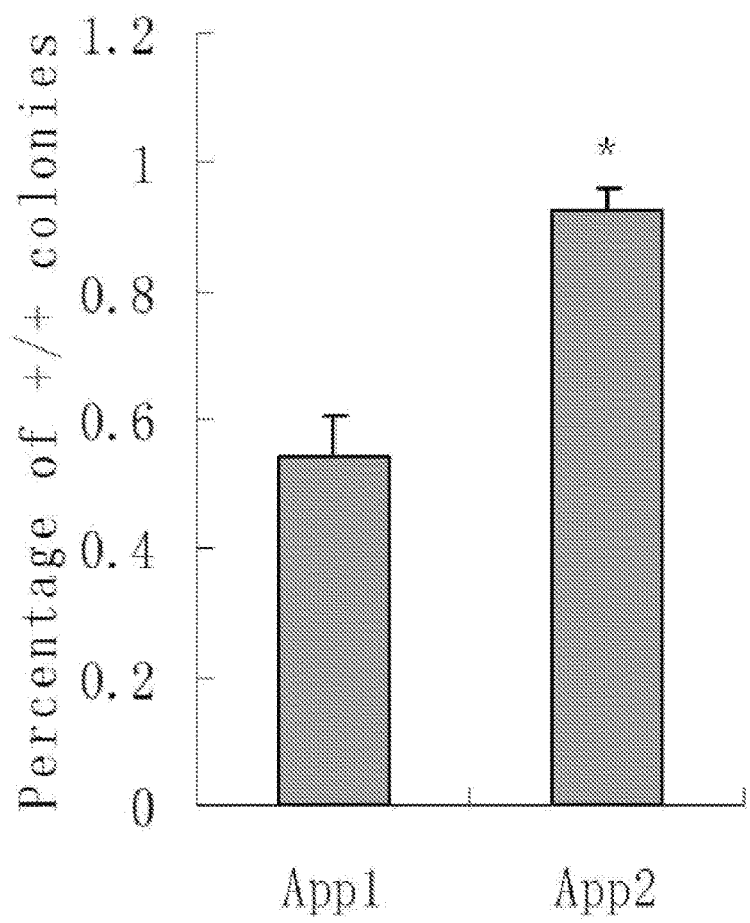
Figure 2A:
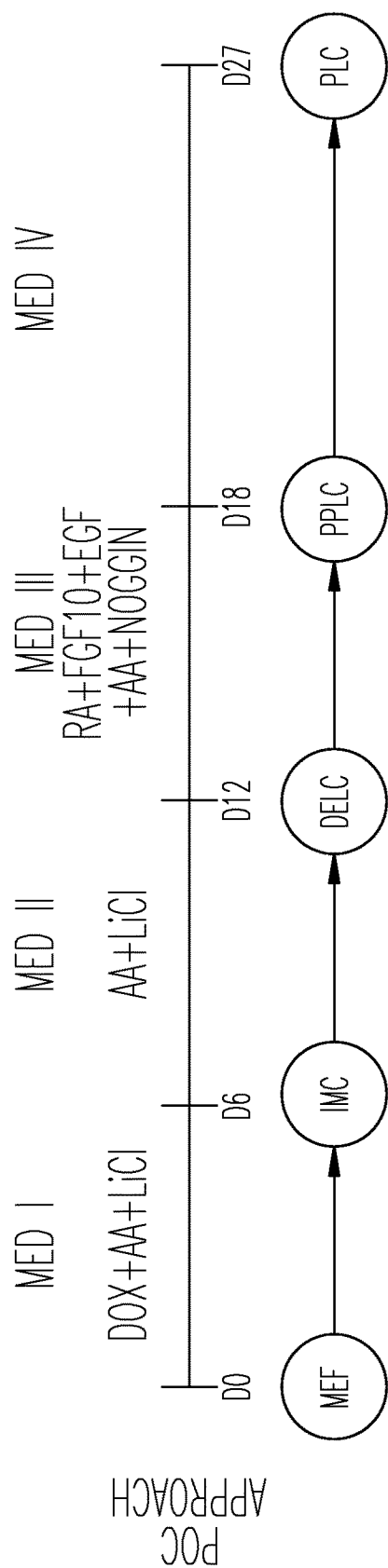
FIGS. 2A-2G illustrate the proof-of-concept (POC) approach described herein for reprogramming mouse embryonic fibroblasts (MEFs) into definitive endodermal like cells (DELCs), then into pancreatic progenitor like cells (PPLCs), and then into pancreatic β-like cells (PLCs).
Figure 2B:
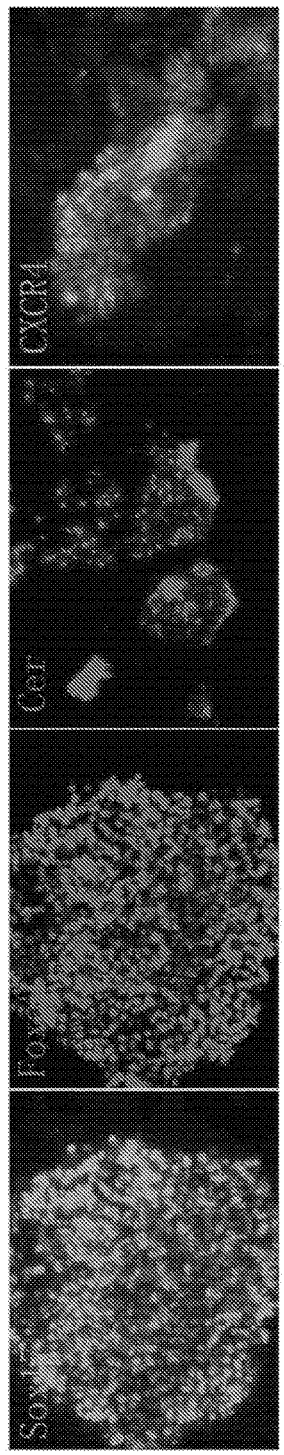
Figure 2C:
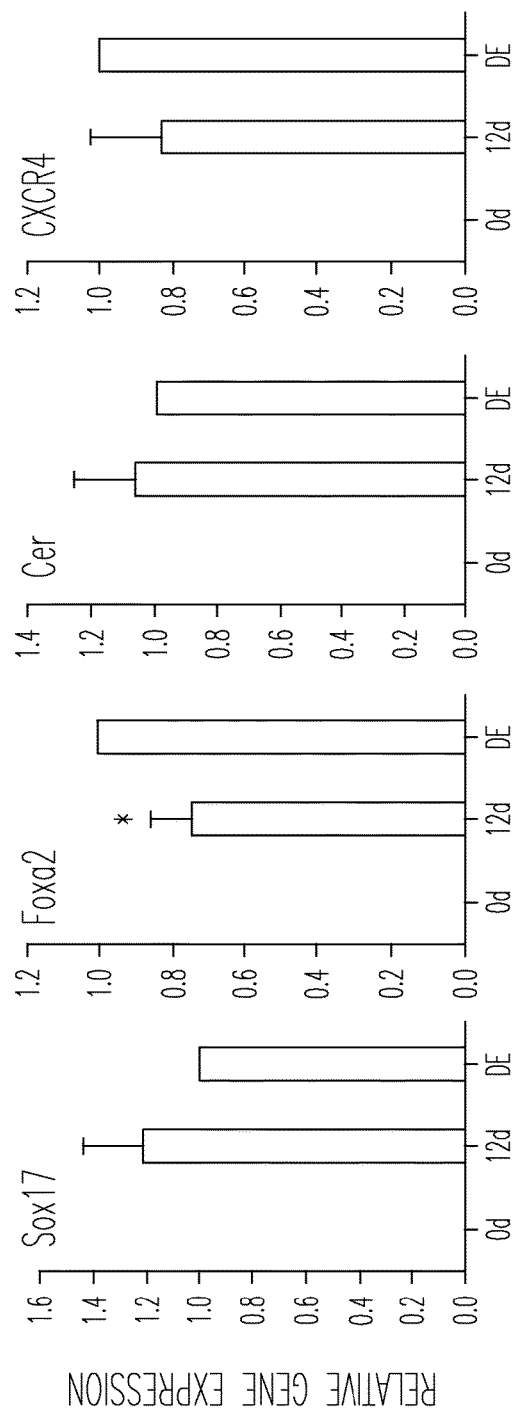

The inventors hypothesized that transcriptional activity downstream of lineage-specific signals, in conjunction with iPSC factors that erase the starting cell's epigenetic identity during early reprogramming, could help set up lineage-specific transcriptional programs. To test this hypothesis, conditions were evaluated in which definitive endoderm induction factors (Activin/Li) were added to fibroblasts either after (Approach-I) or during (Approach II) iPSC factor expression, using Sox17 and Foxa2 expression as a measure of DELC induction (FIG. 1A). In contrast, addition of Activin/Li during the iPSC-factor expression (Approach-II) yielded mRNA levels of Sox17 and Foxa2 1.5 fold greater than strictly separating iPSC factor expression and Activin/Li induction in the two steps (Approach-I) (FIG. 1B). Consistently, addition of Activin/Li during the iPSC-factor expression (Approach-II) also greatly increased the percentage of Sox17/Foxa2 double positive colonies (FIG. 1C-1D). By using the Approach-II, 6-days iPSC factor expression in the presence of Activin/Li followed by Activin/Li treatment for another 6 days, other definitive endoderm marker genes, including Cerberus 1 (Cer) and C-X-C chemokine receptor type 4 (Cxcr4), were highly induced in addition to Sox17 and Foxa2 (FIG. 2B-2C).

These results supported our hypothesis that transcriptional activities downstream of lineage-specific signals could participate early to set up the lineage-specific transcriptional programs in conjunction with iPSC factors.

Figure 2D:
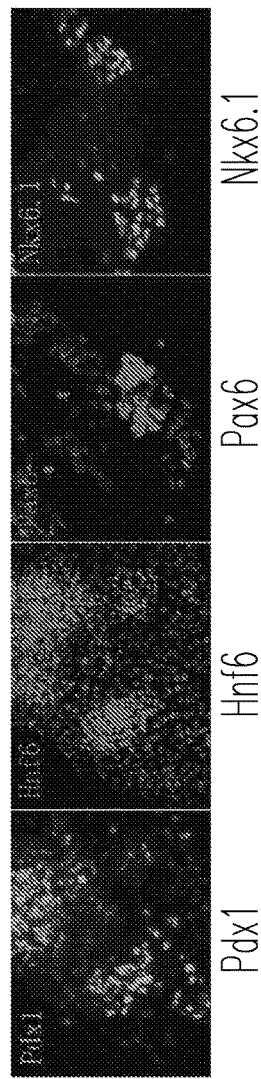
Figure 2E:
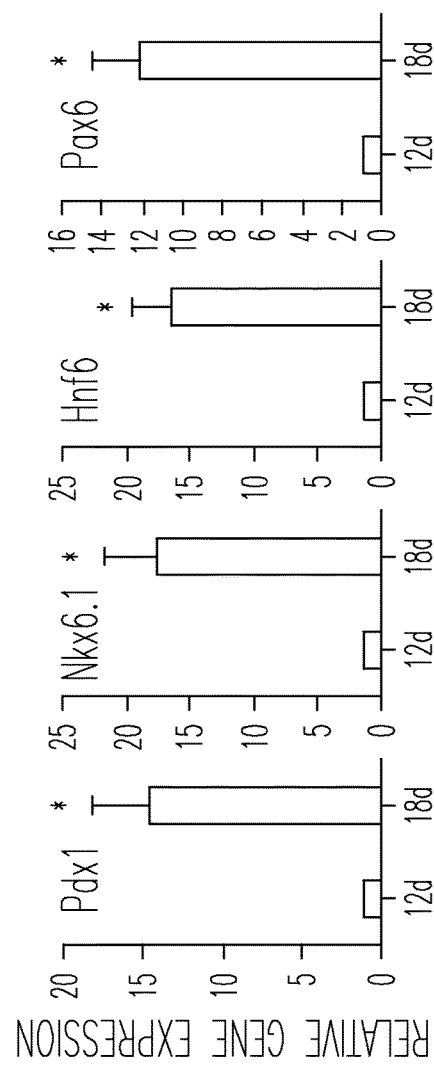
Figure 2F:
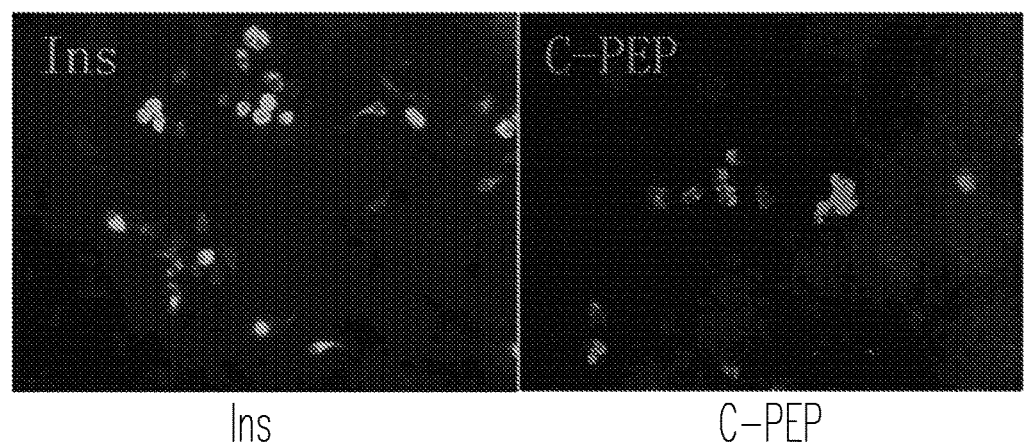
Figure 2G:
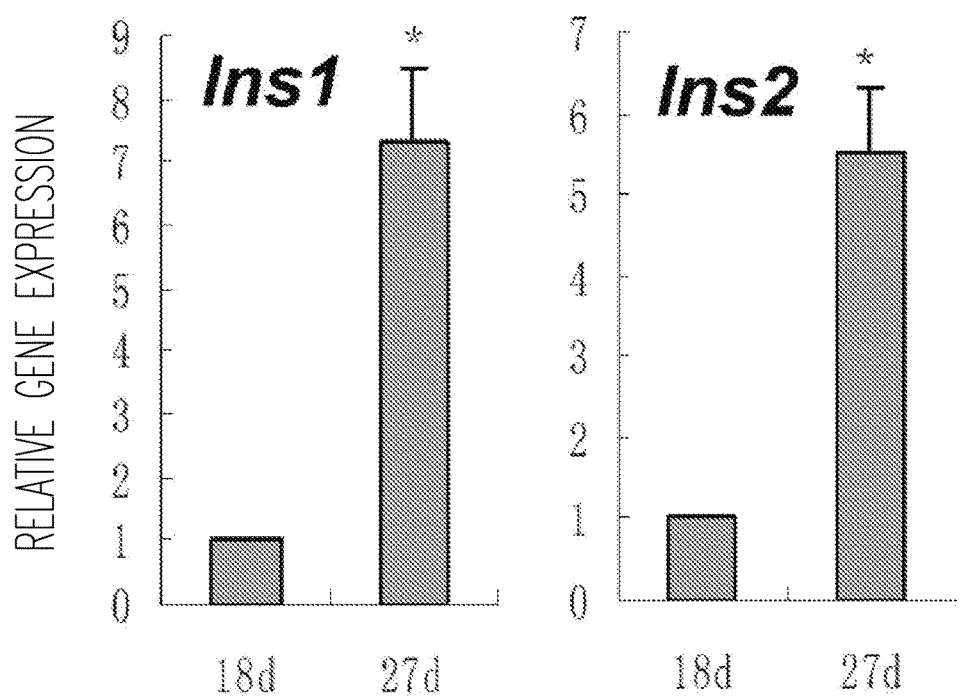

To establish a proof of concept that these DELCs have the differentiation potential toward pancreatic lineages, the DELCs were initially subjected to published pancreatic differentiation conditions (D'Amour et al., 2006; Li et al., 2011). Notably, like definitive endoderm cells derived from mouse embryonic stem (mES) cells, the DELCs generated by the methods described herein also gave rise to cells that expressed specific markers for pancreatic progenitors, including pancreatic and duodenal homeobox gene-1 (Pdx1) (Offield, Jetton et al. 1996), hepatocyte nuclear factor-6 (Hnf6) (Jacquemin, Durviaux et al. 2000), paired-box gene 6 (Pax6) (Sander, Neubuser et al. 1997), and NK homeobox factor 6.1 (Nkx6.1) (Sander, Sussel et al. 2000), as examined by immunostaining and real-time PCR (FIG. 2D-2E). The cells expressing pancreatic progenitor markers are referred to herein as pancreatic progenitor-like cells (PPLCs). Further differentiation of the PPLCs in vitro could give rise to insulin expressing cells, as examined by immunostaining and real-time PCR (FIG. 2F-2G). These results demonstrate that the DELCs generated as described herein could differentiate all the way to pancreatic β-like cells, like definitive endoderm cells derived from mES cells.

However, the efficiency of generating pancreatic-like cells from the DELCs was low, although comparable to differentiation of mES cells using the same conditions. For example, only about 5% and 10% of cells were positive for just Nkx6.1 or Pdx1, respectively, and only about 1% were Pdx1/Nkx6.1 double positive. Further differentiation in vitro gave rise to less than 0.1% insulin expressing cells. And consistent with previous studies (D'Amour et al., 2006), these insulin expressing cells didn't response well to high glucose stimulation. These results indicate that the lineage induction conditions ideally should be further improved. Therefore, the next Example describes efforts for optimizing induction conditions for generating pancreatic-like cells by small molecules.

Example 3: Identification of Novel Combinations of Small Molecules that Enhance Generation of Pancreatic Progenitor-Like Cells This Example describes experiments demonstrating that several small molecules can be used to generate pancreatic progenitor-like cells from cells that express factors such as Cerberus 1 (Cer), C-X-C chemokine receptor type 4 (Cxcr4), Sox17, and/or Foxa2.

Beta cell formation and maturation are impaired in Nkx6.1-null mutant mice and can be restored upon re-expression of Nkx6.1 in multipotential Pdx1+ pancreatic progenitors (Nelson et al., 2007). In other studies, Pdx1+/Nkx6.1+ pancreatic progenitor cells differentiated from human ES cells could be purified with the cell-surface marker CD142, and after transplantation into mice, these purified progenitor cells gave rise to all pancreatic cell lineages, including glucose-responsive, insulin-secreting cells (Kelly et al., 2011). These studies suggest that dual expression of Pdx1 and Nkx6.1 is an indicator that pancreatic progenitor cells can give rise to functional β cells. Induction of Pdx1$^+$ and Nkx6.1$^+$ expression was used in experiments designed to identify conditions that generate pancreatic progenitor-like cells (PPLCs) from the reprogrammed DELCs.

An available drug collection of 400 compounds in the 48-well format was screened to identity small molecules that induce high percentages of Pdx1+/Nkx6.1+ cells in DELC populations. Med-III medium (DMEM supplemented with 1×B27, 2 mM Glutamax) was used as the basal condition and double staining of Pdx1 and Nkx6.1 at 4 days post-induction was used as the readout.

Figure 3A:
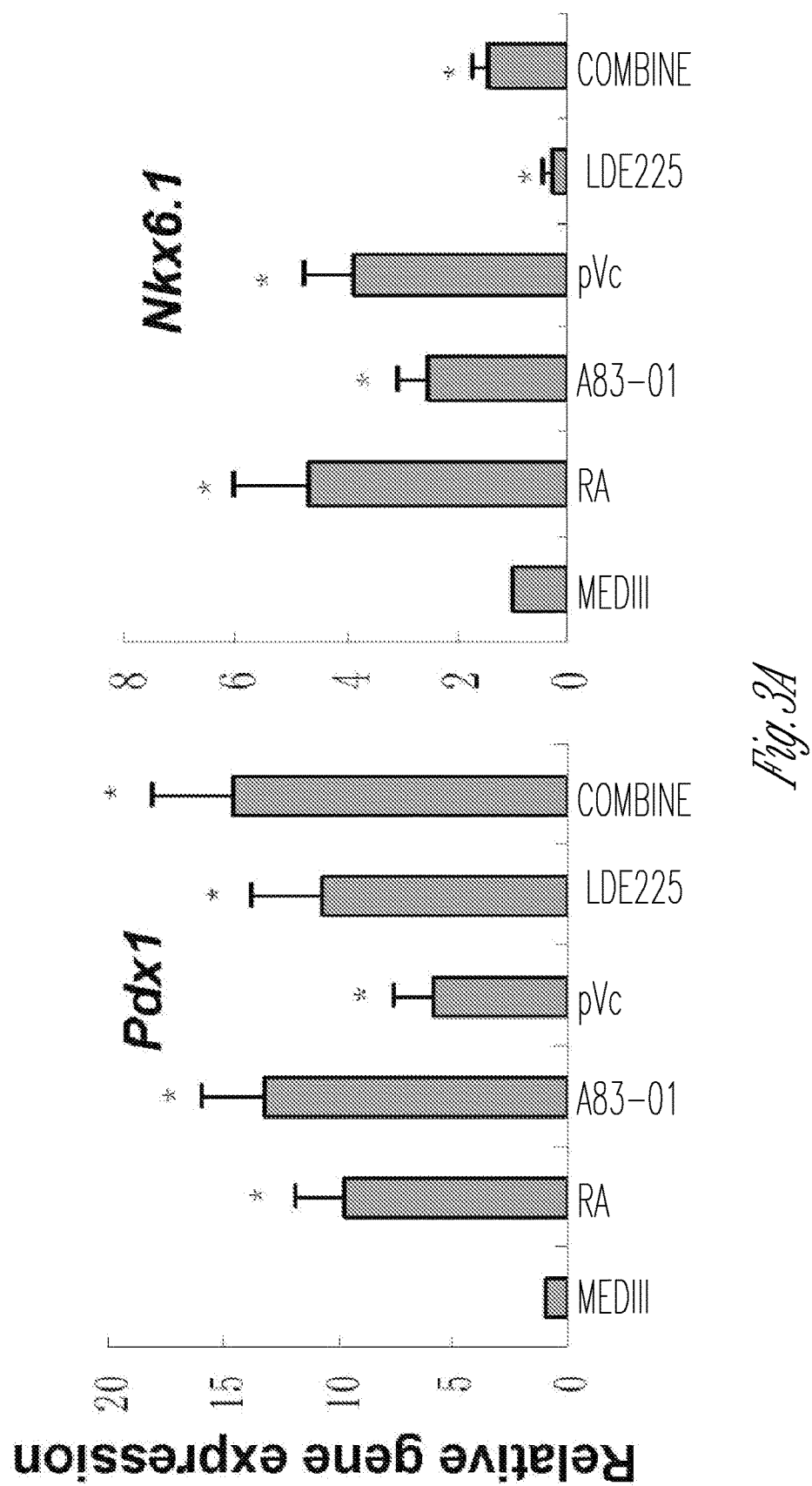
FIGS. 3A-3B show that small molecules enhance induction of definitive endoderm-like cells (DELCs) into pancreatic progenitor like cells (PPLCs).
Figure 3B:
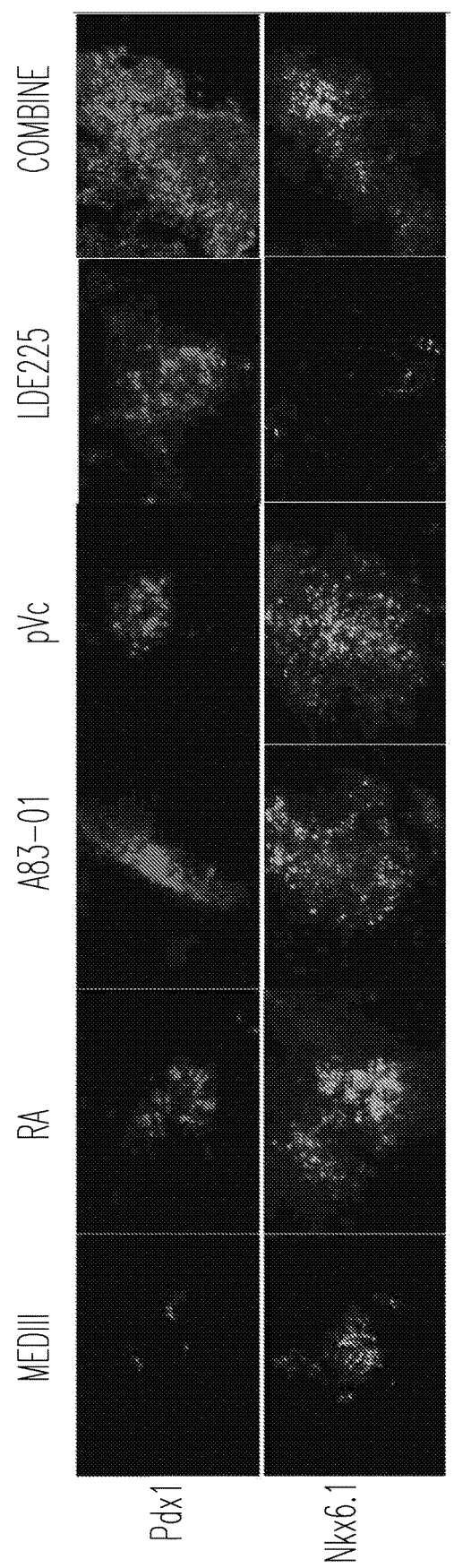
Figure 4B:
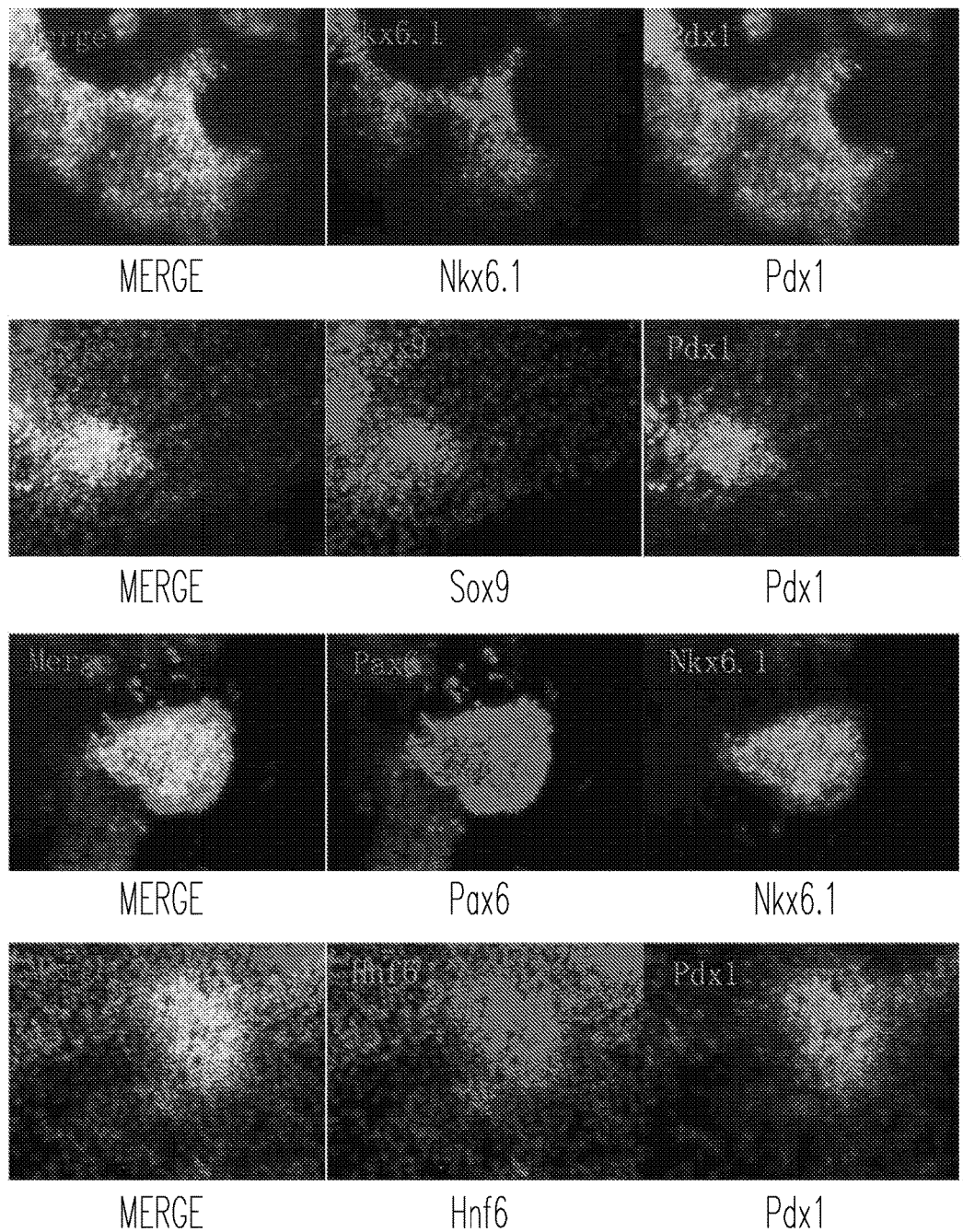
Figure 4C:
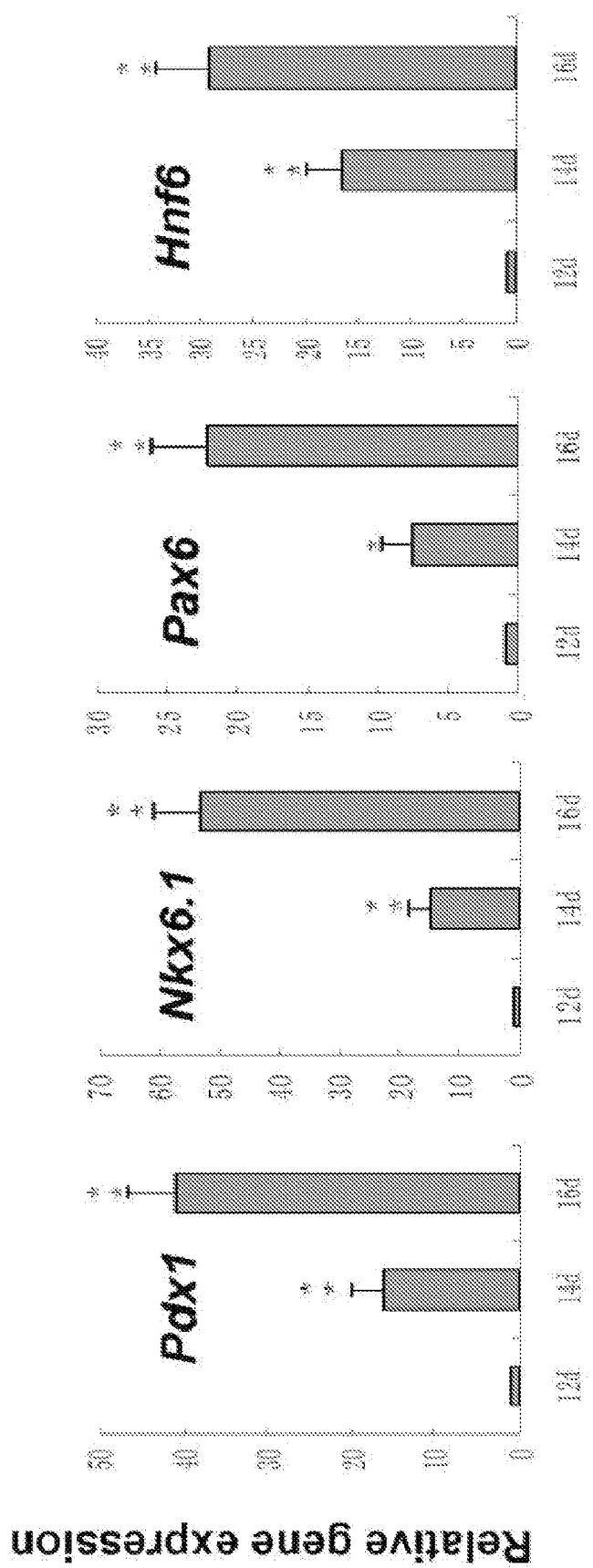

Induction of Pdx1 and Nkx6.1 expression by small molecules is referred herein to the "third step" (step III) of pancreatic induction. Several primary hits that could increase Pdx1 and/or Nkx6.1 expression were further characterized using larger-well cultures. Confirmed hits included retinoic acid (RA, a RAR agonist), A83-01 (a TGFβ receptor inhibitor), 2-phospho-L-ascorbic acid (pVc), and LDE225 (a hedgehog pathway inhibitor) (FIG. 3). After testing various small molecule combinations, significantly improved pancreatic induction was achieved by treating DELCs with 2 µM RA, 1 µM A83-01, 2 µM LDE225 and 280 µM pVc for 1 day, and then 1 µM A83-01, 2 µM LDE225 and 280 µM pVc for another 3 days. Under these conditions, the pancreatic progenitor makers Pdx1, Nkx6.1, Hnf6, Pax6 and Sox9 (Lynn, Smith et al. 2007) were highly expressed and co-localized as detected by co-immunostaining (FIG. 4B). About 35% of the cells expressed Pdx1 and about 30% of the cells expressed Nkx6.1, 2.5-fold and 5-fold increase, respectively, over previous conditions (POC approach). More importantly, about 8% of the cells were Pdx1/Nkx6.1 double positive, a 7-fold increase over previous conditions (POC approach). qRT-PCR analysis further confirmed heightened expression of Pdx1, Nkx6.1, Pax6 and Hnf6 during the pancreatic induction process (FIG. 4C). These results indicate that this novel combination of small molecules promoted differentiation of DELCs into Pdx1+/Nkx6.1+ PPLCs.

Figure 4D:
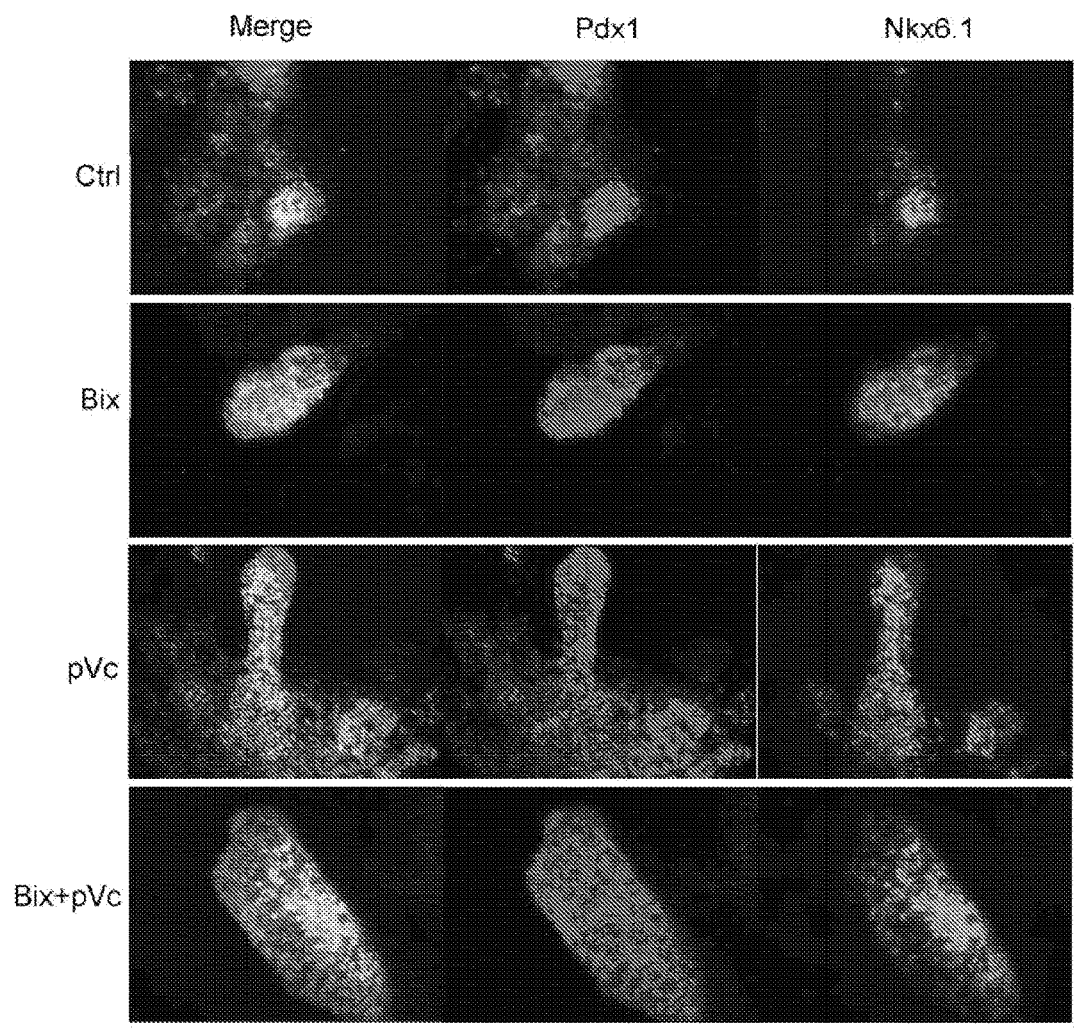
Figure 4E:
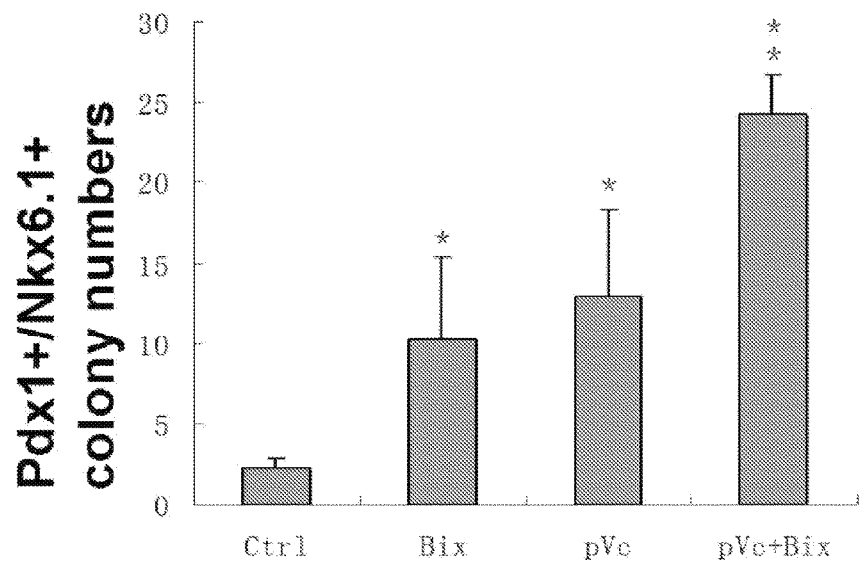
Figure 4F:
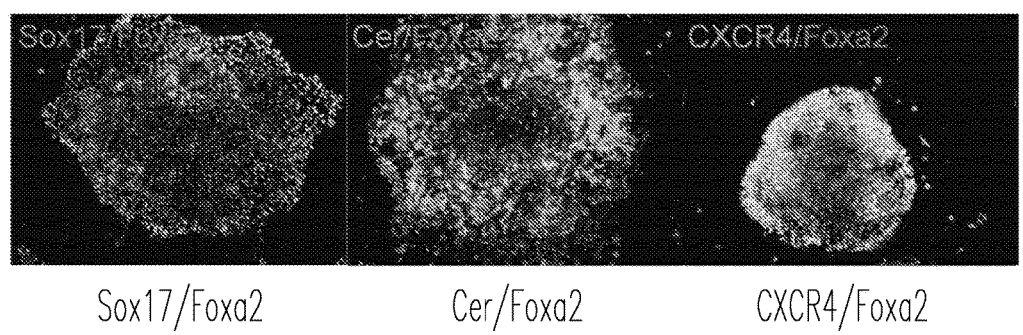

The inventors then hypothesized that overlapping lineage-specific patterning conditions based on small molecules with early reprogramming would enhance pancreatic induction. To this end, further screens of the inventors' drug collection were performed during the first- and second-step inductions, with double staining of Pdx1 and Nkx6.1 at the end of the third step (day 16) as a readout. Remarkably, several small molecules, when applied during the first and/or second steps, greatly enhanced pancreatic induction. In particular, 1 µM Bix-01294 (a G9a histone methyltransferase inhibitor), when added from D0 to D6, and 280 µM pVc, when added from D0 to D12, increased the number of Pdx1+/Nkx6.1+ colonies to about 3 fold and 4 fold respectively (FIG. 4D-4E). Further testing revealed that the combination of 1 µM Bix-01294 (added from D0 to D6) and 280 µM pVc (added from D0 to D12) generated about 8 fold of Pdx1+/Nkx6.1+ colonies (FIG. 4D-4E). Interestingly, treatment with Bix and/or pVc had no significant influence on the numbers of Sox17 and Foxa2 single positive and double positive cells.

Therefore, conditions and small molecules have been identified for efficiently generating pancreatic progenitor-like cells (PPLCs).

Example 4: Pancreatic Progenitor-Like Cells can be Further Differentiated into Mature Pancreatic-Like Cells This Example describes experiments demonstrating that the pancreatic progenitor-like cells generated as described above can be differentiated into more mature pancreatic-like cells.

The pancreatic progenitor-like cells generated as described herein were treated with Med-IV medium containing laminin, nicotinamide, and B27 etc. as previously reported (Schroeder et al., 2006) to determine whether those PPLCs can be further differentiated into mature pancreatic like cells. After 9 days of culture in this medium, a small population (about 0.5%) of insulin and C-peptide double-positive cells was detected.

Figure 5A:
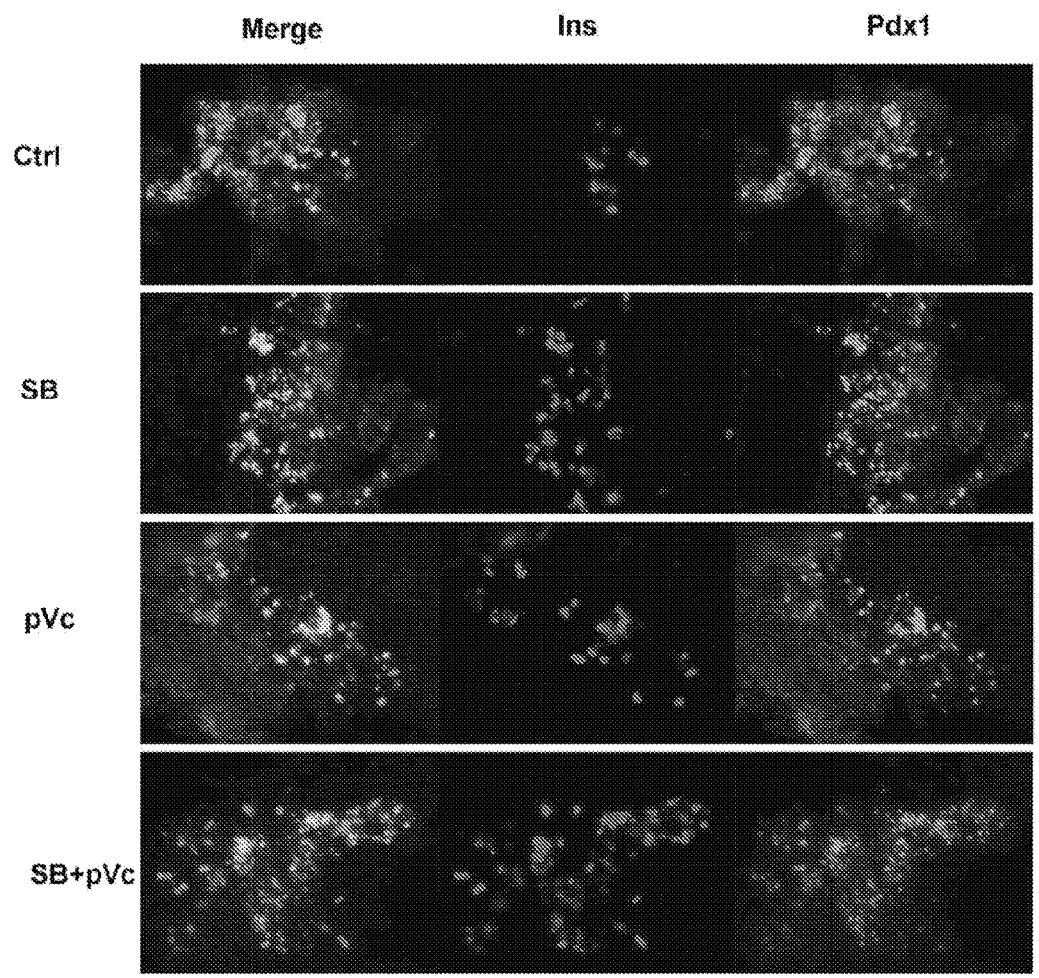
FIGS. 5A-5D show that pancreatic progenitor-like cells can be differentiated into pancreatic-like cells.

To improve efficiency of pancreatic maturation, the inventors' drug collection was further screened in a "fourth" step (step IV) to identify compounds that increase the percentage of cells that express insulin and Pdx1 on day 25. These experiments showed that 5 µM SB203580 and 280 µM pVc significantly increased the number of insulin+/Pdx1+ double-positive cells when used individually, and when combined together these compounds synergistically enhanced the numbers of insulin+/Pdx1+ cells in the population (e.g., to about 2%) (FIG. 5A).

Figure 5B:
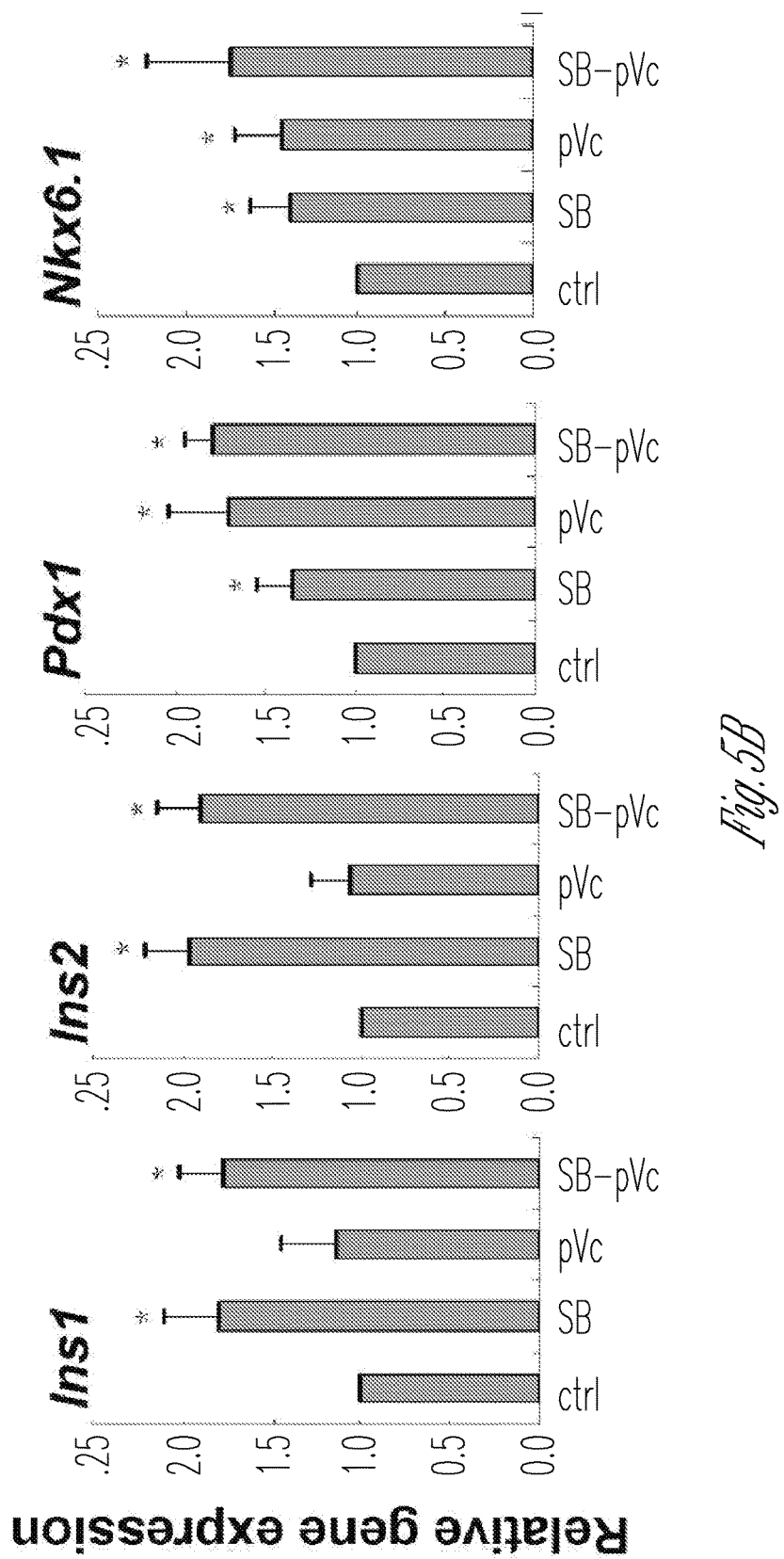
Figure 5C:
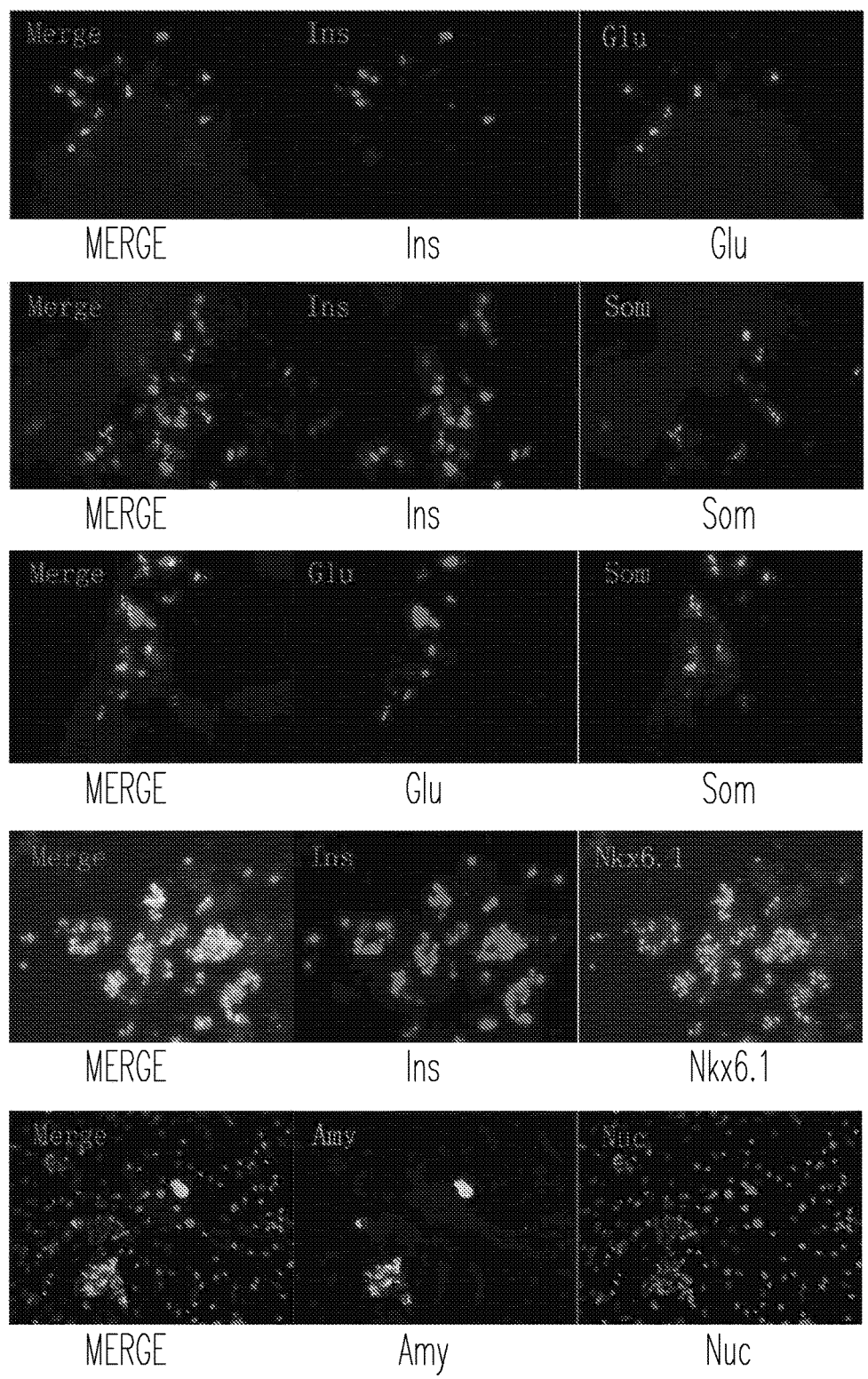
Figure 5D:
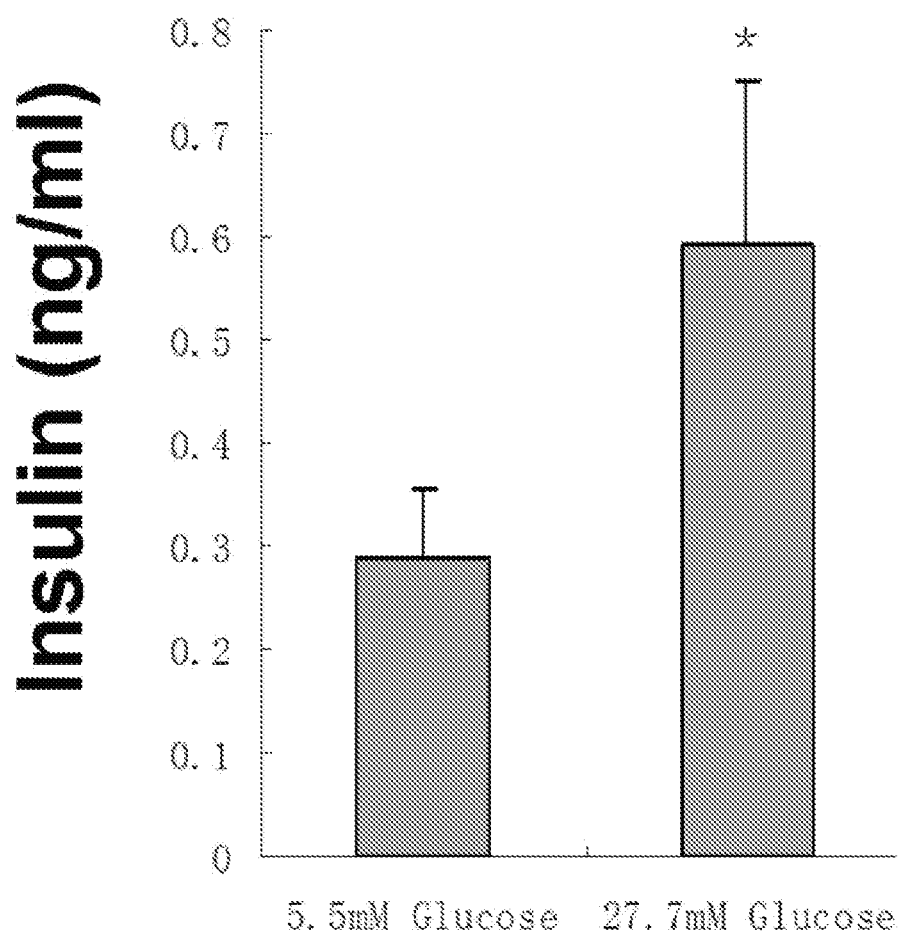

The expression levels of insulin, Pdx1 and Nkx6.1 in the pancreatic progenitor-like cells treated with SB203580 and pVc also increased significantly (FIG. 5B). Glucagon-producing pancreatic alpha-like cells, somatostatin-producing pancreatic delta-like cells, and amylase-producing pancreatic acinar-like cells were also detected on day 25 (FIG. 5C). Importantly, these endocrine-like cells produced only one hormone, a defining characteristic of mature pancreatic endocrine cells. The insulin-positive cells were also Nkx6.1-positive and secreted insulin when stimulated with high level of glucose (FIG. 5C-5D). Thus, these differentiated PPLCs gave rise to pancreatic endocrine and exocrine-like cells in vitro, including functional insulin-secreting beta-like cells.

Example 5: iPSCs were not Generated During the Reprogramming of Fibroblasts to Pancreatic-Like Cells This Example illustrates that the reprogramming procedure described in Example 2 does not generate fully pluripotent stem cells.

Figure 6A:
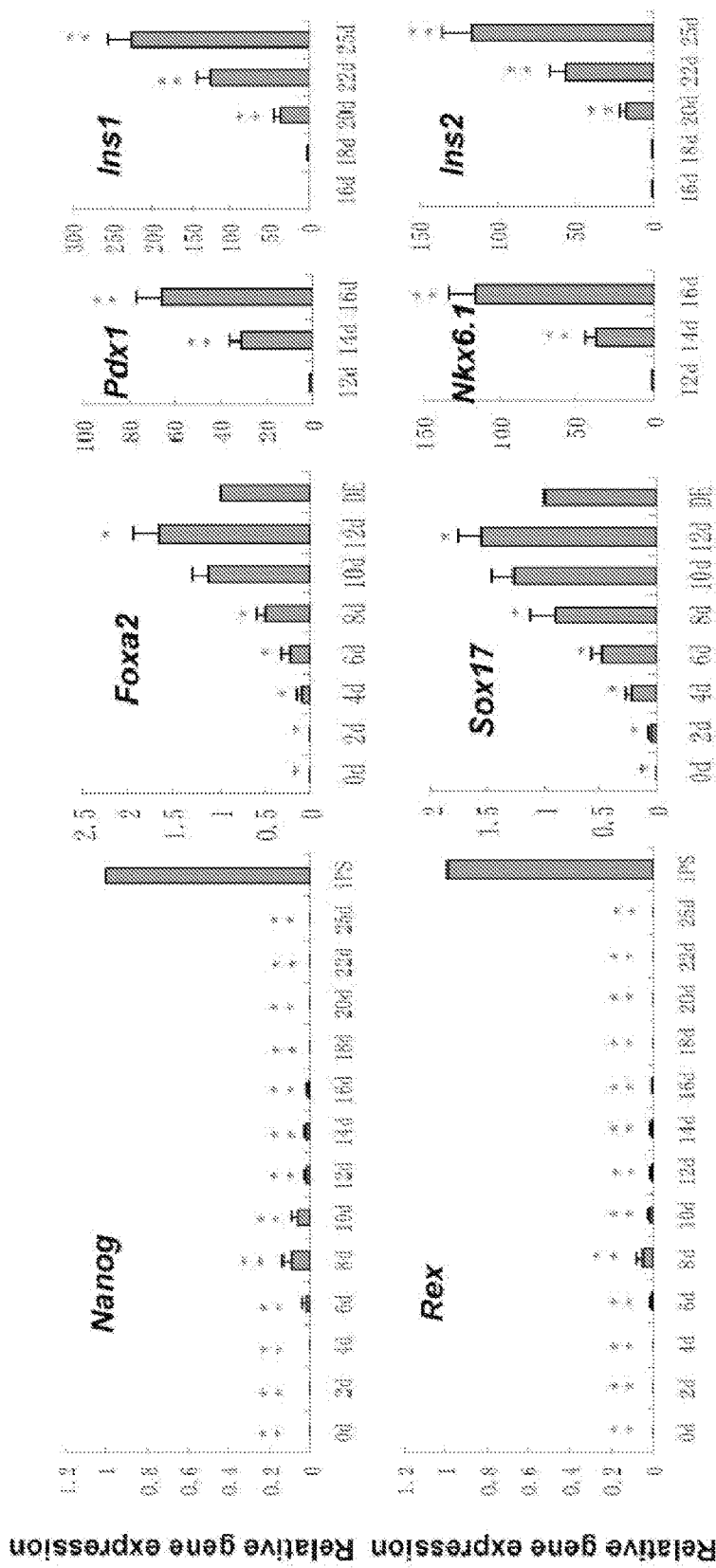
FIGS. 6A-6D shows that induced pluripotent stem cells were not generated during the reprogramming process.
Figure 6B:
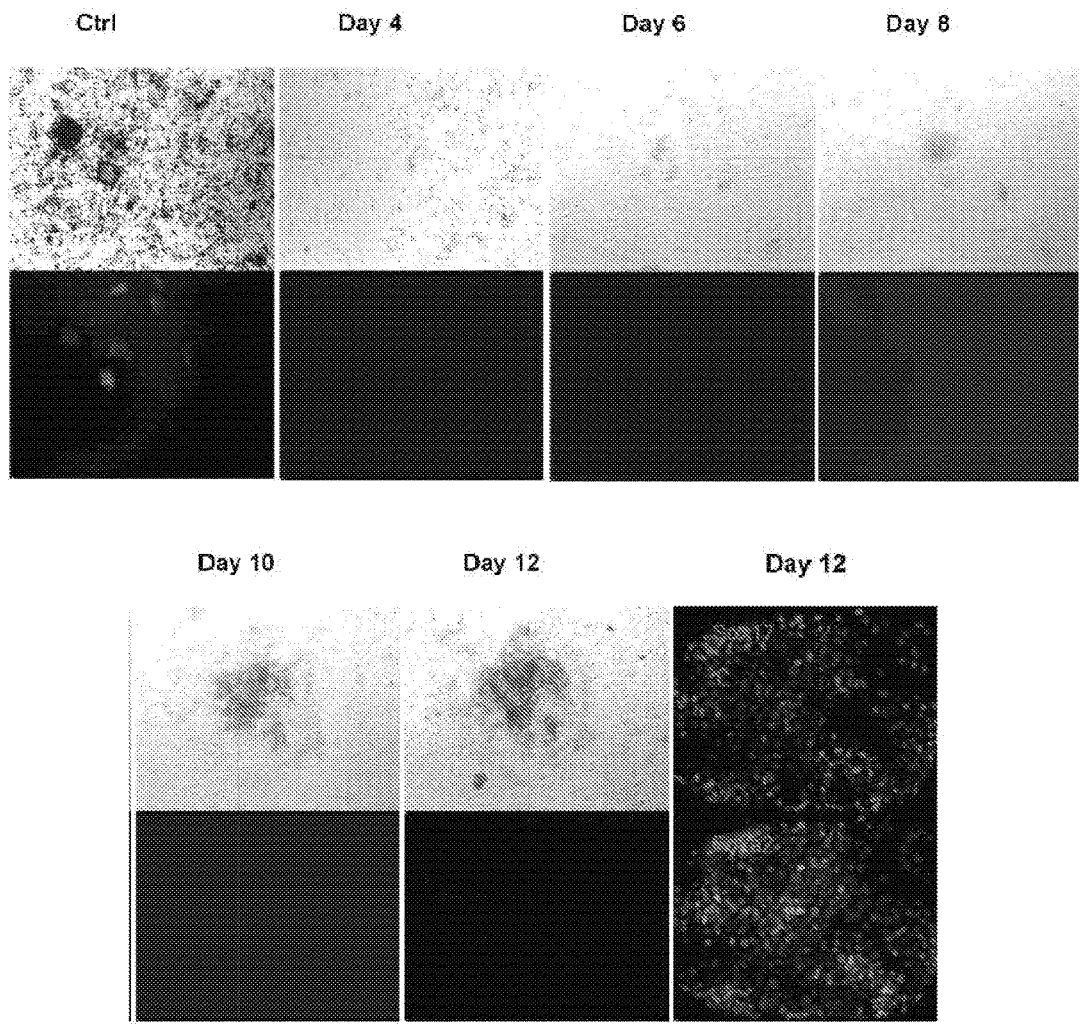

Generating iPSCs from secondary MEFs requires at least 9 days of Dox treatment with LIF, followed by an additional 7-10 days of culture, as confirmed by expression of a knock-in GFP reporter for Nanog, a pluripotency gene (Wernig, Lengner et al. 2008). However, when the procedures described herein were employed, no Nanog-GFP-positive cells were detected during reprogramming of MEFs to DELCs, as assessed via time-lapse imaging (FIG. 6B). This finding is consistent with the inventors' previous studies on direct cardiac, neural and endothelial cell reprogramming. As detected by qRT-PCR, Nanog and Rex1 (another pluripotency gene) expression remained nearly undetectable during the whole process, while endoderm marker genes were induced from day 4 and peaked on day 12 (FIG. 6A). On day 12, the expression levels of these endoderm marker genes were comparable to or higher than those of iPSC-derived definitive endoderm cells (FIG. 6A).

Figure 6C:
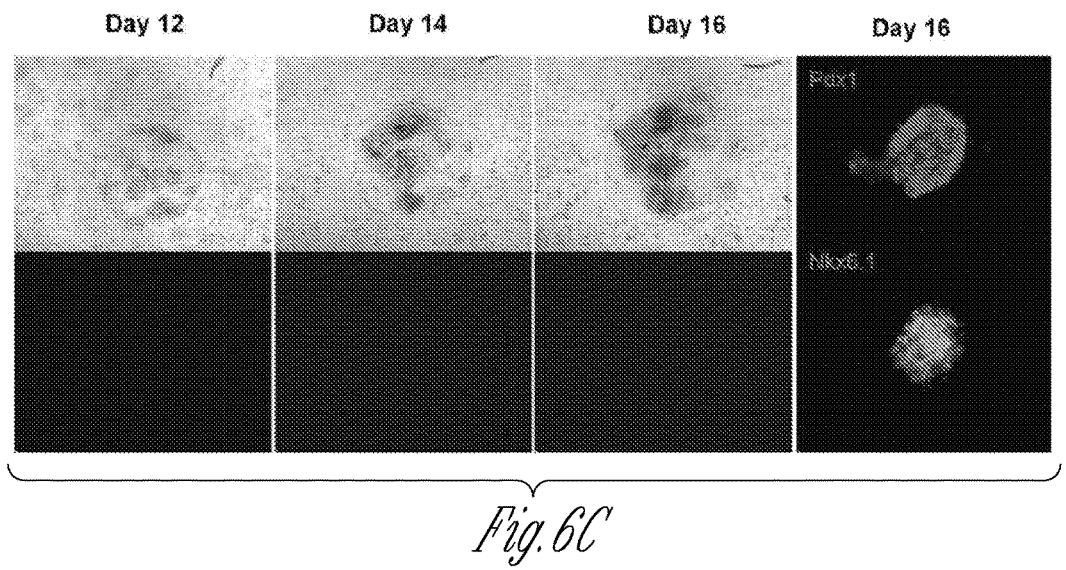
Figure 6D:
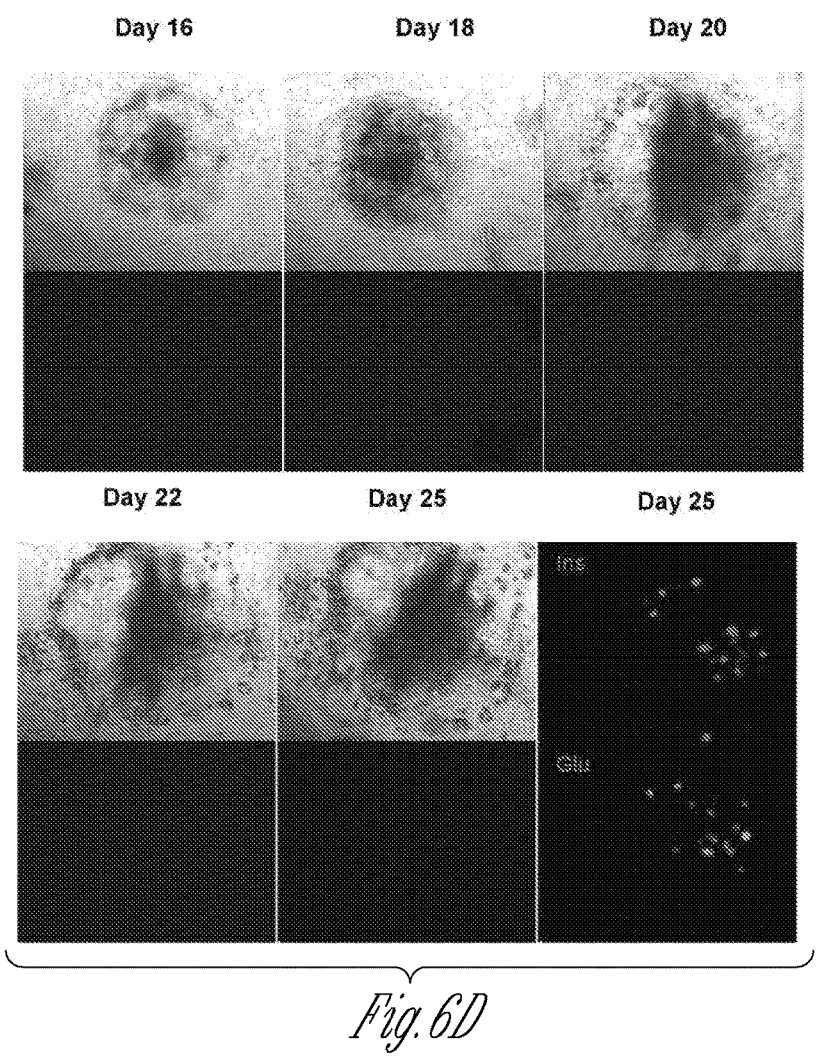

Similarly, Nanog-GFP-positive cells were not detected by time-lapse imaging during the third and fourth steps of differentiation (FIG. 6C-6D). Expression of the pancreatic progenitor markers Pdx1/Nkx6.1 were detected at the end of step III, and the endocrine pancreatic markers insulin and Glucagon were detected at the end of step IV by immunostaining and/or by q-RT-PCR (FIG. 6A, 6C, 6D). These results confirmed that the methods described herein can directly reprogram MEF cells to DELCs and eventually generate pancreatic-like cells without starting from iPSCs.

Example 6: In Vivo Characterizations of Pancreatic Progenitor-Like Cells

This Example shows that the pancreatic progenitor-like cells generated as described above can give rise to insulin secreting pancreatic beta cells that can regulate blood glucose levels in vivo.

To assess PPLC function in vivo, PPLCs were transplanted under the kidney capsules of immunodeficient NOD.Cg-Prkdcscid Il2rgtm1Wjl/SzJ (NSG) mice, which had been induced to become hyperglycemic by intraperitoneal injection of STZ (Streptozocin). Mice were considered diabetic when blood glucose measurements were >300 mg/dl for 4 consecutive days, at which stage they were used as transplant recipients. Each recipient received a renal subcapsular transplant of about $3 \times 10^6$ pancreatic progenitor-like cells or $3 \times 10^6$ MEF cells. Untreated normal and STZ-only-treated NSG mice were used as controls. Blood glucose levels were measured weekly after surgery.

Figure 7A:
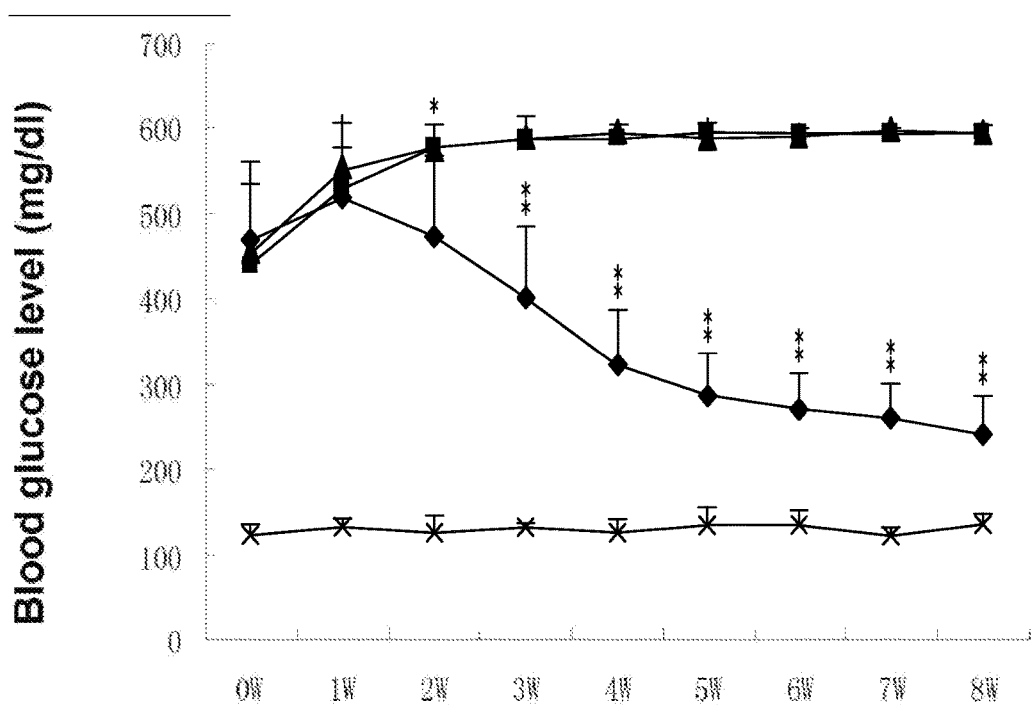
FIGS. 7A-7D shows that pancreatic progenitor like cells can regulate glucose levels and insulin secretion in vivo.

In the untreated control group, blood glucose levels remained normal, as expected (FIG. 7A). The lower line (X symbols) shows the blood glucose levels of normal mice. As shown in FIG. 7A, the STZ-only group (filled triangles), glucose levels increased gradually and peaked by the end of the third week. In the STZ-treated group that received MEF cells (filled squares), glucose levels increased similar to the STZ-only group.

Figure 7B:
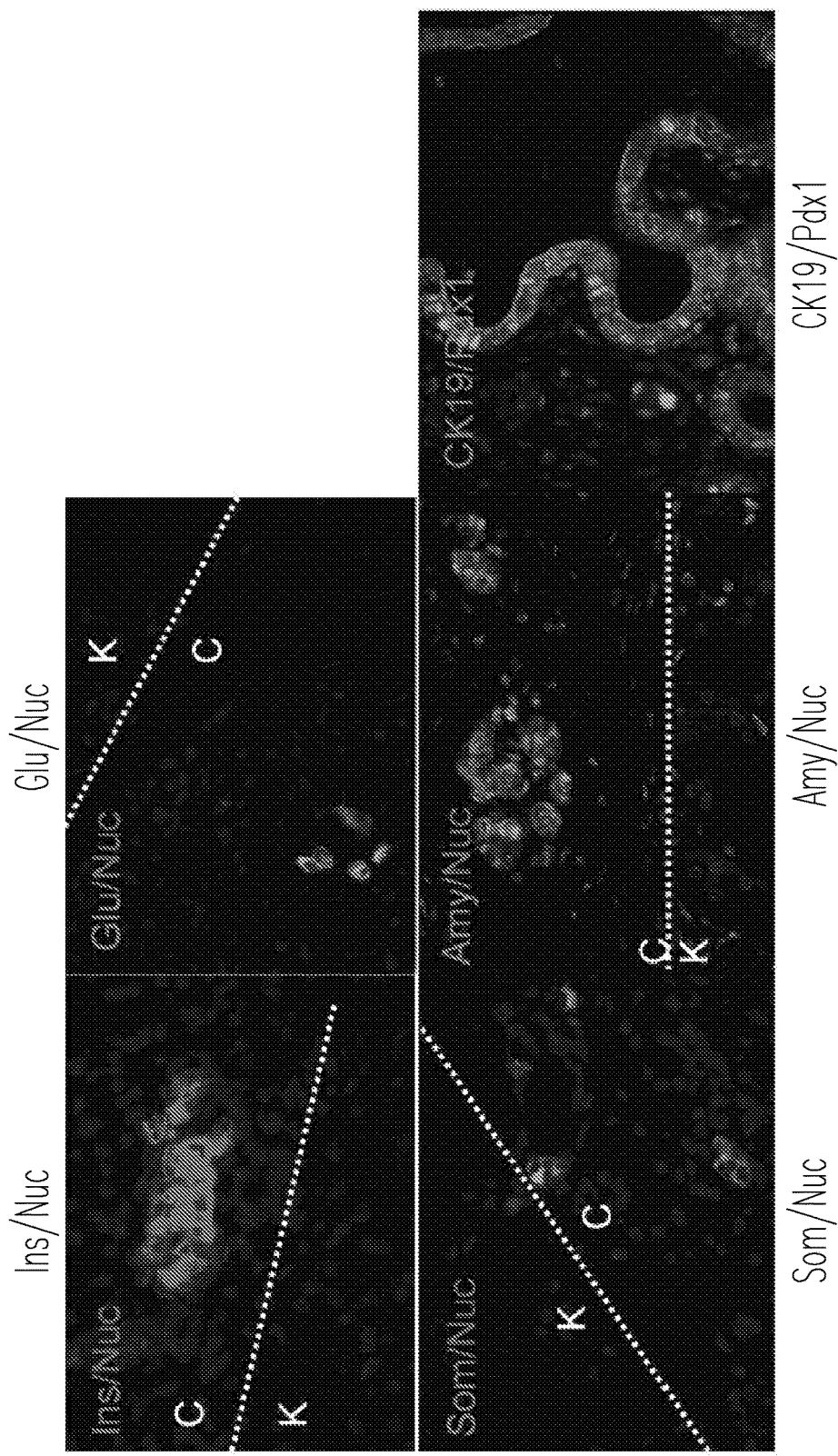
Figure 7C:
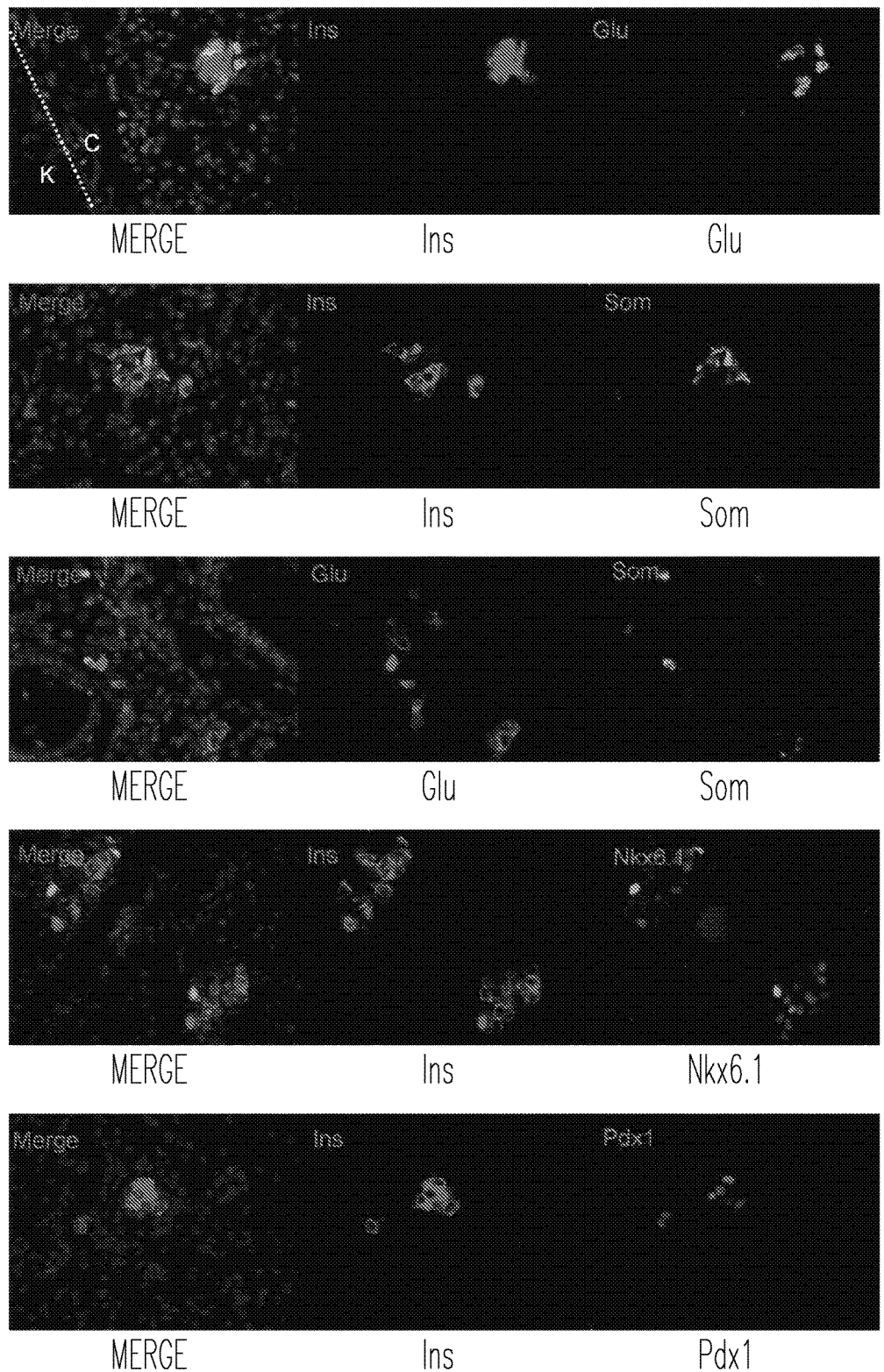

In contrast, STZ-treated mice, who had received transplantation of PPLCs, exhibited a transient increase in glucose levels within the first week that decreased gradually thereafter and that approached levels in normal mice by about week 7 (FIG. 7A, filled diamonds). These data indicate that the implanted PPLCs differentiated into insulin-secreting cells within the first 2 weeks of transplantation. At the end of 3 weeks, the kidneys of three mice from each of the two cell-transplanted groups were harvested for immunofluorescence analyses. In kidney capsules engrafted with PPLCs, glucagon-producing pancreatic alpha-like cells, insulin-producing pancreatic beta-like cells, somatostatin-producing pancreatic delta-like cells, amylase-producing pancreatic acinar-like cells, and Pdx1/Ck19$^+$ pancreatic ductal-like cells were identified (FIG. 7B). In contrast, none of these genes were expressed in kidney capsules engrafted with MEF cells. Furthermore, the detected insulin-positive cells were also Pdx1- and Nkx6.1-positive (FIG. 7C). Importantly, these endocrine-like cells were nearly all singly hormonal, and bi-hormonal cells were rarely detected (FIG. 7C), which is consistent with the in vitro findings described herein.

Figure 7D:
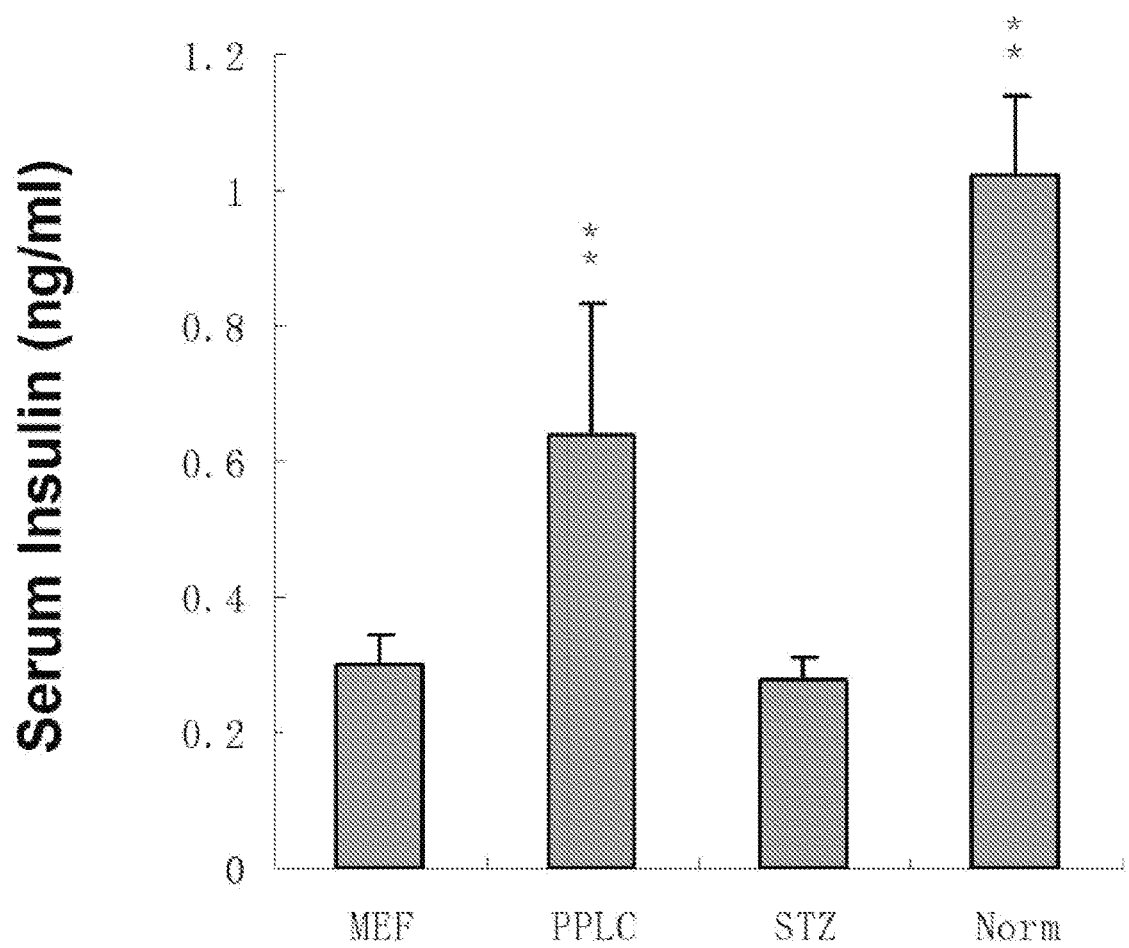

To assess serum insulin levels, blood samples were collected at the end of 8 weeks and analyzed by ELISA. Transplantation of PPLCs to the diabetic mice significantly increased the level of circulating insulin, compared with MEF-grafted mice (FIG. 7D). There was no significant difference in serum insulin levels between STZ-only mice and STZ mice transplanted with MEF cells. These results showed that PPLCs could mature in vivo into cells of all three pancreatic lineages, including functional, insulin-secreting beta cells that help to ameliorate hyperglycemia in vivo.

Example 7: Materials and Methods for Conversion of Human Fibroblasts into Endodermal Progenitor Cells This example describes procedures for generating endodermal progenitor cells from human fibroblasts.

Conversion of Human Fibroblasts into Endodermal Progenitor Cells

All cell culture products were from Invitrogen/Gibco BRL and all chemicals and growth factors were from Stemgent except where mentioned.

Human foreskin fibroblasts (CRL-2097, ATCC) were cultured in a 10 cm tissue culture dish in regular fibroblast culture medium. Reprogramming with episomal vectors was done as described by Okita et al. (2011). Briefly, $4 \times 10^5$ fibroblasts were electroporated with up to 6 μg of episomal vectors (pCXLE-hOCT3/4-shp53-F, pCXLE-hSK and pCXLE-EGFP) using the Microporator Human Dermal Fibroblast (NHDF) Nucleofector™ Kit (Lonza) according to the manufacturer's instructions. Cells were cultured in fibroblast medium for 4 days and then re-plated onto Matrigel-coated 10 cm dishes at a density of 50,000 cells per dish. The cells were then cultured in reprogramming initiation medium (DMEM/F12, 10% Knockout serum replacement, 5% ES-FBS, 1% Glutamax, 1% Non-essential amino acids, 1% penicillin/streptomycin, 0.1 mM β-mercaptoethanol, 10 ng/ml bFGF, 10 ng/ml EGF, 2 μM Parnate, 0.5 μM RG108, 0.1 mM sodium butyrate, 0.5 μM NECA, and 3 μM CHIR99021) for 1 week, followed by endodermal induction medium (Advanced RPMI, 2% ES-FBS, 1% Glutamax, 1% Non-essential amino acids, 1% penicillin/streptomycin, 0.1 mM β-mercaptoethanol, 2 μM Parnate, 0.5 μM RG108, 0.1 mM sodium butyrate, 0.5 μM NECA, 3 μM CHIR99021, and 100 ng/ml Activin A) for another 2-3 weeks. The converted colonies were carefully picked up for expansion in expansion medium (DMEM, 1% Glutamax, 0.5×N2, 0.5×B27 media supplement (Invitrogen), 5 μg/ml BSA, 1% penicillin/streptomycin, 10 ng/ml bFGF, 10 ng/ml EGF, 0.5 μM A83-01, and 3 μM CHIR99021) and were passaged at 1:4-1:6 each time by Accutase treatment. Routinely, 0.5 μM thiazovivin was used during the first 12-24 hour period of each passage to prevent cell death after dissociation.

Differentiation of Posterior Foregut-Like Progenitor Cells (cPF Cells) into Pancreatic Endodermal Progenitor Cells (cPE Cells)

For pancreatic differentiation, posterior foregut-like progenitor cells were cultured in pancreatic differentiation medium (DMEM, 1% Glutamax, B27, 5 μg/ml BSA, 1% penicillin/streptomycin) with 25 ng/ml FGF7, 25 ng/ml FGF10, 0.5 μM A83-01, 0.1 μM Compound E, 2 μM Retinoic acid, 0.1 μM GDC-0449, and 0.1 μM LDN-193189 for 2 days; then 50 ng/ml EGF, 50 ng/ml Exendin-4, 0.5 μM A83-01, 0.1 μM Compound E, 50 nM TPB, 0.1 μM LDN-193189, and 10 mM nicotinamide for another 3 days. After differentiation, the pancreatic endodermal progenitor (cPE) cell population was passaged with Accutase and cultured in cPE expansion medium (DMEM, 1% Glutamax, 1×B27, 5 μg/ml BSA, 1% penicillin/streptomycin, 10 ng/ml bFGF, 50 ng/ml EGF, and 0.5 μM A83-01). Routinely, 0.5 μM thiazovivin was used during the first 12-24 hour period of each passage to prevent cell death after dissociation.

Maturation of Pancreatic Endodermal Progenitor (cPE) Cells into Pancreatic Beta-Like Cells (cPB Cells) In Vitro The pancreatic endodermal progenitor (cPE cells) were differentiated into beta-like cells in the pancreatic maturation media with DMEM, 1% Glutamax, B27, 5 μg/ml BSA, and 1% penicillin/streptomycin, 50 ng/ml Exendin-4, 1 μM A83-01, 10 μM forskolin, 10 μM dexamethasone, 10 mM nicotinamide, 0.1 μM Compound E, 50 μg/ml vitamin C, and 2 μM Bayk-8644 for 10 d, and then cultured as 3D aggregates in low-attachment plates for another 8-12 days.

Immunofluorescence Staining

Figure 8B:
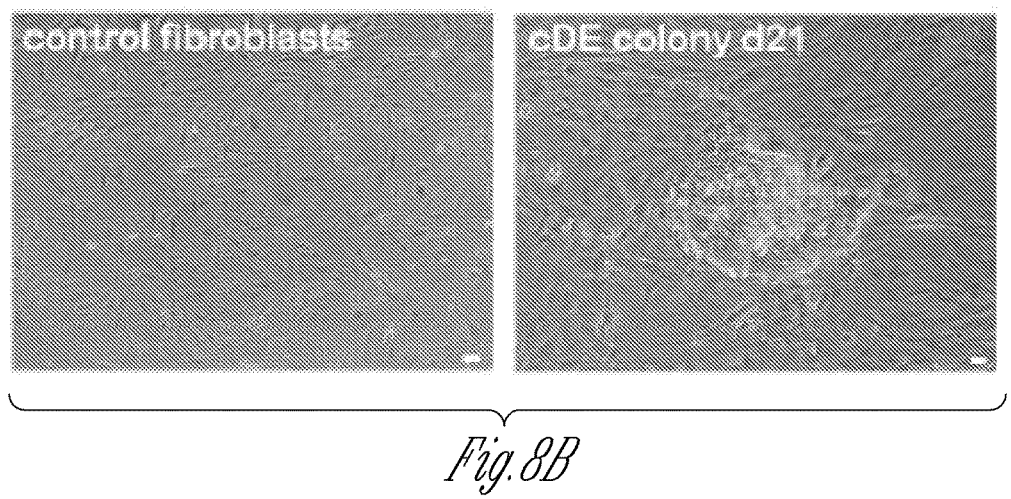
Figure 8C:
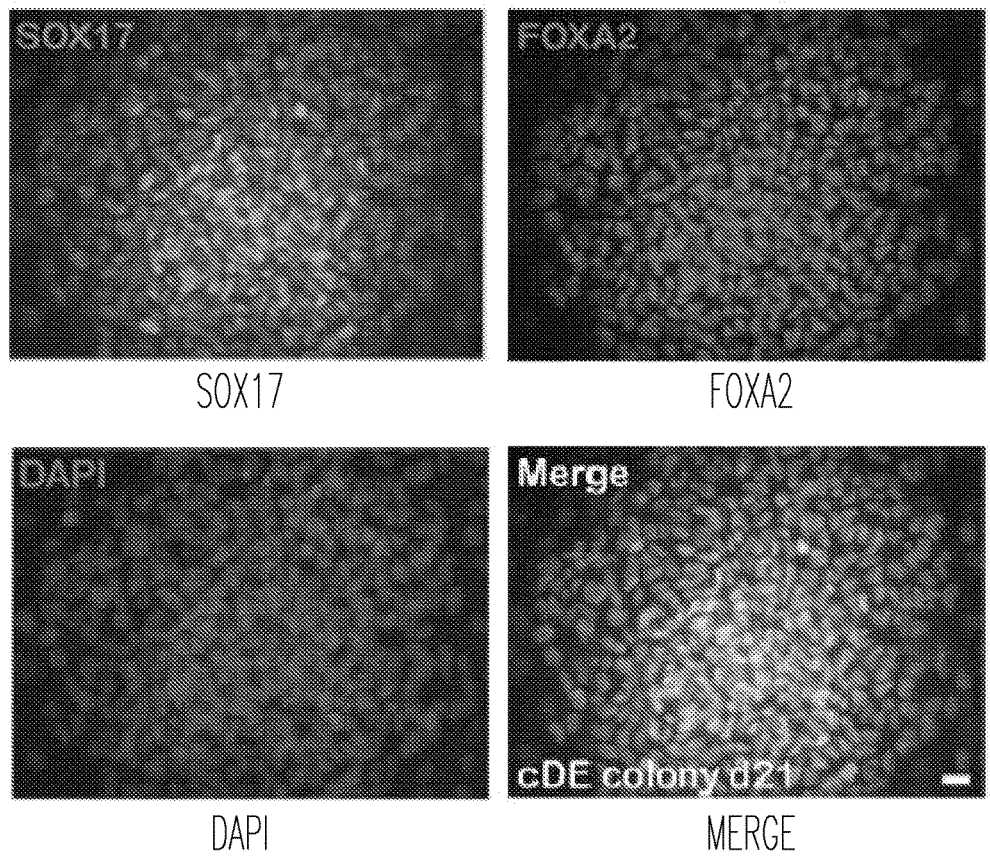
Figure 8G:
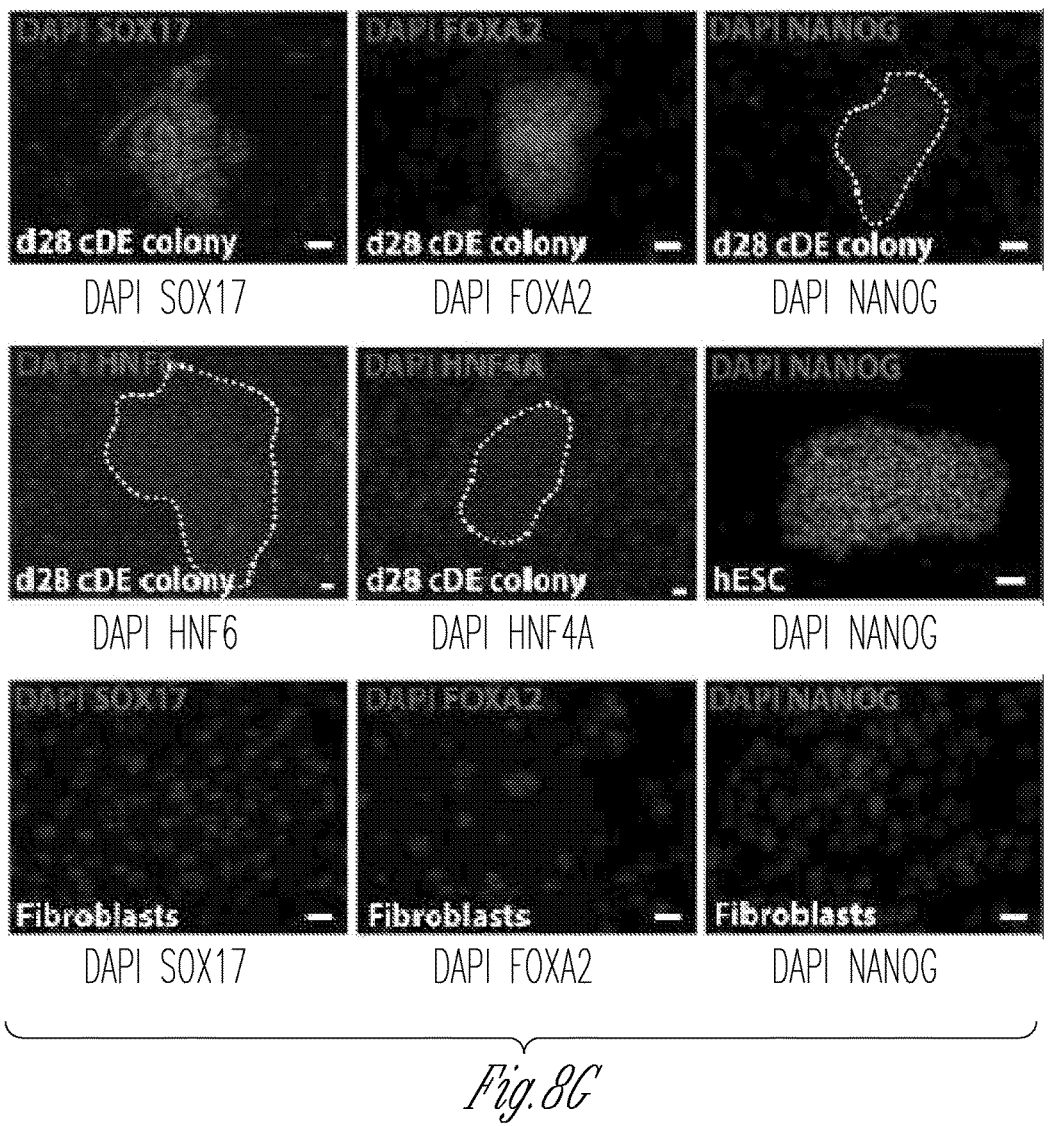
Figure 9A:
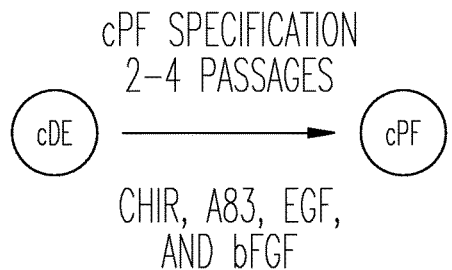
FIGS. 9A-9L illustrate the specificity, expansion and characterization of human posterior foregut-like progenitor cells.
Figure 9B:
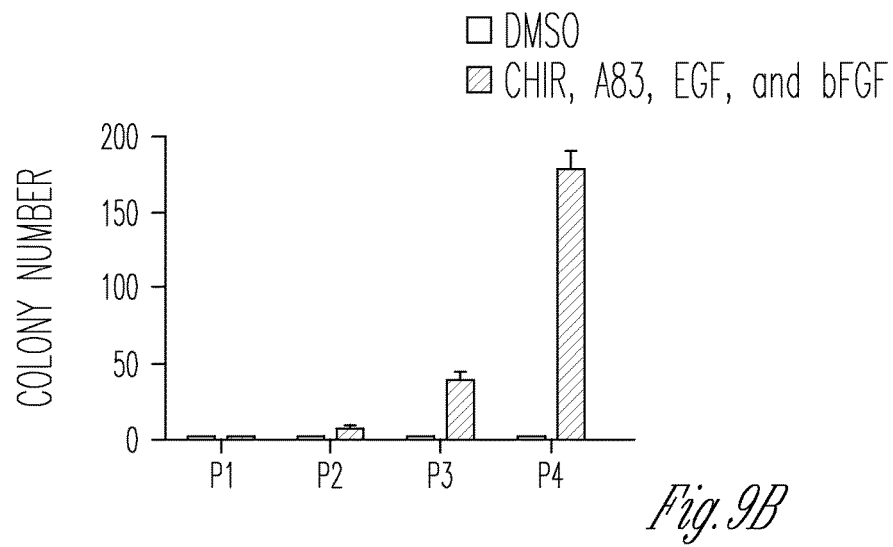
Figure 9C:
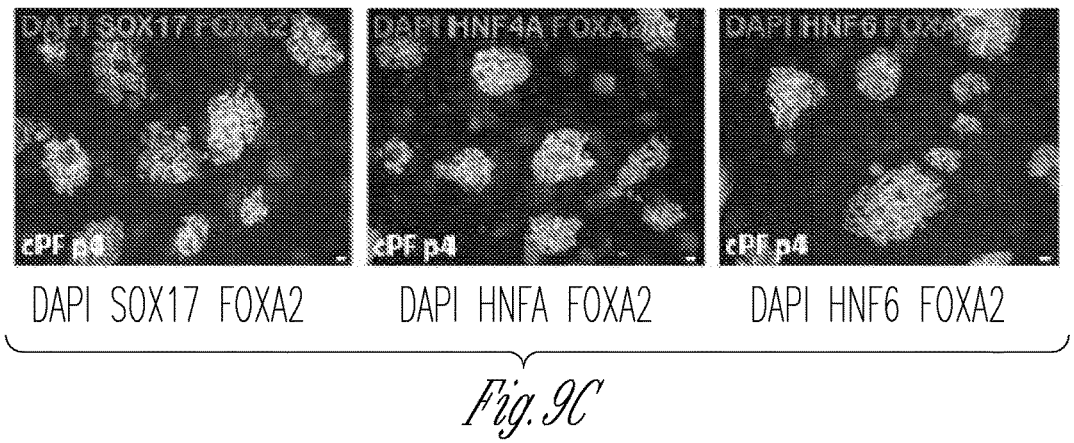
Figure 9D:
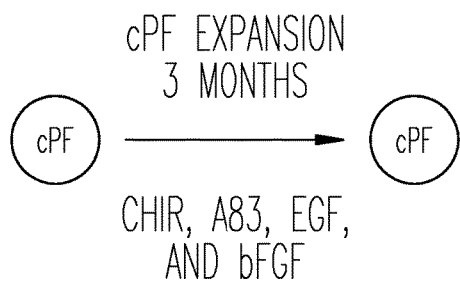
Figure 9E:
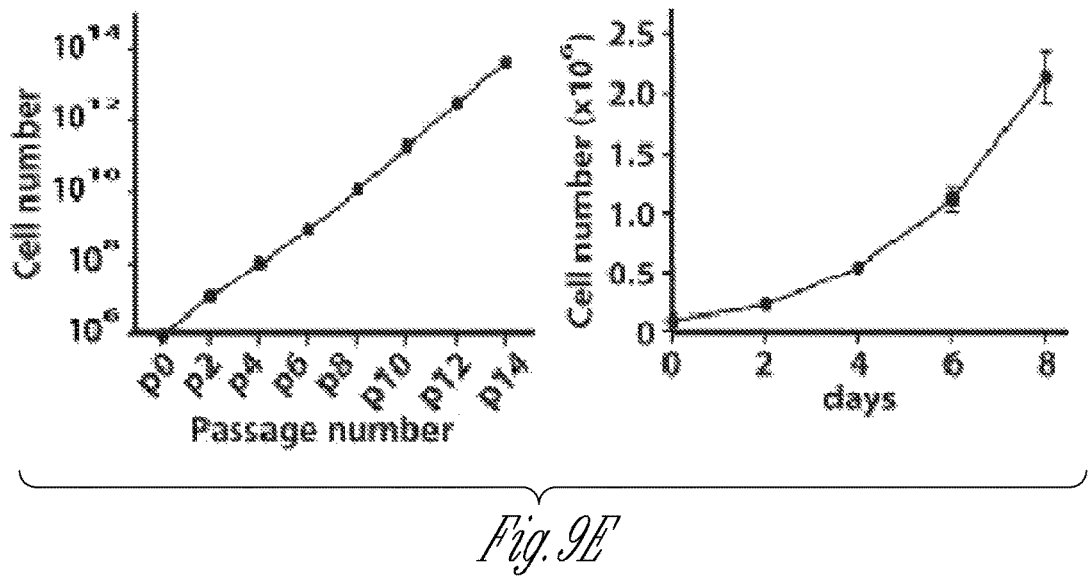
Figure 9F:
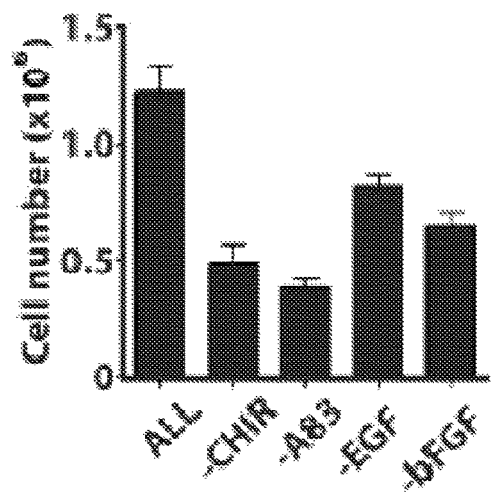
Figure 9G:
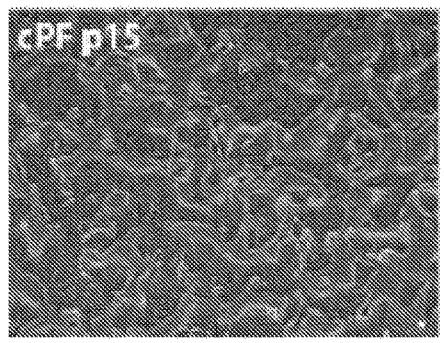
Figure 9H:
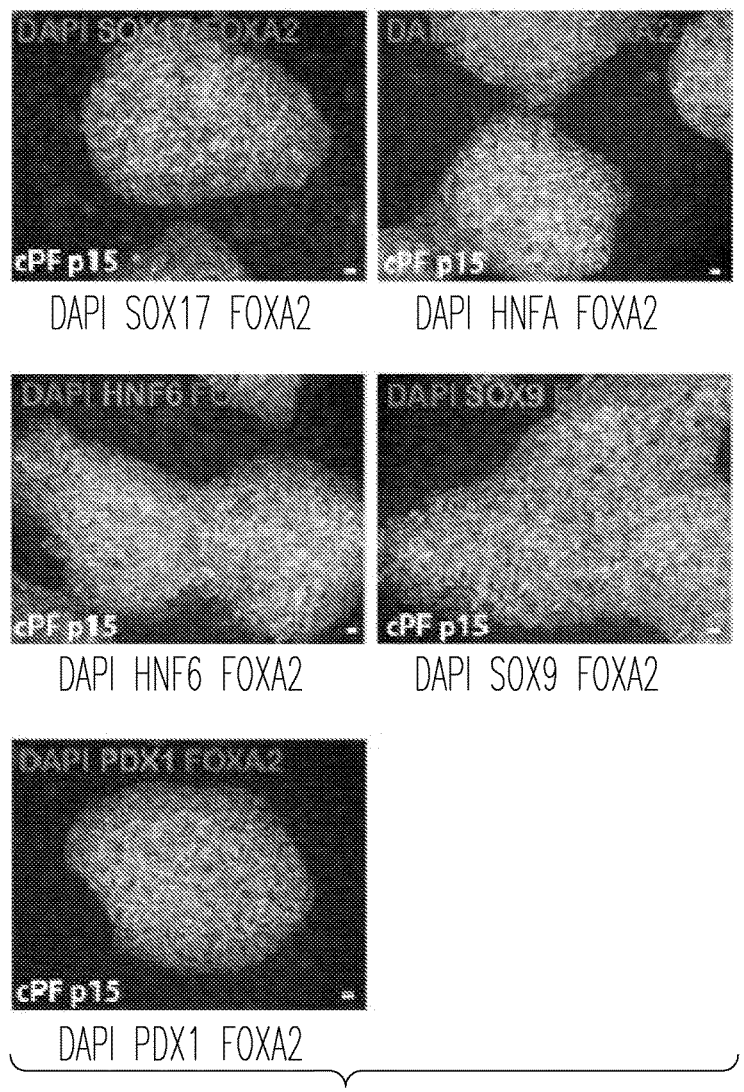
Figure 9I:
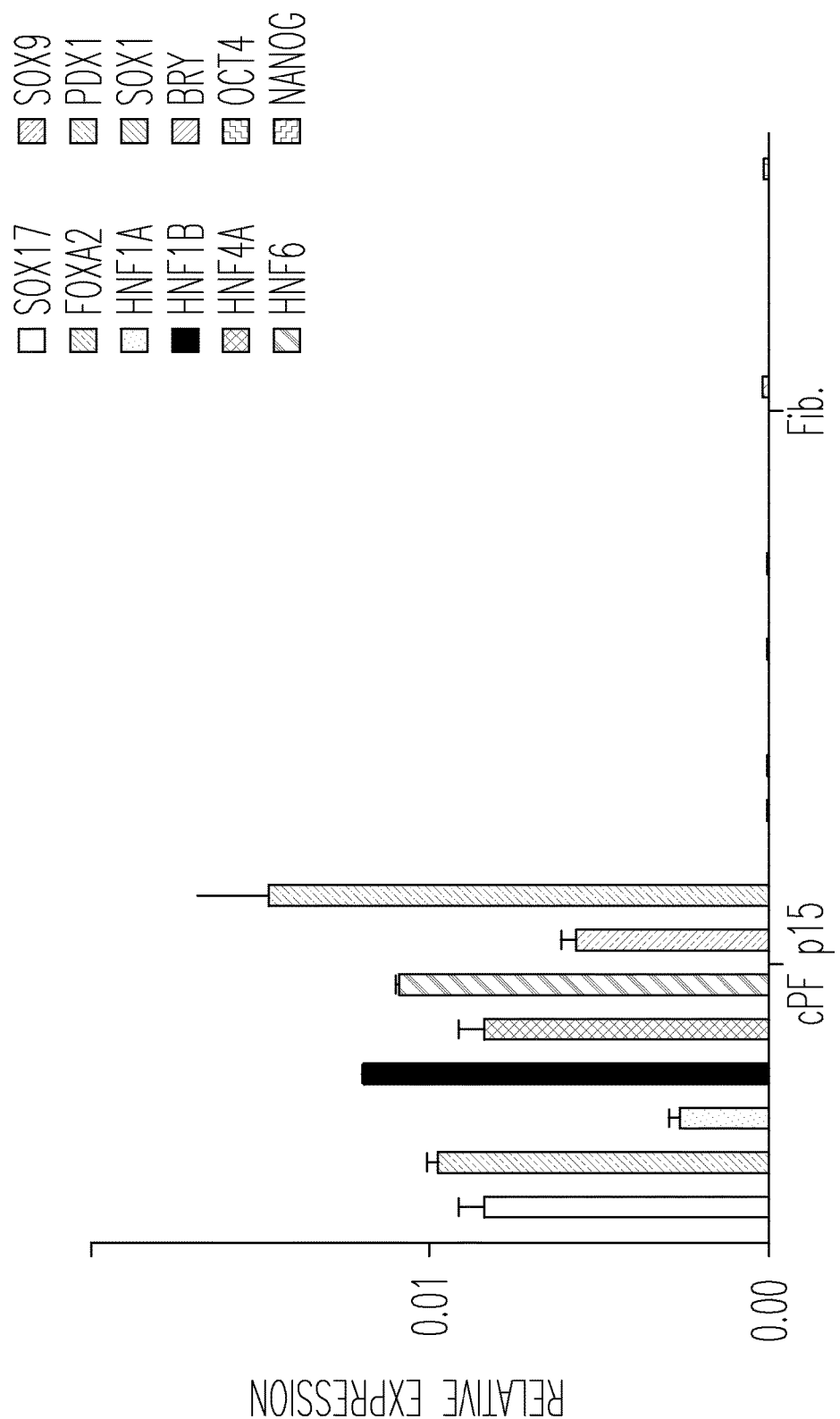
Figure 9J:
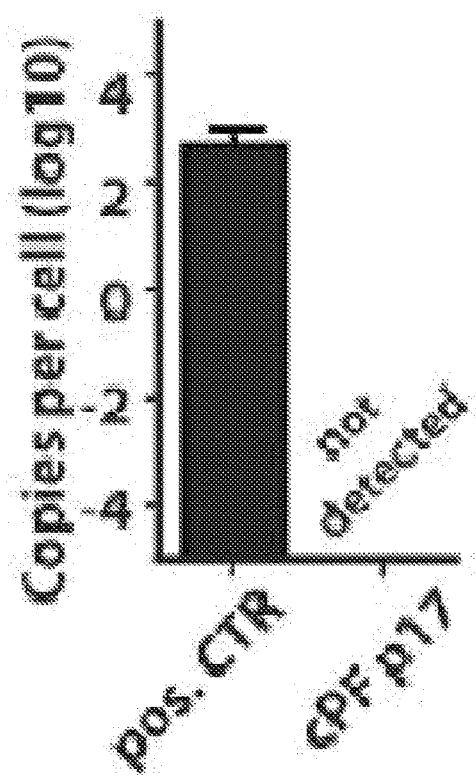
Figure 9K:
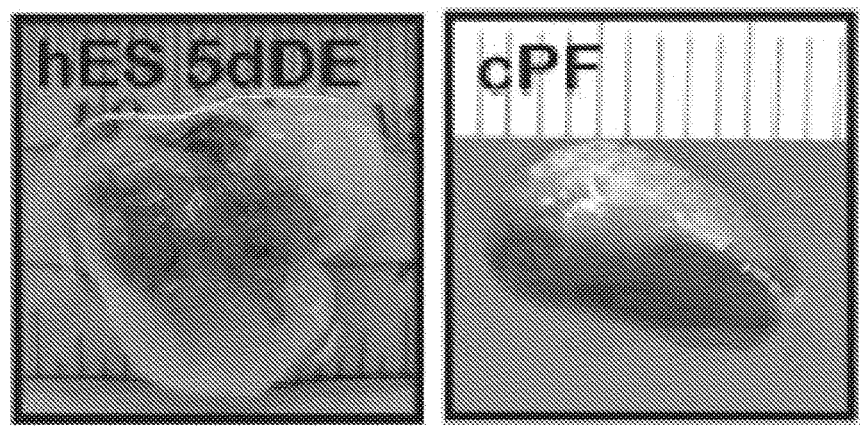
Figure 9L:
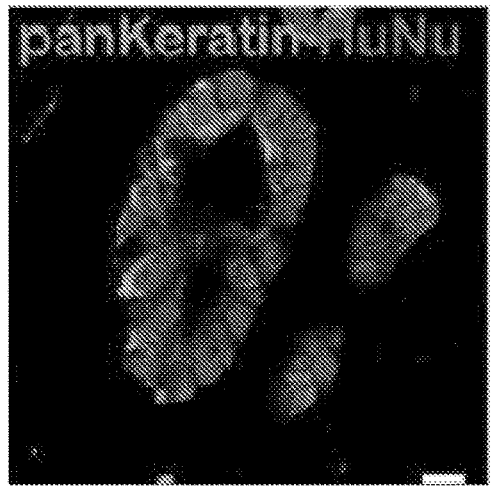
Figure 9L:
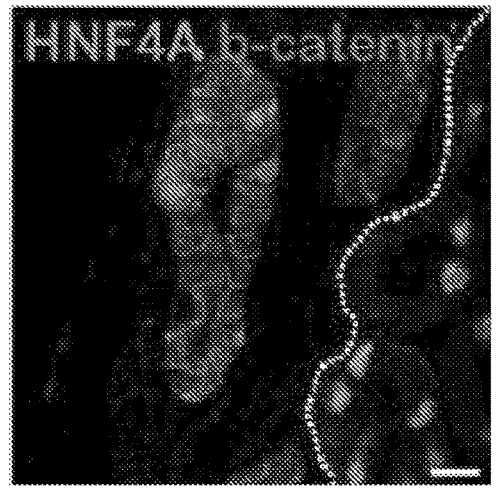
Figure 9L:
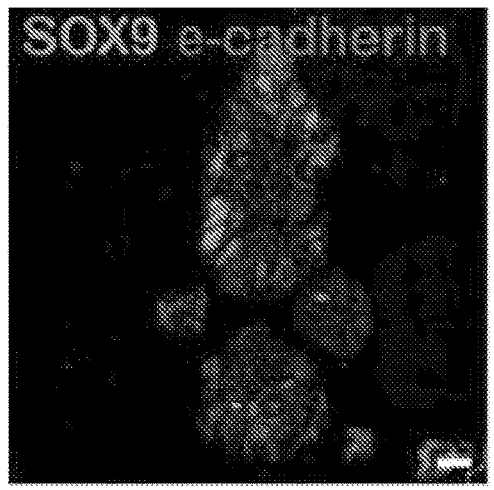
Figure 9L:
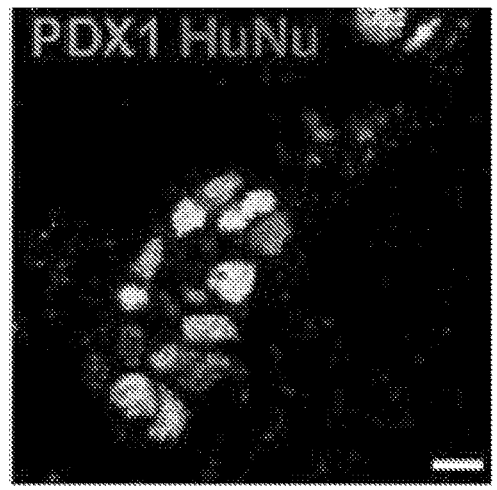
Figure 10A:
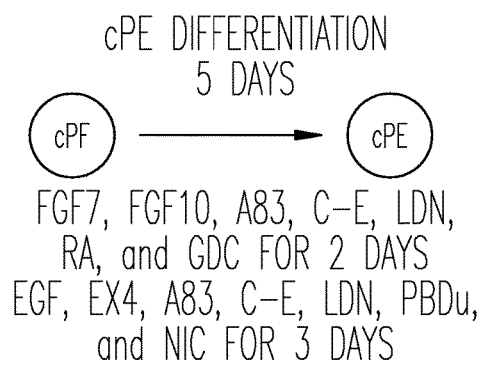
FIGS. 10A-10L illustrate the differentiation of human posterior foregut-like progenitor cells (cPF cells) into expandable pancreatic endodermal progenitor cells with the ability to mature into functional beta-like cells in vivo.
Figure 10B:
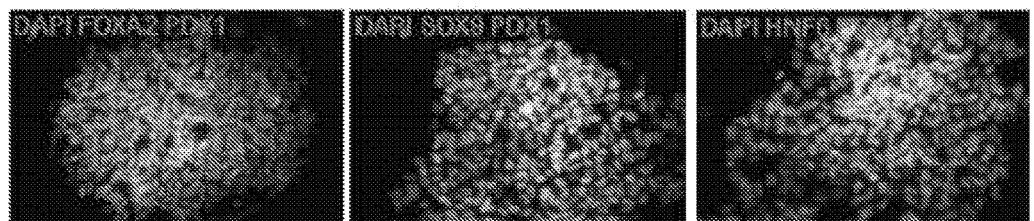
Figure 10C:
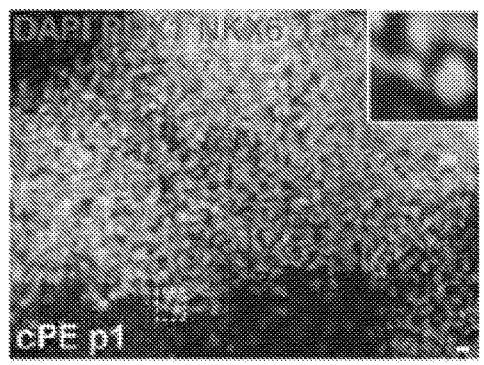
Figure 10D:
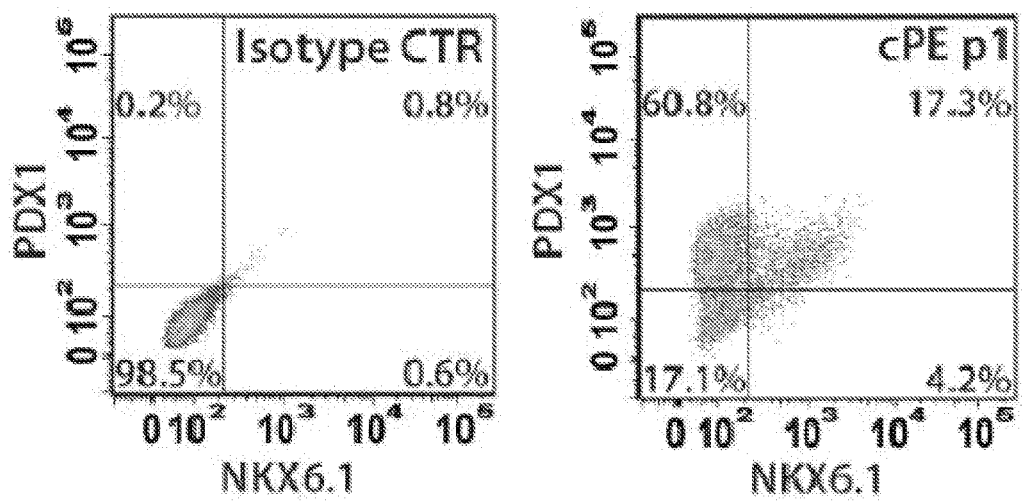
Figure 10E:
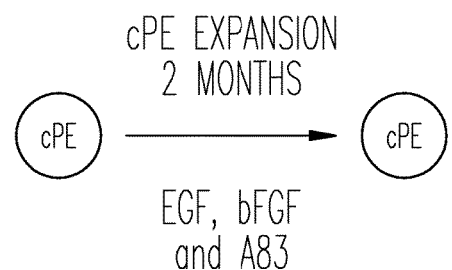
Figure 10F:
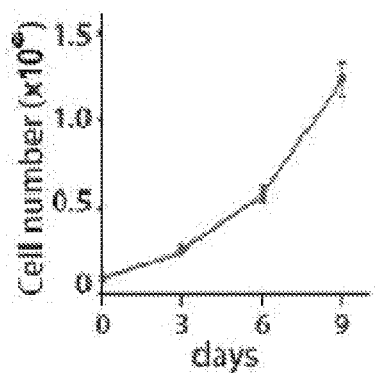
Figure 10G:
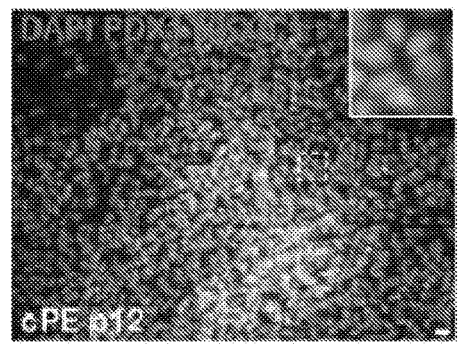
Figure 10H:
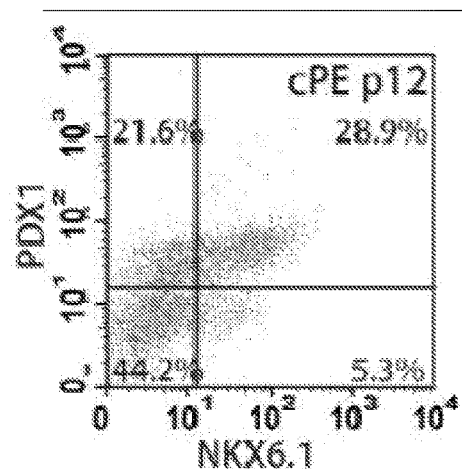
Figure 10I:
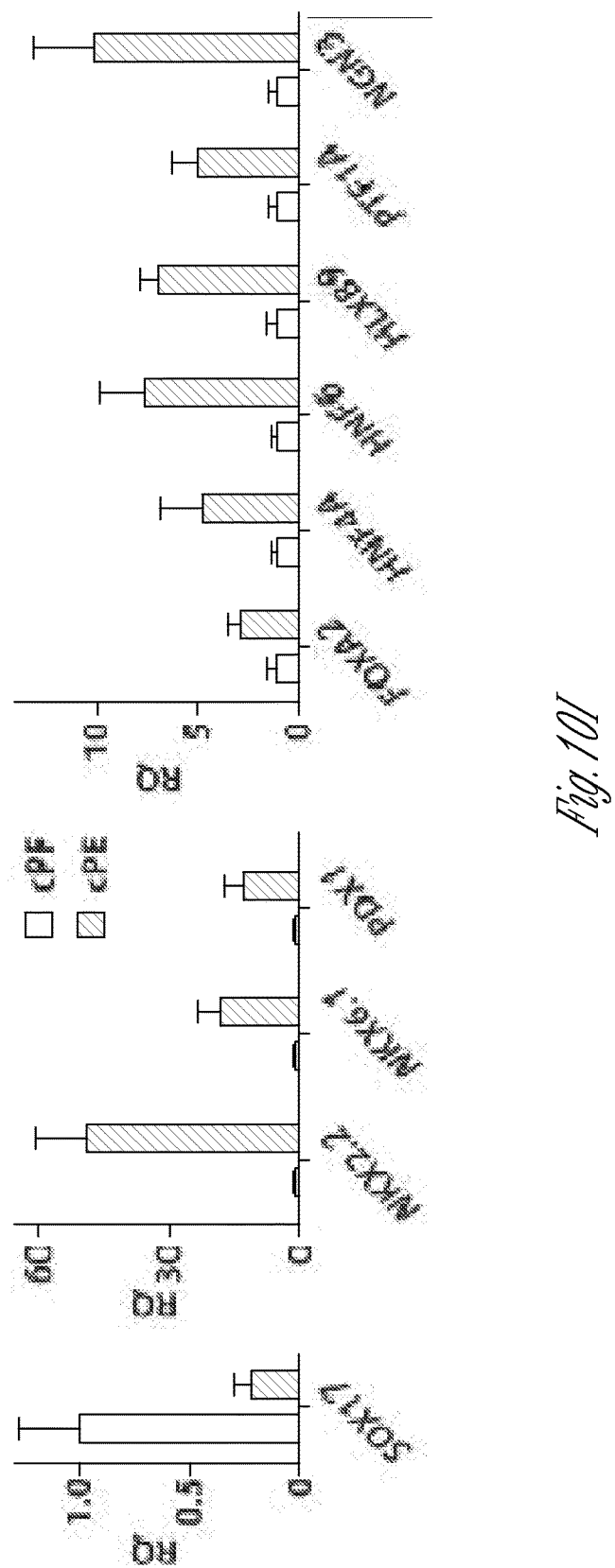
Figure 10J:
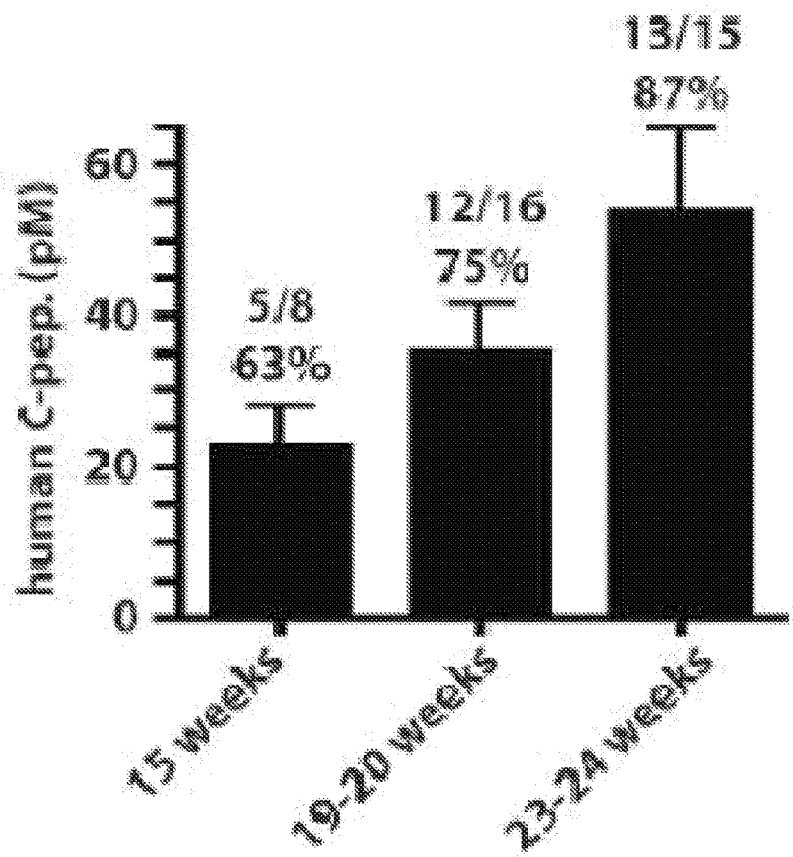
Figure 10K:
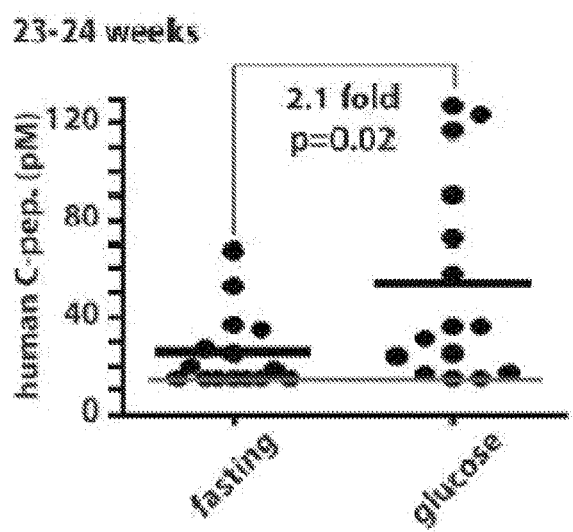
Figure 10L:
Figure 10L:

Standard immune-staining was carried out as previously reported by Russ et al. (*PLoS One* 6, e25566 (2011)). For cell cluster staining primary and secondary antibodies were incubated overnight at 4° C. Secondary antibodies were Alexa Fluor conjugated (1:500-1000) (Invitrogen). Nuclei were visualized by Hoechst (Sigma-Aldrich) staining Images were captured using a Nikon Eclipse TE2000-U microscope or a SP5 confocal microscope. The primary antibodies used included SOX17, FOXA2, NANOG, HNF6, and HNF4A, with DAPI staining for nuclei. Representative images of cells from at least five independent experiments are shown in FIGS. 8B, 8C, 9G, and 9H. A representative image of at least three independent experiments is shown in FIGS. 9C, 9L, 10B, 10C, 10G, and 11B. A representative picture of three independent experiments is shown in FIGS. 8G, 11B, 11G and 11H. A representative image of two independent mice is shown in FIG. 10L.

Flow Cytometry

Cells were harvested at the indicated time points by Accutase treatment, fixed with 4% formaldehyde solution, and washed five times with ice-cold Perm/Wash buffer (BD). Cells were aliquoted and incubated individually or combinatorially with antibodies and isotype controls on ice for two hours. Cells were washed with Perm/Wash buffer for five times and incubated individually with Alexa Fluor 488-conjugated or Alexa Fluor 555-conjugated antibodies (1:500, Invitrogen) on ice for one hour. Cells were washed with Perm/Wash buffer for five times, re-suspended in 0.5 ml ice-cold PBS with 2% FBS, and analyzed by FACSCalibur and CellQuest software (BD). FlowJo software (Tree Star) was used to analyze the data.

Quantitative PCR

For quantitative PCR analysis, total RNA was extracted using the RNeasy Plus Mini Kit in combination with QIAshredder (Qiagen). First strand reverse transcription was performed with 1 μg RNA using iScript™ cDNA Synthesis Kit (BioRad). Quantitative PCR was taken out using iQ SYBR Green Supermix (Bio-Rad). The primers used are detailed in Table S2.

Kidney Capsule Transplantation

Mice used in this study were maintained according to protocols approved by the University of California, San Francisco, Committee on Laboratory Animal Resource Center. The kidney capsule transplantation was done as previously reported[40]. Briefly, cells were collected from culture dishes by cell scraper, and injected under the renal capsule of immune-deficient NSG (NOD.Cg-Prkdc$^{scid}$ Il2rg$^{tm1Wjl}$/SzJ) male mice (six to ten week old). For transplantation assays of established cPF cell lines, hESC-derived definitive endoderm generated by differentiation for 1 day in RPMI containing 100 ng/ml ActivinA and 50 ng/ml WNT3a, followed by 4 days in RPMI containing 0.2% FBS and 100 ng/ml ActivinA served as control. Grafts were dissected and analyzed at the indicated time points.

Glucose Stimulated Insulin Secretion (GSIS) Assays

Cell were pre-incubated for 1 hour in Krebs-Ringer buffer (KRB), followed by incubation for 1 hour in KBR containing 2.8 mM glucose followed by 1 hour incubation in KRB containing 16.7 mM Glucose followed by 30 min in KRB containing 16.7 mM Glucose and 30 mM KCl. Human C-peptide levels were quantified using an ultrasensitive ELISA kit (Mercodia; cross-reactivity with insulin and proinsulin, 0.0006% and 1.8%, respectively).

Statistics.

Indicated P values were obtained using a two-tailed t-test, and all quantitative data are shown as mean±s.e.m. No statistical method was used to predetermine sample size. No samples were excluded. The experiments were not randomized. The investigators were not blinded to allocation during the experiments and outcome assessment.

Figure 8A:
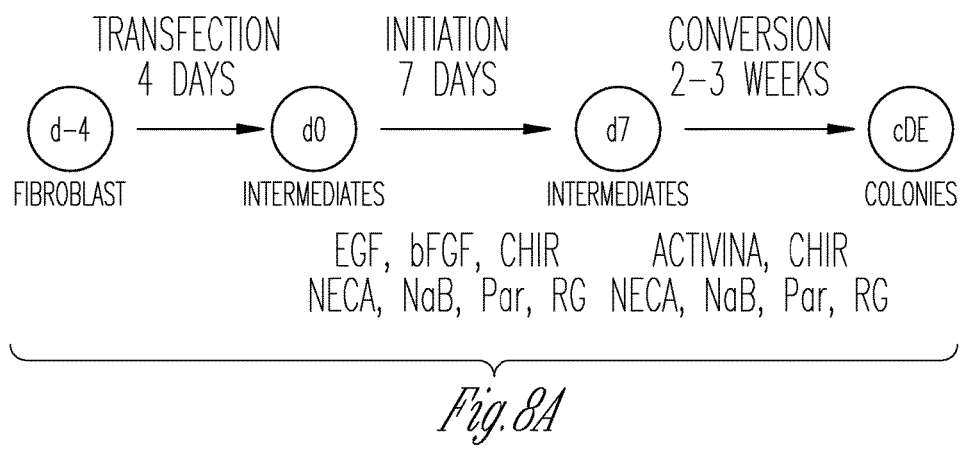
Figure 8D:
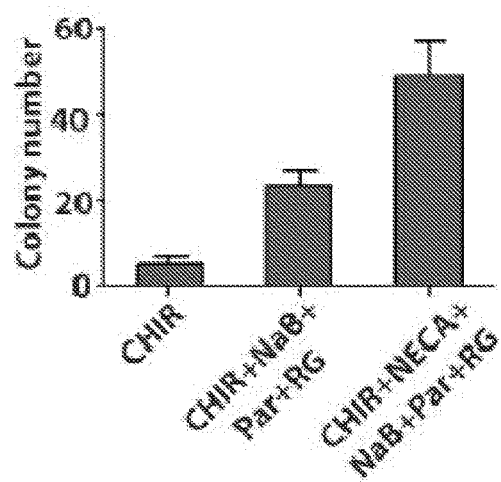
Figure 8E:
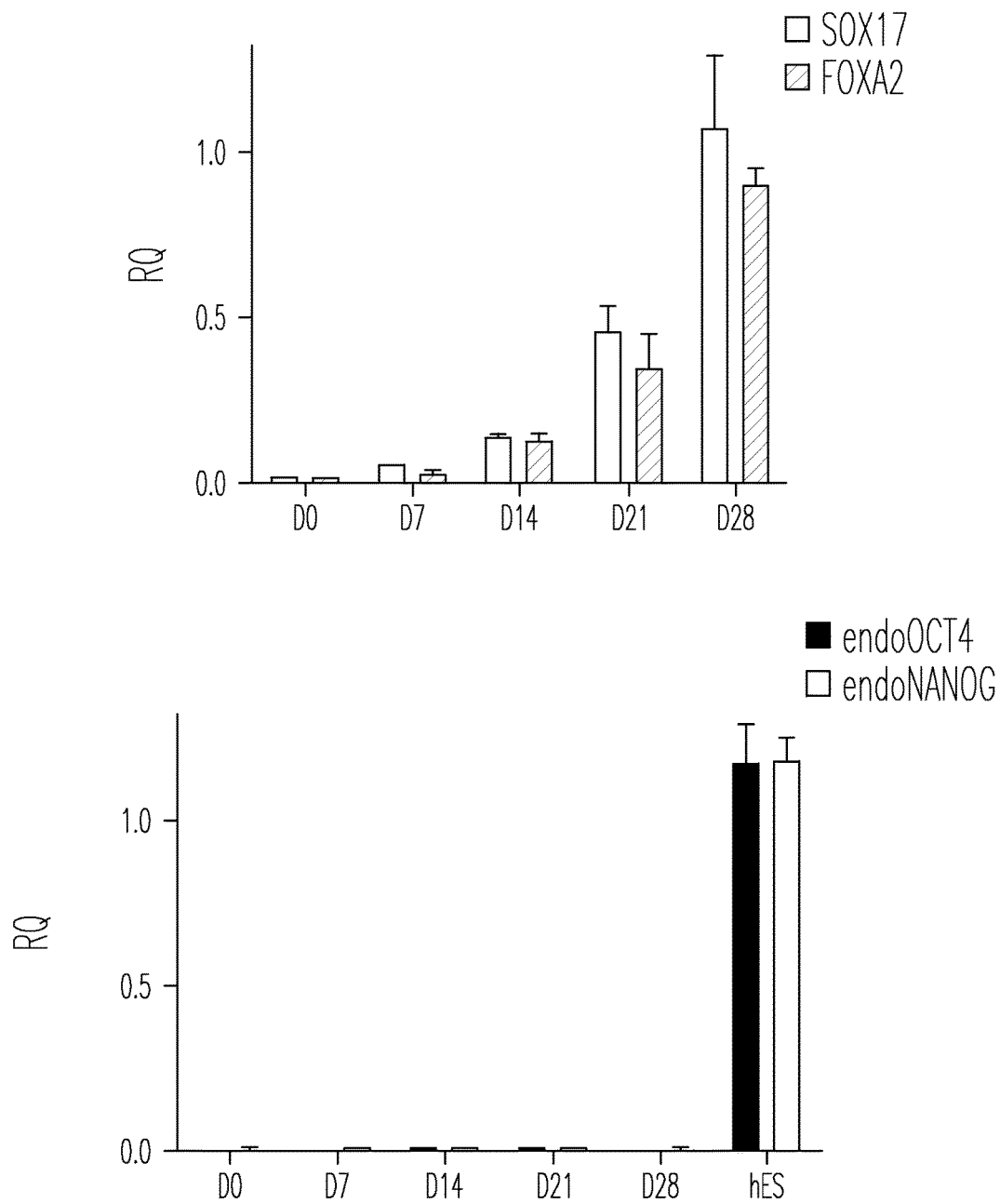

Example 8: Direct Conversion of Human Fibroblasts into Definitive Endodermal Progenitor Cells Human foreskin fibroblasts were transduced with non-integrating episomal reprogramming factors, OCT4, SOX2, KLF4, and a short hairpin RNA against p53 as described in Example 7. The cells were allowed to recover in fibroblast medium for four days, and then they were cultured in initiation medium containing epidermal growth factor (EGF), basic fibroblast growth factor (bFGF) and CHIR99021 (an activator of WNT signaling) to support cell proliferation (FIG. 8A). After seven days, the culture conditions were switched to endodermal conversion media containing CHIR99021 and high level of Activin A (100 ng/ml) to establish converted definitive endodermal progenitor (cDE) cells, based on previous studies demonstrating key roles for the Activin A and WNT signaling pathways in endodermal fate decision in vitro and in vivo (Stainier et al. (2002); Tian et al. (2006); D'Amour et al. (2005)). This basic endodermal conversion protocol gave rise to cell colonies with an epithelial morphology at day 21 to 28 (FIG. 8B). Colonies specifically stained for definitive endodermal progenitor markers SOX17 and FOXA2, but not for the pluripotency marker NANOG or primitive gut marker genes HNF4a and HNF6 (FIGS. 8C and 8G). As expected, control fibroblasts were negative for endodermal and pluripotency markers (FIG. 8G). To increase the efficiency of the endodermal conversion protocol, a small scale screening was performed of chemical compounds known to contain bioactive molecules capable of directing cell differentiation (Zhu et al. (2010). The addition of a combination of epigenetic modulators, including sodium butyrate (NaB, a histone deacetylase inhibitor), Parnate (Par, a histone demethylase inhibitor), and RG108 (RG, a DNA methyltransferase inhibitor), significantly improved the conversion efficiency by 2.5 fold (FIG. 8D). Additional screening using this improved condition revealed that 5'-N-ethylcarboxamidoadenosine (NECA, an adenosine agonist) could further increase the conversion rate by 2-fold, resulting in 5-fold increase over the basal protocol (FIG. 8D). Notably, by employing this optimized condition we could generate approximately fifty FOXA2 and SOX17 double-positive cDE colonies from 400,000 human fibroblasts (FIG. 8D). Quantitative polymerase chain reaction (qPCR) revealed a gradual up-regulation of both SOX17 and FOXA2 gene transcripts starting at day 14 (FIG. 8E). In contrast, endogenous pluripotency gene transcripts NANOG and OCT4 were undetectable during the whole conversion process. Additional flow cytometric analysis revealed a similar gradual increase in FOXA2+ cells starting at day 21, without detection of cells immune-reactive for the pluripotency marker TRA-1-60 at any stage (Chan et al. (2009) (FIG. 8F). These data indicate that human fibroblasts can be directly converted into definitive endodermal progenitor cells without transitioning through a pluripotency state. Thus, the protocol described herein efficiently converts mesodermal human fibroblasts into endodermal progenitors employing the Cell-Activation and Signaling-Directed (CASD) trans-differentiation approach.

Example 9: Specification, Expansion and Characterization of Posterior Foregut-Like Progenitor Cells This Example describes experiments designed to expand definitive endodermal progenitor cells by using a simple expansion media containing two small molecules, CHIR99021 (an activator of WNT signaling) and A83-01 (an inhibitor of TGFβ signaling) and two growth factors, EGF and bFGF that significantly promoted their expansion in serial passages (FIGS. 9A and 9B). Immunofluorescence analysis revealed strong expression of endodermal progenitor markers SOX17 and FOXA2, but also induction of primitive gut tube marker HNF4α and posterior foregut marker HNF6 (FIG. 9C), suggesting further specification towards posterior foregut-like progenitor cells (cPF cells). Employing these culture conditions, several posterior foregut-like progenitor cell lines were successfully established from independent experiments that could be further expanded using the same culture conditions (FIG. 9D). Posterior foregut-like progenitor cells proliferated rapidly with an average doubling time of 2 days. After 15 passages, this represents at least a trillion-fold increase in cell number (FIG. 9E). All four media supplements were important for cPF cell self-renewal (FIG. 9F) and expanded posterior foregut-like progenitor cells maintained their epithelial colony morphology as well as posterior foregut-like phenotype as determined by immunofluorescence staining for SOX17, FOXA2, HNF4a, HNF6, and SOX9 (FIGS. 9G and 9H).

During mouse embryonic development, Pdx1 expression is first detected at embryonic day 8.5 and marks the endodermal region that will give rise to the whole pancreas, as well as the common bile duct, distal stomach, and duodenal epithelium (Oliver-Krasinski & Stoffers (2008); Spence et al. (2009). Interestingly, PDX1 protein (FIG. 9H) was detected but not the more specific pancreatic endoderm (PE) marker NKX6.1 (data not shown). Consistently, qPCR analysis demonstrated the induced high level expression of multiple posterior foregut progenitor gene transcripts, including SOX17, FOXA2, HNF1A, HNF1B, HNF4A, HNF6, SOX9 and PDX1 in foregut-like progenitor cells when compared to parental fibroblasts (FIG. 9I). In contrast, ectodermal marker gene SOX1, mesodermal marker gene BRACHYURY, and pluripotency marker genes OCT4 and NANOG were not induced (FIG. 9I). Collectively, these data confirm the specific posterior foregut identity of cPF cells.

Notably, the episomal vectors were undetectable by qPCR assays in established cPF cells (FIG. 9J), thus overcoming a current safety concern associated with the integration of viral vector based reprogramming/conversion approaches. Another potential safety concern regarding cells with proliferative and stem cell capacity is their potential for tumor formation (Hentze et al. (2009)). Transplantation of an expanded population of posterior foregut-like progenitor cells under the kidney capsule of immune deficient mice did not result in any tumor formation even after prolonged periods up to 12 weeks in vivo (n=10) (FIG. 9K). In contrast, all controls (hESC-derived endoderm progenitor cell populations) formed tumorigenic structures with big cysts and increased graft size 7 weeks after transplantation (n=3) (FIG. 9K). Analysis of the posterior foregut-like progenitor cell grafts demonstrated formation of epithelial structures expressing different endoderm-specific markers, including E-cadherin, HNF4a, PDX1, SOX9, and pan-cytokeratin (FIG. 9L). Thus, these results demonstrate that posterior foregut-like progenitor cells can be greatly expanded in culture while maintaining their posterior foregut endodermal phenotype.

Example 10: Differentiation of cPF Cells into Expandable Pancreatic Endodermal Progenitor Cells with the Ability to Mature into Functional Beta-Like Cells In Vivo Recently, several studies have reported the use of small molecules and growth factors to achieve differentiation of hESC-derived primitive gut tube and posterior foregut endoderm into pancreatic endoderm (Kroon et al. (2008); Rezania et al. (2012), Nostro et al. (2011); Kunisada et al. (2012)). Using a similar approach, different combinations of small molecules and growth factors were screened for differentiation of posterior foregut-like progenitor cells (cPF cells) into more committed pancreatic endodermal progenitor cells (cPE cells). A two-step protocol was optimized in which cPF cells were first exposed to FGF7, FGF10, A83-01, Compound-E (an inhibitor of Notch signaling), retinoic acid (RA), GDC-0449 (an antagonist of Sonic hedgehog), and LDN-193189 (an inhibitor of BMP4 signaling) for 2 days (FIG. 10A). Subsequently, differentiating cells were treated with EGF, Exendin-4 (an agonist of glucagon-like peptide-1), A83-01, LDN-193189, phorbol 12,13-dibutyrate (PBDu; an activator of protein kinase C), Compound-E, and Nicotinamide (an inhibitor of polyADP-ribose synthetase) for another 3 days (FIG. 10A). Resulting cPE cells continued to express high levels of FOXA2, HNF6, SOX9, and PDX1, as is expected for PE progenitor cells (Seymour & Sander (2011); Pan & Wright (2011)) (FIG. 10B). Most importantly, this treatment resulted in the generation of PDX1 and NKX6.1 double-positive cells (FIG. 10C). NKX6.1 expression in common PDX1$^+$ pancreatic progenitors (before NKX6.1 expression becomes further restricted to beta cells) marks their commitment to a more specific endocrine-/ductal-bi-potent progenitor cell type (Henseleit et al. (2005)). Notably, hESC-derived NKX6.1 and PDX1 double-positive PE progenitor cells have been shown to be able to give rise to functional beta cells after transplantation (Kelly et al. (2011)). FACS analysis revealed approximately 78% of PDX1 positive cells, and 17.3% PDX1 and NKX6.1 double-positive cells within cPE populations at passage 1 (FIG. 10D).

Next, the effect of cPF expansion media was tested on cPE cultures in an attempt to expand posterior foregut-like progenitor cells (cPE cells) in a similar fashion. However, cPE colonies easily detached from the plate under the cPF expansion conditions. Omission of CHIR99021 and increasing the EGF concentration to 50 ng/ml reversed this effect and promoted cPE cell expansion pursuant to the method illustrated in FIG. 10E. Under this optimized culture condition, cPE cells were expanded more than two hundred million fold with an approximate doubling time of 3 days for up to 14 passages (FIG. 10F). Of note, expanded cPE cells maintained their bi-potent progenitor identity as evidenced by the presence of PDX1 and NKX6.1 double-positive cells at passage 12 (FIGS. 10G and 10H). Consistently, qPCR results demonstrated the down-regulation of early endodermal marker gene SOX17. The pan-endodermal marker genes FOXA2 and HNF4A, as well as many pancreatic and endocrine marker genes, including HNF6, PTF1A, HLXB9, and NGN3, were up regulated (FIG. 10I). More robust expression was noted for other critical markers also highly expressed in mature beta cells, including PDX1, NKX2.2, and NKX6.1.

To explore whether expanded pancreatic endodermal progenitor cells (cPE cells) can further mature into functional beta cells in vivo, cPE cells were transplanted under the kidney capsule of immune deficient mice. After 15-16, 19-20 and 23-24 weeks, human C-peptide was detected after a glucose challenge in the blood of 62.5%, 75%, and 86.6% of mice analyzed, respectively, albeit at low levels (FIG. 10J). In addition, a 2.1 fold increase in human C-peptide was detected in the serum of mice bearing 23-week old grafts after glucose challenge when compared to fasting levels, a finding illustrating that cPE grafts become functional upon transplantation into host animals (FIG. 10K). Starting at 15 weeks post transplantation, insulin-expressing beta-like cells and PDX1 positive pancreatic progenitor cells were found in some graft sections, while other regions were negative for these and other pancreas markers (FIG. 10L). Insulin-positive cells co-expressed the critical beta cell transcription factors NKX6.1 and PDX1, but did not show expression of other endocrine hormones (FIG. 10L). In summary, our data demonstrates that cPF cells can be differentiated into cPE cells, which can be greatly expanded in vitro while maintaining their specific phenotype. Importantly, cPE cells differentiate further in vivo towards insulin-producing, single-hormonal cells capable of releasing Insulin in response to glucose challenge.

Figure 11A:
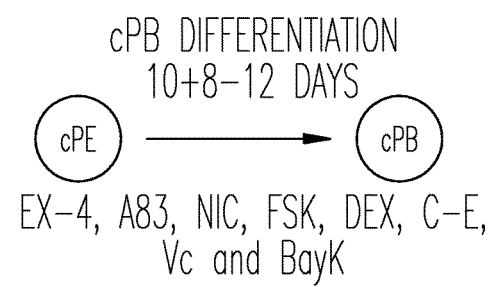
FIGS. 11A-11H illustrate maturation of cPE cells into human insulin-producing, glucose-responsive pancreatic beta-like cells (cPB) in vitro.
Figure 11B:
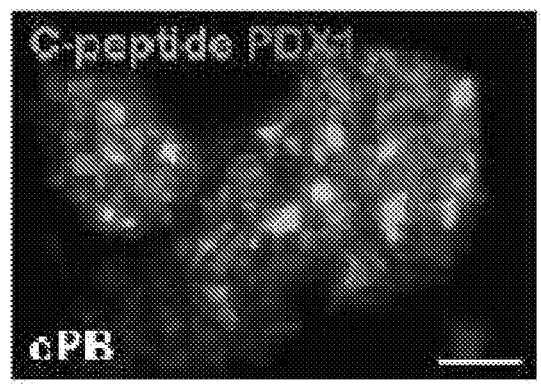

Example 11: Maturation of cPE Cells into Insulin-Producing, Glucose-Responsive Pancreatic Beta-Like Cells In Vitro Full maturation towards glucose responsive cells is optimally illustrated by transplantation of in vitro differentiated pancreas endoderm progenitor cells into immune compromised mice. To address the question of whether the cPE cells generated as described herein can develop into functional beta-like cells under cell culture conditions, cPE cells were incubated in a basal pancreatic differentiation media that has been shown to promote hESC/iPSC-derived pancreatic progenitor differentiation into insulin-producing cells (Kunisada et al. (2012)). This media includes A83-01, Nicotinamide, Forskolin (an activator of adenylyl cyclase), Dexamethasone (an agonist of glucocorticoid receptor), and Exendin-4 (FIG. 11A). While C-peptide positive cells expressing high levels of PDX1 were consistently observed after 10-14 days in culture (FIG. 11B), the relatively low number of cells (~0.5%) indicated further optimization of conditions may improve the frequency of conversion to functional beta-like cells. Chemical compounds able to promote differentiation of definitive endoderm (Borowiak et al. (2009)) and PDX1+ progenitors (Chen et al. (2009) have been identified previously. However, molecules directing the final steps of differentiation into beta-like cells have not been uncovered, likely due to difficulties in generating and maintaining sufficient numbers of differentiation-competent pancreatic endodermal progenitor cells.

Figure 11C:
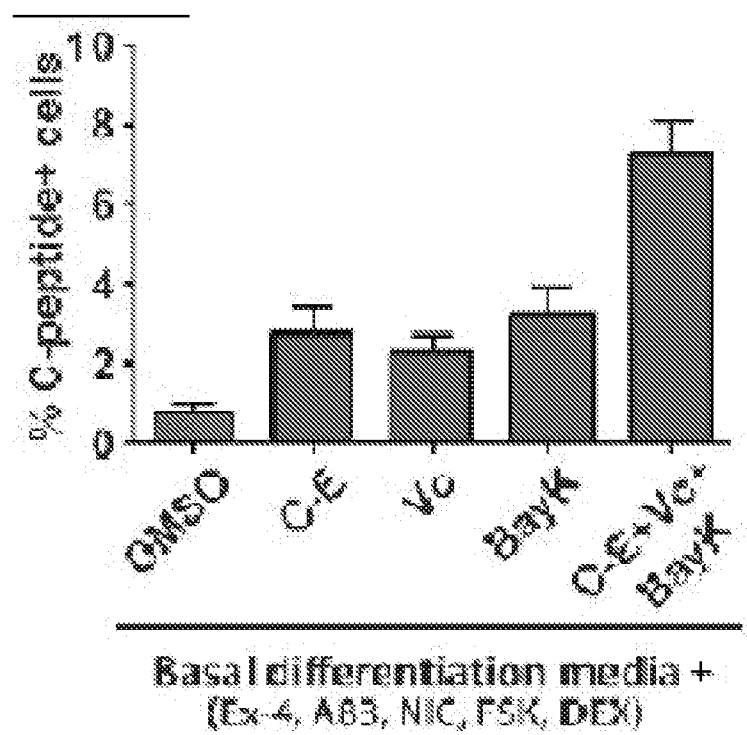

A chemical screen was performed with the intent of identifying factors that would result in the more efficient development of C-peptide positive cells from expanded cPE cells. These experiments revealed that supplementation of the basal pancreatic differentiation media individually with Compound-E (an inhibitor of Notch signaling), Vitamin C, or BayK-8644 (a $Ca^{2+}$ channel agonist), were effective in increasing the percentage of C-peptide positive cells (FIG. 11C). Combined treatment with these compounds had an additive effect (Exendin-4, A83-01, Nicotinamide, Forskolin, Dexamethasone, Compound-E, Vitamin C, and Bayk-8644), resulting in the formation of up to 7% C-peptide positive cells (FIG. 11C).

Insulin-producing cells generated from ESCs/iPSCs under published culture conditions are mostly immature as evidenced by co-expression of endocrine hormones, lack of crucial beta cell transcription factors and the absence of insulin secretion in response to physiological levels of glucose (Nostro & Keller (2012)). The maturation defects may be partly due to the lack of 3D organization normally present in islets of Langerhans (Sasai (2013)).

Figure 11D:
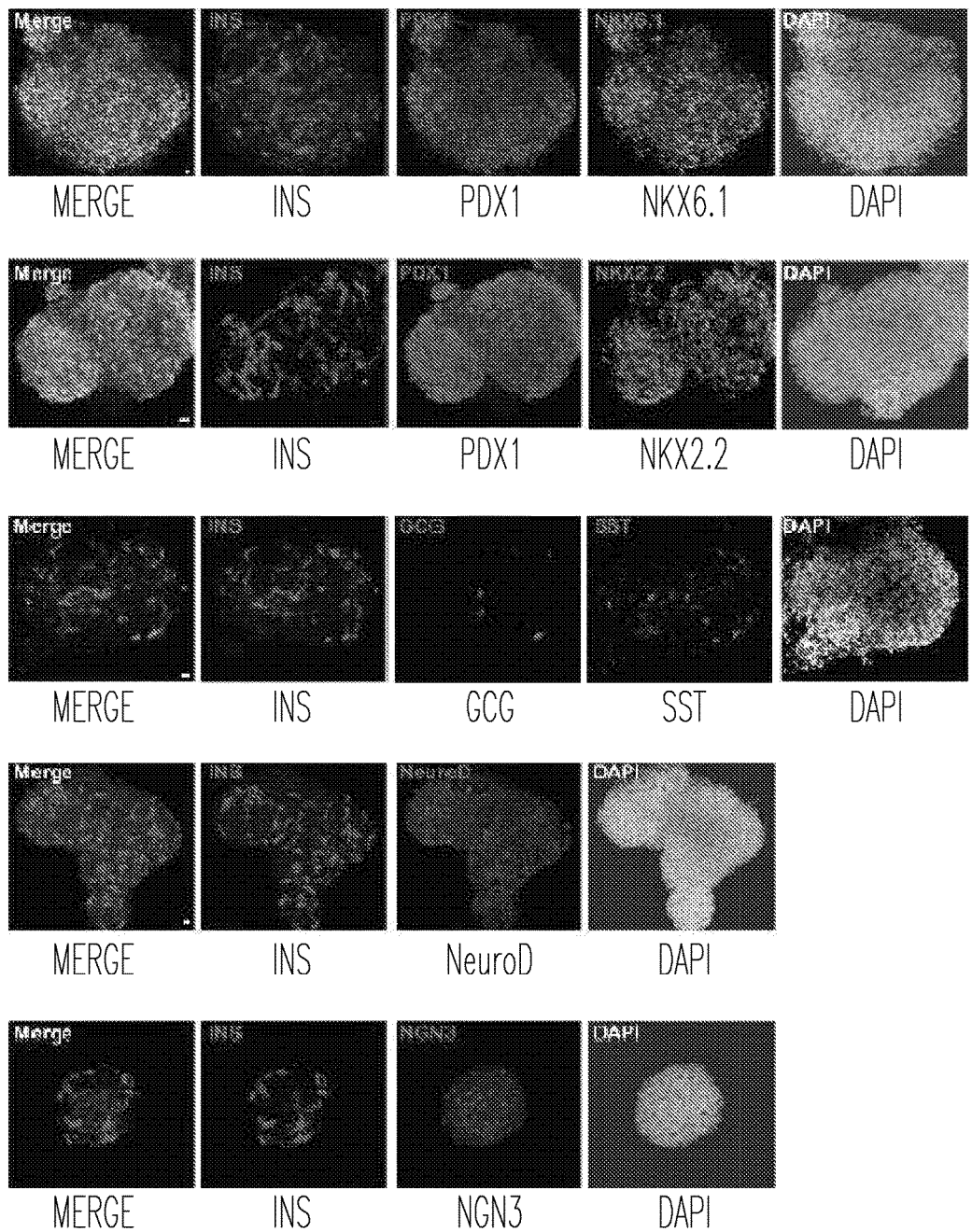
Figure 11E:
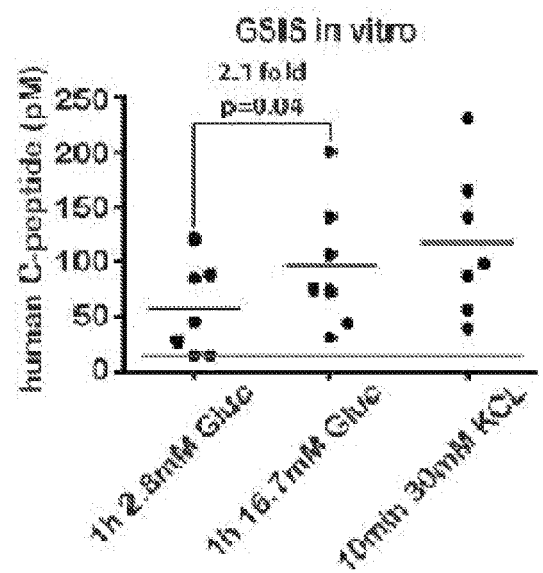
Figure 11F:
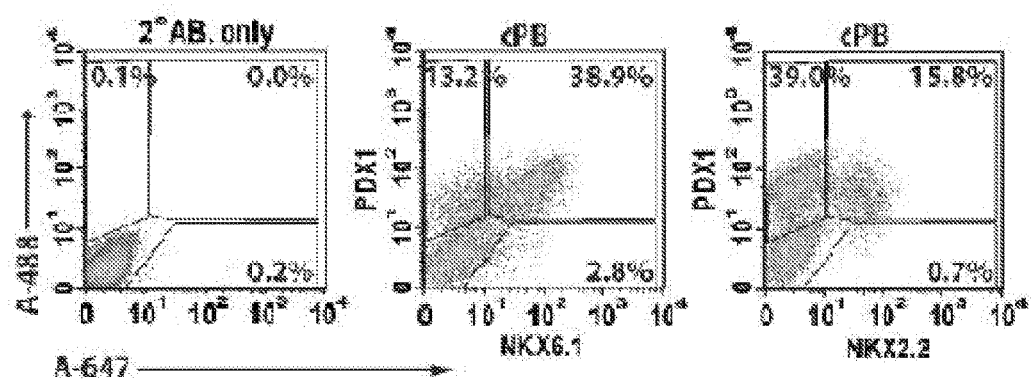
Figure 11G:
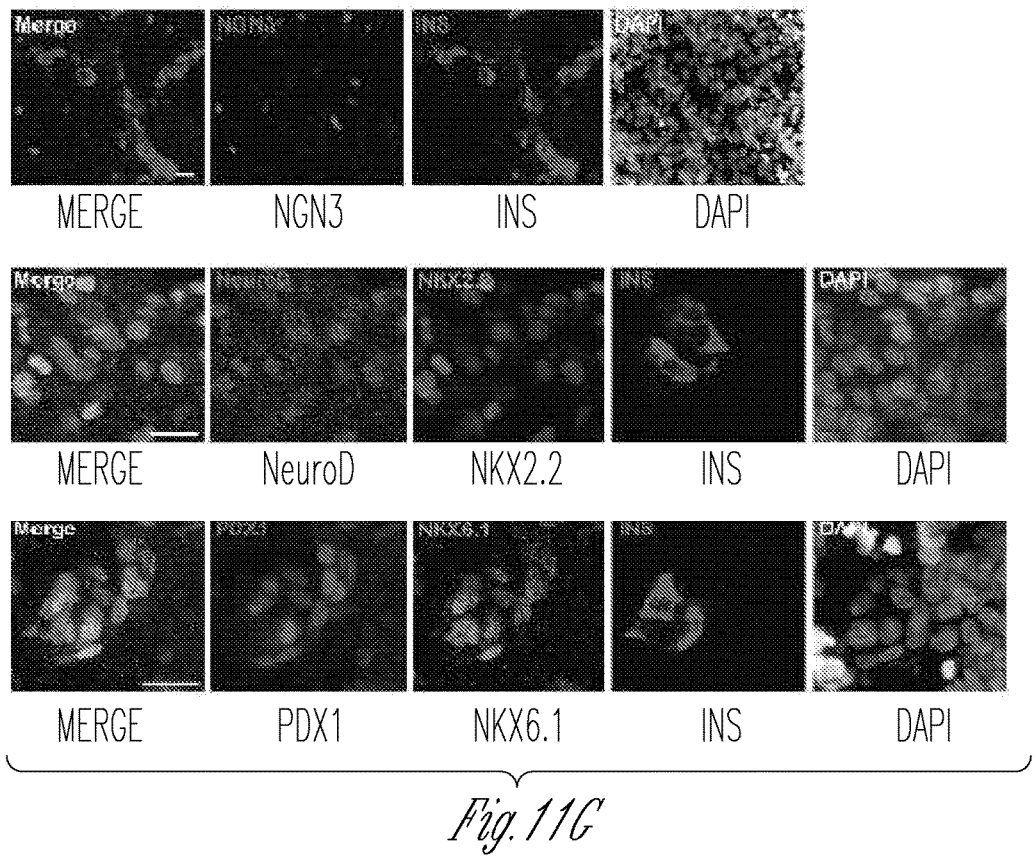
Figure 11H:
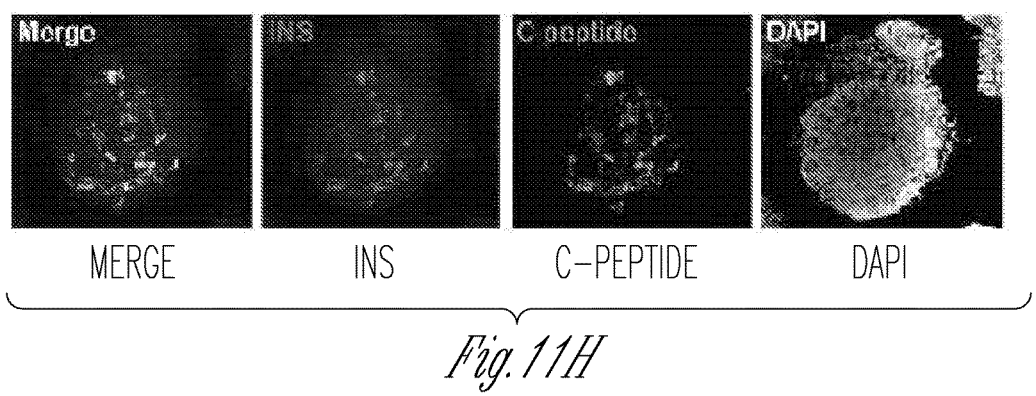

Hence, free floating cell aggregates of cPE cells were generated that had first been incubated as 2D cultures for 10 days in the improved maturation media. The majority of cells within the aggregates expressed the pan-pancreas marker PDX1 after 8-12 days of 3D culture (FIGS. 11D, 11F and 11G). In addition, many insulin-expressing cells co-expressing key beta cell transcription factors including NKX6.1, NKX2.2, and NeuroD were detected (FIGS. 11D and 11G). In contrast, insulin-expressing cells only rarely co-stained for the endocrine progenitor marker NGN3 or other endocrine hormones, including Glucagon (GCG) and Somatostatin (SST) (FIGS. 11D and 11G). Of note, all insulin-positive cells also stained for a human specific C-peptide antibody, thus excluding possible insulin uptake from the media (FIG. 11H).

Considering the expression of key beta cell markers, these cells were designated converted pancreatic beta-like cells (cPB cells). One of the distinguishing hallmarks of pancreatic beta cells is the ability to release insulin upon glucose stimulation. Importantly, glucose stimulated insulin secretion (GSIS) assays demonstrated that in vitro generated cPB cells released insulin (as detected by human C-peptide expression) in response to physiological levels of glucose (n=7, fold increase 2.1±1.3, range 0.9-4.8) (FIG. 11E). Collectively, these findings demonstrate that the in vitro differentiation protocol described herein directed conversion of human fibroblasts into beta-like cells that respond to physiological levels of glucose.

REFERENCES

Aviv, V., Meivar-Levy, I., Rachmut, I. H., Rubinek, T., Mor, E., and Ferber, S. (2009). Exendin-4 promotes liver cell proliferation and enhances the PDX-1-induced liver to pancreas transdifferentiation process. J Biol Chem 284, 33509-33520.

Bar-Nur, O., Russ, H. A., Efrat, S. & Benvenisty, N. Epigenetic memory and preferential lineage-specific differentiation in induced pluripotent stem cells derived from human pancreatic islet beta cells. Cell Stem Cell 9, 17-23 (2011).

Borowiak, M., et al. Small molecules efficiently direct endodermal differentiation of mouse and human embryonic stem cells. Cell Stem Cell 4, 348-358 (2009).

Chan, E. M., et al. Live cell imaging distinguishes bona fide human iPS cells from partially reprogrammed cells. Nat Biotechnol 27, 1033-1037 (2009).

Chen, S., Borowiak, M., Fox, J. L., Maehr, R., Osafune, K., Davidow, L., Lam, K., Peng, L. F., Schreiber, S. L., Rubin, L. L., Melton, D. (2009). A small molecule that directs differentiation of human ESCs into the pancreatic lineage. Nat Chem Biol 5, 258-265.

Cheng, X., et al. Self-renewing endodermal progenitor lines generated from human pluripotent stem cells. Cell Stem Cell 10, 371-384 (2012).

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-1541.

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. Nat Biotechnol 24, 1392-1401.

Efe, J. A., Hilcove, S., Kim, J., Zhou, H., Ouyang, K., Wang, G., Chen, J., and Ding, S. (2011). Conversion of mouse fibroblasts into cardiomyocytes using a direct reprogramming strategy. Nat Cell Biol 13, 215-222.

Ferber, S., Halkin, A., Cohen, H., Ber, I., Einav, Y., Goldberg, I., Barshack, I., Seijffers, R., Kopolovic, J., Kaiser, N., et al. (2000). Pancreatic and duodenal homeobox gene 1 induces expression of insulin genes in liver and ameliorates streptozotocin-induced hyperglycemia. Nat Med 6, 568-572.

Guo, T., Landsman, L., Li, N. & Hebrok, M. Factors Expressed by Murine Embryonic Pancreatic Mesenchyme Enhance Generation of Insulin-Producing Cells From hESCs. Diabetes (2013).

Gouon-Evans, Boussemart et al. (2006). BMP-4 is required for hepatic specification of mouse embryonic stem cell-derived definitive endoderm. Nat. Biotechnol. 24(11): 1402-11.

Green, Chen et al. (2011). Generation of anterior foregut endoderm from human embryonic and induced pluripotent stem cells. Nat. Biotechnol. 29(3): 267-72.

Gu, G., Dubauskaite, J. & Melton, D. A. Direct evidence for the pancreatic lineage: NGN3+ cells are islet progenitors and are distinct from duct progenitors. Development 129, 2447-2457 (2002).

Hanna, J., Markoulaki, S., Schorderet, P., Carey, B. W., Beard, C., Wernig, M., Creyghton, M. P., Steine, E. J., Cassady, J. P., Foreman, R., et al. (2008). Direct reprogramming of terminally differentiated mature B lymphocytes to pluripotency. Cell 133, 250-264.

Hanna, J., Saha, K., Pando, B., van Zon, J., Lengner, C. J., Creyghton, M. P., van Oudenaarden, A., and Jaenisch, R. (2009). Direct cell reprogramming is a stochastic process amenable to acceleration. Nature 462, 595-601.

Henseleit, K. D., et al. NKX6 transcription factor activity is required for alpha- and beta-cell development in the pancreas. Development 132, 3139-3149 (2005).

Hentze, H., et al. Teratoma formation by human embryonic stem cells: evaluation of essential parameters for future safety studies. Stem Cell Res 2, 198-210 (2009).

Jacquemin, P., Durviaux, S. M., Jensen, J., Godfraind, C., Gradwohl, G., Guillemot, F., Madsen, O. D., Carmeliet, P., Dewerchin, M., Collen, D., et al. (2000). Transcription factor hepatocyte nuclear factor 6 regulates pancreatic endocrine cell differentiation and controls expression of the proendocrine gene ngn3. Mol Cell Biol 20, 4445-4454.

Jiang, W., Shi, Y., Zhao, D., Chen, S., Yong, J., Zhang, J., Qing, T., Sun, X., Zhang, P., Ding, M., et al. (2007). In vitro derivation of functional insulin-producing cells from human embryonic stem cells. Cell Res 17, 333-344.

Kaneto, H., Nakatani, Y., Miyatsuka, T., Matsuoka, T. A., Matsuhisa, M., Hori, M., and Yamasaki, Y. (2005). PDX-1/VP16 fusion protein, together with NeuroD or Ngn3, markedly induces insulin gene transcription and ameliorates glucose tolerance. Diabetes 54, 1009-1022.

Kelly, O. G., Chan, M. Y., Martinson, L. A., Kadoya, K., Ostertag, T. M., Ross, K. G., Richardson, M., Carpenter, M. K., D'Amour, K. A., Kroon, E., et al. (2011). Cell-surface markers for the isolation of pancreatic cell types derived from human embryonic stem cells. Nat Biotechnol 29, 750-756.

Kim, J., Ambasudhan, R. & Ding, S. Direct lineage reprogramming to neural cells. Curr Opin Neurobiol 22, 778-784 (2012).

Kim, D., Kim, C. H., Moon, J. I., Chung, Y. G., Chang, M. Y., Han, B. S., Ko, S., Yang, E., Cha, K. Y., Lanza, R., et al. (2009). Generation of human induced pluripotent stem cells by direct delivery of reprogramming proteins. Cell Stem Cell 4, 472-476.

Kim, J., Efe, J. A., Zhu, S., Talantova, M., Yuan, X., Wang, S., Lipton, S. A., Zhang, K., and Ding, S. (2011). Direct reprogramming of mouse fibroblasts to neural progenitors. Proc Natl Acad Sci 108, 7838-7843

Kroon, E., Martinson, L. A., Kadoya, K., Bang, A. G., Kelly, O. G., Eliazer, S., Young, H., Richardson, M., Smart, N. G., Cunningham, J., et al. (2008). Pancreatic endoderm derived from human embryonic stem cells generates glucose-responsive insulin-secreting cells in vivo. Nat Biotechnol 26, 443-452.

Kunisada, Y., Tsubooka-Yamazoe, N., Shoji, M. & Hosoya, M. Small molecules induce efficient differentiation into insulin-producing cells from human induced pluripotent stem cells. Stem Cell Res 8, 274-284 (2012).

Kurian, L., et al. Conversion of human fibroblasts to angioblast-like progenitor cells. Nat Methods 10, 77-83 (2013).

Li, F., He, Z., Li, Y., Liu, P., Chen, F., Wang, M., Zhu, H., Ding, X., Wangensteen, K. J., Hu, Y., et al. (2011). Combined Activin A/LiCl/Noggin treatment improves production of mouse embryonic stem cell-derived definitive endoderm cells. J Cell Biochem 112, 1022-1034.

Li, J., Huang, N. F., Zou, J., Laurent, T. J., Lee, J. C., Okogbaa, J., Cooke, J. P., and Ding, S. (2013). Conversion of Human Fibroblasts to Functional Endothelial Cells by Defined Factors. Arterioscler Thromb Vasc Biol.

Lynn, F. C., Smith, S. B., Wilson, M. E., Yang, K. Y., Nekrep, N., and German, M. S. (2007). Sox9 coordinates a transcriptional network in pancreatic progenitor cells. Proc Natl Acad Sci 104, 10500-10505.

Nelson, S. B., Schaffer, A. E., and Sander, M. (2007). The transcription factors Nkx6.1 and Nkx6.2 possess equivalent activities in promoting beta-cell fate specification in Pdx1+ pancreatic progenitor cells. Development 134, 2491-2500.

Nostro, M. C., et al. Stage-specific signaling through TGF-beta family members and WNT regulates patterning and pancreatic specification of human pluripotent stem cells. Development 138, 861-871 (2011).

Nostro, M. C. & Keller, G. Generation of beta cells from human pluripotent stem cells: Potential for regenerative medicine. Semin Cell Dev Biol 23, 701-710 (2012).

Offield, M. F., Jetton, T. L., Labosky, P. A., Ray, M., Stein, R. W., Magnuson, M. A., Hogan, B. L., and Wright, C. V. (1996). PDX-1 is required for pancreatic outgrowth and differentiation of the rostral duodenum. Development 122, 983-995.

Okita et al. (2011). A more efficient method to generate integration-free human iPS cells. Nat Methods 8: 409-412.

Oliver-Krasinski, J. M. & Stoffers, D. A. On the origin of the beta cell. Genes Dev 22, 1998-2021 (2008).

Oshimori, N. & Fuchs, E. The harmonies played by TGF-beta in stem cell biology. Cell Stem Cell 11, 751-764 (2012).

Pan, F. C. & Wright, C. Pancreas organogenesis: from bud to plexus to gland. Dev Dyn 240, 530-565 (2011).

Qu, X. B., Pan, J., Zhang, C., and Huang, S. Y. (2008). Sox17 facilitates the differentiation of mouse embryonic stem cells into primitive and definitive endoderm in vitro. Dev Growth Differ 50, 585-593.

Rezania, A., et al. Maturation of human embryonic stem cell-derived pancreatic progenitors into functional islets capable of treating pre-existing diabetes in mice. Diabetes 61, 2016-2029 (2012).

Russ, H. A., et al. Insulin-producing cells generated from dedifferentiated human pancreatic beta cells expanded in vitro. PLoS One 6, e25566 (2011).

Sancho-Martinez, I., Baek, S. H. & Izpisua Belmonte, J. C. Lineage conversion methodologies meet the reprogramming toolbox. Nat Cell Biol 14, 892-899 (2012).

Sander, M., Neubuser, A., Kalamaras, J., Ee, H. C., Martin, G. R., and German, M. S. (1997). Genetic analysis reveals that PAX6 is required for normal transcription of pancreatic hormone genes and islet development. Genes Dev 11, 1662-1673.

Sander, M., Sussel, L., Conners, J., Scheel, D., Kalamaras, J., Dela Cruz, F., Schwitzgebel, V., Hayes-Jordan, A., and German, M. (2000). Homeobox gene Nkx6.1 lies downstream of Nkx2.2 in the major pathway of beta-cell formation in the pancreas. Development 127, 5533-5540.

Sasai, Y. Next-generation regenerative medicine: organogenesis from stem cells in 3D culture. Cell Stem Cell 12, 520-530 (2013).

Schaffer, A. E., Taylor, B. L., Benthuysen, J. R., Liu, J., Thorel, F., Yuan, W., Jiao, Y., Kaestner, K. H., Herrera, P. L., Magnuson, M. A., et al. (2013). Nkx6.1 Controls a Gene Regulatory Network Required for Establishing and Maintaining Pancreatic Beta Cell Identity. PLoS Genet 9, e1003274.

Schroeder, I. S., Rolletschek, A., Blyszczuk, P., Kania, G., and Wobus, A. M. (2006). Differentiation of mouse embryonic stem cells to insulin-producing cells. Nat Protoc 1, 495-507.

Seymour, P. A. & Sander, M. Historical perspective: beginnings of the beta-cell: current perspectives in beta-cell development. Diabetes 60, 364-376 (2011).

Shih, H. P., et al. A Notch-dependent molecular circuitry initiates pancreatic endocrine and ductal cell differentiation. Development 139, 2488-2499 (2012).

Sneddon, J. B., Borowiak, M. & Melton, D. A. Self-renewal of embryonic-stem-cell-derived progenitors by organ-matched mesenchyme. Nature 491, 765-768 (2012).

Spence, J. R., et al. Sox17 regulates organ lineage segregation of ventral foregut progenitor cells. Dev Cell 17, 62-74 (2009).

Stainier, D. Y. A glimpse into the molecular entrails of endoderm formation. Genes Dev 16, 893-907 (2002).

Tam, P. P., Kanai-Azuma, M., and Kanai, Y. (2003). Early endoderm development in vertebrates: lineage differentiation and morphogenetic function. Curr Opin Genet Dev 13, 393-400.

Tian, T. & Meng, A. M. Nodal signals pattern vertebrate embryos. Cell Mol Life Sci 63, 672-685 (2006).

Wang, L., et al. Generation of integration-free neural progenitor cells from cells in human urine. Nat Methods 10, 84-89 (2012).

Wang, Z., Oron, E., Nelson, B., Razis, S., and Ivanova, N. (2012) Distinct lineage specification roles for NANOG, OCT4, and SOX2 in human embryonic stem cells. Cell Stem Cell. 10, 440-454.

Warren, L., Manos, P. D., Ahfeldt, T., Loh, Y. H., Li, H., Lau, F., Ebina, W., Mandal, P. K., Smith, Z. D., Meissner, A., et al. (2010). Highly Efficient Reprogramming to Pluripotency and Directed Differentiation of Human Cells with Synthetic Modified mRNA. Cell Stem Cell 7, 618-630.

Wernig, M., Lengner, C. J., Hanna, J., Lodato, M. A., Steine, E., Foreman, R., Staerk, J., Markoulaki, S., and Jaenisch, R. (2008). A drug-inducible transgenic system for direct reprogramming of multiple somatic cell types. Nat Biotechnol 26, 916-924.

Yasunaga, M., Tada, S., Torikai-Nishikawa, S., Nakano, Y., Okada, M., Jakt, L. M., Nishikawa, S., Chiba, T., and Era, T. (2005). Induction and monitoring of definitive and visceral endoderm differentiation of mouse ES cells. Nat Biotechnol 23, 1542-1550.

Zhang, D., et al. Highly efficient differentiation of human ES cells and iPS cells into mature pancreatic insulin-producing cells. Cell Res 19, 429-438 (2009).

Zhou, H., Wu, S., Joo, J. Y., Zhu, S., Han, D. W., Lin, T., Trauger, S., Bien, G., Yao, S., Zhu, Y., et al. (2009). Generation of induced pluripotent stem cells using recombinant proteins. Cell Stem Cell 4, 381-384.

Zhu, S., Wei, W. & Ding, S. Chemical strategies for stem cell biology and regenerative medicine. Annu Rev Biomed Eng 13, 73-90 (2011).

Zhu, S., et al. Reprogramming of human primary somatic cells by OCT4 and chemical compounds. Cell Stem Cell 7, 651-655 (2010).

Zhou, Q., Brown, J., Kanarek, A., Rajagopal, J., and Melton, D. A. (2008). In vivo reprogramming of adult pancreatic exocrine cells to beta-cells. Nature 455, 627-632.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A composition comprising a TGFβ family member, a WNT activator, or a combination thereof
2. The composition of statement 1, further comprising 2-phospho-L-ascorbic acid or vitamin C.
3. The composition of statement 1 or 2, wherein the WNT activator is a lithium salt, CHIR99021, 1-azakenpaullone, AR-A014418, indirubin-3'-monoxime, 5-Iodo-indirubin-3'-monoxime, kenpaullone, SB-415286, SB-216763, 2-anilino-5-phenyl-1,3,4-oxadiazole), (Z)-5-(2,3-Memylenedioxyphenyl)imidazolidine-2,4-dione, TWS119, CHIR98014, SB415286, Tideglusib, LY2090314, or a combination thereof.
4. The composition of any of statements 1-3, wherein the TGFβ family member is a factor of an Activin/Inhibin subfamily, a decapentaplegic-Vg-related (DVR) related subfamily (that includes bone morphogenetic proteins and growth differentiation factors), and/or a TGF-β subfamily.

5. The composition of any of statements 1-4, wherein the TGFβ family member is Activin A.

6. The composition of any of statements 1-5, further comprising a G9a histone methyltransferase inhibitor selected from the group consisting of Bix-01294, chaetocin, 3-deazaneplanocin hydrochloride, UNC 0224, UNC 0638, UNC 0646, and any combination thereof.

7. The composition of any of statements 1-6, further comprising a histone deacetylase inhibitor selected from the group consisting of sodium butyrate, phenyl butyrate, butyrate, Suberoylanilide Hydroxamic Acid (SAHA), BML-210, Depudecin, HC Toxin, Scriptaid, Phenylbutyrate, Valproic Acid, Suramin, Trichostatin A, APHA Compound 8, Apicidin, Trapoxin B, Chlamydocin, Depsipeptide, CI-994, MS-27-275, MGCD0103, NVP-LAQ-824, CBHA, JNJ16241199, Tubacin, A-161906, Proxamide, Oxamflatin, 3Cl-UCHA, AOE, CHAP31, or any combination thereof 8. The composition of any of statements 1-7, further comprising a DNA methyltransferase inhibitor selected from the group consisting of RG108, 5-azacitidine, 5-aza-2'-deoxycytidine, decitabine, doxorubicin, EGCG ((−)-epigallocatechin-3-gallate), zebularine, and any combination thereof.

9. The composition of any of statements 1-8, further comprising an adenosine receptor agonist selected from the group consisting of 5'-N-ethylcarbox-amido-adenosine (NECA), 8-butylamino-adenosine, 2-[p-(2-carboxyethyl)phenethyl-amino]-5'-N-ethylcarboxamido-adenosine (CGS-2 1680), HENECA, 4-(3-[6-amino-9-(5-ethylcarbamoyl-3,4-dihydroxy-tetrahydro-furan-2-yl)-9H-purin-2-yl]-prop-2-ynyl)-cyclohexanecarboxylic acid methyl ester), $N^6$-cyclopentyladenosine (CPA), 2-chloro-$N^6$-cyclopentyl-adenosine (CCPA), (2S)—N6-[2-endo-Norbornyl]adenosine ((S)-ENBA), N-(2-aminoethyl)-2-[4-[[2-[4-[[9-[(2R,3R,4S,5R)-3,4-dihydroxy-5-(hydroxymethyl)oxolan-2-yl]purin-6-yl]amino] phenyl]acetyl]amino]phenyl]acetamide hydrate (ADAC), AMP579, NNC-21-0136, GR79236, CVT-510 (Tecadenoson), SDZ WAG 994, Selodenoson, and any combination thereof 10. The composition of any of statements 1-9, wherein the composition is a cell culture medium or comprises components for a cell culture medium.

11. The composition of any of statements 1-10, wherein the TGFβ family member, the WNT activator, the 2-phospho-L-ascorbic acid, the vitamin C, G9a histone methyltransferase inhibitor, histone deacetylase inhibitor, DNA methyltransferase inhibitor, adenosine receptor agonist, or a combination thereof, is in an amount sufficient to generate definitive endodermal cells from mammalian cells that transiently express pluripotency factors.

12. A mixture comprising the composition of any of statements 1-11, and a selected starting mammalian cell population.

13. The mixture of statement 12, wherein the mammalian cell population transiently expresses at least one pluripotency factor while being incubated in the composition.

14. The mixture of statement 12 or 13, wherein the pluripotency factor comprises OCT4, KLF4, SOX2, or a combination thereof.

15. The mixture of statement 14, wherein the pluripotency further comprises c-MYC, p53 shRNA, or a combination thereof.

16. The mixture of any of statements 12-15, wherein the starting mammalian cell population is non-pluripotent.

17. The mixture of any of statements 12-16, wherein the starting mammalian cell population comprises non-pluripotent fibroblasts, epidermal cells, lymphocytes, hepatocytes, myoblasts, neurons, osteoblasts, osteoclasts, and T-cells.

18. The mixture of any of statements 12-17, wherein the starting mammalian cell population comprises partially and/or fully differentiated cells of epithelial cell lineage, hematopoietic lineage, endothelial cell lineage, muscle cell lineage, neural cell lineage, or any combinations thereof 19. The mixture of any of statements 12-18, wherein the starting mammalian cell population is from a non-pluripotent mammalian cell population previously contacted with one or more pluripotency factors or pluripotency inducing agents, or wherein the non-pluripotent mammalian cell population is induced to express one or more pluripotency factors.

20. The mixture of any of statements 12-19, wherein the starting mammalian cell population comprises pluripotent stem cells.

21. The mixture of any of statements 12-20, wherein the starting mammalian cell population does not express detectable amounts of NANOG.

22. The mixture of any of statements 12-21, wherein the starting mammalian cell population is an isolated mammalian cell population.

23. The mixture of any of statements 12-22, wherein the starting mammalian cell population is an isolated allogeneic mammalian cell population.

24. The mixture of any of statements 12-23, wherein the starting mammalian cell population is an autologous mammalian cell population isolated from a patient.

25. The mixture of any of statements 12-24, wherein the starting mammalian cell population is contacted with the composition for about 4 days to about 28 days.

26. The mixture of any of statements 12-25, wherein a portion of the starting mammalian cell population is converted into definitive endodermal cells after about 7 days, or after about 10 days, or after about 12 days, or after about 14 days, or after about 16 days, or after about 18 days, or after about 20 days of contact with the composition.

27. The mixture of any of statements 12-26, wherein a portion of the starting mammalian cell population express Sox17, Foxa2, Cerberus 1 (Cer), C-X-C chemokine receptor type 4 (Cxcr4), or a combination thereof, after about 7 days, or after about 10 days, or after about 12 days, or after about 14 days, or after about 16 days, or after about 18 days, or after about 20 days of contact with the composition.

28. The mixture of any of statements 12-27, wherein the starting mammalian cell population and cells thereof that convert into definitive endodermal cells do not express detectable levels of NANOG.

29. A composition comprising a TGFβ receptor inhibitor, a hedgehog pathway inhibitor, and a retinoic acid receptor agonist.

30. The composition of statement 29, further comprising epidermal growth factor (EGF), basic fibroblast growth factor (bFGF), fibroblast growth factor 7 (FGF7), fibroblast growth factor 10 (FGF10), or a combination thereof.

31. The composition of statement 29 or 30, further comprising a WNT activator, 2-phospho-L-ascorbic acid, vitamin C, a Notch signaling inhibitor, a BMP4 signaling inhibitor, or a combination thereof 32. The composition of any of statements 29-31, wherein the TGFβ receptor inhibitor, the hedgehog pathway inhibitor, the retinoic acid receptor agonist, the WNT activator, the 2-phospho-L-ascorbic acid, the vitamin C, the Notch signaling inhibitor, the BMP4 signaling inhibitor, or any combination thereof, is in an amount sufficient to generate pancreatic progenitor cells from mammalian cells that express Sox17, Foxa2, Cerberus 1 (Cer), C-X-C chemokine receptor type 4 (Cxcr4), or a combination thereof 33. The composition of any of statements 29-32, wherein the TGFβ receptor inhibitor is selected from the group consisting of A83-01, SB431542, SB 431542, SJN 2511, D 4476, LY 364947, SB505124, SB 525334, SD 208, LDN-193189, and any combination thereof.

34. The composition of any of statements 29-33, wherein the hedgehog pathway inhibitor is selected from the group consisting of LDE 225, cyclopamine, MK-4101, GDC-0449, XL-139 (BMS-833923), PF-04449913, robotnikinin, Cur-61414 (G-024856), and any combination thereof.

35. The composition of any of statements 29-34, wherein the retinoic acid receptor agonist is selected from the group consisting of retinoic acid, 9-cis-retinoic acid, honokiol, magnolol Am80, AM580, TTNPB, AC55649, and any combination thereof 36. The composition of any of statements 29-35, wherein the WNT activator is a lithium salt, CHIR99021, 1-azakenpaullone, AR-A014418, indirubin-3'-monoxime, 5-Iodo-indirubin-3'-monoxime, kenpaullone, SB-415286, SB-216763, 2-anilino-5-phenyl-1,3,4-oxadiazole), (Z)-5-(2,3-Memylenedioxyphenyl)imidazolidine-2,4-dione, TWS119, CHIR98014, SB415286, Tideglusib, LY2090314, or a combination thereof.

37. The composition of any of statements 29-36, wherein the Notch signaling inhibitor is Compound E, RO4929097, DAPT (GSI-IX), Gamma-Secretase Inhibitor I (Z-Leu-Leu-Nle-CHO where Nle is Norleucine), Gamma-Secretase Inhibitor II, or any combination thereof 38. The composition of any of statements 29-37, wherein the BMP4 signaling inhibitor is noggin, chordin, CeM, DAN, Gremlin, K02288, LDN-193189, or any combination thereof.

39. The composition of any of statements 29-38, wherein the composition is a cell culture medium or comprises components for a cell culture medium.

40. A mixture comprising the composition of any of statements 29-39, and a selected mammalian cell population.

41. The mixture of statement 40, wherein the selected mammalian cell population comprises cells that express Sox17, Foxa2, Cerberus 1 (Cer), C-X-C chemokine receptor type 4 (Cxcr4), or a combination thereof.

42. The mixture of statement 40 or 41, wherein the selected mammalian cell population comprises at least 5%, or at least 10%, or at least 12%, or at least 15%, or at least 25%, or at least 50%, or at least 60%, or at least 70%, or at least 80%, or at least 90%, or at least 95% cells that express Sox17, Foxa2, Cerberus 1 (Cer), C-X-C chemokine receptor type 4 (Cxcr4), or a combination thereof 43. The mixture of any of statements 40-43, wherein the selected mammalian cell population is formed from a nonpluripotent cell population or a stem cell population redirected to express Sox17, Foxa2, Cerberus 1 (Cer), C-X-C chemokine receptor type 4 (Cxcr4), or a combination thereof.

44. The mixture of any of statements 40-43, wherein the selected mammalian cell population is formed from cells contacted with a first composition comprising a TGFβ family member, a WNT activator, or a combination thereof.

45. The mixture of statement 44, wherein the first composition further comprises 2-phospho-L-ascorbic acid or vitamin C.

46. The mixture of statement 44 or 45, wherein the first composition has the TGFβ family member, the WNT activator, the 2-phospho-L-ascorbic acid, the vitamin C, or a combination thereof, in an amount sufficient to generate definitive endodermal cells.

47. The mixture of any of statements 40-46, wherein when initially mixed with the composition, cells in the selected mammalian cell population do not express Rex1, Nanog, or a combination thereof 48. The mixture of any of statements 40-47, wherein a portion of the selected mammalian cell population is converted into pancreatic progenitor cells after 4 hours, or after about 8 hours, or after about 12 hours, or after about 1 day, or after about 2 days, or after about 3 days, or after about 4 days, or after about 5 days, or after about 6 days of contact with the composition.

49. The mixture of any of statements 40-48, wherein after mixing the selected mammalian cell population with the composition for at least one day, cells in the selected mammalian cell population express Pdx1, Nkx6.1, or a combination thereof.

50. The mixture of any of statements 40-49, wherein after mixing the selected mammalian cell population with the composition for 2 or more days, cells in the selected mammalian cell population express Pdx1, Nkx6.1, Pax6, Hnf6, or a combination thereof.

51. The mixture of any of statements 40-50, wherein a portion of the selected mammalian cell population is converted into pancreatic progenitor cells after 4 hours, or after about 8 hours, or after about 12 hours, or after about 1 day, or after about 2 days, or after about 3 days, or after about 4 days, or after about 5 days, or after about 6 days of contact with the composition.

52. The mixture of any of statements 40-51, wherein after mixing the selected mammalian cell population with the composition for 2 or more days, at least 5%, or at least about 10%, or at least about 12%, or at least about 16%, or at least about 17%, or at least about 20%, or at least about 25% of cells in the selected mammalian cell population express Pdx1, Nkx6.1, Pax6, Hnf6, or a combination thereof.

53. A method comprising, contacting a selected starting mammalian cell population with a composition comprising a TGFβ family member, a WNT activator, or a combination thereof.

54. The method of statement 53, wherein the composition further comprises 2-phospho-L-ascorbic acid or vitamin C.

55. The method of statement 53 or 54, wherein the WNT activator is a lithium salt, CHIR99021, 1-azakenpaullone, AR-A014418, indirubin-3'-monoxime, 5-Iodo-indirubin-3'-monoxime, kenpaullone, SB-415286, SB-216763, 2-anilino-5-phenyl-1,3,4-oxadiazole), (Z)-5-(2,3-Memylenedioxyphenyl)imidazolidine-2,4-dione, TWS119, CHIR98014, SB415286, Tideglusib, LY2090314, or a combination thereof.

56. The method of any of statements 53-55, wherein the TGFβ family member is a factor of an Activin/Inhibin subfamily, a decapentaplegic-Vg-related (DVR) related subfamily (that includes bone morphogenetic proteins and growth differentiation factors), and/or a TGF-β subfamily.

57. The method of any of statements 53-56, wherein the TGFβ family member is Activin A.

58. The method of any of statements 53-57, wherein the composition further comprises a G9a histone methyltransferase inhibitor selected from the group consisting of Bix-01294, chaetocin, 3-deazaneplanocin hydrochloride, UNC 0224, UNC 0638, UNC 0646, and any combination thereof.

59. The method of any of statements 53-58, wherein the composition further comprises a histone deacetylase inhibitor selected from the group consisting of sodium butyrate, phenyl butyrate, butyrate, Suberoylanilide Hydroxamic Acid (SAHA), BML-210, Depudecin, HC Toxin, Scriptaid, Phenylbutyrate, Valproic Acid, Suramin, Trichostatin A, APHA Compound 8, Apicidin, Trapoxin B, Chlamydocin, Depsipeptide, CI-994, MS-27-275, MGCD0103, NVP-LAQ-824, CBHA, JNJ16241199, Tubacin, A-161906, Proxamide, Oxamflatin, 3C1-UCHA, AOE, CHAP31, or any combination thereof.

60. The method of any of statements 53-59, wherein the composition further comprises a DNA methyltransferase inhibitor selected from the group consisting of RG108, 5-azacitidine, 5-aza-2'-deoxycytidine, decitabine, doxorubicin, EGCG ((−)-epigallocatechin-3-gallate, zebularine, and any combination thereof 61. The method of any of statements 53-60, wherein the composition further comprises an adenosine receptor agonist selected from the group consisting of 5'-N-ethylcarbox-amido-adenosine (NECA), 8-butylaminoadenosine, 2-[p-(2-carboxyethyl)phenethyl-amino]-5'-N-ethylcarboxamidoadenosine (CGS-2 1680), HENECA, 4-(3-[6-amino-9-(5-ethylcarbamoyl-3,4-dihydroxy-tetrahydro-furan-2-yl)-9H-purin-2-yl]-prop-2-ynyl)-cyclohexanecarboxylic acid methyl ester), $N^6$-cyclopentyladenosine (CPA), 2-chloro-$N^6$-cyclopentyl-adenosine (CCPA), (2S)—N6-[2-endo-Norbornyl]adenosine ((S)-ENBA), N-(2-aminoethyl)-2-[4-[[2-[4-[[9-[(2R,3R,4S,5R)-3,4-dihydroxy-5-(hydroxymethyl)oxolan-2-yl]purin-6-yl]amino]phenyl]acetyl]amino]phenyl]acetamide hydrate (ADAC), AMP579, NNC-21-0136, GR79236, CVT-510 (Tecadenoson), SDZ WAG 994, Selodenoson, and any combination thereof 62. The method of any of statements 53-61, wherein the TGFβ family member, the WNT activator, the 2-phospho-L-ascorbic acid, the vitamin C, G9a histone methyltransferase inhibitor, histone deacetylase inhibitor, DNA methyltransferase inhibitor, adenosine receptor agonist, or a combination thereof, is in an amount sufficient to generate definitive endodermal cells from a mammalian cell population that transiently expresses pluripotency factors.

63. The method of any of statements 53-62, wherein the TGFβ family member, the WNT activator, the 2-phospho-L-ascorbic acid, the vitamin C, G9a histone methyltransferase inhibitor, histone deacetylase inhibitor, DNA methyltransferase inhibitor, adenosine receptor agonist, or a combination thereof, is in an amount sufficient to generate mammalian cells that express Sox17, Foxa2, Cerberus 1 (Cer), C-X-C chemokine receptor type 4 (Cxcr4), or a combination thereof, from a mammalian cell population that transiently expresses pluripotency factors.

64. The method of any of statements 53-63, wherein the starting mammalian cell population transiently expresses at least one pluripotency factor while being incubated in the composition.

65. The method of statement 64, wherein the pluripotency factor comprises OCT4, KLF4, SOX2, or a combination thereof.

66. The method of statement 64 or 65, wherein the pluripotency further comprises c-MYC, p53 shRNA, or a combination thereof.

67. The method of any of statements 53-66, wherein the starting mammalian cell population is non-pluripotent.

68. The method of any of statements 53-67, wherein the starting mammalian cell population comprises non-pluripotent fibroblasts, epidermal cells, lymphocytes, hepatocytes, myoblasts, neurons, osteoblasts, osteoclasts, T-cells, or any combination thereof.

69. The method of any of statements 53-68, wherein the starting mammalian cell population comprises partially and/or fully differentiated cells of epithelial cell lineage, hematopoietic lineage, endothelial cell lineage, muscle cell lineage, neural cell lineage, or any combination thereof.

70. The method of any of statements 53-69, wherein the starting mammalian cell population is from a non-pluripotent mammalian cell population previously contacted with one or more pluripotency factors or pluripotency inducing agents, or wherein the non-pluripotent mammalian cell population is induced to express one or more pluripotency factors.

71. The method of any of statements 53-68, wherein the starting mammalian cell population comprises pluripotent stem cells.

72. The method of any of statements 53-70, wherein the starting mammalian cell population does not express detectable amounts of NANOG.

73. The method of any of statements 53-72, wherein the starting mammalian cell population is an isolated mammalian cell population.

74. The method of any of statements 53-73, wherein the starting mammalian cell population is an isolated allogeneic mammalian cell population.

75. The method of any of statements 53-74, wherein the starting mammalian cell population is an autologous mammalian cell population isolated from a patient.

76. The method of any of statements 53-75, wherein the starting mammalian cell population is contacted with the composition for about 4 days to about 28 days.

77. The method of any of statements 53-76, wherein a portion of the starting mammalian cell population is converted into definitive endodermal cells after about 7 days, or after about 10 days, or after about 12 days, or after about 14 days, or after about 16 days, or after about 18 days, or after about 20 days of contact with the composition.

78. The method of any of statements 53-77, wherein a portion of the starting mammalian cell population express Sox17, Foxa2, Cerberus 1 (Cer), C-X-C chemokine receptor type 4 (Cxcr4), or a combination thereof, after about 7 days, or after about 10 days, or after about 12 days, or after about 14 days, or after about 16 days, or after about 18 days, or after about 20 days of contact with the composition.
79. The method of any of statements 53-78, wherein the starting mammalian cell population and cells converting therefrom into definitive endodermal cells do not express detectable levels of NANOG.
80. The method of any of statements 53-79, further comprising administering cells generated by the method to a mammal.
81. The method of any of statements 53-80, further comprising administering to a mammal at least some definitive endodermal cells generated by the method.
82. The method of any of statements 53-81, further comprising administering cells generated by the method to a mammal, wherein the cells express Sox17, Foxa2, Cerberus 1 (Cer), C-X-C chemokine receptor type 4 (Cxcr4), or a combination thereof
83. A method comprising contacting a cell population comprising Sox17 ', Foxa2' cells with one or more growth factors, WNT activators, TGFβ receptor inhibitors, or a combination thereof for a time sufficient to expand the cell number by at least ten-fold and thereby generate an expanded population of posterior foregut-like progenitor cells.
84. The method of statement 83, wherein the expanded population of posterior foregut-like progenitor cells maintains an epithelial colony morphology.
85. The method of statement 83 or 84, wherein the expanded population of posterior foregut-like progenitor cells express SOX17, FOXA2, HNF4a, HNF6, SOX9, or any combination thereof
86. The method of any of statements 83-85, wherein the one or more growth factors is a combination of EGF and bFGF.
87. The method of any of statements 83-86, wherein the WNT activator is a lithium salt, CHIR99021, 1-azakenpaullone, AR-A014418, indirubin-3'-monoxime, 5-Iodo-indirubin-3'-monoxime, kenpaullone, SB-415286, SB-216763, 2-anilino-5-phenyl-1,3,4-oxadiazole), (Z)-5-(2,3-Memylenedioxyphenyl)imidazolidine-2,4-dione, TWS119, CHIR98014, SB415286, Tideglusib, LY2090314, or a combination thereof.
88. The method of any of statements 83-87, wherein the WNT activator is CHIR99021.
89. The method of any of statements 83-88, wherein the TGFβ receptor inhibitor is selected from the group consisting of A83-01, SB431542, SB 431542, SJN 2511, D 4476, LY 364947, SB505124, SB 525334, SD 208, LDN-193189, and any combination thereof.
90. The method of any of statements 83-89, wherein the TGFβ receptor inhibitor is A83-01.
91. The method of any of statements 83-90, wherein the cell number is expanded by at least 100-fold, or at least 1000-fold, or at least 10,000-fold, or at least 100,000-fold, or by at least 1 million-fold, or by at least 10 million-fold, or by at least 100 million-fold.
92. The method of any of statements 83-91, further comprising converting the posterior foregut-like progenitor cells into pancreatic progenitor cells.
93. The method of any of statements 83-92, further comprising contacting the posterior foregut-like progenitor cells with a composition comprising at least one FGF7, FGF10, TGFβ receptor inhibitor, Notch signaling inhibitor, retinoic acid receptor agonist, hedgehog inhibitor, BMP4 signaling inhibitor, or a combination thereof for at least one day to generate differentiating cells.
94. The method of statement 93, further comprising contacting the differentiating cells with EGF, a glucagon-like peptide-1 agonist, a TGFβ receptor inhibitor, a BMP4 signaling inhibitor, an activator of protein kinase C, a Notch signaling inhibitor, a polyADP-ribose synthetase inhibitor, or a combination thereof, for at least 2 days to generate a population of pancreatic progenitor cells.
95. The method of any of statements 83-94, wherein the pancreatic progenitor cells express FOXA2, HNF6, SOX9, PDX1, or any combination thereof
96. The method of any of statements 83-95, further comprising administering the posterior foregut-like progenitor cells, the differentiating cells, the pancreatic progenitor cells, or a combination thereof, to a mammalian subject.
97. The method of any of statements 83-96, wherein the mammalian subject has diabetes.
98. A method comprising contacting pancreatic progenitor cells with a composition comprising vitamin C (or phospho-L-ascorbic acid) and nicotinamide to generate a population of pancreatic beta cells.
99. The method of statement 98, wherein the pancreatic progenitor cells express FOXA2, HNF6, SOX9, PDX1, or any combination thereof
100. The method of statement 98 or 99, wherein the pancreatic beta cells express insulin, glucagon, PDX1, NKX6.1, NEUROD1, NKX2.2, or any combination thereof
101. The method of any of statements 98-100, wherein the composition further comprises a TGFβ receptor inhibitor, a p38 mitogen-activated protein (MAP) kinase inhibitor, a Notch signaling inhibitor, a glucagon-like peptide-1 agonist, a basement membrane protein, an adenylyl cyclase activator, a glucocorticoid receptor agonist, $Ca^{2+}$ channel agonist, or any combination thereof.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed:

1. A method comprising:
(a) contacting starting mammalian cells, after transient expression of OCT4, SOX2 and KLF4 in the cells, with a first composition comprising an effective amount of a TGFβ family member, a WNT activator, sodium butyrate, and parnate, wherein the effective amount is sufficient to generate a first cell population comprising definitive endoderm cells and wherein at least about 5% of the cells in the first population express Sox17 and/or Foxa2, but where the first cell population does not express detectable NANOG; and
(b) contacting cells from the first cell population with a second composition comprising an effective amount of a TGFβ receptor inhibitor, a hedgehog pathway inhibitor, and a retinoic acid receptor agonist to generate a second cell population comprising pancreatic progenitor cells, wherein at least about 10% of the cells in the second population express Pdx1, Nkx6.1, Hnf6, or a combination thereof.

2. The method of claim 1, wherein the pluripotency factors further comprise c-MYC, a p53 inhibitor, or a combination thereof.

3. The method of claim 1, wherein the first composition further comprises epidermal growth factor (EGF), basic fibroblast growth factor (bFGF), or a combination thereof.

4. The method of claim 1, wherein the first composition further comprises a G9a histone methyltransferase inhibitor, 2-phospho-L-ascorbic acid, Vitamin C, a DNA methyltransferase inhibitor, an adenosine agonist, or a combination thereof.

5. The method of claim 1, wherein the TOT family member is Activin A.

6. The method of claim 1, wherein the WNT activator is a lithium salt, CHIR99021, or a combination thereof.

7. The method of claim 1, wherein the starting mammalian cells are non-pluripotent.

8. The method of claim 1, wherein the starting mammalian cells comprise non-pluripotent fibroblasts, epidermal cells, lymphocytes, hepatocytes, myoblasts, neurons, osteoblasts, osteoclasts, T-cells, or any combination thereof.

9. The method of claim 1, wherein the starting mammalian cells comprise partially and/or fully differentiated cells of epithelial cell lineage, hematopoietic lineage, endothelial cell lineage, muscle cell lineage, neural cell lineage, or any combination thereof.

10. The method of claim 1, wherein the mammalian cells are contacted with the first composition for about 4 days to about 21 days.

11. The method of claim 1, wherein at least about 7% of the cells in the first population express Sox17, Foxa2, Cer, Cxcr4, or a combination thereof.

12. The method of claim 1, wherein the second composition further comprises epidermal growth factor (EGF), basic fibroblast growth factor (bFGF), fibroblast growth factor 7 (FGF7), fibroblast growth factor 10 (FGF10), or a combination thereof.

13. The method of claim 1, wherein the second composition further comprises a WNT activator, 2-phospho-L-ascorbic acid, vitamin C, a Notch signaling inhibitor, a BMP4 signaling inhibitor, or a combination thereof.

14. The method of claim 1, wherein the first cell population is contacted with the second composition for about 2 days to about 100 days.

15. The method of claim 1, further comprising contacting the first cell population with an expansion composition comprising EGF and bFGF, a WNT activator, and a TGFβ receptor inhibitor for a time sufficient to expand cell numbers by at least ten-fold and thereby generate an expanded population of posterior foregut-like progenitor cells.

16. The method of claim 15, wherein the expanded population of posterior foregut-like progenitor cells express SOX17, FOXA2, HNF4α, HNF6, SOX9, or any combination thereof.

17. The method of claim 15, wherein the WNT activator is CHIR99021.

18. The method of claim 15, wherein the TGFβ receptor inhibitor is A83-01.

19. The method of claim 15 further comprising contacting the second cell population or the expanded population of posterior foregut-like progenitor cells with a third composition comprising one or more vitamins, TGFβ receptor inhibitors, p38 mitogen-activated protein (MAP) kinase inhibitors, Notch signaling inhibitors, glucagon-like peptide-1 agonists, polyADP ribose synthetase inhibitors, basement membrane proteins, adenylyl cyclase activators, glucocorticoid receptor agonists, calcium channel agonists, or a combination thereof, to generate a third cell population comprising functional pancreatic beta-like cells.

20. The method of claim 19 further comprising administering the second cell population, posterior foregut-like progenitor cells, pancreatic progenitor cells obtained from the second cell population, the third cell population, functional pancreatic beta-like cells or a combination thereof, to a mammal in need thereof.

21. The method of claim 20, wherein the mammal in need thereof has type I diabetes, type II diabetes, or type 1.5 diabetes.

* * * * *

UNITED STATES PATENT AND TRADEMARK OFFICE
CERTIFICATE OF CORRECTION

PATENT NO. : 9,909,104 B2
APPLICATION NO. : 14/907056
DATED : March 6, 2018
INVENTOR(S) : Ding et al.

It is certified that error appears in the above-identified patent and that said Letters Patent is hereby corrected as shown below:

On the Title Page

In Column 2, under "Other Publications", Line 14, delete ""Indolactarn" and insert --"Indolactam-- therefor In the Claims In Column 89, Line 53, in Claim 5, delete "TOT" and insert --TGFβ-- therefor Signed and Sealed this
Eleventh Day of June, 2019

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 426
<212> TYPE: PRT
<213> ORGANISM: Homo sapiens

<400> SEQUENCE: 1

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Arg Gly Leu Glu Cys Asp Gly Lys Val Asn Ile
305                 310                 315                 320
```

-continued

```
Cys Cys Lys Lys Gln Phe Phe Val Ser Phe Lys Asp Ile Gly Trp Asn
            325             330             335

Asp Trp Ile Ile Ala Pro Ser Gly Tyr His Ala Asn Tyr Cys Glu Gly
            340             345             350

Glu Cys Pro Ser His Ile Ala Gly Thr Ser Gly Ser Ser Leu Ser Phe
        355             360             365

His Ser Thr Val Ile Asn His Tyr Arg Met Arg Gly His Ser Pro Phe
        370             375             380

Ala Asn Leu Lys Ser Cys Cys Val Pro Thr Lys Leu Arg Pro Met Ser
385             390             395             400

Met Leu Tyr Tyr Asp Asp Gly Gln Asn Ile Ile Lys Lys Asp Ile Gln
            405             410             415

Asn Met Ile Val Glu Glu Cys Gly Cys Ser
            420             425
```